US006825023B1

(12) United States Patent
Gurney et al.

(10) Patent No.: US 6,825,023 B1
(45) Date of Patent: Nov. 30, 2004

(54) ALZHEIMER'S DISEASE SECRETASE, APP SUBSTRATES THEREFOR, AND USES THEREFOR

(75) Inventors: Mark E. Gurney, Grand Rapids, MI (US); Michael J. Bienkowski, Portage, MI (US); Robert L. Heinrikson, Plainwell, MI (US); Luis A. Parodi, Stockholm (SE); Riqiang Yan, Kalamazoo, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/548,368

(22) Filed: Apr. 12, 2000

Related U.S. Application Data

(60) Division of application No. 09/416,901, filed on Oct. 13, 1999, now Pat. No. 6,699,671, which is a continuation-in-part of application No. 09/404,133, filed on Sep. 23, 1999, now abandoned, and a continuation-in-part of application No. PCT/US99/20881, filed on Sep. 23, 1999.

(60) Provisional application No. 60/155,493, filed on Sep. 23, 1999, and provisional application No. 60/101,594, filed on Sep. 24, 1998.

(51) Int. Cl.[7] ............................ C12N 9/64; C12N 9/00; C07K 7/00; C07K 1/00

(52) U.S. Cl. ........................ 435/226; 435/183; 530/300; 530/324; 530/350

(58) Field of Search ................................ 530/300, 350, 530/324; 435/325, 252.3, 67.1, 183, 226

(56) References Cited

U.S. PATENT DOCUMENTS

| | | | |
|---|---|---|---|
| 5,424,205 A | 6/1995 | Dovey et al. | 435/226 |
| 5,455,169 A | 10/1995 | Mullan | 435/240.2 |
| 5,593,846 A | 1/1997 | Schenk et al. | 435/7.9 |
| 5,710,248 A * | 1/1998 | Grose | 530/327 |
| 5,733,768 A | 3/1998 | Dixon et al. | 435/226 |
| 5,744,346 A | 4/1998 | Chrysler et al. | 435/226 |
| 5,750,349 A | 5/1998 | Suzuki et al. | 435/7.1 |
| 5,766,846 A | 6/1998 | Schlossmacher et al. | 435/6 |
| 5,795,963 A | 8/1998 | Mullan | 435/350 |
| 5,837,672 A | 11/1998 | Schenk et al. | 514/2 |
| 5,849,560 A | 12/1998 | Abraham | 435/219 |
| 5,877,015 A | 3/1999 | Hardy et al. | 435/325 |
| 5,942,400 A | 8/1999 | Anderson et al. | 435/7.1 |
| 6,025,180 A | 2/2000 | Powell et al. | 435/219 |
| 6,162,630 A | 12/2000 | Powell et al. | 435/219 |
| 6,211,428 B1 | 4/2001 | Singh et al. | 800/13 |
| 6,221,645 B1 | 4/2001 | Chrysler et al. | 435/226 |
| 6,245,884 B1 | 6/2001 | Hook | 530/300 |
| 6,245,964 B1 | 6/2001 | McLonlogue et al. | 800/12 |
| 6,313,268 B1 | 11/2001 | Hook | 530/350 |
| 6,319,689 B1 | 11/2001 | Powell et al. | 435/69.1 |
| 6,358,725 B1 | 3/2002 | Christie et al. | 435/212 |
| 6,361,975 B1 | 3/2002 | Christie et al. | 435/69.1 |
| 6,545,127 B1 | 4/2003 | Tang et al. | 530/350 |

FOREIGN PATENT DOCUMENTS

| | | |
|---|---|---|
| EP | 0848 062 A2 | 6/1998 |
| EP | 0855 444 A2 | 7/1998 |
| WO | WO 96/31122 | 10/1996 |
| WO | WO 96/40885 | 12/1996 |
| WO | WO 98/13488 | 4/1998 |
| WO | WO 98/21589 | 5/1998 |
| WO | WO 98/26059 | 6/1998 |
| WO | WO 99/31236 | 6/1999 |
| WO | WO 99/34004 | 8/1999 |
| WO | WO 99/46281 | 9/1999 |
| WO | WO 99/64587 | 12/1999 |
| WO | WO 00/23576 | 4/2000 |
| WO | WO 00/47618 | 8/2000 |
| WO | WO 00/56871 | 9/2000 |
| WO | WO 00/58479 | 10/2000 |
| WO | WO 00/68266 | 11/2000 |
| WO | WO 00/69262 | 11/2000 |
| WO | WO 01/00663 | 1/2001 |
| WO | WO 01/00665 | 1/2001 |
| WO | WO 01/29563 | 4/2001 |
| WO | WO 01/31054 | 5/2001 |
| WO | WO 01/36600 | 5/2001 |
| WO | WO 01/38487 | 5/2001 |

OTHER PUBLICATIONS

Skolnick et al., Trends in Biotech., 18(1):34–39, 2000.*

Chyung et al. Novel β–Secretase Cleavage of β–Amyloid Precursor Protein in the Endoplasmic Reticulum/Intermediate Compartment of NT2N Cells, *Journal of Cell Biology*, 138: 671–680 (Aug. 11, 1997.

Evin et al.,. Alzheimer's disease amyloid precursor protein (AβPP): proteolytic processing, secretases and βA4 amyloid production, *Amyloid: Int. J. Exp. Clin. Invest.* 1: 263–280 (Sep. 8, 1994).

Haass et al., Amyloid β–peptide is Produced by Cultured Cells During Normal Metabolism, *Nature*, 359: 322–325 (Sep. 24, 1992).

Haass et al., β–Amyloid Peptide and 3–kDa Fragment are Derived by Distinct Cellular Mechanisms, *Journal of Biochemistry*, 268: 3021–3024 (Feb. 15, 1993).

Haass et al., The Swedish Mutation Causes Early–Onset Alzheimer's Disease by β–Secretase Cleavage Within the Secretory Pathway, *Nature Medicine*, 12: 1291–1296 (Dec. 1995).

(List continued on next page.)

*Primary Examiner*—Sharon Turner
(74) *Attorney, Agent, or Firm*—Pharmacia & Upjohn Company; Thomas A. Wootton

(57) ABSTRACT

The present invention provides the enzyme and enzymatic procedures for cleaving the β secretase cleavage site of the APP protein and associated nucleic acids, peptides, vectors, cells and cell isolates and assays. The invention further provides a modified APP protein and associated nucleic acids, peptides, vectors, cells, and cell isolates, and assays that are particularly useful for identifying candidate therapeutics for treatment or prevention of Alzheimer's disease.

4 Claims, 18 Drawing Sheets

OTHER PUBLICATIONS

Hirosawa et al., Characterization of cDNA Clones Selected by the GeneMark Analysis from Size–Fractionated cDNA Libraries From Human Brain, *DNA Res.*, 6(5): 329–336 (Oct. 29, 1999).

Hussain et al., Identification of a Novel Aspartic Protease (Asp 2) as β–Secretase, *Molecular and Cellular Neuroscience*, 14: 419–427 (1999).

Kang et al., The Precursor of Alzheimer's Disease Amyloid A4 Protein Resembles a Cell–Surface Receptor, *Nature*, 325: 733–736 (Feb. 19, 1987).

Kitaguchi et al., Novel Precursor of Alzheimer's Disease Amyloid Protein Shows Protease Inhibitory Activity, *Nature*, 331: 532–532 (Feb. 11, 1988).

Knops et al., Cell–type and Amyloid Precursor Protein–type Specific Inhibition of Aβ Release by Bafilomycin A1, a Selective Inhibitor of Vacuolar ATPases, *Journal of Biological Chemistry*, 270: 2419–2422 (Feb. 10, 1995).

Koo and Squazzo, Evidence that Production and Release of Amyloid β–Protein Involves the Endocytic Pathway, *Journal of Biological Chemistry*, 269: 17386–17389 (Jul. 1, 1994).

Ponte et al., A New A4 Amyloid mRNA Contains a Domain Homologous to Serine Proteinase Inhibitors, *Nature*, 331: 525–527 (Feb. 11, 1988).

Seubert et al. Secretion of β–amyloid Precursor Protein Cleaved at the Amino Terminus of the β–amyloid Peptide, *Nature*, 361: 260–263 (Jan. 21, 1993).

Sinha et al., Purification and Cloning of Amyloid Precursor Protein β–Secretase from Human Brain, *Nature*, 402: 537–540 (Dec., 2, 1999).

Szecsi, The Aspartic Proteases, *Scand. J. Clin. Lab. Invest.*, 52 (suppl. 210): 5–22 (1992).

Tanzi et al., Protease Inhibitor Domain Encoded by an Amyloid Protein Precursor mRNA Associated with Alzheimer's Disease, *Nature*, 331: 528–530 (Feb. 11, 1988).

Vasser et al., β–secretase Cleavage of Alzheimer's Amyloid Precursor Protein by the Transmembrane Aspartic Protease BACE, *Science*, 286 (5440): 735–41 (Oct. 22, 1999).

Yan et al., Membrane–anchored Aspartyl Protease with Alzheimer's Disease β–Secretase Activity, *Nature*, 402: 533–537 (Dec. 2, 1999).

Zhao et al., β–Secretase Processing of the β–Amyloid Precursor Protein in Transgenic Mice Is Efficient in Neurons but Inefficient in Astrocytes, *Journal of Biological Chemistry*, 271: 31407–31411 (Dec. 6, 1996).

Mullan et al., A Pathogenic Mutation for Probable Alzheimer's Disease in the APP Gene at the N–Terminus of β–Amyloid, *Nature Genetics* 1: 345–347, (Aug. 1992).

Elan and Pharmacia form Alzheimer's disease research collaboration in the area of Beta–Secretase, News Aug. 9, 2000, www.elancorp.com.

* cited by examiner

FIGURE 1A

```
ATGGGCGCACTGGCCCGGGCGCTGCTGCTGCCTCTGCTGGCCCAGTGGCTCCTGCGCGCC
 M   G   A   L   A   R   A   L   L   L   P   L   L   A   Q   W   L   L   R   A
CCCCGGAGCTGGCCCCCGCGCCCTTCACGCTGCCCCTCCGGGTGGCCGCGGCCACGAAC
 A   P   E   L   A   P   A   P   F   T   L   P   L   R   V   A   A   A   T   N
CGCGTAGTTGCGCCCACCCCGGGACCCGGGACCCCTGCCGAGCGCCACGCCGACGGCTTG
 R   V   V   A   P   T   P   G   P   G   T   P   A   E   R   H   A   D   G   L
GCGCTCGCCCTGGAGCCTGCCCTGGCGTCCCCGCGGGCGCCGCCAACTTCTTGGCCATG
 A   L   A   L   E   P   A   L   S   P   A   G   A   A   N   F   L   A   M
GTAGACAACCTGCAGGGGACTCTGGCCGCGGCTACTACCTGGAGATGCTGATCGGGACC
 V   D   N   L   Q   G   D   S   G   R   G   Y   Y   L   E   M   L   I   G   T
CCCCCGCAGAAGCTACAGATTCTCGTTGACACTGGAAGCAGTAACTTTGCCGTGGCAGGA
 P   P   Q   K   L   Q   I   L   V   D   T   G   S   S   N   F   A   V   A   G
ACCCCGCACTCCTACATAGACACGTACTTTGACACAGAGAGGTCTAGCACATACCGCTCC
 T   P   H   S   Y   I   D   T   Y   F   D   T   E   R   S   S   T   Y   R   S
AAGGGCTTTGACGTCACAGTGAAGTACACACAAGGAAGCTGGACGGGCTTCGTTGGGGAA
 K   G   F   D   V   T   V   K   Y   T   Q   G   S   W   T   G   F   V   G   E
GACCTCGTCACCATCCCCAAAGGCTTCAATACTTCTTTTCTTGTCAACATTGCCACTATT
 D   L   V   T   I   P   K   G   F   N   T   S   F   L   V   N   I   A   T   I
TTTGAATCAGAGAATTTCTTTTTGCCTGGGATTAAATGGAATGGAATACTTGGCCTAGCT
 F   E   S   E   N   F   F   L   P   G   I   K   W   N   G   I   L   G   L   A
TATGCCACACTTGCCAAGCCATCAAGTTCTCTGGAGACCTTCTTCGACTCCCTGGTGACA
 Y   A   T   L   A   K   P   S   S   S   L   E   T   F   F   D   S   L   V   T
CAAGCAAACATCCCCAACGTTTTCTCCATGCAGATGTGTGGAGCCGGCTTGCCCGTTGCT
 Q   A   N   I   P   N   V   F   S   M   Q   M   C   G   A   G   L   P   V   A
GGATCTGGGACCAACGGAGGTAGTCTTGTCTTGGGTGGAATTGAACCAAGTTTGTATAAA
 G   S   G   T   N   G   G   S   L   V   L   G   G   I   E   P   S   L   Y   K
GGAGACATCTGGTATACCCCTATTAAGGAAGAGTGGTACTACCAGATAGAAATTCTGAAA
 G   D   I   W   Y   T   P   I   K   E   E   W   Y   Y   Q   I   E   I   L   K
TTGGAAATTGGAGGCCAAAGCCTTAATCTGGACTGCAGAGAGTATAACGCAGACAAGGCC
 L   E   I   G   G   Q   S   L   N   L   D   C   R   E   Y   N   A   D   K   A
ATCGTGGACAGTGGCACCACGCTGCTGCGCCTGCCCCAGAAGGTGTTTGATGCGGTGGTG
 I   V   D   S   G   T   T   L   L   R   L   P   Q   K   V   F   D   A   V   V
GAAGCTGTGGCCCGCGCATCTCTGATTCCAGAATTCTCTGATGGTTTCTGGACTGGGTCC
 E   A   V   A   R   A   S   L   I   P   E   F   S   D   G   F   W   T   G   S
CAGCTGGCGTGCTGGACGAATTCGGAAACACCTTGGTCTTACTTCCCTAAAATCTCCATC
 Q   L   A   C   W   T   N   S   E   T   P   W   S   Y   F   P   K   I   S   I
TACCTGAGAGATGAGAACTCCAGCAGGTCATTCCGTATCACAATCCTGCCTCAGCTTTAC
 Y   L   R   D   E   N   S   S   R   S   F   R   I   T   I   L   P   Q   L   Y
ATTCAGCCCATGATGGGGGCCGGCCTGAATTATGAATGTTACCGATTCGGCATTTCCCCA
 I   Q   P   M   M   G   A   G   L   N   Y   E   C   Y   R   F   G   I   S   P
```

FIGURE 1B

```
TCCACAAATGCGCTGGTGATCGGTGCCACGGTGATGGAGGGCTTCTACGTCATCTTCGAC
 S   T   N   A   L   V   I   G   A   T   V   M   E   G   F   Y   V   I   F   D
AGAGCCCAGAAGAGGGTGGGCTTCGCAGCGAGCCCCTGTGCAGAAATTGCAGGTGCTGCA
 R   A   Q   K   R   V   G   F   A   A   S   P   C   A   E   I   A   G   A   A
GTGTCTGAAATTTCCGGGCCTTTCTCAACAGAGGATGTAGCCAGCAACTGTGTCCCCGCT
 V   S   E   I   S   G   P   F   S   T   E   D   V   A   S   N   C   V   P   A
CAGTCTTTGAGCGAGCCCATTTTGTGGATTGTGTCCTATGCGCTCATGAGCGTCTGTGGA
 Q   S   L   S   E   P   I   L   W   I   V   S   Y   A   L   M   S   V   C   G
GCCATCCTCCTTGTCTTAATCGTCCTGCTGCTGCTGCCGTTCCGGTGTCAGCGTCGCCCC
 A   I   L   L   V   L   I   V   L   L   L   P   F   R   C   Q   R   R   P
CGTGACCCTGAGGTCGTCAATGATGAGTCCTCTCTGGTCAGACATCGCTGGAAATGAATA
 R   D   P   E   V   V   N   D   E   S   S   L   V   R   H   R   W   K

GCCAGGCCTGACCTCAAGCAACCATGAACTCAGCTATTAAGAAAATCACATTTCCAGGGC
AGCAGCCGGGATCGATGGTGGCGCTTTCTCCTGTGCCCACCCGTCTTCAATCTCTGTTCT
GCTCCCAGATGCCTTCTAGATTCACTGTCTTTTGATTCTTGATTTTCAAGCTTTCAAATC
CTCCCTACTTCCAAGAAAAATAATTAAAAAAAAAACTTCATTCTAAACCAAAAAAAAAA
AAAA
```

FIGURE 2A

```
ATGGCCCAAGCCCTGCCCTGGCTCCTGCTGTGGATGGGCGCGGGAGTGCTGCCTGCCCAC
 M   A   Q   A   L   P   W   L   L   L   W   M   G   A   G   V   L   P   A   H
GGCACCCAGCACGGCATCCGGCTGCCCCTGCGCAGCGGCCTGGGGGGCGCCCCCCTGGGG
 G   T   Q   H   G   I   R   L   P   L   R   S   G   L   G   G   A   P   L   G
CTGCGGCTGCCCCGGGAGACCGACGAAGAGCCCGAGGAGCCCGGCCGGAGGGGCAGCTTT
 L   R   L   P   R   E   T   D   E   E   P   E   E   P   G   R   R   G   S   F
GTGGAGATGGTGGACAACCTGAGGGGCAAGTCGGGGCAGGGCTACTACGTGGAGATGACC
 V   E   M   V   D   N   L   R   G   K   S   G   Q   G   Y   Y   V   E   M   T
GTGGGCAGCCCCCCGCAGACGCTCAACATCCTGGTGGATACAGGCAGCAGTAACTTTGCA
 V   G   S   P   P   Q   T   L   N   I   L   V   D   T   G   S   S   N   F   A
GTGGGTGCTGCCCCCCACCCCTTCCTGCATCGCTACTACCAGAGGCAGCTGTCCAGCACA
 V   G   A   A   P   H   P   F   L   H   R   Y   Y   Q   R   Q   L   S   S   T
TACCGGGACCTCCGGAAGGGTGTGTATGTGCCCTACACCCAGGGCAAGTGGGAAGGGGAG
 Y   R   D   L   R   K   G   V   Y   V   P   Y   T   Q   G   K   W   E   G   E
CTGGGCACCGACCTGGTAAGCATCCCCCATGGCCCCAACGTCACTGTGCGTGCCAACATT
 L   G   T   D   L   V   S   I   P   H   G   P   N   V   T   V   R   A   N   I
GCTGCCATCACTGAATCAGACAAGTTCTTCATCAACGGCTCCAACTGGGAAGGCATCCTG
 A   A   I   T   E   S   D   K   F   F   I   N   G   S   N   W   E   G   I   L
GGGCTGGCCTATGCTGAGATTGCCAGGCTTTGTGGTGCTGGCTTCCCCCTCAACCAGTCT
 G   L   A   Y   A   E   I   A   R   L   C   G   A   G   F   P   L   N   Q   S
GAAGTGCTGGCCTCTGTCGGAGGGAGCATGATCATTGGAGGTATCGACCACTCGCTGTAC
 E   V   L   A   S   V   G   G   S   M   I   I   G   G   I   D   H   S   L   Y
ACAGGCAGTCTCTGGTATACACCCATCCGGCGGGAGTGGTATTATGAGGTGATCATTGTG
 T   G   S   L   W   Y   T   P   I   R   R   E   W   Y   Y   E   V   I   I   V
CGGGTGGAGATCAATGGACAGGATCTGAAAATGGACTGCAAGGAGTACAACTATGACAAG
 R   V   E   I   N   G   Q   D   L   K   M   D   C   K   E   Y   N   Y   D   K
AGCATTGTGGACAGTGGCACCACCAACCTTCGTTTGCCCAAGAAAGTGTTTGAAGCTGCA
 S   I   V   D   S   G   T   T   N   L   R   L   P   K   K   V   F   E   A   A
GTCAAATCCATCAAGGCAGCCTCCTCCACGGAGAAGTTCCCTGATGGTTTCTGGCTAGGA
 V   K   S   I   K   A   A   S   S   T   E   K   F   P   D   G   F   W   L   G
GAGCAGCTGGTGTGCTGGCAAGCAGGCACCACCCCTTGGAACATTTTCCCAGTCATCTCA
 E   Q   L   V   C   W   Q   A   G   T   T   P   W   N   I   F   P   V   I   S
CTCTACCTAATGGGTGAGGTTACCAACCAGTCCTTCCGCATCACCATCCTTCCGCAGCAA
 L   Y   L   M   G   E   V   T   N   Q   S   F   R   I   T   I   L   P   Q   Q
TACCTGCGGCCAGTGGAAGATGTGGCCACGTCCCAAGACGACTGTTACAAGTTTGCCATC
 Y   L   R   P   V   E   D   V   A   T   S   Q   D   D   C   Y   K   F   A   I
TCACAGTCATCCACGGGCACTGTTATGGGAGCTGTTATCATGGAGGGCTTCTACGTTGTC
 S   Q   S   S   T   G   T   V   M   G   A   V   I   M   E   G   F   Y   V   V
TTTGATCGGGCCCGAAAACGAATTGGCTTTGCTGTCAGCGCTTGCCATGTGCACGATGAG
 F   D   R   A   R   K   R   I   G   F   A   V   S   A   C   H   V   H   D   E
```

FIGURE 2B

```
TTCAGGACGGCAGCGGTGGAAGGCCCTTTTGTCACCTTGGACATGGAAGACTGTGGCTAC
 F  R  T  A  A  V  E  G  P  F  V  T  L  D  M  E  D  C  G  Y
AACATTCCACAGACAGATGAGTCAACCCTCATGACCATAGCCTATGTCATGGCTGCCATC
 N  I  P  Q  T  D  E  S  T  L  M  T  I  A  Y  V  M  A  A  I
TGCGCCCTCTTCATGCTGCCACTCTGCCTCATGGTGTGTCAGTGGCGCTGCCTCCGCTGC
 C  A  L  F  M  L  P  L  C  L  M  V  C  Q  W  R  C  L  R  C
CTGCGCCAGCAGCATGATGACTTTGCTGATGACATCTCCCTGCTGAAGTGAGGAGGCCCA
 L  R  Q  Q  H  D  D  F  A  D  D  I  S  L  L  K

TGGGCAGAAGATAGAGATTCCCCTGGACCACACCTCCGTGGTTCACTTTGGTCACAAGTA
GGAGACACAGATGGCACCTGTGGCCAGAGCACCTCAGGACCCTCCCCACCCACCAAATGC
CTCTGCCTTGATGGAGAAGGAAAAGGCTGGCAAGGTGGGTTCCAGGGACTGTACCTGTAG
GAAACAGAAAAGAGAAGAAAGAAGCACTCTGCTGGCGGGAATACTCTTGGTCACCTCAAA
TTTAAGTCGGGAAATTCTGCTGCTTGAAACTTCAGCCCTGAACCTTTGTCCACCATTCCT
TTAAATTCTCCAACCCAAAGTATTCTTCTTTTCTTAGTTTCAGAAGTACTGGCATCACAC
GCAGGTTACCTTGGCGTGTGTCCCTGTGGTACCCTGGCAGAGAAGAGACCAAGCTTGTTT
CCCTGCTGGCCAAAGTCAGTAGGAGAGGATGCACAGTTTGCTATTTGCTTTAGAGACAGG
GACTGTATAAACAAGCCTAACATTGGTGCAAAGATTGCCTCTTGAAAAAAAAAAAA
```

FIGURE 3A

```
ATGGCCCAAGCCCTGCCCTGGCTCCTGCTGTGGATGGGCGCGGGAGTGCTGCCTGCCCAC
 M   A   Q   A   L   P   W   L   L   L   W   M   G   A   G   V   L   P   A   H
GGCACCCAGCACGGCATCCGGCTGCCCCTGCGCAGCGGCCTGGGGGGCGCCCCCCTGGGG
 G   T   Q   H   G   I   R   L   P   L   R   S   G   L   G   G   A   P   L   G
CTGCGGCTGCCCCGGGAGACCGACGAAGAGCCCGAGGAGCCCGGCCGGAGGGGCAGCTTT
 L   R   L   P   R   E   T   D   E   E   P   E   E   P   G   R   R   G   S   F
GTGGAGATGGTGGACAACCTGAGGGGCAAGTCGGGGCAGGGCTACTACGTGGAGATGACC
 V   E   M   V   D   N   L   R   G   K   S   G   Q   G   Y   Y   V   E   M   T
GTGGGCAGCCCCCCGCAGACGCTCAACATCCTGGTGGATACAGGCAGCAGTAACTTTGCA
 V   G   S   P   P   Q   T   L   N   I   L   V   D   T   G   S   S   N   F   A
GTGGGTGCTGCCCCCCACCCCTTCCTGCATCGCTACTACCAGAGGCAGCTGTCCAGCACA
 V   G   A   A   P   H   P   F   L   H   R   Y   Y   Q   R   Q   L   S   S   T
TACCGGGACCTCCGGAAGGGTGTGTATGTGCCCTACACCCAGGGCAAGTGGGAAGGGGAG
 Y   R   D   L   R   K   G   V   Y   V   P   Y   T   Q   G   K   W   E   G   E
CTGGGCACCGACCTGGTAAGCATCCCCCATGGCCCCAACGTCACTGTGCGTGCCAACATT
 L   G   T   D   L   V   S   I   P   H   G   P   N   V   T   V   R   A   N   I
GCTGCCATCACTGAATCAGACAAGTTCTTCATCAACGGCTCCAACTGGGAAGGCATCCTG
 A   A   I   T   E   S   D   K   F   F   I   N   G   S   N   W   E   G   I   L
GGGCTGGCCTATGCTGAGATTGCCAGGCCTGACGACTCCCTGGAGCCTTTCTTTGACTCT
 G   L   A   Y   A   E   I   A   R   P   D   D   S   L   E   P   F   F   D   S
CTGGTAAAGCAGACCCACGTTCCCAACCTCTTCTCCCTGCAGCTTTGTGGTGCTGGCTTC
 L   V   K   Q   T   H   V   P   N   L   F   S   L   Q   L   C   G   A   G   F
CCCCTCAACCAGTCTGAAGTGCTGGCCTCTGTCGGAGGGAGCATGATCATTGGAGGTATC
 P   L   N   Q   S   E   V   L   A   S   V   G   G   S   M   I   I   G   G   I
GACCACTCGCTGTACACAGGCAGTCTCTGGTATACACCCATCCGGCGGGAGTGGTATTAT
 D   H   S   L   Y   T   G   S   L   W   Y   T   P   I   R   R   E   W   Y   Y
GAGGTCATCATTGTGCGGGTGGAGATCAATGGACAGGATCTGAAAATGGACTGCAAGGAG
 E   V   I   I   V   R   V   E   I   N   G   Q   D   L   K   M   D   C   K   E
TACAACTATGACAAGAGCATTGTGGACAGTGGCACCACCAACCTTCGTTTGCCCAAGAAA
 Y   N   Y   D   K   S   I   V   D   S   G   T   T   N   L   R   L   P   K   K
GTGTTTGAAGCTGCAGTCAAATCCATCAAGGCAGCCTCCTCCACGGAGAAGTTCCCTGAT
 V   F   E   A   A   V   K   S   I   K   A   A   S   S   T   E   K   F   P   D
GGTTTCTGGCTAGGAGAGCAGCTGGTGTGCTGGCAAGCAGGCACCACCCCTTGGAACATT
 G   F   W   L   G   E   Q   L   V   C   W   Q   A   G   T   T   P   W   N   I
TTCCCAGTCATCTCACTCTACCTAATGGGTGAGGTTACCAACCAGTCCTTCCGCATCACC
 F   P   V   I   S   L   Y   L   M   G   E   V   T   N   Q   S   F   R   I   T
ATCCTTCCGCAGCAATACCTGCGGCCAGTGGAAGATGTGGCCACGTCCCAAGACGACTGT
 I   L   P   Q   Q   Y   L   R   P   V   E   D   V   A   T   S   Q   D   D   C
TACAAGTTTGCCATCTCACAGTCATCCACGGGCACTGTTATGGGAGCTGTTATCATGGAG
 Y   K   F   A   I   S   Q   S   S   T   G   T   V   M   G   A   V   I   M   E
```

FIGURE 3B

```
GGCTTCTACGTTGTCTTTGATCGGGCCCGAAAACGAATTGGCTTTGCTGTCAGCGCTTGC
 G  F  Y  V  V  F  D  R  A  R  K  R  I  G  F  A  V  S  A  C
CATGTGCACGATGAGTTCAGGACGGCAGCGGTGGAAGGCCCTTTTGTCACCTTGGACATG
 H  V  H  D  E  F  R  T  A  A  V  E  G  P  F  V  T  L  D  M
GAAGACTGTGGCTACAACATTCCACAGACAGATGAGTCAACCCTCATGACCATAGCCTAT
 E  D  C  G  Y  N  I  P  Q  T  D  E  S  T  L  M  T  I  A  Y
GTCATGGCTGCCATCTGCGCCCTCTTCATGCTGCCACTCTGCCTCATGGTGTGTCAGTGG
 V  M  A  A  I  C  A  L  F  M  L  P  L  C  L  M  V  C  Q  W
CGCTGCCTCCGCTGCCTGCGCCAGCAGCATGATGACTTTGCTGATGACATCTCCCTGCTG
 R  C  L  R  C  L  R  Q  Q  H  D  D  F  A  D  D  I  S  L  L
AAGTGAGGAGGCCCATGGGCAGAAGATAGAGATTCCCCTGGACCACACCTCCGTGGTTCA
 K
```

```
CTTTGGTCACAAGTAGGAGACACAGATGGCACCTGTGGCCAGAGCACCTCAGGACCCTCC
CCACCCACCAAATGCCTCTGCCTTGATGGAGAAGGAAAAGGCTGGCAAGGTGGGTTCCAG
GGACTGTACCTGTAGGAAACAGAAAAGAGAAGAAAGAAGCACTCTGCTGGCGGGAATACT
CTTGGTCACCTCAAATTTAAGTCGGGAAATTCTGCTGCTTGAAACTTCAGCCCTGAACCT
TTGTCCACCATTCCTTTAAATTCTCCAACCCAAAGTATTCTTCTTTTCTTAGTTTCAGAA
GTACTGGCATCACACGCAGGTTACCTTGGCGTGTGTCCCTGTGGTACCCTGGCAGAGAAG
AGACCAAGCTTGTTTCCCTGCTGGCCAAAGTCAGTAGGAGAGGATGCACAGTTTGCTATT
TGCTTTAGAGACAGGGACTGTATAAACAAGCCTAACATTGGTGCAAAGATTGCCTCTTGA
ATTAAAAAAAAAAAAAAAAAAAAAAAAAA
```

FIGURE 4

```
ATGGCCCCAGCGCTGCACTGGCTCCTGCTATGGGTGGGCTCGGGAATGCTGCCTGCCCAG
 M  A  P  A  L  H  W  L  L  L  W  V  G  S  G  M  L  P  A  Q
GGAACCCATCTCGGCATCCGGCTGCCCCTTCGCAGCGGCCTGGCAGGGCCACCCCTGGGC
 G  T  H  L  G  I  R  L  P  L  R  S  G  L  A  G  P  P  L  G
CTGAGGCTGCCCCGGGAGACTGACGAGGAATCGGAGGAGCCTGGCCGGAGAGGCAGCTTT
 L  R  L  P  R  E  T  D  E  E  S  E  E  P  G  R  R  G  S  F
GTGGAGATGGTGGACAACCTGAGGGGAAAGTCCGGCCAGGGCTACTATGTGGAGATGACC
 V  E  M  V  D  N  L  R  G  K  S  G  Q  G  Y  Y  V  E  M  T
GTAGGCAGCCCCCCACAGACGCTCAACATCCTGGTGGACACGGGCAGTAGTAACTTTGCA
 V  G  S  P  P  Q  T  L  N  I  L  V  D  T  G  S  S  N  F  A
GTGGGGGCTGCCCCACACCCTTTCCTGCATCGCTACTACCAGAGGCAGCTGTCCAGCACA
 V  G  A  A  P  H  P  F  L  H  R  Y  Y  Q  R  Q  L  S  S  T
TATCGAGACCTCCGAAAGGGTGTGTATGTGCCCTACACCCAGGGCAAGTGGGAGGGGAA
 Y  R  D  L  R  K  G  V  Y  V  P  Y  T  Q  G  K  W  E  G  E
CTGGGCACCGACCTGGTGAGCATCCCTCATGGCCCCAACGTCACTGTGCGTGCCAACATT
 L  G  T  D  L  V  S  I  P  H  G  P  N  V  T  V  R  A  N  I
GCTGCCATCACTGAATCGGACAAGTTCTTCATCAATGGTTCCAACTGGGAGGGCATCCTA
 A  A  I  T  E  S  D  K  F  F  I  N  G  S  N  W  E  G  I  L
GGGCTGGCCTATGCTGAGATTGCCAGGCCCGACGACTCTTTGGAGCCCTTCTTTGACTCC
 G  L  A  Y  A  E  I  A  R  P  D  D  S  L  E  P  F  F  D  S
CTGGTGAAGCAGACCCACATTCCCAACATCTTTTCCCTGCAGCTCTGTGGCGCTGGCTTC
 L  V  K  Q  T  H  I  P  N  I  F  S  L  Q  L  C  G  A  G  F
CCCCTCAACCAGACCGAGGCACTGGCCTCGGTGGGAGGGAGCATGATCATTGGTGGTATC
 P  L  N  Q  T  E  A  L  A  S  V  G  G  S  M  I  I  G  G  I
GACCACTCGCTATACACGGGCAGTCTCTGGTACACACCCATCCGGCGGGAGTGGTATTAT
 D  H  S  L  Y  T  G  S  L  W  Y  T  P  I  R  R  E  W  Y  Y
GAAGTGATCATTGTACGTGTGGAAATCAATGGTCAAGATCTCAAGATGGACTGCAAGGAG
 E  V  I  I  V  R  V  E  I  N  G  Q  D  L  K  M  D  C  K  E
TACAACTACGACAAGAGCATTGTGGACAGTGGGACCACCAACCTTCGCTTGCCCAAGAAA
 Y  N  Y  D  K  S  I  V  D  S  G  T  T  N  L  R  L  P  K  K
GTATTTGAAGCTGCCGTCAAGTCCATCAAGGCAGCCTCCTCGACGGAGAAGTTCCCGGAT
 V  F  E  A  A  V  K  S  I  K  A  A  S  S  T  E  K  F  P  D
GGCTTTTGGCTAGGGGAGCAGCTGGTGTGCTGGCAAGCAGGCACGACCCCTTGGAACATT
 G  F  W  L  G  E  Q  L  V  C  W  Q  A  G  T  T  P  W  N  I
TTCCCAGTCATTTCACTTTACCTCATGGGTGAAGTCACCAATCAGTCCTTCCGCATCACC
 F  P  V  I  S  L  Y  L  M  G  E  V  T  N  Q  S  F  R  I  T
ATCCTTCCTCAGCAATACCTACGGCCGGTGGAGGACGTGGCCACGTCCCAAGACGACTGT
 I  L  P  Q  Q  Y  L  R  P  V  E  D  V  A  T  S  Q  D  D  C
TACAAGTTCGCTGTCTCACAGTCATCCACGGGCACTGTTATGGGAGCCGTCATCATGGAA
 Y  K  F  A  V  S  Q  S  S  T  G  T  V  M  G  A  V  I  M  E
GGTTTCTATGTCGTCTTCGATCGAGCCCGAAAGCGAATTGGCTTTGCTGTCAGCGCTTGC
 G  F  Y  V  V  F  D  R  A  R  K  R  I  G  F  A  V  S  A  C
CATGTGCACGATGAGTTCAGGACGGCGGCAGTGGAAGGTCCGTTTGTTACGGCAGACATG
 H  V  H  D  E  F  R  T  A  A  V  E  G  P  F  V  T  A  D  M
GAAGACTGTGGCTACAACATTCCCCAGACAGATGAGTCAACACTTATGACCATAGCCTAT
 E  D  C  G  Y  N  I  P  Q  T  D  E  S  T  L  M  T  I  A  Y
GTCATGGCGGCCATCTGCGCCCTCTTCATGTTGCCACTCTGCCTCATGGTATGTCAGTGG
 V  M  A  A  I  C  A  L  F  M  L  P  L  C  L  M  V  C  Q  W
CGCTGCCTGCGTTGCCTGCGCCACCAGCACGATGACTTTGCTGATGACATCTCCCTGCTC
 R  C  L  R  C  L  R  H  Q  H  D  D  F  A  D  D  I  S  L  L
AAGTAAGGAGGCTCGTGGGCAGATGATGGAGACGCCCCTGGACCACATCTGGGTGGTTCC
 K
CTTTGGTCACATGAGTTGGAGCTATGGATGGTACCTGTGGCCAGAGCACCTCAGGACCCT
CACCAACCTGCCAATGCTTCTGGCGTGACAGAACAGAGAAATCAGGCAAGCTGGATTACA
GGGCTTGCACCTGTAGGACACAGGAGAGGGAAGGAAGCAGCGTTCTGGTGGCAGGAATAT
CCTTAGGCACCACAAACTTGAGTTGGAAATTTTGCTGCTTGAAGCTTCAGCCCTGACCCT
CTGCCCAGCATCCTTTAGAGTCTCCAACCTAAAGTATTCTTTATGTCCTTCCAGAAGTAC
TGGCGTCATACTCAGGCTACCCGGCATGTGTCCCTGTGGTACCCTGGCAGAGAAAGGGCC
AATCTCATTCCCTGCTGGCCAAAGTCAGCAGAAGAAGGTGAAGTTTGCCAGTTGCTTTAG
TGATAGGGACTGCAGACTCAAGCCTACACTGGTACAAAGACTGCGTCTTGAGATAAACAA
GAA
```

FIGURE 5

```
  1 MAQALPWLLLWMGAGVLPAHGTQHGIRLPLRSGLGGAPLGLRLPRETDEE  50
    || || |||||·|·|·||| ||  ||||||||||| | |||||||||||||
  1 MAPALHWLLLWVGSGMLPAQGTHLGIRLPLRSGLAGPPLGLRLPRETDEE  50

51 PEEPGRRGSFVEMVDNLRGKSGQGYYVEMTVGSPPQTLNILVDTGSSNFA 100
    |||||||||||||||||||||||||||||||||||||||||||||||||
 51 SEEPGRRGSFVEMVDNLRGKSGQGYYVEMTVGSPPQTLNILVDTGSSNFA 100

101 VGAAPHPFLHRYYQRQLSSTYRDLRKGVYVPYTQGKWEGELGTDLVSIPH 150
    |||||||||||||||||||||||||||||||||||||||||||||||||
101 VGAAPHPFLHRYYQRQLSSTYRDLRKGVYVPYTQGKWEGELGTDLVSIPH 150

151 GPNVTVRANIAAITESDKFFINGSNWEGILGLAYAEIARPDDSLEPFFDS 200
    |||||||||||||||||||||||||||||||||||||||||||||||||
151 GPNVTVRANIAAITESDKFFINGSNWEGILGLAYAEIARPDDSLEPFFDS 200

201 LVKQTHVPNLFSLQLCGAGFPLNQSEVLASVGGSMIIGGIDHSLYTGSLW 250
    ||||||:||:|||||||||||||·| ||||||||||||||||||||||||
201 LVKQTHIPNIFSLQLCGAGFPLNQTEALASVGGSMIIGGIDHSLYTGSLW 250

251 YTPIRREWYYEVIIVRVEINGQDLKMDCKEYNYDKSIVDSGTTNLRLPKK 300
    |||||||||||||||||||||||||||||||||||||||||||||||||
251 YTPIRREWYYEVIIVRVEINGQDLKMDCKEYNYDKSIVDSGTTNLRLPKK 300

301 VFEAAVKSIKAASSTEKFPDGFWLGEQLVCWQAGTTPWNIFPVISLYLMG 350
    |||||||||||||||||||||||||||||||||||||||||||||||||
301 VFEAAVKSIKAASSTEKFPDGFWLGEQLVCWQAGTTPWNIFPVISLYLMG 350

351 EVTNQSFRITILPQQYLRPVEDVATSQDDCYKFAISQSSTGTVMGAVIME 400
    ||||||||||||||||||||||||||||||||||:||||||||||||||
351 EVTNQSFRITILPQQYLRPVEDVATSQDDCYKFAVSQSSTGTVMGAVIME 400

401 GFYVVFDRARKRIGFAVSACHVHDEFRTAAVEGPFVTLDMEDCGYNIPQT 450
    ||||||||||||||||||||||||||||||||||||| |||||||||||
401 GFYVVFDRARKRIGFAVSACHVHDEFRTAAVEGPFVTADMEDCGYNIPQT 450

451 DESTLMTIAYVMAAICALFMLPLCLMVCQWRCLRCLRQQHDDFADDISLL 500
    |||||||||||||||||||||||||||||||||||||| ||||||||||
451 DESTLMTIAYVMAAICALFMLPLCLMVCQWRCLRCLRHQHDDFADDISLL 500

```
ATGGCTAGCATGACTGGTGGACAGCAAATGGGTCGCGGATCCACCCAGCACGGCATCCGG
 M  A  S  M  T  G  G  Q  Q  M  G  R  G  S  T  Q  H  G  I  R
CTGCCCCTGCGCAGCGGCCTGGGGGGCGCCCCCCTGGGGCTGCGGCTGCCCCGGGAGACC
 L  P  L  R  S  G  L  G  G  A  P  L  G  L  R  L  P  R  E  T
GACGAAGAGCCCGAGGAGCCCGGCCGGAGGGGCAGCTTTGTGGAGATGGTGGACAACCTG
 D  E  E  P  E  E  P  G  R  R  G  S  F  V  E  M  V  D  N  L
AGGGGCAAGTCGGGGCAGGGCTACTACGTGGAGATGACCGTGGGCAGCCCCCCGCAGACG
 R  G  K  S  G  Q  G  Y  Y  V  E  M  T  V  G  S  P  P  Q  T
CTCAACATCCTGGTGGATACAGGCAGCAGTAACTTTGCAGTGGGTGCTGCCCCCCACCCC
 L  N  I  L  V  D  T  G  S  S  N  F  A  V  G  A  A  P  H  P
TTCCTGCATCGCTACTACCAGAGGCAGCTGTCCAGCACATACCGGGACCTCCGGAAGGGC
 F  L  H  R  Y  Y  Q  R  Q  L  S  S  T  Y  R  D  L  R  K  G
GTGTATGTGCCCTACACCCAGGGCAAGTGGGAAGGGGAGCTGGGCACCGACCTGGTAAGC
 V  Y  V  P  Y  T  Q  G  K  W  E  G  E  L  G  T  D  L  V  S
ATCCCCCATGGCCCCAACGTCACTGTGCGTGCCAACATTGCTGCCATCACTGAATCAGAC
 I  P  H  G  P  N  V  T  V  R  A  N  I  A  A  I  T  E  S  D
AAGTTCTTCATCAACGGCTCCAACTGGGAAGGCATCCTGGGGCTGGCCTATGCTGAGATT
 K  F  F  I  N  G  S  N  W  E  G  I  L  G  L  A  Y  A  E  I
GCCAGGCCTGACGACTCCCTGGAGCCTTTCTTTGACTCTCTGGTAAAGCAGACCCACGTT
 A  R  P  D  D  S  L  E  P  F  F  D  S  L  V  K  Q  T  H  V
CCCAACCTCTTCTCCCTGCAGCTTTGTGGTGCTGGCTTCCCCCTCAACCAGTCTGAAGTG
 P  N  L  F  S  L  Q  L  C  G  A  G  F  P  L  N  Q  S  E  V
CTGGCCTCTGTCGGAGGGAGCATGATCATTGGAGGTATCGACCACTCGCTGTACACAGGC
 L  A  S  V  G  G  S  M  I  I  G  G  I  D  H  S  L  Y  T  G
AGTCTCTGGTATACACCCATCCGGCGGGAGTGGTATTATGAGGTCATCATTGTGCGGGTG
 S  L  W  Y  T  P  I  R  R  E  W  Y  Y  E  V  I  I  V  R  V
GAGATCAATGGACAGGATCTGAAAATGGACTGCAAGGAGTACAACTATGACAAGAGCATT
 E  I  N  G  Q  D  L  K  M  D  C  K  E  Y  N  Y  D  K  S  I
GTGGACAGTGGCACCACCAACCTTCGTTTGCCCAAGAAAGTGTTTGAAGCTGCAGTCAAA
 V  D  S  G  T  T  N  L  R  L  P  K  K  V  F  E  A  A  V  K
TCCATCAAGGCAGCCTCCTCCACGGAGAAGTTCCCTGATGGTTTCTGGCTAGGAGAGCAG
 S  I  K  A  A  S  S  T  E  K  F  P  D  G  F  W  L  G  E  Q
CTGGTGTGCTGGCAAGCAGGCACCACCCCTTGGAACATTTTCCCAGTCATCTCACTCTAC
 L  V  C  W  Q  A  G  T  T  P  W  N  I  F  P  V  I  S  L  Y
CTAATGGGTGAGGTTACCAACCAGTCCTTCCGCATCACCATCCTTCCGCAGCAATACCTG
 L  M  G  E  V  T  N  Q  S  F  R  I  T  I  L  P  Q  Q  Y  L
CGGCCAGTGGAAGATGTGGCCACGTCCCAAGACGACTGTTACAAGTTTGCCATCTCACAG
 R  P  V  E  D  V  A  T  S  Q  D  D  C  Y  K  F  A  I  S  Q
TCATCCACGGGCACTGTTATGGGAGCTGTTATCATGGAGGGCTTCTACGTTGTCTTTGAT
 S  S  T  G  T  V  M  G  A  V  I  M  E  G  F  Y  V  V  F  D
```

FIGURE 6B

```
CGGGCCCGAAAACGAATTGGCTTTGCTGTCAGCGCTTGCCATGTGCACGATGAGTTCAGG
 R   A   R   K   R   I   G   F   A   V   S   A   C   H   V   H   D   E   F   R
ACGGCAGCGGTGGAAGGCCCTTTTGTCACCTTGGACATGGAAGACTGTGGCTACAACATT
 T   A   A   V   E   G   P   F   V   T   L   D   M   E   D   C   G   Y   N   I
CCACAGACAGATGAGTCATGA
 P   Q   T   D   E   S   *
```

FIGURE 7A

```
ATGGCTAGCATGACTGGTGGACAGCAAATGGGTCGCGGATCGATGACTATCTCTGACTCT
 M   A   S   M   T   G   G   Q   Q   M   G   R   G   S   M   T   I   S   D   S
CCGCGTGAACAGGACGGATCCACCCAGCACGGCATCCGGCTGCCCCTGCGCAGCGGCCTG
 P   R   E   Q   D   G   S   T   Q   H   G   I   R   L   P   L   R   S   G   L
GGGGGCGCCCCCCTGGGGCTGCGGCTGCCCCGGGAGACCGACGAAGAGCCCGAGGAGCCC
 G   G   A   P   L   G   L   R   L   P   R   E   T   D   E   E   P   E   E   P
GGCCGGAGGGGCAGCTTTGTGGAGATGGTGGACAACCTGAGGGGCAAGTCGGGGCAGGGC
 G   R   R   G   S   F   V   E   M   V   D   N   L   R   G   K   S   G   Q   G
TACTACGTGGAGATGACCGTGGGCAGCCCCCCGCAGACGCTCAACATCCTGGTGGATACA
 Y   Y   V   E   M   T   V   G   S   P   P   Q   T   L   N   I   L   V   D   T
GGCAGCAGTAACTTTGCAGTGGGTGCTGCCCCCCACCCCTTCCTGCATCGCTACTACCAG
 G   S   S   N   F   A   V   G   A   A   P   H   P   F   L   H   R   Y   Y   Q
AGGCAGCTGTCCAGCACATACCGGGACCTCCGGAAGGGCGTGTATGTGCCCTACACCCAG
 R   Q   L   S   S   T   Y   R   D   L   R   K   G   V   Y   V   P   Y   T   Q
GGCAAGTGGGAAGGGGAGCTGGGCACCGACCTGGTAAGCATCCCCCATGGCCCCAACGTC
 G   K   W   E   G   E   L   G   T   D   L   V   S   I   P   H   G   P   N   V
ACTGTGCGTGCCAACATTGCTGCCATCACTGAATCAGACAAGTTCTTCATCAACGGCTCC
 T   V   R   A   N   I   A   A   I   T   E   S   D   K   F   F   I   N   G   S
AACTGGGAAGGCATCCTGGGGCTGGCCTATGCTGAGATTGCCAGGCCTGACGACTCCCTG
 N   W   E   G   I   L   G   L   A   Y   A   E   I   A   R   P   D   D   S   L
GAGCCTTTCTTTGACTCTCTGGTAAAGCAGACCCACGTTCCCAACCTCTTCTCCCTGCAG
 E   P   F   F   D   S   L   V   K   Q   T   H   V   P   N   L   F   S   L   Q
CTTTGTGGTGCTGGCTTCCCCCTCAACCAGTCTGAAGTGCTGGCCTCTGTCGGAGGGAGC
 L   C   G   A   G   F   P   L   N   Q   S   E   V   L   A   S   V   G   G   S
ATGATCATTGGAGGTATCGACCACTCGCTGTACACAGGCAGTCTCTGGTATACACCCATC
 M   I   I   G   G   I   D   H   S   L   Y   T   G   S   L   W   Y   T   P   I
CGGCGGGAGTGGTATTATGAGGTCATCATTGTGCGGGTGGAGATCAATGGACAGGATCTG
 R   R   E   W   Y   Y   E   V   I   I   V   R   V   E   I   N   G   Q   D   L
AAAATGGACTGCAAGGAGTACAACTATGACAAGAGCATTGTGGACAGTGGCACCACCAAC
 K   M   D   C   K   E   Y   N   Y   D   K   S   I   V   D   S   G   T   T   N
CTTCGTTTGCCCAAGAAAGTGTTTGAAGCTGCAGTCAAATCCATCAAGGCAGCCTCCTCC
 L   R   L   P   K   K   V   F   E   A   A   V   K   S   I   K   A   A   S   S
ACGGAGAAGTTCCCTGATGGTTTCTGGCTAGGAGAGCAGCTGGTGTGCTGGCAAGCAGGC
 T   E   K   F   P   D   G   F   W   L   G   E   Q   L   V   C   W   Q   A   G
ACCACCCCTTGGAACATTTTCCCAGTCATCTCACTCTACCTAATGGGTGAGGTTACCAAC
 T   T   P   W   N   I   F   P   V   I   S   L   Y   L   M   G   E   V   T   N
CAGTCCTTCCGCATCACCATCCTTCCGCAGCAATACCTGCGGCCAGTGGAAGATGTGGCC
 Q   S   F   R   I   T   I   L   P   Q   Q   Y   L   R   P   V   E   D   V   A
ACGTCCCAAGACGACTGTTACAAGTTTGCCATCTCACAGTCATCCACGGGCACTGTTATG
 T   S   Q   D   D   C   Y   K   F   A   I   S   Q   S   S   T   G   T   V   M
```

FIGURE 7B

```
GGAGCTGTTATCATGGAGGGCTTCTACGTTGTCTTTGATCGGGCCCGAAAACGAATTGGC
 G   A  V  I  M  E  G  F  Y  V  V  F  D  R  A  R  K  R  I  G
TTTGCTGTCAGCGCTTGCCATGTGCACGATGAGTTCAGGACGGCAGCGGTGGAAGGCCCT
 F  A  V  S  A  C  H  V  H  D  E  F  R  T  A  A  V  E  G  P
TTTGTCACCTTGGACATGGAAGACTGTGGCTACAACATTCCACAGACAGATGAGTCATGA
 F  V  T  L  D  M  E  D  C  G  Y  N  I  P  Q  T  D  E  S  *
```

FIGURE 8A

```
ATGACTCAGCATGGTATTCGTCTGCCACTGCGTAGCGGTCTGGGTGGTGCTCCACTGGGT
 M  T  Q  H  G  I  R  L  P  L  R  S  G  L  G  G  A  P  L  G  -
CTGCGTCTGCCCCGGGAGACCGACGAAGAGCCCGAGGAGCCCGGCCGGAGGGGCAGCTTT
 L  R  L  P  R  E  T  D  E  E  P  E  E  P  G  R  R  G  S  F  -
GTGGAGATGGTGGACAACCTGAGGGGCAAGTCGGGGCAGGGCTACTACGTGGAGATGACC
 V  E  M  V  D  N  L  R  G  K  S  G  Q  G  Y  Y  V  E  M  T  -
GTGGGCAGCCCCCCGCAGACGCTCAACATCCTGGTGGATACAGGCAGCAGTAACTTTGCA
 V  G  S  P  P  Q  T  L  N  I  L  V  D  T  G  S  S  N  F  A  -
GTGGGTGCTGCCCCCCACCCCTTCCTGCATCGCTACTACCAGAGGCAGCTGTCCAGCACA
 V  G  A  A  P  H  P  F  L  H  R  Y  Y  Q  R  Q  L  S  S  T  -
TACCGGGACCTCCGGAAGGGCGTGTATGTGCCCTACACCCAGGGCAAGTGGGAAGGGGAG
 Y  R  D  L  R  K  G  V  Y  V  P  Y  T  Q  G  K  W  E  G  E  -
CTGGGCACCGACCTGGTAAGCATCCCCCATGGCCCCAACGTCACTGTGCGTGCCAACATT
 L  G  T  D  L  V  S  I  P  H  G  P  N  V  T  V  R  A  N  I  -
GCTGCCATCACTGAATCAGACAAGTTCTTCATCAACGGCTCCAACTGGGAAGGCATCCTG
 A  A  I  T  E  S  D  K  F  F  I  N  G  S  N  W  E  G  I  L  -
GGGCTGGCCTATGCTGAGATTGCCAGGCCTGACGACTCCCTGGAGCCTTTCTTTGACTCT
 G  L  A  Y  A  E  I  A  R  P  D  D  S  L  E  P  F  F  D  S  -
CTGGTAAAGCAGACCCACGTTCCCAACCTCTTCTCCCTGCAGCTTTGTGGTGCTGGCTTC
 L  V  K  Q  T  H  V  P  N  L  F  S  L  Q  L  C  G  A  G  F  -
CCCCTCAACCAGTCTGAAGTGCTGGCCTCTGTCGGAGGGAGCATGATCATTGGAGGTATC
 P  L  N  Q  S  E  V  L  A  S  V  G  G  S  M  I  I  G  G  I  -
GACCACTCGCTGTACACAGGCAGTCTCTGGTATACACCCATCCGGCGGGAGTGGTATTAT
 D  H  S  L  Y  T  G  S  L  W  Y  T  P  I  R  R  E  W  Y  Y  -
GAGGTCATCATTGTGCGGGTGGAGATCAATGGACAGGATCTGAAAATGGACTGCAAGGAG
 E  V  I  I  V  R  V  E  I  N  G  Q  D  L  K  M  D  C  K  E  -
TACAACTATGACAAGAGCATTGTGGACAGTGGCACCACCAACCTTCGTTTGCCCAAGAAA
 Y  N  Y  D  K  S  I  V  D  S  G  T  T  N  L  R  L  P  K  K  -
GTGTTTGAAGCTGCAGTCAAATCCATCAAGGCAGCCTCCTCCACGGAGAAGTTCCCTGAT
 V  F  E  A  A  V  K  S  I  K  A  A  S  S  T  E  K  F  P  D  -
GGTTTCTGGCTAGGAGAGCAGCTGGTGTGCTGGCAAGCAGGCACCACCCCTTGGAACATT
 G  F  W  L  G  E  Q  L  V  C  W  Q  A  G  T  T  P  W  N  I  -
TTCCCAGTCATCTCACTCTACCTAATGGGTGAGGTTACCAACCAGTCCTTTCGCATCACC
 F  P  V  I  S  L  Y  L  M  G  E  V  T  N  Q  S  F  R  I  T  -
ATCCTTCCGCAGCAATACCTGCGGCCAGTGGAAGATGTGGCCACGTCCCAAGACGACTGT
 I  L  P  Q  Q  Y  L  R  P  V  E  D  V  A  T  S  Q  D  D  C  -
```

FIGURE 8B

```
TACAAGTTTGCCATCTCACAGTCATCCACGGGCACTGTTATGGGAGCTGTTATCATGGAG
 Y   K   F   A   I   S   Q   S   S   T   G   T   V   M   G   A   V   I   M   E   -
GGCTTCTACGTTGTCTTTGATCGGGCCCGAAAACGAATTGGCTTTGCTGTCAGCGCTTGC
 G   F   Y   V   V   F   D   R   A   R   K   R   I   G   F   A   V   S   A   C   -
CATTAG
 H   *
```

FIGURE 11

MAQALPWLLLWMGAGVLPAHG TQHGIRLPLRSGLGGAPLGLRLPRETDEE
PEEPGRRGSFVEMVDNLRGKSGQGYYVEMTVGSPPQTLNILVDTGSSNFA
VGAAPHPFLHRYYQRQLSSTYRDLRKGVYVPYTQGKWEGELGTDLVSIPH
GPNVTVRANIAAITESDKFFINGSNWEGILGLAYAEIARPDDSLEPFFDS
LVKQTHVPNLFSLQLCGAGFPLNQSEVLASVGGSMIIGGIDHSLYTGSLW
YTPIRREWYYEVIIVRVEINGQDLKMDCKEYNYDKSIVDSGTTNLRLPKK
VFEAAVKSIKAASSTEKFPDGFWLGEQLVCWQAGTTPWNIFPVISLYLMG
EVTNQSFRITILPQQYLRPVEDVATSQDDCYKFAISQSSTGTVMGAVIME
GFYVVFDRARKRIGFAVSACHVHDEFRTAAVEGPFVTLDMEDCGYNIPQT
DES

FIGURE 12

MAQALPWLLLWMGAGVLPAHG TQHGIRLPLRSGLGGAPLGLRLPRETDEE
PEEPGRRGSFVEMVDNLRGKSGQGYYVEMTVGSPPQTLNILVDTGSSNFA
VGAAPHPFLHRYYQRQLSSTYRDLRKGVYVPYTQGKWEGELGTDLVSIPH
GPNVTVRANIAAITESDKFFINGSNWEGILGLAYAEIARPDDSLEPFFDS
LVKQTHVPNLFSLQLCGAGFPLNQSEVLASVGGSMIIGGIDHSLYTGSLW
YTPIRREWYYEVIIVRVEINGQDLKMDCKEYNYDKSIVDSGTTNLRLPKK
VFEAAVKSIKAASSTEKFPDGFWLGEQLVCWQAGTTPWNIFPVISLYLMG
EVTNQSFRITILPQQYLRPVEDVATSQDDCYKFAISQSSTGTVMGAVIME
GFYVVFDRARKRIGFAVSACHVHDEFRTAAVEGPFVTLDMEDCGYNIPQT
DESHHHHHH

ALZHEIMER'S DISEASE SECRETASE, APP SUBSTRATES THEREFOR, AND USES THEREFOR

This is a divisional application of U.S. application Ser. No. 09/416,901, filed on Oct. 13, 1999, now U.S. Pat. No. 6,699,671, which claims priority benefit of U.S. Provisional Patent Application No. 60/155,493, filed Sep. 23, 1999. The present application also claims priority benefit as a continuation-in-part of U.S. patent application Ser. No. 09/404,133 now abandoned and PCT/US99/20881, both filed Sep. 23, 1999, both of which in turn claim priority benefit of U.S. Provisional Patent Application No. 60/101,594, filed Sep. 24, 1998. All of these priority applications are hereby incorporated by reference in their entirety.

FIELD OF THE INVENTION

The present invention relates to Alzheimer's Disease, amyloid protein precursor, amyloid beta peptide, and human aspartyl proteases, as well as a method for the identification agents that modulate the activity of these polypeptides and thereby are candidates to modulate the progression of Alzheimer's disease.

BACKGROUND OF THE INVENTION

Alzheimer's disease (AD) causes progressive dementia with consequent formation of amyloid plaques, neurofibrillary tangles, gliosis and neuronal loss. The disease occurs in both genetic and sporadic forms whose clinical course and pathological features are quite similar. Three genes have been discovered to date which, when mutated, cause an autosomal dominant form of Alzheimer's disease. These encode the amyloid protein precursor (APP) and two related proteins, presenilin-1 (PS1) and presenilin-2 (PS2), which, as their names suggest, are structurally and functionally related. Mutations in any of the three proteins have been observed to enhance proteolytic processing of APP via an intracellular pathway that produces amyloid beta peptide (Aβ peptide, or sometimes here as Abeta), a 40–42 amino acid long peptide that is the primary component of amyloid plaque in AD.

Dysregulation of intracellular pathways for proteolytic processing may be central to the pathophysiology of AD. In the case of plaque formation, mutations in APP, PS1 or PS2 consistently alter the proteolytic processing of APP so as to enhance formation of Aβ 1-42, a form of the Aβ peptide which seems to be particularly amyloidogenic, and thus very important in AD. Different forms of APP range in size from 695–770 amino acids, localize to the cell surface, and have a single C-terminal transmembrane domain. Examples of specific isotype of APP which are currently known to exist in humans are the 695-amino acid polypeptide described by Kang et. al. (1987), Nature 325: 733–736 which is designated as the "normal" APP; the 751 amino acid polypeptide described by Ponte et al (1988), Nature 331: 525–527 (1988) and Tanzi et al. (1988), Nature 331: 528–530; and the 770 amino acid polypeptide described by Kitaguchi et; al. (1988), Nature 331: 530–532. The Abeta peptide is derived from a region of APP adjacent to and containing a portion of the transmembrane domain. Normally, processing of APP at the αβ-secretase site cleaves the midregion of the Aβ sequence adjacent to the membrane and releases the soluble, extracellular domain of APP from the cell surface. This α-secretase APP processing creates soluble APP-α, which is normal and not thought to contribute to AD. Pathological processing of APP at the β- and γ-secretase sites, which are located N-terminal and C-terminal to the α-secretase site, respectively, produces a very different result than processing at the α site. Sequential processing at the β- and γ-secretase sites releases the Aβ peptide, a peptide possibly very important in AD pathogenesis. Processing at the β- and γ-secretase sites can occur in both the endoplasmic reticulum (in neurons) and in the endosomal/lysosomal pathway after reinternalization of cell surface APP (in all cells). Despite intense efforts, for 10 years or more, to identify the enzymes responsible for processing APP at the β and γ sites, to produce the Aβ peptide, those proteases remained unknown until this disclosure.

SUMMARY OF THE INVENTION

Here, for the first time, we report the identification and characterization of the β secretase enzyme, termed Aspartyl Protease 2 (Asp2). We disclose some known and some novel human aspartic proteases that can act as β-secretase proteases and, for the first time, we explain the role these proteases have in AD. We describe regions in the proteases critical for their unique function and for the first time characterize their substrate. This is the first description of expressed isolated purified active protein of this type, assays that use the protein addition to the identification and creation of useful cell lines and inhibitors.

Here we disclose a number of variants of the Asp2 gene and peptide.

In one aspect, the invention provides any isolated or purified nucleic acid polynucleotide that codes for a protease capable of cleaving the beta (β) secretase cleavage site of APP that contains two or more sets of special nucleic acids, where the special nucleic acids are separated by nucleic acids that code for about 100 to 300 amino acid positions, where the amino acids in those positions may be any amino acids, where the first set of special nucleic acids consists of the nucleic acids that code for the peptide DTG, where the first nucleic acid of the first special set of nucleic acids is the first special nucleic acid, and where the second set of nucleic acids code for either the peptide DSG or DTG, where the last nucleic acid of the second set of nucleic acids is the last special nucleic acid, with the proviso that the nucleic acids disclosed in SEQ ID NO. 1 and SEQ ID NO. 3 are not included. In a preferred embodiment, the two sets of special nucleic acids are separated by nucleic acids that code for about 125 to 222 amino acid positions, which may be any amino acids. In a highly preferred embodiment, the two-sets of special nucleic acids are separated by nucleic acids that code for about 150 to 196, or 150–190, or 150 to 172 amino acid positions, which may be any amino acids. In a particular preferred embodiment, the two sets are separated by nucleic acid that code for about 172 amino acid positions, which may be any amino acids. An exemplary nucleic acid polynucleotide comprises the acid nucleotide sequence in SEQ ID NO. 5. In another particular preferred embodiment, the two sets are separated by nucleic acids that code for about 196 amino acids. An exemplary polynucleotide comprises the nucleotide sequence in SEQ ID NO. 5. In another particular embodiment, the two sets of nucleotides are separated by nucleic acids that code for about 190 amino acids. An exemplary polynucleotide comprises the nucleotide sequence in SEQ ID NO. 1. Preferably, the first nucleic acid of the first special set of amino acids, that is, the first special nucleic acid, is operably linked to any codon where the nucleic acids of that codon codes for any peptide comprising from 1 to 10,000 amino acid (positions). In one variation, the first special nucleic acid is operably linked to nucleic acid polymers that code for any peptide selected from the group consisting of: any reporter proteins or proteins which facilitate purification. For example, the first special nucleic acid is operably linked to nucleic acid polymers that code for any peptide selected from the group consisting of: immunoglobin-heavy chain, maltose binding protein, glutathione S transferase, Green Fluorescent protein, and ubiquitin. In another variation, the last nucleic acid of the second set of special amino acids, that is, the last special nucleic acid, is operably linked to nucleic acid polymers that code for any peptide comprising any amino acids from 1 to 10,000 amino acids. In still another variation, the last special nucleic acid is operably led to nucleic acid polymers that code for any peptide selected from the group consisting of: any reporter proteins or proteins which facilitate purification. For example, the last special nucleic acid is operably linked to nucleic acid polymers that code for any peptide selected from the group consisting of immunoglobin-heavy chain, maltose binding protein, glutathione S transferase, Green Fluorescent protein, and ubiquitin.

In a related aspect, the invention provides any isolated or purified nucleic acid polynucleotide that codes for a protease capable of cleaving the beta secretase cleavage site of APP that contains two or more sets of special nucleic acids, where the special nucleic acids are separated by nucleic acids that code for about 100 to 300 amino acid positions, where the amino acids in those positions may be any amino acids, where the first set of special nucleic acids consists of the nucleic acids that code for DTG, where the first nucleic acid of the first special set of nucleic acids is the first special nucleic acid, and where the second set of nucleic acids code for either DSG or DTG, where the last nucleic acid of the second set of special nucleic acids is the last special nucleic acid, where the first special nucleic acid is operably linked to nucleic acids that code for any number of amino acids from zero to 81 amino acids and where each of those codons may code for any amino acid. In a preferred embodiment, the first special nucleic acid is operably linked to nucleic acids that code for any number of from 64 to 77 amino acids where each codon may code for any amino acid. In a particular embodiment, the first special nucleic acid is operably linked to nucleic acids that code for 71 amino acids. For example, the first special nucleic acid is operably linked to 71 amino acids and where the first of those 71 amino acids is the amino acid T. In a preferred embodiment, the polynucleotide comprises a sequence that is at least 95% identical to a human Asp1 or Asp2 sequence as taught herein. In another preferred embodiment, the first special nucleic acid is operably linked to nucleic acids that code for any number of from 30 to 54 amino acids, or 35 to 47 amino acids, or 40 to 54 amino acids where each codon may code for any amino acid. In a particular embodiment, the first special nucleic acid is operably linked to nucleic acids that code for 47 amino acids. For example, the first special nucleic acid is operably linked to 47 codons where the first those 47 amino acids is, amino acid E.

In another related aspect, the invention provides for any isolated or purified nucleic acid polynucleotide that codes for a protease capable of cleaving the beta (β) secretase cleavage site of APP and that contains two or more sets of special nucleic acids, where the special nucleic acids are separated by nucleic acids that code for about 100 to 300 amino acid positions, where the amino acids in those positions may be any amino acids, where the first set of special nucleic acids consists of the nucleic acids that code for the peptide DTG, where the first nucleic acid of the first special set of amino acids is, the first special nucleic acid, and where the second set of special nucleic acids code for either the peptide DSG or DTG, where the last nucleic acid of the second set of special nucleic acids, the last special nucleic acid, is operably linked to nucleic acids that code for any number of codons from 50 to 170 codons. In a preferred embodiment, the last special nucleic acid is operably linked to nucleic acids comprising from 100 to 170 codons. In a highly preferred embodiment, the last special nucleic acid is operably linked to nucleic acids comprising from 142 to 163 codons. In a particular embodiment, the last special nucleic acid is operably linked to nucleic acids comprising about 142 codons, or about 163 codons, or about 170 codons. In a highly preferred embodiment, the polynucleotide comprises a sequence that is at least 95% identical to aspartyl-protease encoding sequences taught herein. In one variation, the second set of special nucleic acids code for the peptide DSG. In another variation, the first set of nucleic acid polynucleotide is operably linked to a peptide purification tag. For example, the nucleic acid polynucleotide is operably linked to a peptide purification tag which is six histidine. In still another variation, the first set of special nucleic acids are on one polynucleotide and the second set of special nucleic acids are on a second polynucleotide, where both first and second polynucleotides have at lease 50 codons. In one embodiment of this type, both of the polynucleotides are in the same solution. In a related aspect, the invention provides a vector which contains a polynucleotide as described above, or a cell or cell line which is transformed or transfected with a polynucleotide as described above or with a vector containing such a polynucleotide.

In still another aspect, the invention provides an isolated or purified peptide or protein comprising an amino acid polymer that is a protease capable of cleaving the beta (β) secretase cleavage site of APP that contains two or more sets of special amino acids, where the special amino acids are separated by about 100 to 300 amino acid positions, where each amino acid position can be any amino acid, where the first set of special amino acids consists of the peptide DTG, where the first amino acid of the first special set of amino acids is, the first special amino acid, where the second set of amino acids is selected from the peptide comprising either DSG or DTG, where the last amino acid of the second set of special amino acids is the last special amino acid, with the proviso that the proteases disclosed in SEQ ID NO. 2 and SEQ ID NO. 4 are not included. In preferred embodiments, the two sets of amino acids are separated by about 125 to 222 amino acid positions or about 150 to 196 amino acids, or about 150–190 amino acids, or about 150 to 172 amino acids, where in each position it may be any amino acid. In a particular embodiment, the two sets of amino acids are separated by about 172 amino acids. For example, the protease has the amino acid sequence described in SEQ ID NO 6. In another particular embodiment, the two sets of amino acids are separated by about 196 amino acids. For example, the two sets of amino acids are separated by the same amino acid sequences that separate the same set of special amino acids in SEQ ID NO 4. In another particular embodiment, the two sets of nucleotides are separated by about 190 amino acids. For example, the two sets of nucleotides are separated by the same amino acid sequences that separate the same set of special amino acids in SEQ ID NO 2. In one embodiment, the first amino acid of the first special set of amino acids, that is, the first special amino acid, is operably linked to any peptide comprising from 1 to 10,000 amino acids. In another embodiment, the first special amino acid is operably linked to any peptide selected from the group consisting of any reporter proteins or proteins which facilitate purification. In particular embodiments, the first special amino acid is operably linked to any peptide selected from the group consisting of immunoglobin-heavy chain, maltose binding protein, glutathione S transferase, Green Fluorescent protein, and ubiquitin. In still another variation, the last amino acid of the second set of special amino acids, that is, the last special amino acid, is operably linked to any peptide comprising any amino acids from 1 to 10,000 amino acids. By way of nonlimiting example, the last special amino acid is operably linked any peptide selected from the group consisting of any reporter proteins or proteins which facilitate purification. In particular embodiments, the last special amino acid is operably linked to any peptide selected from the group consisting of: immunoglobin-heavy chain, maltose binding protein, glutathione S transferase, Green Fluorescent protein, and ubiquitin.

In a related aspect, the invention provides any isolated or purified peptide or protein comprising an amino acid polypeptide that codes for a protease capable of cleaving the beta secretase cleavage site of APP that contains two or more sets of special amino acids, where the special amino acids are separated by about 100 to 300 amino acid positions, where each amino acid in each position can be any amino acid, where the first set of special amino acids consists of the amino acids DTG, where the first amino acid of the first special set of amino acids is, the first special amino acid, D, and where the second set of amino acids is either DSG or DTG, where the last amino acid of the second set of special amino acids is the last special amino acid, G, where the first special amino acid is operably linked to amino acids that code for any number of amino acids from zero to 81 amino acid positions where in each position it may be any amino acid. In a preferred embodiment, the first special amino acid is operably linked to a peptide from about 30–77 or about 64 to 77 amino acids positions where each amino acid position may be any amino acid. In a particular embodiment, the first special amino acid is operably linked to a peptide 35, 47, 71, or 77 amino acids. In a very particular embodiment, the first special amino acid is operably linked to 71 amino acids and the first of those 71 amino acids is the amino acid T. For example, the polypeptide comprises a sequence that is at least 95% identical to an aspartyl protease sequence as described herein. In another embodiment, the first special amino acid is operably linked to any number of from 40 to 54 amino acids (positions) where each amino acid position may be any amino acid. In a particular embodiment, the first special amino acid is operably linked to amino acids that code for a peptide of 47 amino acids. In a very particular embodiment, the first special amino acid is operably linked to a 47 amino acid peptide where the first those 47 amino acids is the amino acid E. In another particular embodiment, the first special amino acid is operably linked to the same corresponding peptides from SEQ ID NO. 3 that are 35, 47, 71, or 77 peptides in length, beginning counting with the amino acids on the first special sequence, DTG, towards the N-terminal of SEQ ID NO. 3. In another particular embodiment, the polypeptide comprises a sequence that is at least 95% identical to the same corresponding amino acids in SEQ ID NO. 4, that is, identical to that portion of the sequences in SEQ ID NO. 4, including all the sequences from both the first and or the second special nucleic acids, toward the—terminal, through and including 71, 47, 35 amino acids before the first special amino acids. For example, the complete polypeptide comprises the peptide of 71 amino acids, where the first of the amino acid is T and the second is Q.

In still another related aspect, the invention provides any isolated or purified amino acid polypeptide that is a protease capable of cleaving the beta (p) secretase cleavage site of APP that contains two or more sets of special amino acids, where the special amino acids are separated by about 100 to 300 amino acid positions, where each amino acid in each position can be any amino acid, where the first set of special amino acids consists of the amino acids that code for DTG, where the first amino acid of the first special set of amino acids is, the first special amino acid, D, and where the second set of amino acids are either DSG or DTG, where the last amino acid of the second set of special amino acids is the last special amino acid, G, which is operably linked to any number of amino acids from 50 to 170 amino acids, which may be any amino acids. In preferred embodiments, the last special amino acid is operably linked to a peptide of about 100 to 170 amino acids or about 142–163 amino acids. In particular embodiments, the last special amino acid is operably linked to a peptide of about 142 amino acids, or about 163 amino acids, or about 170 amino acids. For example, the polypeptide comprises a sequence that is at least 95% identical (and preferably 100% identical) to an aspartyl protease sequence as described herein. In one particular embodiment, the second set of special amino acids is comprised of the peptide with the amino acid sequence DSG. Optionally, the amino acid polypeptide is operably linked to a peptide purification tag, such as purification tag which is six histidine. In one variation, the first set of special amino acids are on one polypeptide and the second set of special amino acids are on a second polypeptide, where both first and second polypeptide have at lease 50 amino acids, which may be any amino acids. In one embodiment of this type, both of the polypeptides are in the same vessel. The invention further includes a process of making any of the polynucleotides, vectors, or cells described herein; and a process of making any of the polypeptides described herein.

In yet another related aspect, the invention provides a purified polynucleotide comprising a nucleotide sequence that encodes a polypeptide having aspartyl protease activity, wherein the polypeptide has an amino acid sequence characterized by: (a) a first tripeptide sequence DTG; (b) a second tripeptide sequence selected from the group consisting of DSG and DTG; and (c) about 100 to 300 amino acids separating the first and second tripeptide sequences, wherein the polypeptide cleaves the beta secretase cleavage site of amyloid protein precursor. In one embodiment, the polypeptide comprises an amino acid sequence depicted in SEQ ID NO: 2 or 4, whereas in another embodiment, the polypeptide comprises an amino acid sequence other than the amino acid sequences set forth in SEQ ID NOs: 2 and 4. Similarly, the invention provides a purified polynucleotide comprising a nucleotide sequence that encodes a polypeptide that cleaves the beta secretase cleavage site of amyloid protein precursor, wherein the polynucleotide includes a strand that hybridizes to one or more of SEQ ID NOs: 3, 5, and 7 under the following hybridization conditions: hybridization overnight at 42° C. for 2.5 hours in 6×SSC/0.1% SDS, followed by washing in 1.0×SSC at 65° C., 0.1% SDS. In one embodiment, the polypeptide comprises an amino acid sequence depicted in SEQ ID NO: 2 or 4, whereas in another embodiment, the polypeptide comprises an amino acid sequence other than the amino acid sequences set forth in SEQ ID NOs: 2 and 4. Likewise, the invention provides a purified polypeptide having aspartyl protease activity, wherein the polypeptide is encoded by polynucleotides as described in the preceding sentences. The invention also provides a vector or host cell comprising such polynucleotides, and a method of making the polypeptides using the vectors or host cells to recombinantly express the polypeptide.

In yet another aspect, the invention provides an isolated nucleic acid molecule comprising a polynucleotide, said polynucleotide encoding a Hu-Asp polypeptide and having a nucleotide sequence at least 95% identical to a sequence selected from the group consisting of:

(a) a nucleotide sequence encoding a Hu-Asp polypeptide selected from the group consisting of Hu-Asp1, Hu-Asp2(a), and Hu-Asp2(b), wherein said Hu-Asp1, Hu-Asp2(a) and Hu-Asp2(b) polypeptides have the complete amino acid sequence of SEQ ID NO. 2, SEQ ID NO. 4, and SEQ ID NO. 6, respectively; and (b) a nucleotide sequence complementary to the nucleotide sequence of (a).

Several species are particularly contemplated. For example, the invention provides a nucleic acid molecule wherein said Hu-Asp polypeptide is Hu-Asp1, and said polynucleotide molecule of (a) comprises the nucleotide sequence of SEQ ID NO. 1; and a nucleic acid molecule wherein said Hu-Asp polypeptide is Hu-Asp2(a), and said polynucleotide molecule of (a) comprises the nucleotide sequence of SEQ ID NO. 3; and a nucleic acid molecule wherein said Hu-Asp polypeptide is Hu-Asp2(b), and said polynucleotide molecule of (a) comprises the nucleotide sequence of SEQ ID NO. 5. In addition to the foregoing, the invention provides an isolated nucleic acid molecule comprising a polynucleotide which hybridizes under stringent conditions to a polynucleotide having the nucleotide sequence in (a) or (b) as described above.

Additionally, the invention provides a vector comprising a nucleic acid molecule as described in the preceding paragraph. In a preferred embodiment, the nucleic acid molecule is operably linked to a promoter for the expression of a Hu-Asp polypeptide. Individual vectors which encode Hu-Asp1, and Hu-Asp2(a), and Hu-Asp2(b) are all contemplated. Likewise, the invention contemplates a host cell comprising any of the foregoing vectors, as well as a method of obtaining a Hu-Asp polypeptide comprising culturing such a host cell and isolating the Hu-Asp polypeptide. Host cells of the invention include bacterial cells, such as *E. coli*, and eukaryotic cells. Among the eukaryotic cells that are contemplated are insect cells, such as sf9 or High 5 cells; and mammalian cells, such as human, rodent, lagomorph, and primate. Preferred human cells include HEK293, and IMR-32 cells. Other preferred mammalian cells include COS-7, CHO-K1, Neuro-2A, and 3T3 cells. Also among the eukaryotic cells that are contemplated are a yeast cell and an avian cell.

In a related aspect, the invention provides an isolated Hu-Asp1 polypeptide comprising an amino acid sequence at least 95% identical to a sequence comprising the amino acid sequence of SEQ ID NO. 2. The invention also provides an isolated Hu-Asp2(a) polypeptide comprising an amino acid sequence at least 95% identical to a sequence comprising the amino acid sequence of SEQ ID NO. 4. The invention also provides an isolated Hu-Asp2(a) polypeptide comprising an amino acid sequence at least 95% identical to a sequence comprising the amino acid sequence of SEQ ID NO. 8.

In still another aspect, the invention provides an isolated antibody that binds specifically to any Hu-Asp polypeptide described herein, especially the polypeptide described in the preceding paragraphs.

The invention also provides several assays involving aspartyl protease enzymes of the invention. For example, the invention provides a method to identify a cell that can be used to screen for inhibitors of β secretase activity comprising:

(a) identifying a cell that expresses a protease capable of cleaving APP at the β secretase site, comprising:

i) collect the cells or the supernatant from the cells to be identified ii) measure the production of a critical peptide, where the critical peptide is selected from the group consisting of either the APP C-terminal peptide or soluble APP, iii) select the cells which produce the critical peptide.

In one variation, the cells are collected and the critical peptide is the APP C-terminal peptide created as a result of the β secretase cleavage. In another variation, the supernatant is collected and the critical peptide is soluble APP, where the soluble APP has a C-terminus created by β secretase cleavage. In preferred embodiments, the cells contain any of the nucleic acids or polypeptides described above and the cells are shown to cleave the β secretase site of any peptide having the following peptide structure, P2, P1, P1', P2' (SEQ ID NO: 72), where P2 is K or N, where P1 is M or L, where P1' is D, where P2' is A. In one embodiment P2 is K and P1 is M and in another embodiment P2 is N and P1 is L.

In still another aspect, the invention provides novel isoforms of amyloid protein precursor (APP) where the last two carboxy terminus amino acids of that isoform are both lysine residues. In this context, the term "isoform" is defined as any APP polypeptide, including APP variants (including mutations), and APP fragments that exists in humans, such as those described in U.S. Pat. No. 5,766,846, col 7, lines 45–67, incorporated into this document by reference, modified as described herein by the inclusion of two C-terminal lysine residues. For example, the invention provides a polypeptide comprising the isoform known as APP695, modified to include two lysine residues as its last two carboxy terminus amino acids. An exemplary polypeptide comprises the amino acid sequence set forth in SEQ ID NO. 16. The invention further includes APP isoform variants as set forth in SEQ ID NOs. 18 and 20. The invention further includes all polynucleotides that encode an APP protein that has been modified to include two C-terminal lysines; as well has any eukaryotic cell line comprising such nucleic acids or polypeptides. Preferred cell lines include a mammalian cell line (e.g., HEK293, Neuro2a).

Thus, in one embodiment, the invention provides a polypeptide comprising the amino acid sequence of a mammalian amyloid protein precursor (APP) or fragment thereof containing an APP cleavage site recognizable by a mammalian βsecretase, and further comprising two lysine residues at the carboxyl terminus of the amino acid sequence of the mammalian APP or APP fragment. As taught herein in detail, the addition of two additional lysine residues to APP sequences has been found to greatly increase Aβ processing of the APP in APP processing assays. Thus, the di-lysine modified APP reagents of the invention are particularly useful in assays to identify modulators of Aβ production, for use in designing therapeutics for the treatment or prevention of Alzheimer's disease. In one embodiment, the polypeptide comprises the complete amino acid sequence of a mammalian amyloid protein precursor (APP), and further comprises the two lysine residues at the carboxyl terminus of the amino acid sequence of the mammalian amyloid protein precursor. In an alternative embodiment, the polypeptide comprises only a fragment of the APP, the fragment containing at least a, that portion of APP that is cleaved by a mammalian β-secretase in the formation of Aβ peptides.

The practice of assays that monitor cleavage of APP can be facilitated by attaching a marker to a portion of the APP. Measurment of retained or liberated marker can be used to quantitate the amount of APP cleavage that occurs in the assay, e.g., in the presence or absence of a putative modulator of cleavage activity. Thus, in one preferred embodiment, the polypeptide of the invention further includes a marker. For example, the marker comprises a reporter protein amino acid sequence attached to the APP amino acid sequence. Exemplary reporter proteins include a fluorescing protein (e.g., green fluorescing proteins, luciferase) or an enzyme that is used to cleave a substrate to produce a calorimetric cleavage product. Also contemplated are tag sequences which are commonly used as epitopes for quantitative immunoassays.

In a preferred embodiment, the di-lysine-modified APP of the invention is a human APP. For example, human APP isoforms such as APP695, APP751, and APP770, modified to include the two lysines, are contemplated. In a preferred embodiment, the APP isoform comprises at least one variation selected from the group consisting of a Swedish KM-NL mutation and a London V717→F mutation, or any other mutation that has been observed in a subpopulation that is particularly prone to development of Alzheimer's disease. These mutations are recognized as mutations that influence APP processing into Aβ. In a highly preferred embodiment, the APP protein or fragment hereof comprises the APP-Sw β-secretase peptide sequence NLDA, (SEQ ID NO:66) with increased levels of Aβ processing and therefore is particularly useful in assays relating to Alzheimer's research. More particularly, the APP protein or fragment thereof preferably comprises the APP-Sw β-secretase peptide sequence SEVNLDAEFR (SEQ ID NO: 63).

In one preferred embodiment, the APP protein or fragment thereof further includes an APP transmembrane domain carboxy-terminal to the APP-Sw β-secretase peptide sequence. Polypeptides that include the TM domain are particularly useful in cell-based APP processing assays. In contrast, embodiments lacking the TM domain are useful in cell-free assays of APP processing.

In addition to working with APP from humans and various animal models, researchers in the field of Alzheimer's also have construct chimeric APP polypeptides which include stretches of amino acids from APP of one species (e.g., humans) fused to streches of APP from one or more other species (e.g., rodent). Thus, in another embodiment of the polypeptide of the invention, the APP protein or fragment thereof comprises a chimeric APP, the chimeric APP including partial APP amino acid sequences from at least two species. A chimeric APP that includes amino acid sequence of a human APP and a rodent APP is particularly contemplated.

In a related aspect, the invention provides a polynucleotide comprising a nucleotide sequence that encodes a polypeptide as described in the preceding paragraphs. Such a polynucleotide is useful for recombinant expression of the polypeptide of the invention for use in APP processing assays. In addition, the polynucleotide is useful for transforming into cells to produce recombinant cells that express the polypeptide of the invention, which cells are useful in cell-based assays to identify modulators of APP processing. Thus, in addition to polynucleotides, the invention provides a vector comprising such polynucleotides, especially expression vectors where the polynucleotide is operably linked to a promoter to promote expression of the polypeptide encoded by the polynucleotide in a host cell. The invention further provides a host cell transformed or transfected with a polynucleotide of the invention or a vector comprising a polynucleotide of the invention. Among the preferred host cells are mammalian cells, especially human cells.

In another, related embodiment, the invention provides a polypeptide useful for assaying for modulators of β-secretase activity, said polypeptide comprising an amino acid sequence of the formula NH$_2$—X—Y-Z-KK-COOH; wherein X, Y, and Z each comprise an amino acid sequence of at least one amino acid; wherein—NH$_2$—X comprises an carboxy-terminal amino acid sequence having at least one amino acid residue; wherein Y comprises an amino acid sequence of a β-secretase recognition site of a mammalian amyloid protein precursor (APP); and wherein Z-KK-COOH comprises a carboxy-terminal amino acid sequence ending in two lysine (K) residues. In one preferred variation, the carboxyl-terminal amino acid sequence Z includes a hyrdrophobic domain that is a transmembrane domain in host cells that express the polypeptide. Host cells that express such a polypeptide are particularly useful in assays described herein for identifying modulators of APP processing. In another preferred variation, the amino-terminal amino acid sequence X includes an amino acid sequence of a reporter or marker protein, as described above. In still another preferred variation, the β-secretase recognition site Y comprises the human APP-Sw β-secretase peptide sequence NLDA It will be apparent that these preferred variations are not mutually exclusive of each other—they may be combined in a single polypeptide. The invention further provides a polynucleotide comprising a nucleotide sequence that encodes such polypeptides, vectors which comprise such polynucleotides, and host cells which comprises such vectors, polynucleotides, and/or polypeptides.

In yet another aspect, the invention provides a method for identifying inhibitors of an enzyme that cleaves the beta secretase cleavable site of APP comprising:

a) culturing cells in a culture medium under conditions in which the enzyme causes processing of APP and release of amyloid beta-peptide into the medium and causes the accumulation of CTF99 fragments of APP in cell lysates, b) exposing the cultured cells to a test compound; and specifically determining whether the test compound inhibits the function of the enzyme by measuring the amount of amyloid beta-peptide released into the medium and/or the amount of CTF99 fragments of APP in cell lysates;

c) identifying test compounds diminishing the amount of soluble amyloid beta peptide present in the culture medium and diminution of CTF99 fragments of APP in cell lysates as Asp2 inhibitors. In preferred embodiments, the cultured cells are a human, rodent or insect cell line. It is also preferred that the human or rodent cell line exhibits P secretase activity in which processing of APP occurs with release of amyloid beta-peptide into the culture medium and accumulation of CTF99 in cell lysates. Among the contemplated test compounds are antisense oligomers directed against the enzyme that exhibits β secretase activity, which oligomers reduce release of soluble amyloid beta-peptide into the culture medium and accumulation of CTF99 in cell lysates.

In yet another aspect, the invention provides a method for the identification of an agent that decreases the activity of a. Hu-Asp polypeptide selected from the group consisting of Hu-Asp 1, Hu-Asp2(a), and Hu-Asp2(b), the method comprising:

a) determining the activity of said Hu-Asp polypeptide in the presence of a test agent and in the absence of a test agent; and b) comparing the activity of said Hu-Asp polypeptide determined in the presence of said test agent to the activity of said Hu-Asp polypeptide determined in the absence of said test agent; whereby a lower level of activity in the presence of said test agent than in the absence of said test agent indicates that said test agent has decreased the activity of said Hu-Asp polypeptide.

In a related aspect, the invention provides a method for assaying for modulators of β-secretase activity, comprising the steps of:

(a) contacting a first composition with a second composition both in the presence and in the absence of a putative modulator compound, wherein the first composition comprises a mammalian β-secretase polypeptide or biologically active fragment thereof, and wherein the second composition comprises a substrate polypeptide having an amino acid sequence comprising a β-secretase cleavage site; (b) measuring cleavage of the substrate polypeptide in the presence and in the absence of the putative modulator compound; and (c) identifying modulators of β-secretase activity from a difference in cleavage in the presence versus in the absence of the putative modulator compound. A modulator that is a β-secrete antagonist (inhibitor) reduces such cleavage, whereas a modulator that is a β-secretase agonist increases such cleavage. Since such assays are relevant to development of Alzheimer's disease therapeutics for humans, it will be readily apparent that, in one preferred embodiment, the first composition comprises a purified human Asp2 polypeptide. In one variation, the first composition comprises a soluble fragment of a human Asp2 polypeptide that retains Asp2 β-secretase activity. Several such fragments (including ΔTM fragments) are described herein in detail. Thus, in a particular embodiment, the soluble fragment is a fragment lacking an Asp2 transmembrane domain.

The β-secretase cleavage site in APP is known, and it will be appreciated that the assays of the invention can be performed with either intact APP or fragments or analogs of APP that retain the β-secretase recognition and cleavage site. Thus, in one variation, the substrate polypeptide of the second composition comprises the amino acid sequence SEVNLDAEFR (SEQ ID NO:63), which includes the β-secretase recognition site of human APP that contains the "Swiss" mutation. In another variation, the substrate polypeptide of the second composition comprises the amino acid sequence EVKMDAEF (SEQ ID NO:67). In another variation, the second composition comprises a polypeptide having an amino acid sequence of a human amyloid precursor protein (APP). For example, the human amyloid precursor protein is selected from the group consisting of. APP695, APP751, and APP770. Preferably, the human amyloid precursor protein (irrespective of isoform selected) includes at least on mutation selected from a KM→NL Swiss mutation and a V→F London mutation. As explained elsewhere, one preferred embodiment involves a variation wherein the polypeptide having an amino acid sequence of a human APP further comprises an amino acid sequence comprising a marker sequence attached amino-terminal to the amino acid sequence of the human amyloid precursor protein. Preferably, the polypeptide having an amino acid sequence of a human APP further comprises two lysine residues attached to the carboxyl terminus of the amino acid sequence of the human APP. The assays can be performed in a cell free setting, using cell-free enzyme and cell-free substrate, or can be performed in a cell-based assay wherein the second composition comprises a eukaryotic cell that that the β-expresses amyloid precursor protein (APP) or a fragment thereof containing a β-secretase cleavage site. Preferably, the APP expressed by the host cell is an APP variant that includes two carboxyl-terminal lysine residues. It will also be appreciated that the β-secretase enzyme can be an enzyme that is expressed on the surface of the same cells.

The present invention provides isolated nucleic acid molecules comprising a polynucleotide that codes for a polypeptide selected from the group consisting of human aspartyl proteases. In particular, human aspartyl protease 1 (Hu-Asp1) and two alternative splice variants of human aspartyl protease-2 (Hu-Asp2), a "long" (L) form designated herein as Hu-Asp2(a) and a "short" (S) form designated Hu-Asp2 (b). As used herein, all references to "Hu-Asp" should be understood to refer to all of Hu-Asp1, Hu-Asp2(a), and Hu-Asp2(b). In addition, as used herein, all references to "Hu-Asp2" should be understood to refer to both Hu-Asp2 (a) and Hu-Asp2(b). Hu-Asp1 is expressed most abundantly in pancreas and prostate tissues, while Hu-Asp2(a) and Hu-Asp2(b) are expressed most abundantly in pancreas and brain tissues. The invention also provides isolated Hu-Asp1, Hu-Asp2(a), and Hu-Asp2(b) polypeptides, as well as fragments thereof which exhibit aspartyl protease activity.

In a preferred embodiment, the nucleic acid molecules comprise a polynucleotide having a nucleotide sequence selected from the group consisting of residues 1–1554 of SEQ ID NO. 1, encoding Hu-Asp1, residues 1–1503 of SEQ If) NO. 3, encoding Hu-Asp2(a), and residues 1–1428 of SEQ ID NO.5, encoding Hu-Asp2(b). In another aspect, the invention provides an isolated nucleic acid molecule comprising a polynucleotide which hybridizes under stringent conditions to a polynucleotide encoding Hu-Asp1, Hu-Asp2 (a), Hu-Asp-2(b), or fragments thereof. European patent application EP 0 848 062 discloses a polypeptide referred to as "Asp 1," that bears substantial homology to Hu-Asp1, while international application WO 98/22597 discloses a polypeptide referred to as "Asp 2," that bears substantial homology to Hu-Asp2(a).

The present invention also provides vectors comprising the isolated nucleic acid molecules of the invention, host cells into which such vectors have been introduced, and recombinant methods of obtaining a Hu-Asp1, Hu-Asp2(a), or Hu-Asp2(b) polypeptide comprising culturing the above-described host cell and isolating the relevant polypeptide.

In another aspect, the invention provides isolated Hu-Asp1, Hu-Asp2(a), and Hu-Asp2(b) polypeptides, as well as fragments thereof. In a preferred embodiment, the Hu-Asp1, Hu-Asp2(a), and Hu-Asp2(b) polypeptides have the amino acid sequence given in SEQ ID NO. 2, SEQ ID NO. 4, or SEQ ID NO.6, respectively. The present invention C3 also describes active forms of Hu-Asp2, methods for preparing such active forms, methods for preparing soluble forms, methods for measuring Hu-Asp2 activity, and substrates for Hu-Asp2 cleavage. The invention also describes antisense oligomers targeting the Hu-Asp1, Hu-Asp2(a) and Hu-Asp2(b) mRNA transcripts and the use of such antisense reagents to decrease such mRNA and consequently the production of the corresponding polypeptide. Isolated antibodies, both polyclonal and monoclonal, that binds specifically to any of the Hu-Asp 1, Hu-Asp2(a), and Hu-Asp2(b) polypeptides of the invention are also provided.

The invention also provides a method for the identification of an agent that modulates the activity of any of Hu-Asp-1, Hu-Asp2(a), and Hu-Asp2(b). The inventions describes methods to test such agents in cell-free assays to which Hu-Asp2 polypeptide is added, as well as methods to test such agents in human or other mammalian cells in which Hu-Asp2 is present.

Additional features and variations of the invention will be apparent to those skilled in the art from the entirety of this application, including the drawing and detailed description, and all such features are intended as aspects of the invention. Likewise, features of the invention described herein can be re-combined into additional embodiments that are also intended as aspects of the invention, irrespective of whether the combination of features is specifically mentioned above as an aspect or embodiment of the invention. Also, only such limitations which are described herein as critical to the invention should be viewed as such; variations of the invention lacking limitations which have not been described herein as critical are intended as aspects of the invention.

In addition to the foregoing, the invention includes, as an additional aspect, all embodiments of the invention narrower in scope in any way than the variations specifically mentioned above. Although the applicant(s) invented the full scope of the claims appended hereto, the claims appended hereto are not intended to encompass within their scope the prior art work of others. Therefore, in the event that statutory prior art within the scope of a claim is brought to the attention of the applicants by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention.

BRIEF DESCRIPTION OF THE SEQUENCE LISTING

Sequence ID No. 1: Human Asp-1, nucleotide sequence.

Sequence ID No. 2: Human Asp-1, predicted amino acid sequence.

Sequence ID No. 3: Human Asp-2(a), nucleotide sequence.

Sequence ID No. 4: Human Asp2(a), predicted amino acid sequence. The Asp2(a) amino acid sequence includes a putative signal peptide comprising residues 1 to 21; and a putative pre-propeptide after the signal peptide that extends through residue 45 (as assessed by processing observed of recombinant Asp2(a) in CHO cells), and a putative propeptide that may extend to at least about residue 57, based on the observation of an observed GRR↓GS (SEQ ID NO: 68) sequence which has characteristics of a protease recognition sequence. The Asp2(a) further includes a transmembrane domain comprising residues 455–477, a cytoplasmic domain comprising residues 478–501, and a putative alpha-helical spacer region, comprising residues 420–454, believed to be unnecessary for proteolytic activity, between the protease catalytic domain and the transmembrane domain.

Sequence ID No. 5: Human Asp-2(b), nucleotide sequence.

Sequence ID No. 6: Human Asp-2(b), predicted amino acid sequence. The Asp2(b) amino acid sequence includes a putative signal peptide, pre-propeptide, and propeptide as described above for Asp2(a). The Asp2(b) further includes a transmembrane domain comprising residues 430–452, a cytoplasmic domain comprising residues 453–476, and a putative alpha-helical spacer region, comprising residues 395–429, believed to be unnecessary for proteolytic activity, between the protease catalytic domain and the transmembrane domain.

Sequence ID No. 7: Murine Asp-2(a), nucleotide sequence.

Sequence ID No. 8: Murine Asp-2(a), predicted amino acid sequence. The proteolytic processing of murine Asp2(a) is believed to be analogous to the processing described above for human Asp2(a). In addition, a variant lacking amino acid residues 190–214 of SEQ ID NO: 8 is specifically contemplated as a murine Asp2(b) polypeptide (SEQ ID NO: 73).

Sequence ID No. 9: Human APP695, nucleotide sequence.

Sequence ID No.10: Human APP695, predicted amino acid sequence.

Sequence ID No.11: Human APP695-Sw, nucleotide sequence.

Sequence ID No.12: Human APP695-Sw, predicted amino acid sequence. In the APP695 isoform, the Sw mutation is characterized by a KM→NL alteration at positions 595–596 (compared to normal APP695).

Sequence ID No.13: Human APP695-VF, nucleotide sequence.

Sequence ID No.14: Human APP695-VF, predicted amino acid sequence. In the APP 695 isoform, the VF mutation is characterized by a V→F alteration at position 642 (compared to normal APP 695).

Sequence ID No.15: Human APP695-KK, nucleotide sequence.

Sequence ID No.16: Human APP695-KK, predicted amino acid sequence. (APP695 with two carboxy-terminal lysine residues.)

Sequence ID No.17: Human APP695-Sw-KK, nucleotide sequence.

Sequence ID No.18: Human APP695-Sw-KK, predicted amino acid sequence

Sequence ID No.19: Human APP695-VF-KK, nucleotide sequence

Sequence ID No.20: Human APP695-VF-KK, predicted amino acid sequence

Sequence ID No.21: T7-Human-pro-Asp-2(a)ΔTM nucleotide sequence

Sequence ID No.22: T7-Human-pro-Asp-2(a)ΔTM amino acid sequence

Sequence ID No.23: T7-Caspase-Human-pro-Asp-2(a)ΔTM, nucleotide sequence

Sequence ID No.24: T7-Caspase-Human-pro-Asp-2(a)ΔTM amino acid sequence

Sequence ID No.25: Human-pro-Asp-2(a)ΔTM (low GC), nucleotide sequence

Sequence ID No.26: Human-pro-Asp-2(a)ΔTM, (low GC), amino acid sequence

Sequence ID No.27: T7-Caspase-Caspase 8 cleavage-Human-pro-Asp-2(a)ΔTM, nucleotide sequence Sequence ID No.28: T7-Caspase-Caspase 8 cleavage-Human-pro-Asp-2(a)ΔTM, amino acid sequence Sequence ID No.29: Human Asp-2(a)ΔTM, nucleotide sequence Sequence ID No.30: Human Asp-2(a)ΔTM, amino acid sequence Sequence ID No.31: Human Asp-2(a)ΔTM(His)$_6$, nucleotide sequence Sequence ID No. 32: Human Asp-2(a)ΔTM(His)$_6$, amino acid sequence Sequence ID Nos. 33–49 are short synthetic peptide and oligonucleotide sequences that are described below in the Detailed Description of the Invention.

Sequence ID No. 50: Human Asp2(b)ΔTM polynucleotide sequence.

Sequence ID No. 51: Human Asp2(b)ΔTM polypeptide sequence (exemplary variant of Human Asp2(b) lacking transmembrane and intracellular domains of Hu-Asp2(b) set forth in SEQ ID NO: 6.

Sequence ID No. 52: Human Asp2(b)ΔTM(His)$_6$ polynucleotide sequence.

Sequence ID No. 53: Human Asp2(b)ΔTM(His)$_6$ polypeptide sequence (Human Asp2(b)ΔTM with six histidine tag attached to C-terminus).

Sequence ID No. 54: Human APP770-encoding polynucleotide sequence.

Sequence ID No. 55: Human APP770 polypeptide sequence. To introduce the KM-NL Swedish mutation, residues KM at positions 670–71 are changed to NL. To introduce the V→F London mutation, the V residue at position 717 is changed to F.

Sequence ID No. 56: Human APP751 encoding polynucleotide sequence.

Sequence ID No. 57: Human APP751 polypeptide sequence (Human APP751 isoform).

Sequence ID No. 58: Human APP770-KK encoding polynucleotide sequence.

Sequence ID No. 59: Human APP770-KK polypeptide sequence. (Human APP770 isoform to which two C-terminal lysines have been added).

Sequence ID No. 60: Human APP751-KK encoding polynucleotide sequence.

Sequence ID No. 61: Human APP751-KK polypeptide sequence (Human APP751 isoform to which two C-terminal lysines have been added).

Sequence ID No. 62–65: Various short peptide sequences described in detail in detailed description.

BRIEF DESCRIPTION OF THE FIGURES

FIGS. 1A–1B: FIGS. 1A–1B show the nucleotide (SEQ ID NO:1) and predicted amino acid sequence (SEQ ID NO:2) of human Asp1.

FIGS. 2A–2B: FIGS. 2A–2B shows show the nucleotide (SEQ ID NO:3) and predicted amino acid sequence (SEQ ID NO:4) of human Asp2(a).

FIGS. 3A–3B: FIGS. 3A–3B show the nucleotide (SEQ ID NO:5) and predicted amino acid sequence (SEQ ID NO:6) of human Asp2(b).

FIG. 4: FIG. 4 shows the nucleotide (SEQ ID No. 7) and predicted amino acid sequence (SEQ ID No. 8) of murine Asp2(a)

FIG. 5: FIG. 5 shows the BestFit alignment of the predicted amino acid sequences of Hu-Asp2(a) (SEQ ID NO: 4) and murine Asp2(a) (SEQ ID NO: 9)

FIGS. 6A–6B: FIGS. 6A–6B shows show the nucleotide (SEQ ID No. 21) and predicted amino acid sequence (SEQ ID No. 22) of T7-Human-pro-Asp-2(a)ΔTM.

FIG. 7: FIG. 7 shows the nucleotide (SEQ ID No. 23) and predicted amino acid sequence (SEQ ID No. 24) of T7-caspase-Human-pro-Asp-2(a)ΔTM FIG. 8: FIG. 8 shows the nucleotide (SEQ ID No. 25) and predicted amino acid sequence (SEQ ID No. 26) of Human-pro-Asp-2(a)ΔTM (low GC)

FIG. 11: FIG. 11 shows the predicted amino acid sequence (SEQ ID No. 30) of Human-Asp2(a)ΔTM FIG. 12: FIG. 11 shows the predicted amino acid sequence (SEQ ID No. 30) of Human-Asp2(a)ΔTM(His)$_6$

DETAILED DESCRIPTION OF THE INVENTION

Figure 9:
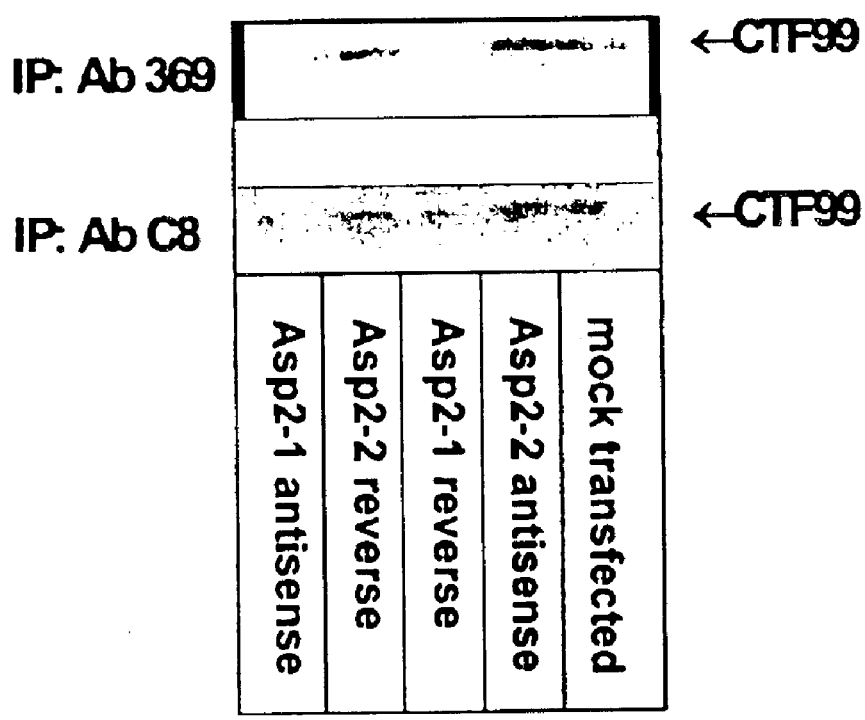
FIG. 9: Western blot showing reduction of CTF99 production by HEK125.3 cells transfected with antisense oligomers targeting the Hu-Asp2 mRNA

A few definitions used in this invention follow, most definitions to be used are those that would be used by one ordinarily skilled in the art.

The term "β amyloid peptide" means any peptide resulting from beta secretase cleavage of APP. This includes peptides of 39, 40, 41, 42 and 43 amino acids, extending from the β-secretase cleavage site to 39, 40, 41, 42 and 43 amino acids C-terminal to the β-secretase cleavage site. β amyloid peptide also includes sequences 1–6, SEQ ID NOs. 1–6 of U.S. Pat. No. 5,750,349, issued 12 May 1998 (incorporated into this document by reference). A β-secretase cleavage fragment disclosed here is called CTF-99, which extends from β-secretase cleavage site to the carboxy terminus of APP.

When an isoform of APP is discussed then what is meant is any APP polypeptide, including APP variants (including mutations), and APP fragments that exists in humans such as those described in U.S. Pat. No. 5,766,846, col 7, lines 45–67, incorporated into this document by reference.

The term "β-amyloid precursor protein" (APP) as used herein is defined as a polypeptide that is encoded by a gene of the same name localized in humans on the long arm of chromosome 21 and that includes "βAP—here "β-amyloid protein" see above, within its carboxyl third. APP is a glycosylated, single-membrane spanning protein expressed in a wide variety of cells in many mammalian tissues. Examples of specific isotypes of APP which are currently known to exist in humans are the 695 amino acid polypeptide described by Kang et. al. (1987) Nature 325:733–736 which is designated as the "normal" APP (SEQ ID NOs: 9–10); the 751 amino acid polypeptide describe by Ponte et al. (1988) Nature 331:525–527 (1988) and Tanzi et al. (1988) Nature 331:528–530 (SEQ ID NOs: 56–57); and the 770-amino acid polypeptide described by Kitaguchi et. al. (1988) Nature 331:530532 (SEQ ID NOs: 54–55). Examples of specific variants of APP include point mutation which can differ in both position and phenotype (for review of known variant mutation see Hardy (1992) Nature Genet. 1:233–234). All references cited here incorporated by reference. The term "APP fragments" as used herein refers to fragments of APP other than those which consist solely of PAP or PAP fragments. That is, APP fragments will include amino acid sequences of APP in addition to those which form intact βAP or a fragment of βAP.

When the term "any amino acid" is used, the amino acids referred to are to be selected from the following, three letter and single letter abbreviations which may also be used, are provided as follows:

Alanine, Ala, A; Arginine, Arg, R; Asparagine, Asn, N; Aspartic acid, Asp, D; Cysteine, Cys, C; Glutamine, Gln, Q; Glutamic Acid, Glu, E; Glycine, Gly, G; Histidine, His, H; Isoleucine, Ile, I; Leucine, Leu, L;

Lysine, Lys, K; Methionine, Met, M; Phenylalanine, Phe, F; Proline, Pro, P; Serine, Ser, S; Threonine, Thr, T; Tryptophan, Trp, W; Tyrosine, Tyr, Y; Valine, Val, V; Aspartic acid or Asparagine, Asx, B; Glutamic acid or Glutamic, Glx, Z; Any amino acid, Xaa, X.

The present invention describes a method to scan gene databases for the simple active site motif characteristic of aspartyl proteases. Eukaryotic aspartyl proteases such as pepsin and renin possess a two-domain structure which folds to bring two aspartyl residues into proximity within the active site. These are embedded in the short tripeptide motif DTG, or more rarely, DSG. Most aspartyl proteases occur as proenzyme whose N-terminus must be cleaved for activation. The DTG or DSG active site motif appears at about residue 65–70 in the proenzyme (prorenin, pepsinogen), but at about residue 25–30 in the active enzyme after cleavage of the N-terminal prodomain. The limited length of the active site motif makes it difficult to search collections of short, expressed sequence tags (EST) for novel aspartyl proteases. EST sequences typically average 250 nucleotides or less, and so would encode 80–90 amino acid residues or less. That would be too short a sequence to span the two active site motifs. The preferred method is to scan databases of hypothetical or assembled protein coding sequences. The present invention describes a computer method to identify candidate aspartyl proteases in protein sequence databases. The method was used to identify seven candidate aspartyl protease sequences in the *Caenorhabditis elegans* genome. These sequences were then used to identify by homology search Hu-Asp1 and two alternative splice variants of Hu-Asp2, designated herein as Hu-Asp2(a) and Hu-Asp2 (b).

In a major aspect of the invention disclosed here we provide new information about APP processing. Pathogeneic processing of the amyloid precursor protein (APP) via the Aβ pathway requires the sequential action of two proteases referred to as β-secretase and γ-secretase. Cleavage of APP by the β-secretase and γ-secretase generates the N-terminus and C-terminus of the Aβ peptide, respectively. Because over production of the Aβ peptide, particularly the $A\beta_{1-42}$, has been implicated in the initiation of Alzheimer's disease, inhibitors of either the β-secretase and/or the γ-secretase have potential in the treatment of Alzheimer's disease. Despite the importance of the β-secretase and β-secretase in the pathogenic processing of APP, molecular definition of these enzymes has not been accomplished to date. That is, it was not known what enzymes were required for cleavage at either the β-secretase or the γ-secretase cleavage site. The sites themselves were known because APP was known and the $A\beta_{1-42}$, peptide was known, see U.S. Pat. No. 5,766,846 and U.S. Pat. No. 5,837,672, (incorporated by reference, with the exception to reference to "soluble" peptides). But what enzyme was involved in producing the $A\beta_{1-42}$, peptide was unknown.

Alignment of the amino acid sequences of Hu-Asp2 with other known aspartyl proteases reveals a similar domain organization. All of the sequences contain a signal sequence followed by a pro-segment and the catalytic domain containing 2 copies of the aspartyl protease active site motif (DTG/DSG) separated by approximately 180 amino acid residues. Comparison of the processing site for proteolytic removal of the pro-segment in the mature forms of pepsin A, pepsin C, cathepsin D, cathepsin E and renin reveals that the mature forms of these enzymes contain between 31–35 amino acid residues upstream of the first DTG motif. Inspection of this region in the Hu-Asp-2 amino acid sequence indicates a preferred processing site within the sequence GRR↓GS (SEQ ID NO:68) as proteolytic processing of pro-protein precursors commonly occurs at site following dibasic amino acid pairs (eg. RR). Also, processing at this site would yield a mature enzyme with 35 amino acid residues upstream of the first DTG, consistent with the processing sites for other aspartyl proteases. In the absence of self-activation of Hu-Asp2 or a knowledge of the endogenous protease that processes Hu-Asp2 at this site, a recombinant form was engineered by introducing a recognition site for the PreSission protease (LEVLFQ↓GP (SEQ ID NO:62)) into the expression plasmids for bacterial, insect cell, and mammalian cell expression of pro-Hu-Asp2. In each case, the Gly residue in P1' position corresponds to the Gly residue 35 amino acids upstream of the first DTG motif in Hu-Asp2.

The present invention involves the molecular definition of several novel human aspartyl proteases and one of these, referred to as Hu-Asp-2(a) and Hu-Asp2(b), has been characterized in detail. Previous forms of asp1 and asp 2 have been disclosed, see EP 0848062 A2 and EP 0855444A2, inventors David Powel et al., assigned to Smith Kline Beecham Corp. (incorporated by reference). Herein are disclosed old and new forms of Hu-Asp 2. For the first time they are expressed in active form their substrates are disclosed, and their specificity is disclosed. Prior to this disclosure cell or cell extracts were required to cleave the β-secretase site, now purified protein can be used in assays, also described here. Based on the results of (1) antisense knock out experiments, (2) transient transfection knock in experiments, and (3) biochemical experiments using purified recombinant Hu-Asp-2, we demonstrate that Hu-Asp-2 is the β-secretase involved in the processing of APP. Although the nucleotide and predicted amino acid sequence of Hu-Asp-2(a) has been reported, see above, see EP 0848062 A2 and EP 0855444A2, no functional characterization of the enzyme was disclosed. Here the authors characterize the Hu-Asp-2 enzyme and are able to explain why it is a critical and essential enzyme required in the formation of $A\beta_{1-42}$, peptide and possible a critical step in the development of AD.

In another embodiment the present invention also describes a novel splice variant of Hu-Asp2, referred to as Hu-Asp-2(b), that has never before been disclosed.

In another embodiment, the invention provides isolated nucleic acid molecules comprising a polynucleotide encoding a polypeptide selected from the group consisting of human aspartyl protease 1 (Hu-Asp1) and two alternative splice variants of human aspartyl protease-2 (Hu-Asp2), designated herein as Hu-Asp2(a) and Hu-Asp2(b). As used herein, all references to "Hu-Asp2" should be understood to refer to both Hu-Asp2(a) and Hu-Asp2(b). Hu-Asp1 is expressed most abundantly in pancreas and prostate tissues, while Hu-Asp2(a) and Hu-Asp2(b) are expressed most abundantly in pancreas and brain tissues. The invention also provides isolated Hu-Asp1, Hu-Asp2(a), and Hu-Asp2(b) polypeptides, as well as fragments thereof which exhibit aspartyl protease activity.

The predicted amino acid sequences of Hu-Asp 1, Hu-Asp2(a) and Hu-Asp2) share significant homology with previously identified mammalian aspartyl proteases such as pepsinogen A, pepsinogen B, cathepsin D, cathepsin E, and renin. P. B. Szecs, *Scand. J. Clin. Lab. Invest.* 52:(Suppl. 210 5–22 (1992)). These enzymes are characterized by the presence of a duplicated DTG/DSG sequence motif. The Hu-Asp1 and HuAsp2 polypeptides disclosed herein also exhibit extremely high homology with the ProSite consensus motif for aspartyl proteases extracted from the SwissProt database.

The nucleotide sequence given as residues 1–1554 of SEQ ID NO: 1 corresponds to the nucleotide sequence encoding Hu-Asp1, the nucleotide sequence given as residues 1–1503 of SEQ ID NO:3 corresponds to the nucleotide sequence encoding Hu-Asp2(a), and the nucleotide sequence given as residues 1–1428 of SEQ ID NO:5 corresponds to the nucleotide sequence encoding Hu-Asp2(b). The isolation and sequencing of DNA encoding Hu-Asp1, Hu-Asp2(a), and Hu-Asp2(b) is described below in Examples 1 and 2.

As is described in Examples 1 and 2, automated sequencing methods were used to obtain the nucleotide sequence of Hu-Asp1, Hu-Asp2(a), and Hu-Asp-2(b). The Hu-Asp nucleotide sequences of the present invention were obtained for both DNA strands, and are believed to be 100% accurate. However, as is known in the art, nucleotide sequence obtained by such automated methods may contain some errors. Nucleotide sequences determined by automation are typically at least about 90%, more typically at least about 95% to at least about 99.9% identical to the actual nucleotide sequence of a given nucleic acid molecule. The actual sequence may be more precisely determined using manual sequencing methods, which are well known in the art. An error in sequence which results in an insertion or deletion of one or more nucleotides may result in a frame shift in translation such that the predicted amino acid sequence will differ from that which would be predicted from the actual nucleotide sequence of the nucleic acid molecule, starting at the point of the mutation. The Hu-Asp DNA of the present invention includes cDNA, chemically synthesized DNA, DNA isolated by PCR, genomic DNA, and combinations thereof. Genomic Hu-Asp DNA may be obtained by screening a genomic library with the Hu-Asp2 cDNA described herein, using methods that are well known in the art, or with oligonucleotides chosen from the Hu-Asp2 sequence that will prime the polymerase chain reaction (PCR). RNA transcribed from Hu-Asp DNA is also encompassed by the present invention.

Due to the degeneracy of the genetic code, two DNA sequences may differ and yet encode identical amino acid sequences. The present invention thus provides isolated nucleic acid molecules having a polynucleotide sequence encoding any of the Hu-Asp polypeptides of the invention, wherein said polynucleotide sequence encodes a Hu-Asp polypeptide having the complete amino acid sequence of SEQ ID NO:2, SEQ ID NO:4, SEQ ID NO:6, or fragments thereof.

Also provided herein are purified Hu-Asp polypeptides, both recombinant and non-recombinant. Most importantly, methods to produce Hu-Asp2 polypeptides in active form are provided. These include production of Hu-Asp2 polypeptides and variants thereof in bacterial cells, insect cells, and mammalian cells, also in forms that allow secretion of the Hu-Asp2 polypeptide from bacterial, insect or mammalian cells into the culture medium, also methods to produce variants of Hu-Asp2 polypeptide incorporating amino acid tags that facilitate subsequent purification. In a preferred embodiment of the invention the Hu-Asp2 polypeptide is converted to a proteolytically active form either in transformed cells or after purification and cleavage by a second protease in a cell-free system, such active forms of the Hu-Asp2 polypeptide beginning with the N-terminal sequence TQHGIR (SEQ ID NO: 69) or ETDEEP (SEQ ID NO: 70). The sequence TQHGIR (SEQ ID NO: 69) represents the amino-terminus of Asp2(a) or Asp2(b) beginning with residue 22 of SEQ ID NO: 4 or 6, after cleavage of a putative 21 residue signal peptide. Recombinant Asp2(a) expressed in and purified from insect cells was observed to have this amino terminus, presumably as a result of cleavage by a signal peptidase. The sequence ETDEEP (SEQ ID NO: 70) represents amino-terminus of Asp2(a) or Asp2(b) beginning with residue 46 of SEQ ID NO: 4 or 6, as observed when Asp2(a) has been recombinantly produced in CHO cells (presumably after cleavage by both a rodent signal peptidase and another rodent peptidase that removes a propeptide sequence). The Asp2(a) produced in the CHO cells possesses β-secretase activity, as described in greater detail in Examples 11 and 12. Variants and derivatives, including fragments, of Hu-Asp proteins having the native amino acid sequences given in SEQ ID Nos: 2, 4, and 6 that retain any of the biological activities of Hu-Asp are also within the scope of the present invention. Of course, one of ordinary skill in the art will readily be able to determine whether a variant, derivative, or fragment of a Hu-Asp protein displays Hu-Asp activity by subjecting the variant, derivative, or fragment to a standard aspartyl protease assay. Fragments of Hu-Asp within the scope of this invention include those that contain the active site domain containing the amino acid sequence DTG, fragments that contain the active site domain amino acid sequence DSG, fragments containing both the DTG and DSG active site sequences, fragments in which the spacing of the DTG and DSG active site sequences has been lengthened, fragments in which the spacing has been shortened. Also within the scope of the invention are fragments of Hu-Asp in which the transmembrane domain has been removed to allow production of Hu-Asp2 in a soluble form. In another embodiment of the invention, the two halves of Hu-Asp2, each containing a single active site DTG or DSG sequence can be produced independently as recombinant polypeptides, then combined in solution where they 4; reconstitute an active protease.

Thus, the invention provides a purified polypeptide comprising a fragment of a mammalian Asp2 protein, wherein said fragment lacks the Asp2 transmembrane domain of said Asp2 protein, and wherein the polypeptide and the fragment retain the β-secretase activity of said mammalian Asp2 protein. In a preferred embodiment, the purified polypeptide comprises a fragment of a human Asp2 protein that retains the β-secretase activity of the human Asp2 protein from which it was derived. Examples include:

a purified polypeptide that comprises a fragment of Asp2 (a) having the amino acid sequence set forth in SEQ ID NO: 4, wherein the polypeptide lacks transmembrane domain amino acids 455 to 477 of SEQ ID NO: 4;

a purified polypeptide as described in the preceding paragraph that further lacks cytoplasmic domain amino acids 478 to 501 of SEQ ID NO: 4;

a purified polypeptide as described in either of the preceding paragraphs that further lacks amino acids 420–454 of SEQ ID NO: 4, which constitute a putative alpha helical region between the catalytic domain and the transmembrane domain that is believed to be unnecessary for β-secretase activity;

a purified polypeptide that comprises an amino acid sequence that includes amino acids 58 to 419 of SEQ ID NO: 4, and that lacks amino acids 22 to 57 of SEQ ID NO: 4;

a purified polypeptide that comprises an amino acid sequence that includes amino acids 46 to 419 of SEQ ID NO: 4, and that lacks amino acids 22 to 45 of SEQ D NO: 4;

a purified polypeptide that comprises an amino acid sequence that includes amino acids 22 to 454 of SEQ ID NO: 4.

a purified polypeptide that comprises a fragment of Asp2 (b) having the amino acid sequence set forth in SEQ ID NO: 6, and wherein said polypeptide lacks transmembrane domain amino acids 430 to 452 of SEQ ID NO: 6;

a purified polypeptide as described in the preceding paragraph that further lacks cytoplasmic domain amino acids 453 to 476 of SEQ ID NO: 6;

a purified polypeptide as described in either of the preceding two paragraphs that further lacks amino acids 395–429 of SEQ ID NO: 4, which constitute a putative alpha helical region between the catalytic domain and the transmembrane domain that is believed to be unnecessary for β-secretase activity;

a purified polypeptide comprising an amino acid sequence that includes amino acids 58 to 394 of SEQ ID NO: 4, and that lacks amino acids 22 to 57 of SEQ ID NO: 4;

a purified polypeptide comprising an amino acid sequence that includes amino acids 46 to 394 of SEQ ID NO: 4, and that lacks amino acids 22 to 45 of SEQ ID NO: 4; and a purified polypeptide comprising an amino acid sequence that includes amino acids 22 to 429 of SEQ ID NO: 4.

Also included as part of the invention is a purified polynucleotide comprising a nucleotide sequence that encodes such polypeptides; a vector comprising a polynucleotide that encodes such polypeptides; and a host cell transformed or transfected with such a polynucleotide or vector.

Hu-Asp variants may be obtained by mutation of native Hu-Asp-encoding nucleotide sequences, for example. A Hu-Asp variant, as referred to herein, is a polypeptide substantially homologous to a native Hu-Asp polypeptide but which has an amino acid sequence different from that of native Hu-Asp because of one or more deletions, insertions, or substitutions in the amino acid sequence. The variant amino acid or nucleotide sequence is preferably at least about 80% identical, more preferably at least about 90% identical, and most preferably at least about 95% identical, to a native Hu-Asp sequence. Thus, a variant nucleotide sequence which contains, for example, 5 point mutations for every one hundred nucleotides, as compared to a native Hu-Asp gene, will be 95% identical to the native protein. The percentage of sequence identity, also termed homology, between a native and a variant Hu-Asp sequence may also be determined, for example, by comparing the two sequences using any of the computer programs commonly employed for this purpose, such as the Gap program (Wisconsin Sequence Analysis Package, Version 8 for Unix, Genetics Computer Group, University Research Park, Madison Wis.), which uses the algorithm of Smith and Waterman (*Adv. Appl. Math.* 2: 482–489 (1981)).

Alterations of the native amino acid sequence may be accomplished by any of a number of known techniques. For example, mutations may be introduced at particular locations by procedures well known to the skilled artisan, such as oligonucleotide-directed mutagenesis, which is described by Walder et at. (*Gene* 42:133 (1986)); Bauer et al. (*Gene* 37:73 (1985)); Craik (*BioTechniques*, January 1985, pp. 12–19); Smith et al. (*Genetic Engineering: Principles and Methods*, Plenum Press (1981)); and U.S. Pat. Nos. 4,518,584 and 4,737,462.

Hu-Asp variants within the scope of the invention may comprise conservatively substituted sequences, meaning that one or more amino acid residues of a Hu-Asp polypeptide are replaced by different residues that do not alter the secondary and/or tertiary structure of the Hu-Asp polypeptide. Such substitutions may include the replacement of an amino acid by a residue having similar physicochemical properties, such as substituting one aliphatic residue (Ile, Val, Leu or Ala) for another, or substitution between basic residues Lys and Arg, acidic residues Glu and Asp, amide residues Gln and Asn, hydroxyl residues Ser and Tyr, or aromatic residues Phe and Tyr. Further information regarding making phenotypically silent amino acid exchanges may be found in Bowie et al., *Science* 247:1306–1310 (1990). Other Hu-Asp variants which might retain substantially the biological activities of Hu-Asp are those where amino acid substitutions have been made in areas outside functional regions of the protein.

In another aspect, the invention provides an isolated nucleic acid molecule comprising a polynucleotide which hybridizes under stringent conditions to a portion of the nucleic acid molecules described above, e.g., to at least about 15 nucleotides, preferably to at least about 20 nucleotides, more preferably to at least about 30 nucleotides, and still more preferably to at least about from 30 to at least about 100 nucleotides, of one of the previously described nucleic acid molecules. Such portions of nucleic acid molecules having the described lengths refer to, e.g., at least about 15 contiguous nucleotides of the reference nucleic acid molecule. By stringent hybridization conditions is intended overnight incubation at about 42° C. for about 2.5 hours in 6×SSC/0.1% SDS, followed by washing of the filters four times for 15 minutes in 1.0×SSC at 65° C., 0.1% SDS.

Fragments of the Hu-Asp encoding nucleic acid molecules described herein, as well as polynucleotides capable of hybridizing to such nucleic acid molecules may be used as a probe or as primers in a polymerase chain reaction (PCR). Such probes may be used, e.g., to detect the presence of Hu-Asp nucleic acids in in vitro assays, as well as in Southern and northern blots. Cell types expressing Hu-Asp may also be identified by the use of such probes. Such procedures are well known, and the skilled artisan will be able to choose a probe of a length suitable to the particular application. For PCR, 5' and 3' primers corresponding to the termini of a desired Hu-Asp nucleic acid molecule are employed to isolate and amplify that sequence using conventional techniques.

Other useful fragments of the Hu-Asp nucleic acid molecules are antisense or sense oligonucleotides comprising a single stranded nucleic acid sequence capable of binding to a target Hu-Asp mRNA (using a sense strand), or Hu-Asp DNA (using an antisense strand) sequence. In a preferred embodiment of the invention these Hu-Asp antisense oligonucleotides reduce Hu-Asp mRNA and consequent production of Hu-Asp polypeptides.

In another aspect, the invention includes Hu-Asp polypeptides with or without associated native pattern glycosylation. Both Hu-Asp1 and Hu-Asp2 have canonical acceptor sites for Asn-linked sugars, with Hu-Asp1 having two of such sites, and Hu-Asp2 having four. Hu-Asp expressed in yeast or mammalian expression systems (discussed below) may be similar to or significantly different from a native Hu-Asp polypeptide in molecular weight and glycosylation pattern. Expression of Hu-Asp in bacterial expression systems will provide non-glycosylated Hu-Asp.

The polypeptides of the present invention are preferably provided in an isolated form, and preferably are substantially purified. Hu-Asp polypeptides may be recovered and purified from tissues, cultured cells, or recombinant cell cultures by well-known methods, including ammonium sulfate or ethanol precipitation, anion or cation exchange chromatography, phosphocellulose chromatography, hydrophobic interaction chromatography, affinity chromatography, hydroxylapatite chromatography, lectin chromatography, and high performance liquid chromatography (HPLC). In a preferred embodiment, an amino acid tag is added to the Hu-Asp polypeptide using genetic engineering techniques that are well known to practitioners of the art which include addition of six histidine amino acid residues to allow purification by binding to nickel immobilized on a suitable support, epitopes for polyclonal or monoclonal antibodies including but not limited to the T7 epitope, the myc epitope, and the V5a epitope, and fusion of Hu-Asp2 to suitable protein partners including but not limited to glutathione-S-transferase or maltose binding protein. In a preferred embodiment these additional amino acid sequences are added to the C-terminus of Hu-Asp but may be added to the N-terminus or at intervening positions within the Hu-Asp2 polypeptide.

The present invention also relates to vectors comprising the polynucleotide molecules of the invention, as well as host cell transformed with such vectors. Any of the polynucleotide molecules of the invention may be joined to a vector, which generally includes a selectable marker and an origin of replication, for propagation in a host. Because the invention also provides Hu-Asp polypeptides expressed from the polynucleotide molecules described above, vectors for the expression of Hu-Asp are preferred. The vectors include DNA encoding any of the Hu-Asp polypeptides described above or below, operably linked to suitable transcriptional or translational regulatory sequences, such as those derived from a mammalian, microbial, viral, or insect gene. Examples of regulatory sequences include transcriptional promoters, operators, or enhancers, mRNA ribosomal binding sites, and appropriate sequences which control transcription and translation. Nucleotide sequences are operably linked when the regulatory sequence functionally relates to the DNA encoding Hu-Asp. Thus, a promoter nucleotide sequence is operably linked to a Hu-Asp DNA sequence if the promoter nucleotide sequence directs the transcription of the Hu-Asp sequence.

Selection of suitable vectors to be used for the cloning of polynucleotide molecules encoding Hu-Asp, or for the expression of Hu-Asp polypeptides, will of course depend upon the host cell in which the vector will be transformed, and, where applicable, the host cell from which the Hu-Asp polypeptide is to be expressed. Suitable host cells for expression of Hu-Asp polypeptides include prokaryotes, yeast, and higher eukaryotic cells, each of which is discussed below.

The Hu-Asp polypeptides to be expressed in such host cells may also be fusion proteins which include regions from heterologous proteins. Such regions may be included to allow, e.g., secretion, improved stability, or facilitated purification of the polypeptide. For example, a sequence encoding an appropriate signal peptide can be incorporated into expression vectors. A DNA sequence for a signal peptide (secretory leader) may be fused inframe to the Hu-Asp sequence so that Hu-Asp is translated as a fusion protein comprising the signal peptide. A signal peptide that is functional in the intended host cell promotes extracellular secretion of the Hu-Asp polypeptide. Preferably, the signal sequence will be cleaved from the Hu-Asp polypeptide upon secretion of Hu-Asp from the cell. Nonlimiting examples of signal sequences that can be used in practicing the invention include the yeast Ifactor and the honeybee melatin leader in sf9 insect cells.

In a preferred embodiment, the Hu-Asp polypeptide will be a fusion protein which includes a heterologous region used to facilitate purification of the polypeptide. Many of the available peptides used for such a function allow selective binding of the fusion protein to a binding partner. For example, the Hu-Asp polypeptide may be modified to comprise a peptide to form a fusion protein which specifically binds to a binding partner, or peptide tag. Nonlimiting examples of such peptide tags include the 6-His tag, thioredoxin tag, hemaglutinin tag, GST tag, and OmpA signal sequence tag. As will be understood by one of skill in the art, the binding partner which recognizes and binds to the peptide may be any molecule or compound including metal ions (e.g., metal affinity columns), antibodies, or fragments thereof, and any protein or peptide which binds the peptide, such as the FLAG tag.

Suitable host cells for expression of Hu-Asp polypeptides includes prokaryotes, _yeast, and higher eukaryotic cells. Suitable prokaryotic hosts to be used for the expression of Hu-Asp include bacteria of the genera Escherichia, Bacillus, and Salmonella, as well as members of the genera Pseudomonas, Streptomyces, and Staphylococcus. For expression in, e.g., *E. coli*, a Hu-Asp polypeptide may include an N-terminal methionine residue to facilitate expression of the recombinant polypeptide in a prokaryotic host. The N-terminal Met may optionally then be cleaved from the expressed Hu-Asp polypeptide. Other N-terminal amino acid residues can be added to the Hu-Asp polypeptide to facilitate expression in *Escherichia coli* including but not limited to the T7 leader sequence, the T7 caspase 8 leader sequence, as well as others leaders including tags for purification such as the 6-His tag (Example 9). Hu-Asp polypeptides expressed in *E. coli* may be shortened by removal of the cytoplasmic tail, the transmembrane domain, or the membrane proximal region. Hu-Asp polypeptides expressed in *E. coli* may be obtained in either a soluble form or as an insoluble form which may or may not be present as an inclusion body. The insoluble polypeptide may be rendered soluble by guanidine HCl, urea or other protein denaturants, then refolded into a soluble form before or after purification by dilution or dialysis into a suitable aqueous buffer. If the inactive proform of the Hu-Asp was produced using recombinant methods, it may be rendered active by cleaving off the prosegment with a second suitable protease such as human immunodeficiency virus protease.

Expression vectors for use in prokaryotic hosts generally comprises one or more phenotypic selectable marker genes. Such genes generally encode, e.g., a protein that confers antibiotic resistance or that supplies an auxotrophic requirement. A wide variety of such vectors are readily available from commercial sources. Examples include pSPORT vectors, pGEM vectors (Promega), pPROEX vectors (LTI, Bethesda, Md.), Bluescript vectors (Stratagene), pET vectors (Novagen) and pQE vectors (Qiagen).

Hu-Asp may also be expressed in yeast host cells from genera including Saccharomyces, Pichia, and Kluveromyces. Preferred yeast hosts are *S. cerevisiae* and *P. pastoris*. Yeast vectors will often contain an origin of replication sequence from a 2T yeast plasmid, an autonomously replicating sequence (ARS), a promoter region, sequences for polyadenylation, sequences for transcription termination, and a selectable marker gene. Vectors replicable in both yeast and *E. coli* (termed shuttle vectors) may also be used. In addition to the above-mentioned features of yeast vectors, a shuttle vector will also include sequences for replication and selection in *E. coli*. Direct secretion of Hu-Asp polypeptides expressed in yeast hosts may be accomplished by the inclusion of nucleotide sequence encoding the yeast I-factor leader sequence at the 5' end of the Hu-Asp-encoding nucleotide sequence.

Insect host cell culture systems may also be used for the expression of Hu-Asp polypeptides. In a preferred embodiment, the Hu-Asp polypeptides of the invention are expressed using an insect cell expression system (see Example 10). Additionally, a baculovirus expression system can be used for expression in insect cells as reviewed by Luckow and Summers, *Biotechnology* 6:47 (1988).

In another preferred embodiment, the Hu-Asp polypeptide is expressed in mammalian host cells. Nonlimiting examples of suitable mammalian cell lines include the COS7 line of monkey kidney cells (Gluzman et al., *Cell* 23:175 (1981)), human embyonic kidney cell line 293, and Chinese hamster ovary (CHO) cells. Preferably, Chinese hamster ovary (CHO) cells are used for expression of Hu-Asp proteins (Example 11).

The choice of a suitable expression vector for expression of the Hu-Asp polypeptides of the invention will of course depend upon the specific mammalian host cell to be used, and is within the skill of the ordinary artisan. Examples of suitable expression vectors include pcDNA3 (Invitrogen) and pSVL (Pharmacia Biotech). A preferred vector for expression of Hu-Asp polypeptides is pcDNA3.1-Hygro (Invitrogen). Expression vectors for use in mammalian host cells may include transcriptional and translational control sequences derived from viral genomes. Commonly used promoter sequences and enhancer sequences which may be used in the present invention include, but are not limited to, those derived from human cytomegalovirus (CMV), Adenovirus 2, Polyoma virus, and Simian virus 40 (SV40). Methods for the construction of mammalian expression vectors are disclosed, for example, in Okayama and Berg (*Mol. Cell. Biol.* 3:280 (1983)); Cosman et al. (*Mol. Immunol.* 23:935 (1986)); Cosman et al. (*Nature* 312:768 (1984)); EP-A-0367566; and WO 91/18982.

The polypeptides of the present invention may also be used to raise polyclonal and monoclonal antibodies, which are useful in diagnostic assays for detecting Hu-Asp polypeptide expression. Such antibodies may be prepared by conventional techniques. See, for example, *Antibodies: A Laboratory Manual*, Harlow and Land (eds.), Cold Spring Harbor Laboratory Press, Cold Spring Harbor, N.Y., (1988); *Monoclonal Antibodes, Hybridomas: A New Dimension in Biological Analyses*, Kennet et al. (eds.), Plenum Press, New York (1980). Synthetic peptides comprising portions of Hu-Asp containing 5 to 20 amino acids may also be used for the production of polyclonal or monoclonal antibodies after linkage to a suitable carrier protein including but not limited to keyhole limpet hemacyanin (KLH), chicken ovalbumin, or bovine serum albumin using various cross-linking reagents including carbodimides, glutaraldehyde, or if the peptide contains a cysteine, N-methylmaleimide. A preferred peptide for immunization when conjugated to KLH contains the C-terminus of Hu-Asp1 or Hu-Asp2 comprising QRRPRDPEVVNDESSLVRHRWK (SEQ ID NO: 2, residues 497–518) or LRQQHDDFADDISLLK (SEQ ID NO:4, residues 486–501), respectively. See SEQ ID Nos. 33–34.

The Hu-Asp nucleic acid molecules of the present invention are also valuable for chromosome identification, as they can hybridize with a specific location on a human chromosome. Hu-Asp1 has been localized to chromosome 21, while Hu-Asp2 has been localized to chromosome 11q23.3–24.1. There is a current need for identifying particular sites on the chromosome, as few chromosome marking reagents based on actual sequence data (repeat polymorphisms) are presently available for marking chromosomal location. Once a sequence has been mapped to a precise chromosomal location, the physical position of the sequence on the chromosome can be correlated with genetic map data. The relationship between genes and diseases that have been mapped to the same chromosomal region can then be identified through linkage analysis, wherein the coinheritance of physically adjacent genes is determined. Whether a gene appearing to be related to a particular disease is in fact the cause of the disease can then be determined by comparing the nucleic acid sequence between affected and unaffected individuals.

In another embodiment, the invention relates to a method of assaying Hu-Asp function, specifically Hu-Asp2 function which involves incubating in solution the Hu-Asp polypeptide with a suitable substrate including but not limited to a synthetic peptide containing the β-secretase cleavage site of APP, preferably one containing the mutation found in a Swedish kindred with inherited AD in is changed to NL, such peptide comprising the sequence SEVNLDAEFR (SEQ ID NO: 64) in an acidic buffering solution, preferably an acidic buffering solution of pH5.5 (see Example 12) using cleavage of the peptide monitored by high performance liquid chromatography as a measure of Hu-Asp proteolytic activity. Preferred assays for proteolytic activity utilize internally quenched peptide assay substrates. Such suitable substrates include peptides which have attached a paired flurophore and quencher including but not limited to 7-amino-4-methyl coumarin and dinitrophenol, respectively, such that cleavage of the peptide by the Hu-Asp results in increased fluorescence due to physical separation of the flurophore and quencher. Other paired flurophores and quenchers include bodipy-tetramethylrhodamine and QSY-5 (Molecular Probes, Inc.). In a variant of this assay, biotin or another suitable tag may be placed on one end of the peptide to anchor the peptide to a substrate assay plate and a flurophore may be placed at the other end of the peptide. Useful flurophores include those listed above as well as Europium labels such as W8044 (EG&g Wallac, Inc.). Cleavage of the peptide by Asp2 will release the flurophore or other tag from the plate, allowing compounds to be assayed for inhibition of Asp2 proteolytic cleavage as shown by an increase in retained fluorescence. Preferred colorimetric assays of Hu-Asp proteolytic activity utilize other suitable substrates that include the P2 and P1 amino acids comprising the recognition site for cleavage linked to o-nitrophenol through an amide linkage, such that cleavage by the Hu-Asp results in an increase in optical density after altering the assay buffer to alkaline pH.

In another embodiment, the invention relates to a method for the identification of an agent that increases the activity of a Hu-Asp polypeptide selected from the group consisting of Hu-Asp1, Hu-Asp2(a), and Hu-Asp2(b), the method comprising (a) determining the activity of said Hu-Asp polypeptide in the presence of a test agent and in the absence of a test agent; and (b) comparing the activity of said Hu-Asp polypeptide determined in the presence of said test agent to the activity of said Hu-Asp polypeptide determined in the absence of said test agent;

whereby a higher level of activity in the presence of said test agent than in the absence of said test agent indicates that said test agent has increased the activity of said Hu-Asp polypeptide. Such tests can be performed with Hu-Asp polypeptide in a cell free system and with cultured cells that express Hu-Asp as well as variants or isoforms thereof.

In another embodiment, the invention relates to a method for the identification of an agent that decreases the activity of a Hu-Asp polypeptide selected from the group consisting of Hu-Asp1, Hu-Asp2(a), and Hu-Asp2(b), the method comprising (a) determining the activity of said Hu-Asp polypeptide in the presence of a test agent and in the absence of a test agent; and (b) comparing the activity of said Hu-Asp polypeptide determined in the presence of said test agent to the activity of said Hu-Asp polypeptide determined in the absence of said test agent;

whereby a lower level of activity in the presence of said test agent than in the absence of said test agent indicates that said test agent has decreased the activity of said Hu-Asp polypeptide. Such tests can be performed with Hu-Asp polypeptide in a cell free system and with cultured cells that express Hu-Asp as well as variants or isoforms thereof.

In another embodiment, the invention relates to a novel cell line (HEK125.3 cells) for measuring processing of amyloid β peptide (Aβ) from the amyloid protein precursor (APP). The cells are stable transformants of human embryonic kidney 293 cells (HEK293) with a bicistronic vector derived from pIRES-EGFP (Clontech) containing a modified human APP cDNA, an internal ribosome entry site and an enhanced green fluorescent protein (EGFP) cDNA in the second cistron. The APP cDNA was modified by adding two lysine codons to the carboxyl terminus of the APP coding sequence. This increases processing of Aβ peptide from human APP by 24 fold. This level of 4 peptide processing is 60 fold higher than is seen in nontransformed HEK293 cells. HEK125.3 cells will be useful for assays of compounds that inhibit Aβ peptide processing. This invention also includes addition of two lysine residues to the C-terminus of other APP isoforms including the 751 and 770 amino acid isoforms, to isoforms of APP having mutations found in human AD including the Swedish KM→NL and V717→F mutations, to C-terminal fragments of APP, such as those beginning with the β-secretase cleavage site, to C-terminal fragments of APP containing the β-secretase cleavage site which have been operably linked to an N-terminal signal peptide for membrane insertion and secretion, and to C-terminal fragments of APP which have been operably linked to an N-terminal signal peptide for membrane insertion and secretion and a reporter sequence including but not limited to green fluorescent protein or alkaline phosphatase, such that β-secretase cleavage releases the reporter protein from the surface of cells expressing the polypeptide.

Having generally described the invention, the same will be more readily understood by reference to the following examples, which are provided by way of illustration and are not intended as limiting.

EXAMPLE 1

Development of a Search Algorithm Useful for the Identification of Aspartyl Proteases, and Identification of C. elegans Aspartyl Protease Genes in Wormpep 12

Materials and Methods:

Classical aspartyl proteases such as pepsin and renin possess a two-domain structure which folds to bring two aspartyl residues into proximity within the active site. These are embedded in the short tripeptide motif DTG, or more rarely, DSG. The DTG or DSG active site motif appears at about residue 25–30 in the enzyme, but at about 65–70 in the proenzyme (prorenin, pepsinogen). This motif appears again about 150–200 residues downstream. The proenzyme is activated by cleavage of the N-terminal prodomain. This pattern exemplifies the double domain structure of the modern day aspartyl enzymes which apparently arose by gene duplication and divergence. Thus;

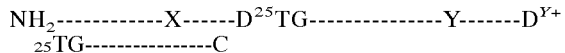

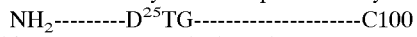

where X denotes the beginning of the enzyme, following the N-terminal prodomain, and Y denotes the center of the molecule where the gene repeat begins again.

In the case of the retroviral enzymes such as the HIV protease, they represent only a half of the two-domain structures of well-known enzymes like pepsin, cathepsin D, renin, etc. They have no prosegment, but are carved out of a polyprotein precursor containing the gag and pol proteins of the virus. They can be represented by:

$$NH_2\text{---------}D^{25}TG\text{--------------------}C100$$

This "monomer" only has about 100 aa, so is extremely parsimonious as compared to the other aspartyl protease "dimers" which have of the order of 330 or so aa, not counting the N-terminal prodomain.

The limited length of the eukaryotic aspartyl protease active site motif makes it difficult to search EST collections for novel sequences. EST sequences typically average 250 nucleotides, and so in this case would be unlikely to span both aspartyl protease active site motifs. Instead, we turned to the C. elegans genome. The C. elegans genome is estimated to contain around 13,000 genes. Of these, roughly 12,000 have been sequenced and the corresponding hypothetical open reading frame (ORF) has been placed in the database Wormpep12. We used this database as the basis for a whole genome scan of a higher eukaryote for novel aspartyl proteases, using an algorithm that we developed specifically for this purpose. The following AWK script for locating proteins containing two DTG or DSG motifs was used for the search, which was repeated four times to recover all pairwise combinations of the aspartyl motif.

```
BEGIN{RS=">"}    /* defines ">" as record separator for
FASTA format */
{
pos = index($0,"DTG")    /*finds "DTG" in record*/
if (pos>0) {
   rest = substr($0,pos+3)    /*get rest of record after first DTG*/
   pos2 = index(rest,"DTG")   /*find second DTG*/
   if (pos2>0) printf ("%s%s\n",">",$0) }   /*report hits*/
}
}
```

The AWK script shown above was used to search Wormpep 12, which was downloaded from ftp.sanger.ac.uk/pub/databases/wormpep, for sequence entries containing at least two DTG or DSG motifs. Using AWK limited each record to 3000 characters or less. Thus, 35 or so larger records were eliminated manually from Wormpep 12 as in any case these were unlikely to encode aspartyl proteases.

Results and Discussion:

The Wormpep 12 database contains 12,178 entries, although some of these (<10%) represent alternatively spliced transcripts from the same gene. Estimates of the number of genes encoded in the C. elegans genome is on the order of 13,000 genes, so Wormpep 12 may be estimated to cover greater than 90% a of the C. elegans genome.

Eukaryotic aspartyl proteases contain a two-domain structure, probably arising from ancestral gene duplication. Each domain contains the active site motif D(S/T)G located from 20–25 amino acid residues into each domain. The retroviral (e.g., MV protease) or retrotransposon proteases are homodimers of subunits which are homologous to a single eukaryotic aspartyl protease domain. An AWK script was used to search the Wormpep12 database for proteins in which the D(S/T)G motif occurred at least twice. This identified >60 proteins with two DTG or DSG motifs. Visual inspection was used to select proteins in which the position of the aspartyl domains was suggestive of a two-domain structure meeting the criteria described above.

In addition, the PROSITE eukaryotic and viral aspartyl protease active site pattern PS00141 was used to search Wormpep12 for candidate aspartyl proteases. (Bairoch A, Bucher P., Hofmann K., The PROSITE database: its status in 1997, *Nucleic Acids Res.* 24:217–221(1997)). This generated an overlapping set of Wormpep12 sequences. Of these, seven sequences contained two DTG or DSG motifs and the PROSITE aspartyl protease active site pattern. Of these seven, three were found in the same cosmid clone (F21F8.3, F21F8.4, and F21F8.7) suggesting that they represent a family of proteins that arose by ancestral gene duplication. Two other ORFs with extensive homology to F21F8.3, F21F8.4 and F21F8.7 are present in the same gene cluster (F21F8.2 and F21F8.6), however, these contain only a single DTG motif. Exhaustive BLAST searches with these seven sequences against Wormpep12 failed to reveal additional candidate aspartyl proteases in the *C. elegans* genome containing two repeats of the DTG or DSG motif.

BLASTX search with each *C. elegans* sequence against SWISS-PROT, GenPep and TREMBL revealed that R12H7.2 was the closest worm homologue to the known mammalian aspartyl proteases, and that T18H9.2 was somewhat more distantly related, while CEASP1, F21F8.3, F21F8.4, and F21F8.7 formed a subcluster which had the least sequence homology to the mammalian sequences.

Discussion:

APP, the presenilins, and p35, the activator of cdk5, all undergo intracellular proteolytic processing at sites which conform to the substrate specificity of the HIV protease. Dysregulation of a cellular aspartyl protease with the same substrate specificity, might therefore provide a unifying mechanism for causation of the plaque and tangle pathologies in AD. Therefore, we sought to identify novel human aspartyl proteases. A whole genome scan in *C. elegans* identified seven open reading frames that adhere to the aspartyl protease profile that we had identified. These seven aspartyl proteases probably comprise the complete complement of such proteases in a simple, multicellular eukaryote. These include four closely related aspartyl proteases unique to *C. elegans* which probably arose by duplication of an ancestral gene. The other three candidate aspartyl proteases (T18H9.2, R12H7.2 and Cl1D2.2) were found to have homology to mammalian gene sequences.

EXAMPLE 2

Identification of Novel Human Aspartyl Proteases Using Database Mining by Genome Bridging Materials and Methods:

Computer-Assisted Analysis of EST Databases, cDNA, and Predicted Polypeptide Sequences:

Exhaustive homology searches of EST databases with the CEASP1, F21F8.3, F21F8.4, and F21F8.7 sequences failed to reveal any novel mammalian homologues. TBLASTN searches with R12H7.2 showed homology to cathepsin D, cathepsin E, pepsinogen A, pepsinogen C and renin, particularly around the DTG motif within the active site, but also failed to identify any additional novel mammalian aspartyl proteases. This indicates that the *C. elegans* genome probably contains only a single lysosomal aspartyl protease which in mammals is represented by a gene family that arose through duplication and consequent modification of an ancestral gene.

TBLASTN searches with T18H9.2, the remaining *C. elegans* sequence, identified several ESTs which assembled into a contig encoding a novel human aspartyl protease (Hu-ASP1). As is described above in Example 1, BLASTX search with the Hu-ASP1 contig against SWISS-PROT revealed that the active site motifs in the sequence aligned with the active sites of other aspartyl proteases. Exhaustive, repetitive rounds of BLASTN searches against LifeSeq, LifeSeqFL, and the public EST collections identified 102 EST from multiple cDNA libraries that assembled into a single contig. The 51 sequences in this contig found in public EST collections also have been assembled into a single contig (THC213329) by The Institute for Genome Research (TIGR). The TIGR annotation indicates that they failed to find any hits in the database for the contig. Note that the TIGR contig is the reverse complement of the LifeSeq contig that we assembled. BLASTN search of Hu-ASP1 against the rat and mouse EST sequences in ZooSeq revealed one homologous EST in each database (Incyte clone 700311523 and IMAGE clone 313341, GenBank accession number W10530, respectively).

TBLASTN searches with the assembled DNA sequence for Hu-ASP1 against both LifeSeqFL and the public EST databases identified a second, related human sequence-(Hu-Asp2) represented by a single EST (2696295). Translation of this partial cDNA sequence reveals a single DTG motif which has homology to the active site motif of a bovine aspartyl protease, NM1.

BLAST searches, contig assemblies and multiple sequence alignments were performed using the bioinformatics tools provided with the LifeSeq, LifeSeqFL and LifeSeq Assembled databases from Incyte. Predicted protein motifs were identified using either the ProSite dictionary (Motifs in GCG 9) or the Pfam database.

Full-Length cDNA Cloning of Hu-Asp1

The open reading frame of *C. elegans* gene T18H9.2CE was used to query Incyte LifeSeq and LifeSeq-FL databases and a single electronic assembly referred to as 1863920CE1 was detected. The 5' most cDNA clone in this contig, 1863920, was obtained from Incyte and completely sequenced on both strands. Translation of the open reading frame contained within clone 1863920 revealed the presence of the duplicated aspartyl protease active site motif (DTG/DSG) but the 5' end was incomplete. The remainder of the Hu-Asp1 coding sequence was determined by 5' Marathon RACE analysis using a human placenta Marathon ready cDNA template (Clontech). A 3'-antisense oligonucleotide primer specific for the 5' end of clone 1863920 was paired with the 5'-sense primer specific for the Marathon ready cDNA synthetic adaptor in the PCR. Specific PCR products were directly sequenced by cycle sequencing and the resulting sequence assembled with the sequence of clone 1863920 to yield the complete coding sequence of Hu-Asp1 (SEQ ID No.1).

Several interesting features are present in the primary amino acid sequence of Hu-Asp1 (FIG. 1, SEQ ID No. 2). The sequence contains a signal peptide (residues 1–20 in SEQ ID No. 2), a pro-segment, and a catalytic domain containing two copies of the aspartyl protease active site motif (DTG/DSG). The spacing between the first and second active site motifs is about 200 residues which should correspond to the expected size of a single, eukaryotic aspartyl protease domain. More interestingly, the sequence contains a predicted transmembrane domain (residues 469–492 in SEQ ID No.2) near its C-terminus which suggests that the protease is anchored in the membrane. This feature is not found in any other aspartyl protease.

Cloning of a Full-Length Hu-Asp2 cDNAs:

As is described above in Example 1, genome wide scan of the *Caenorhabditis elegans* database WormPep12 for putative aspartyl proteases and subsequent mining of human EST databases revealed a human ortholog to the *C. elegans* gene T18H9.2 referred to as Hu-Asp1. The assembled contig for Hu-Asp1 was used to query for human paralogs using the BLAST search tool in human EST databases and a single significant match (2696295CE1) with approximately 60% shared identity was found in the LifeSeq FL database. Similar queries of either gb105PubEST or the family of human databases available from TIGR did not identify similar EST clones. cDNA clone 2696295, identified by single pass sequence analysis from a human uterus cDNA library, was obtained from Incyte and completely sequence on both strands. This clone contained an incomplete 1266 bp open-reading frame that encoded a 422 amino acid polypeptide but lacked an initiator ATG on the 5' end. Inspection of the predicted sequence revealed the presence of the duplicated aspartyl protease active site motif DTG/DSG, separated by 194 amino acid residues. Subsequent queries of later releases of the LifeSeq EST database identified an additional ESTs, sequenced from a human astrocyte cDNA library (4386993), that appeared to contain additional 5' sequence relative to clone 2696295. Clone 4386993 was obtained from Incyte and completely sequenced on both strands. Comparative analysis of clone 4386993 and clone 2696295 confirmed that clone 4386993 extended the open-reading frame by 31 amino acid residues including two in-frame translation initiation codons. Despite the presence of the two in-frame ATGs, no in-frame stop codon was observed upstream of the ATG indicating that the 4386993 may not be full-length. Furthermore, alignment of the sequences of clones 2696295 and 4386993 revealed a 75 base pair insertion in clone 2696295 relative to clone 4386993 that results in the insertion of 25 additional amino acid residues in 2696295. The remainder of the Hu-Asp2 coding sequence was determined by 5' Marathon RACE analysis using a human hippocampus Marathon ready cDNA template (Clontech). A 3'-antisense oligonucleotide primer specific for the shared 5'-region of clones 2696295 and 4386993 was paired with the 5'-sense primer specific for the Marathon ready cDNA synthetic adaptor in the PCR. Specific PCR products were directly sequenced by cycle sequencing and the resulting sequence assembled with the sequence of clones 2696295 and 4386993 to yield the complete coding sequence of Hu-Asp2(a) (SEQ ID No. 3) and Hu-Asp2(b) (SEQ ID No. 5), respectively.

Several interesting features are present in the primary amino acid sequence of Hu-Asp2(a) (FIG. 3 and SEQ ID No. 4) and Hu-Asp-2(b) (FIG. 2, SEQ ID No. 6). Both sequences contain a signal peptide (residues 1–21 in SEQ ID No. 4 and SEQ ID No. 6), a pro-segment, and a catalytic domain containing two copies of the aspartyl protease active site motif (DTG/DSG). The spacing between the first and second active site motifs is variable due to the 25 amino acid residue deletion in Hu-Asp-2(b) and consists of 168-versus-194 amino acid residues, for Hu-Asp2(b) and Hu-Asp-2(a), respectively. More interestingly, both sequences contains a predicted transmembrane domain (residues 455–477 in SEQ ID No.4 and 430–452 in SEQ ID No. 6) near their C-termini which indicates that the protease is anchored in the membrane. This feature is not found in any other aspartyl protease except Hu-Asp1.

EXAMPLE 3

Molecular Cloning of Mouse Asp2 cDNA and Genomic DNA

Cloning and Characterization of Murine Asp2 cDNA.

The murine ortholog of Hu-Asp2 was cloned using a combination of cDNA library screening, PCR, and genomic cloning. Approximately 500,000 independent clones from a mouse brain cDNA library were screened using a $^{32}$P-labeled coding sequence probe prepared from Hu-Asp2. Replicate positives were subjected to DNA sequence analysis and the longest cDNA contained the entire 3' untranslated region and 47 amino acids in the coding region. PCR amplification of the same mouse brain cDNA library with an antisense oligonucleotide primer specific for the 5'-most cDNA sequence determined above and a sense primer specific for the 5' region of human Asp2 sequence followed by DNA sequence analysis gave an additional 980 bp of the coding sequence. The remainder of the 5' sequence of murine Asp-2 was derived from genomic sequence (see below).

Isolation and Sequence Analysis of the Murine Asp-2 Gene.

A murine EST sequence encoding a portion of the murine Asp2 cDNA was identified in the GenBank EST database using the BLAST search tool and the Hu-Asp2 coding sequence as the query. Clone g3160898 displayed 88% shared identity to the human sequence over 352 bp. Oligonucleotide primer pairs specific for this region of murine Asp2 were then synthesized and used to amplify regions of the murine gene. Murine genomic DNA, derived from strain 129/SvJ, was amplified in the PCR (25 cycles) using various primer sets specific for murine Asp2 and the products analyzed by agarose gel electrophoresis. The primer set Zoo-1 and Zoo-4 amplified a 750 bp fragment that contained approximately 600 bp of intron sequence based on comparison to the known cDNA sequence. This primer set was then used to screen a murine BAC library by PCR, a single genomic clone was isolated and this cloned was confirmed contain the murine Asp2 gene by DNA sequence analysis. Shotgun DNA sequencing of this Asp2 genomic clone and comparison to the cDNA sequences of both Hu-Asp2 and the partial murine cDNA sequences defined the full-length sequence of murine Asp2 (SEQ ID No. 7). The predicted amino acid sequence of murine Asp2 (SEQ ID No. 8) showed 96.4% shared identity (GCG BestFit algorithm) with 18/501 amino acid residue substitutions compared to the human sequence (FIG. 4). The proteolytic processing of murine Asp2(a) is believed to be analogous to the processing described above for human Asp2(a). In addition, a variant lacking amino acid residues 190–214 of SEQ ID NO: 8 is specifically contemplated as a murine Asp2(b) polypeptide and is set out as SEQ ID NO: 73. All forms of murine Asp2(b) gene and protein are intended as aspects of the invention.

EXAMPLE 4

Tissue Distribution of Expression of Hu-Asp2 Transcripts

Materials and Methods:

The tissue distribution of expression of Hu-Asp2 was determined using multiple tissue Northern blots obtained from Clontech (Palo Alto, Calif.). Incyte clone 2696295 in the vector pINCY was digested to completion with EcoRI/NotI and the 1.8 kb cDNA insert purified by preparative agarose gel electrophoresis. This fragment was radiolabeled to a specific activity >1×10$^9$ dpm/µg by random priming in the presence of [α-$^{32}$P-dATp] (>3000 Ci/mmol, Amersham, Arlington Heights, Ill.) and Klenow fragment of DNA polymerase 1. Nylon filters containing denatured, size fractionated poly A$^+$ RNAs isolated from different human tissues were hybridized with 2×10$^6$ dpm/ml probe in ExpressHyb buffer (Clontech, Palo Alto, Calif.) for 1 hour at 68° C. and washed as recommended by the manufacture. Hybridization signals were visualized by autoradiography using BioMax XR film (Kodak, Rochester, N.Y.) with intensifying screens at −80° C.

Results and Discussion:

Limited information on the tissue distribution of expression of Hu-Asp-2 transcripts was obtained from database analysis due to the relatively small number of ESTs detected using the methods described above (<5). In an effort to gain further information on the expression of the Hu-Asp2 gene, Northern analysis was employed to determine both the size(s) and abundance of Hu-Asp2 transcripts. PolyA$^+$ RNAs isolated from a series of peripheral tissues and brain regions were displayed on a solid support following separation under denaturing conditions and Hu-Asp2 transcripts were visualized by high stringency hybridization to radio-labeled insert from clone 2696295. The 2696295 cDNA probe visualized a constellation of transcripts that migrated with apparent sizes of 3.0 kb, 4.4 kb and 8.0 kb with the latter two transcript being the most abundant.

Across the tissues surveyed, Hu-Asp2 transcripts were most abundant in pancreas and brain with lower but detectable levels observed in all other tissues examined except thymus and PBLs. Given the relative abundance of Hu-Asp2 transcripts in brain, the regional expression in brain regions was also established. A similar constellation of transcript sizes were detected in all brain regions examined [cerebellum cerebral cortex, occipital pole, frontal lobe, temporal lobe and putamen] with the highest abundance in the medulla and spinal cord.

EXAMPLE 5

Northern Blot Detection of HuAsp-1 and HuAsp-2 Transcripts in Human Cell Lines A variety of human cell lines were tested for their ability to produce Hu-Asp1 and Asp2 mRNA Human embryonic kidney (HEK-293) cells, African green monkey (Cos-7) cells, Chinese hamster ovary (CHO) cells, HELA cells, and the neuroblastoma cell line IMR-32 were all obtained from the ATCC. Cells were cultured in DME containing 10% FCS except CHO cells which were maintained in α-MEM/10% FCS at 37° C. in 5% $CO_2$ until they were near confluence. Washed monolayers of cells ($3 \times 10^7$) were lysed on the dishes and poly A$^+$ RNA extracted using the Qiagen Oligotex Direct mRNA kit. Samples containing 2 μg of poly A$^+$ RNA from each cell line were fractionated under denaturing conditions (glyoxal-treated), transferred to a solid nylon membrane support by capillary action, and transcripts visualized by hybridization with random-primed labeled ($^{32}$P) coding sequence probes derived from either Hu-Asp1 or Hu-Asp2. Radioactive signals were detected by exposure to X-ray film and by image analysis with a PhosphorImager.

The Hu-Asp1 cDNA probe visualized a similar constellation of transcripts (2.6 kb and 3.5 kb) that were previously detected is human tissues. The relative abundance determined by quantification of the radioactive signal was Cos-7>HEK 292=HELA>MR32.

The Hu-Asp2 cDNA probe also visualized a similar constellation of transcripts compared to tissue (3.0 kb, 4.4 kb, and 8.0 kb) with the following relative abundance; HEK 293>Cos 7>IMR32>HELA.

EXAMPLE 6

Modification of APP to Increase Aβ Processing for In Vitro Screening

Human cell lines that process Aβ peptide from APP provide a means to screen in cellular assays for inhibitors of β- and γ-secretase. Production and release of Aβ peptide into the culture supernatant is monitored by an enzyme-linked immunosorbent assay (EIA). Although expression of APP is widespread and both neural and non-neuronal cell lines process and release Aβ peptide, levels of endogenous APP processing are low and difficult to detect by EIA. Aβ processing can be increased by expressing in transformed cell lines mutations of APP that enhance Aβ processing. We made the serendipitous observation that addition of two lysine residues to the carboxyl terminus of APP695 increases Aβ processing still further. This allowed us to create a transformed cell line that releases Aβ peptide into the culture medium at the remarkable level of 20,000 pg/ml.

Materials And Methods

Materials:

Human embryonic kidney cell line 293 (HEK293 cells) were obtained internally. The vector pIRES-EGFP was purchased from Clontech. Oligonucleotides for mutation using the polymerase chain reaction (PCR) were purchased from Genosys. A plasmid containing human APP695 (SEQ ID No. 9 [nucleotide] and SEQ ID No. 10 [amino acid]) was obtained from Northwestern University Medical School. This was subcloned into pSK (Stratagene) at the Not1 site creating the plasmid pAPP695.

Mutagenesis Protocol:

The Swedish mutation (K670N, M671L) was introduced into pAPP695 using the Stratagene Quick Change Mutagenesis Kit to create the plasmid pAPP695NL (SEQ ID No. 11 [nucleotide] and SEQ ID No. 12 [amino acid]). To introduce a di-lysine motif at the C-terminus of APP695, the forward primer #276 5' GACTGACCACTCGACCAGGTTC (SEQ ID No. 47) was used with the "patch" primer #274 5' CGAATTAAATTCCAGCACACTGGCTACTTCTT-GTTCTGCATCTCAAAGAAC (SEQ ID No. 48) and the flanking primer #275 CGAATTMATTCCAGCACACTG-GCTA (SEQ ID No. 49) to modify the 3' end of the APP695 cDNA (SEQ ID No. 15 [nucleotide] and SEQ ID No. 16 [amino acid]). This also added a BstX1 restriction site that will be compatible with the BstX1 site in the multiple cloning site of pIRES-EGFP. PCR amplification was performed with a Clontech HF Advantage cDNA PCR kit using the polymerase mix and buffers supplied by the manufacturer. For "patch" PCR, the patch primer was used at ½0th the molar concentration of the flanking primers. PCR amplification products were purified using a QIAquick PCR purification kit (Qiagen). After digestion with restriction enzymes, products were separated on 0.8% agarose gels and then excised DNA fragments were purified using a QIAquick gel extraction kit (Qiagen).

To reassemble a modified APP695-Sw cDNA the 5' Not1-Bgl2 fragment of the APP695-Sw cDNA and the 3' Bgl2-BstX1 APP695 cDNA fragment obtained by PCR were ligated into pIRES-EGFP plasmid DNA opened at the Not1 and BstX1 sites. Ligations were performed for 5 minutes at room temperature using a Rapid DNA Ligation kit (Boehringer Mannheim) and transformed into Library Efficiency DH5a Competent Cells (GibcoBRL Life Technologies). Bacterial colonies were screened for inserts by PCR amplification using primers #276 and #275. Plasmid DNA was purified for mammalian cell transfection using a QIAprep Spin Miniprep kit (Qiagen). The construct obtained was designated pMG125.3 (APPSW-KK, SEQ ID No. 17 [nucleotide] and SEQ ID No. 18 [amino acid]).

Mammalian Cell Transfection:

HEK293 cells for transfection were grown to 80% confluence in Dulbecco's modified Eagle's medium (DMEM) with 10% fetal bovine serum. Cotransfections were performed using LipofectAmine (Gibco-BRL) with 3 μg pMG125.3 DNA and 9 μg pcDNA3.1 DNA per $10 \times 10^6$ cells. Three days posttransfection, cells were passaged into medium containing G418 at a concentration of 400 μg/ml. After three days growth in selective medium, cells were sorted by their fluorescence. Clonal Selection of 125.3 cells by FACS:

Cell samples were analyzed on an EPICS Elite ESP flow cytometer (Coulter, Hialeah, Fla.) equipped with a 488 nm excitation line supplied by an air-cooled argon laser. EGFP emission was measured through a 525 nm band-pass filter and fluorescence intensity was displayed on a 4-decade log scale after gating on viable cells as determined by forward and right angle light scatter. Single green cells were separated into each well of one 96 well plate containing growth medium without G418. After a four day recovery period, G418 was added to the medium to a final concentration of 400 µg/ml. After selection, 32% of the wells contained expanding clones. Wells with clones were expanded from the 96 well plate to a 24 well plate and then a 6 well plate with the fastest growing colonies chosen for expansion at each passage. The final cell line selected was the fastest growing of the final six passaged. This clone, designated 125.3, has been maintained in G418 at 400 µg/ml with passage every four days into fresh medium. No loss of Aβ production or EGFP fluorescence has been seen over 23 passages.

AβEIA Analysis (Double Antibody Sandwich ELISA for hAβ 1-40/42):

Cell culture supernatants harvested 48 hours after transfection were analyzed in a standard AP EIA as follows. Human Aβ 1-40 or 1-42 was measured using monoclonal antibody (mAb) 6E10 (Senetek St. Louis, Mo.) and biotinylated rabbit antiserum 162 or 164 (New York State Institute for Basic Research, Staten Island, N.Y.) in a double antibody sandwich ELISA The capture antibody 6E 10 is specific to an epitope present on the N-terminal amino acid residues 1–16 of hAβ. The conjugated detecting antibodies 162 and 164 are specific for hAβ 1-40 and 1-42, respectively. Briefly, a Nunc Maxisorp 96 well immunoplate was coated with 100 µl/well of mAb 6E10 (5 µg/ml) diluted in 0.1M carbonate-bicarbonate buffer, pH 9.6 and incubated at 4° C. overnight. After washing the plate 3×with 0.01M DPBS (Modified Dulbecco's Phosphate Buffered Saline (0.008M sodium phosphate, 0.002M potassium phosphate, 0.14M sodium chloride, 0.01 M potassium chloride, pH 7.4) from Pierce, Rockford, Ill.) containing 0.05% of Tween-20 (DPBST), the plate was blocked for 60 minutes with 200 µl of 10% normal sheep serum (Sigma) in 0.01M DPBS to avoid non-specific binding. Human Aβ 1-40 or 1-42 standards 100 µl/well (Bachem, Torrance, Calif.) diluted, from a 1 mg/ml stock solution in DMSO, in culture medium was added after washing the plate, as well as 100 µl/well of sample, e.g., conditioned medium of transfected cells.

The plate was incubated for 2 hours at room temperature and 4° C. overnight. The next day, after washing the plate, 100 µl/well biotinylated rabbit antiserum 162 1:400 or 164 1:50 diluted in DPBST+0.5% BSA was added and incubated at room temperature for 1 hour, 15 minutes. Following washes, 100 µl/well neutravidin-horseradish peroxidase (Pierce, Rockford, Ill.) diluted 1:10,000 in DPBST was applied and incubated for 1 hour at room temperature. After the last washes 100 µl/well of o-phenylnediamine dihydrochloride (Sigma Chemicals, St. Louis, Mo.) in 50 mM citric acid/100 mM sodium phosphate buffer (Sigma Chemicals, St. Louis, Mo.), pH 5.0, was added as substrate and the color development was monitored at 450 nm in a kinetic microplate reader for 20 minutes using Soft max Pro software. All standards and samples were run in triplicates. The samples with absorbance values falling within the standard curve were extrapolated from the standard curves using Soft max Pro software and expressed in pg/ml culture medium.

Results:

Addition of two lysine residues to the carboxyl terminus of APP695 greatly increases Aβ processing in HEK293 cells as shown by transient expression (Table 1). Addition of the di-lysine motif to APP695 increases Aβ processing to that seen with the APP695 containing the Swedish mutation. Combining the di-lysine motif with the Swedish mutation further increases processing by an additional 2.8 fold.

Cotransformation of HEK293 cells with pMG125.3 and pcDNA3.1 allowed dual selection of transformed cells for G418 resistance and high level expression of EGFP. After clonal selection by FACS, the cell line obtained, produces a remarkable 20,000 pg Aβ peptide per ml of culture medium after growth for 36 hours in 24 well plates. Production of Aβ peptide under various growth conditions is summarized in Table 2.

TABLE 1

Release of Aβ peptide into the culture medium 48 hours after transient transfection of HEK293 cells with the indicated vectors containing wildtype or modified APP. Values tabulated are mean + SD and P-value for pairwise comparison using Student's t-test assuming unequal variances.

| APP Construct | Aβ 1-40 peptide (pg/ml) | Fold Increase | P-value |
|---|---|---|---|
| pIRES-EGFP vector | 147 + 28 | 1.0 | |
| wt APP695 (142.3) | 194 + 15 | 1.3 | 0.051 |
| wt APP695-KK (124.1) | 424 + 34 | 2.8 | $3 \times 10^{-5}$ |
| APP695-Sw (143.3) | 457 + 65 | 3.1 | $2 \times 10^{-3}$ |
| APP695-SwKK (125.3) | 1308 + 98 | 8.9 | $3 \times 10^{-4}$ |

TABLE 2

Release of Aβ peptide from HEK125.3 cells under various growth conditions.

| Type of Culture Plate | Volume of Medium | Duration of Culture | Aβ 1–40 (pg/ml) | Aβ 1–42 (pg/ml) |
|---|---|---|---|---|
| 24 well plate | 400 ul | 36 hr | 28,036 | 1,439 |

EXAMPLE 7

Antisense Oligomer Inhibition of Abeta Processing in HEK125.3 Cells

The sequences of Hu-Asp1 and Hu-Asp2 were provided to Sequitur, Inc (Natick, Mass.) for selection of targeted sequences and design of 2nd generation chimeric antisense oligomers using prorietary technology (Sequitur Ver. D Pat pending #3002). Antisense oligomers Lot# S644, S645, S646 and S647 were targeted against Asp1. Antisense oligomers Lot# S648, S649, S650 and S651 were targeted against Asp2. Control antisense oligomers Lot# S652, S653, S655, and S674 were targeted against an irrelevant gene and antisense oligomers Lot #S656, S657, S658, and S659 were targeted against a second irrelevant gene.

For transfection with the antisense oligomers, HEK125.3 cells were grown to about 50% confluence in 6 well plates in Minimal Essential Medium (MEM) supplemented with 10% fetal calf serum. A stock solution of oligofectin G (Sequitur Inc., Natick, Mass.) at 2 mg/ml was diluted to 50 λg/ml in serum free MEM. Separately, the antisense oligomer stock solution at 100 µM was diluted to 800 nM in Opti-MEM (GIBCO-BRL, Grand Island, N.Y.). The diluted stocks of oligofectin G and antisense oligomer were then mixed at a ratio of 1:1 and incubated at room temperature. After 15 minutes incubation, the reagent was diluted 10 fold into MEM: containing 10% fetal calf serum and 2 ml was added to each well of the 6 well plate after first removing the old medium. After transfection, cells were grown in the continual presence of the oligofectin G/antisense oligomer. To monitor Aβ peptide release, 400 µl of conditioned medium was removed periodically from the culture well and replaced with fresh medium beginning 24 hours after transfection. Aβ peptides in the conditioned medium were assayed via immunoprecipitation and Western blotting. Data reported are from culture supernatants harvested 48 hours after transfection.

The 16 different antisense oligomers obtained from Sequitur Inc. were transfected separately into HEK 125.3 cells to determine their affect on Aβ peptide processing. Only antisense oligomers targeted against Asp2 significantly reduced Abeta processing by HEK125.3 cells. Both Aβ (1-40) and Aβ (1-42) were inhibited by the same degree. In Table 3, percent inhibition is calculated with respect to untransfected cells. Antisense oligomer reagents giving greater than 50% inhibition are marked with an asterisk. For ASP2, 4 of 4 antisense oligomers gave greater than 50% inhibition with an average inhibition of 62% for Aβ 1-40 processing and 60% for Aβ 1-42 processing.

TABLE 3

Inhibition of Aβ peptide release from HEK125.3 cells treated with antisense oligomers.

| Gene Targeted | Antisense Oligomer | Abeta (1–40) | Abeta (1–42) |
|---|---|---|---|
| Asp2-1 | S648 | 71%* | 67%* |
| Asp2-2 | S649 | 83%* | 76%* |
| Asp2-3 | S650 | 46%* | 50%* |
| Asp2-4 | S651 | 47%* | 46%* |
| Con1-1 | S652 | 13% | 18% |
| Con1-2 | S653 | 35% | 30% |
| Con1-3 | S655 | 9% | 18% |
| Con1-4 | S674 | 29% | 18% |
| Con2-1 | S656 | 12% | 18% |
| Con2-2 | S657 | 16% | 19% |
| Con2-3 | S658 | 8% | 35% |
| Con2-4 | S659 | 3% | 18% |

Since HEK293 cells derive from kidney, the experiment was extended to human IMR-32 neuroblastoma cells which express all three APP isoforms and which release Aβ peptides into conditioned medium at measurable levels. [See Neill et al., *J. NeuroSci. Res.*, (1994) 39: 482–93; and Asami-Odaka et al., *Biochem.*, (1995) 34:10272–8.] Essentially identical results were obtained in the neuroblastoma cells as the HEK293 cells. As shown in Table 3B, the pair of Asp2 antisense oligomers reduced Asp2 mRNA by roughly one-half, while the pair of reverse control oligomers lacked this effect (Table 3B).

TABLE 3B

Reduction of Aβ40 and Aβ42 in human neuroblastoma IMR-32 cells and mouse neuroblastoma Neuro-2A cells treated with Asp2 antisense and control oligomers as indicated. Oligomers were transfected in quadruplicate cultures. Values tabulated are normalized against cultures treated with oligofectin-G ™ only (mean + SD, ** p < 0.001 compared to reverse control oligomer).

| Asp2 | | IMR-32 cells | | Neuro-2A cells | |
|---|---|---|---|---|---|
| | mRNA | Aβ40 | Aβ42 | Aβ40 | Aβ42 |
| Asp2-1A | −75% | −49 + 2%** | −42 + 14%** | −70 + 7%** | −67 + 2%** |
| Asp2-1R | 0.16 | −0 + 3% | 21.26 | −9 + 15% | 1.05 |
| Asp2-2A | −39% | −43 + 3%** | −44 + 18%** | −61 + 12%** | −61 + 12%** |
| Asp2-2R | 0.47 | 12.2 | 19.22 | 6.15 | −8 + 10% |

Together with the reduction in Asp2 mRNA there was a concomitant reduction in the release of Aβ40 and Aβ42 peptides into the conditioned medium. Thus, Asp2 functions directly or indirectly in a human kidney and a human neuroblastoma cell line to facilitate the processing of APP into Aβ peptides. Molecular cloning of the mouse Asp2 cDNA revealed a high degree of homology to human (>96% amino acid identity, see Example 3), and indeed, complete nucleotide identity at the sites targeted by the Asp2-1A and Asp2-2A antisense oligomers. Similar results were obtained in mouse Neuro-2a cells engineered to express APP-Sw-KK. The Asp2 antisense oligomers reduced release of Aβ peptides into the medium while the reverse control oligomers did not (Table 3B). Thus, the three antisense experiments with HEK293, IMR-32 and Neuro-2a cells indicate that Asp2 acts directly or indirectly to facilitate Aβ processing in both somatic and neural cell lines.

EXAMPLE 8

Demonstration of Hu-Asp2 β-Secretase Activity in Cultured Cells

Several mutations in APP associated with early onset Alzheimer's disease have been shown to alter Aβ peptide processing. These flank the—and C-terminal cleavage sites that release Aβ from APP. These cleavage sites are referred to as the β-secretase and γ-secretase cleavage sites, respectively. Cleavage of APP at the β-secretase site creates a C-terminal fragment of APP containing 99 amino acids of 11,145 daltons molecular weight. The Swedish KM-NL mutation immediately upstream of the β-secretase cleavage site causes a general increase in production of both the 1-40 and 1-42 amino acid forms of Aβ peptide. The London VF mutation (V717-F in the APP770 isoform) has little effect on total Aβ peptide production, but appears to preferentially increase the percentage of the longer 1-42 amino acid form of Aβ peptide by affecting the choice of β-secretase cleavage site used during APP processing. Thus, we sought to determine if these mutations altered the amount and type of Aβ peptide produced by cultured cells cotransfected with a construct directing expression of Hu-Asp2.

Figure 10:
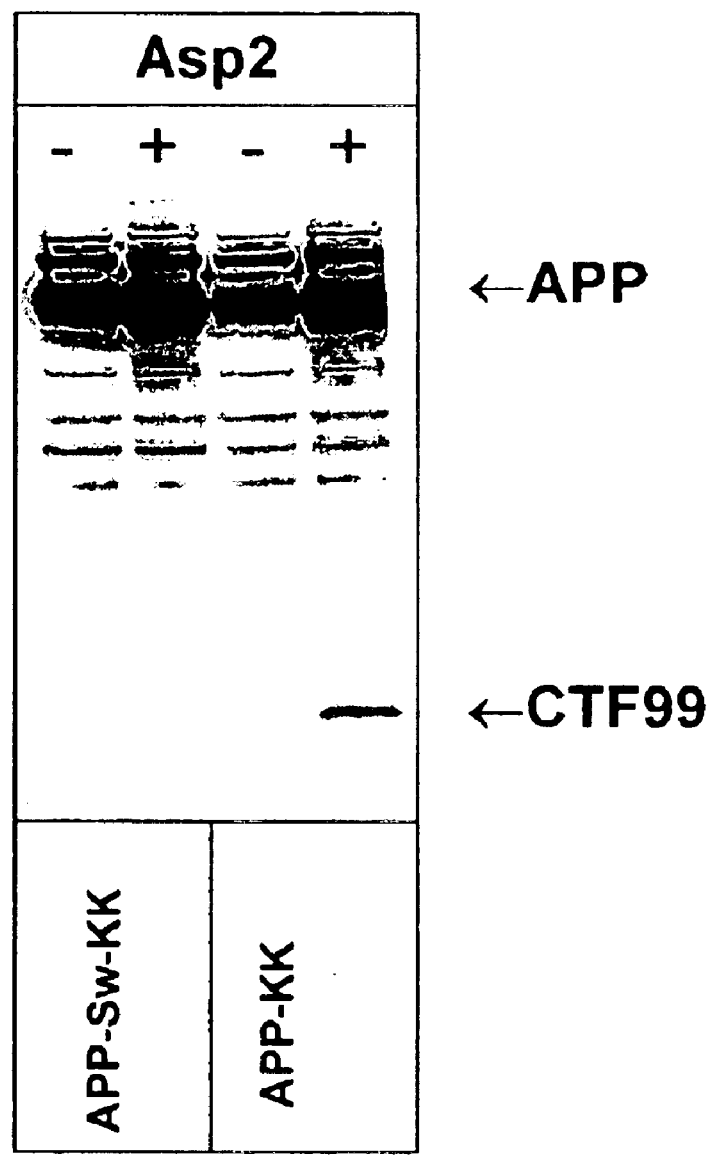
FIG. 10: Western blot showing increase in CTF99 production in mouse Neuro-2a cells cotransfected with APP-KK with and without Hu-Asp2 only in those cells cotransfected with Hu-Asp2. A farther increase in CTF99 production is seen in cells cotransfected with APP-Sw-KK with and without Hu-Asp2 only in those cells cotransfected with Hu-Asp2

Two experiments were performed which demonstrate Hu-Asp2 β-secretase activity in cultured cells. In the first experiment, treatment of HEK125.3 cells with antisense oligomers directed against Hu-Asp2 transcripts as described in Example 7 was found to decrease the amount of the C-terminal fragment of APP created by β-secretase cleavage (CTF99) (FIG. 9). This shows that Hu-Asp2 acts directly or indirectly to facilitate β-secretase cleavage. In the second experiment, increased expression of Hu-Asp2 in transfected mouse Neuro2A cells is shown to increase accumulation of the CTF99 β-secretase cleavage fragment (FIG. 10). This increase is seen most easily when a mutant APP-KK clone containing a C-terminal di-lysine motif is used for transfection. A further increase is seen when Hu-Asp2 is cotransfected with APP-Sw-KK containing the Swedish mutation KM→NL. The Swedish mutation is known to increase cleavage of APP by the β-secretase.

A second set of experiments demonstrate Hu-Asp2 facilitates γ-secretase activity in cotransfection experiments with human embryonic kidney HEK293 cells. Cotransfection of Hu-Asp2 with an APP-KK clone greatly increases production and release of soluble Aβ1-40 and Aβ1-42 peptides from HEK293 cells. There is a proportionately greater increase in the release of Aβ1-42. A further increase in production of Aβ1-42 is seen when Hu-Asp2 is cotransfected with APP-VF (SEQ ID No. 13 [nucleotide] and SEQ ID No. 14 [amino acid]) or APP-VF-KK SEQ ID No. 19 [nucleotide] and SEQ ID No. 20 [amino acid]) clones containing the London mutation V717-F. The V717-F mutation is known to alter cleavage specificity of the APP γ-secretase such that the preference for cleavage at the Aβ42 site is increased. Thus, Asp2 acts directly or indirectly to facilitate γ-secretase processing of APP at the β42 cleavage site.

Materials

Antibodies 6E10 and 4G8 were purchased from Senetek (St. Louis, Mo.). Antibody 369 was obtained from the laboratory of Paul Greengard at the Rockefeller University. Antibody C8 was obtained from the laboratory of Dennis Selkoe at the Harvard Medical School and Brigham and Women's Hospital.

APP Constructs Used

The APP constructs used for transfection experiments comprised the following

APP: wild-type APP695 (SEQ ID No. 9 and No. 10)

APP-Sw: APP695 containing the Swedish KM-NL mutation (SEQ ID No. 11 and No. 12, wherein the lysine (K) at residue 595 of APP695 is changed to asparagine (N) and the methionine (M) at residue 596 of APP695 is changed to leucine (L).), APP-VF: APP695 containing the London V→F mutation (SEQ ID Nos. 13 & 14) (Affected residue 717 of the APP770 isoform corresponds with residue 642 of the APP695 isoform. Thus, APP-VF as set in SEQ ID NO: 14 comprises the APP695 sequence, wherein the valine (V) at residue 642 is changed to phenylalanine (F).)

APP-KK: APP695 containing a C-terminal KK motif (SEQ D Nos. 15 & 16),

APP-Sw-KK: APP695-Sw containing a C-terminal KK motif (SEQ ID No. 17 & 18),

APP-VF-KK: APP695-VF containing a C-terminal KK motif (SEQ ID Nos. 19&20).

These were inserted into the vector pIRES-EGFP (Clontech, Palo Alto Calif.) between the Not1 and BstX1 sites using appropriate linker sequences introduced by PCR Transfection of Antisense Oligomers or Plasmid DNA Constructs in HEK293 Cells, HEK125.3 Cells and Neuro-2A Cells, Human embryonic kidney HEK293 cells and mouse Neuro-2a cells were transfected with expression constructs using the Lipofectamine Plus reagent from Gibco/BRL. Cells were seeded in 24 well tissue culture plates to a density of 70–80% confluence. Four wells per plate were transfected with 2 µg DNA (3:1, APP:cotransfectant), 8 µl Plus reagent, and 4 µl Lipofectamine in OptiMEM. OptiMEM was added to a total volume of 1 ml, distributed 200 µl per well and incubated 3 hours. Care was taken to hold constant the ratios of the two plasmids used for cotransfection as well as the total amount of DNA used in the transfection. The transfection media was replaced with DMEM, 10% FBS, NaPyruvate, with antibiotic/antimycotic and the cells were incubated under normal conditions (37° C., 5% $CO_2$) for 48 hours. The conditioned media were removed to polypropylene tubes and stored at −80° C. until assayed for the content of Aβ1-40 and Aβ1-42 by EIA as described in the preceding examples. Transfection of antisense oligomers into HEK125.3 cells was as described in Example 7.

Preparation of Cell Extracts, Western Blot Protocol

Cells were harvested after being transfected with plasmid DNA for about 60 hours. First, cells were transferred to 15-ml conical tube from the plate and centrifuged at 1,500 rpm for 5 minutes to remove the medium. The cell pellets were washed once with PBS. We then lysed the cells with lysis buffer (10 mM HEPES, pH 7.9, 150 mM NaCl, 10% glycerol, 1 mM EGTA, 1 mM EDTA, 0.1 mM sodium vanadate and 1% NP-40). The lysed cell mixtures were centrifuged at 5000 rpm and the supernatant was stored at −20° C. as the cell extracts. Equal amounts of extracts from HEK125.3 cells transfected with the Asp2 antisense oligomers and controls were precipitated with antibody 369 that recognizes the C-terminus of APP and then CTF99 was detected in the immunoprecipitate with antibody 6E10. The experiment was repeated using C8, a second precipitating antibody that also recognizes the C-terminus of APP. For Western blot of extracts from mouse Neuro-2a cells cotransfected with Hu-Asp2 and APP-KK, APP-Sw-KK, APP-VF-KK or APP-VF, equal amounts of cell extracts were electrophoresed through 4–10% or 10–20% Tricine gradient gels (NOVEX, San Diego, Calif.). Full length APP and the CTF99 β-secretase product were detected with antibody 6E10.

Results

Transfection of HEK125.3 cells with Asp2-1 or Asp2-2 antisense oligomers reduces production of the CTF β-secretase product in comparison to cells similarly transfected with control oligomers having the reverse sequence (Asp2-1 reverse & Asp2-2 reverse), see FIG. 9. Correspondingly, contransfection of Hu-Asp2 into mouse Neuro-2a cells with the APP-KK construct increased the formation of CTF99. (See FIG. 10.) This was further increased if Hu-Asp2 was coexpressed with APP-Sw-KK, a mutant form of APP containing the Swedish KM-NL mutation that increases β-secretase processing.

Effects of Asp2 on the production of Ab peptides from endogenously expressed APP isoforms were assessed in HEK293 cells transfected with a construct expressing Asp2 or with the empty vector after selection of transformants with the antibiotic G418. Aβ40 production was increased in cells transformed with the Asp2 construct in comparison to those transformed with the empty vector DNA. Aβ40 levels in conditioned medium collected from the Asp2 transformed and control cultures was 424±45 pg/ml and 113±58 pg/ml, respectively (p<0.001). Aβ42 release was below the limit of detection by the EIA, while the release of sAPPα was unaffected, 112±8 ng/ml versus 111±40 ng/ml. This further indicates that Asp2 acts directly or indirectly to facilitate the processing and release of AP from endogenously expressed APP.

Co-transfection of Hu-Asp2 with APP has little effect on Aβ40 production but increases Aβ42 production above background (Table 4). Addition of the di-lysine motif to the C-terminus of APP increases Aβ peptide processing about two fold, although Aβ40 and Aβ42 production remain quite low (352 pg/ml and 21 pg/ml, respectively). Cotransfection of Asp2 with APP-KK further increases both Aβ40 and Aβ42 production.

The APP V717→F mutation has been shown to increase γ-secretase processing at the Aβ42 cleavage site. Cotransfection of Hu-Asp2 with the APP-VF or APP-VF-KK constructs increased Aβ42 production (a two fold increase with APP-VF and a four-fold increase with APP-VF-KK, Table 4), but had mixed effects on Aβ40 production (a slight decrease with APP-VF, and a two fold increase with APP-VF-KK in comparison to the pcDNA cotransfection control. Thus, the effect of Asp2 on Aβ42 production was proportionately greater leading to an increase in the ratio of Aβ42/total Ab. Indeed, the ratio of Aβ42/total Aβ reaches a very high value of 42% in HEK293 cells cotransfected with Hu-Asp2 and APP-VF-KK.

TABLE 4

Results of cotransfecting Hu-Asp2 or pcDNA plasmid DNA with various APP constructs containing the V717-F mutation that modifies γ-secretase processing. Cotransfection with Asp2 consistently increases the ratio of Aβ42/total Aβ. Values tabulated are Aβ peptide pg/ml.

|  | pcDNA Cotransfection | | | Asp2 Cotransfection | | |
| --- | --- | --- | --- | --- | --- | --- |
|  | Aβ40 | Aβ42 | Aβ42/Total | Aβ40 | Aβ42 | Aβ42/Total |
| APP | 192 ± 18 | <4 | <2% | 188 ± 40 | 8 ± 10 | 3.9% |
| APP-VF | 118 ± 15 | 15 ± 19 | 11.5% | 85 ± 7 | 24 ± 12 | 22.4% |
| APP-KK | 352 ± 24 | 21 ± 6 | 5.5% | 1062 ± 101 | 226 ± 49 | 17.5% |
| APP-VF-KK | 230 ± 31 | 88 ± 24 | 27.7% | 491 ± 35 | 355 ± 36 | 42% |

EXAMPLE 9

Bacterial Expression of Human Asp2(a)
Expression of Recombinant Hu-Asp2(a) in E coli.

Hu-Asp2(a) can be expressed in E. coli after addition of N-terminal sequences such as a T7 tag (SEQ ID No. 21 and No. 22) or a T7 tag followed by a caspase 8 leader sequence (SEQ ID No. 23 and No. 24). Alternatively, reduction of the GC content of the 5' sequence by site directed mutagenesis can be used to increase the yield of Hu-Asp2 (SEQ D No. 25 and No. 26). In addition, Asp2(a) can be engineered with a proteolytic cleavage site (SEQ ID No. 27 and No. 28). To produce a soluble protein after expression and refolding, deletion of the transmembrane domain and cytoplasmic tail, or deletion of the membrane proximal region, transmembrane domain, and cytoplasmic tail is preferred. Any materials (vectors, host cells, etc.) and methods described herein to express Hu-Asp2(a) should in principle be equally effective for expression of Hu-Asp2(b).

Methods

PCR with primers containing appropriate linker sequences was used to assemble fusions of Asp2(a) coding sequence with N-terminal sequence modifications including a T7 tag (SEQ ID Nos. 21 and 22) or a T7-caspase 8 leader (SEQ ID Nos. 23 and 24). These constructs were cloned into the expression vector pet23a(+) [Novagen] in which a T7 promoter directs expression of a T7 tag preceding a sequence of multiple cloning sites. To clone Hu-Asp2 sequences behind the T7 leader of pet23a+, the following oligonucleotides were used for amplification of the selected Hu-Asp2(a) sequence: #553=GTGGATCCACCCAGC-ACGGCATCCGGCTG (SEQ ID No. 35), #554= GAAAGCTTTCATGACTCATCTGTCTGTGGAATGTTG (SEQ ID No. 36) which placed BamHI and HindIII sites flanking the 5' and 3' ends of the insert, respectively. The Asp2(a) sequence was amplified from the full length Asp2(a) cDNA cloned into pcDNA3.1 using the Advantage-GC cDNA PCR [Clontech] following the manufacturer's supplied protocol using annealing & extension at 68° C. in a two-step PCR cycle for 25 cycles. The insert and vector were cut with BamHI and HindIII, purified by electrophoresis through an agarose gel, then ligated using the if Rapid DNA Ligation kit [Boerhinger Mannheim]. The ligation reaction was used to transform the E. coli strain JM109 (Promega) and colonies were picked for the purification of plasmid (Qiagen, Qiaprep minispin) and DNA sequence analysis. For inducible expression using induction with isopropyl b-D-thiogalactopyranoside (IPTG), the expression vector was transferred into E. coli strain BL21 (Statagene). Bacterial cultures were grown in LB broth in the presence of ampicillin at 100 ug/ml, and induced in log phase growth at an OD600 of 0.6–1.0 with 1 mM IPTG for 4 hour at 37° C. The cell pellet was harvested by centrifugation.

To clone Hu-Asp2 sequences behind the T7 tag and caspase leader (SEQ ID Nos. 23 and 24), the construct created above containing the T7-Hu-Asp2 sequence (SEQ ID Nos. 21 and 22) was opened at the BamHI site, and then the phosphorylated caspase 8 leader oligonucleotides #559= GATCGATGACTATCTCTGACTCTCCGCGTGAA-CAGGACG (SEQ ID No. 37), #560= GATCCGTCCTGTTCACGCGGAGAGTCAGAGAT-AGTCATC (SEQ ID No. 38) were annealed and ligated to the vector DNA. The 5' overhang for each set of oligonucleotides was designed such that it allowed ligation into the BamHI site but not subsequent digestion with BamHI. The ligation reaction was transformed into JM109 as above for analysis of protein expression after transfer to E. coli strain BL21.

In order to reduce the GC content of the 5' terminus of asp2(a), a pair of antiparallel oligos were designed to change degenerate codon bases in 15 amino acid positions from G/C to A/T (SEQ ID Nos. 25 and 26). The new nucleotide sequence at the 5' end of asp2 did not change the encoded amino acid and was chosen to optimize E. Coli expression. The sequence of the sense linker is 5' CGGCATCCGGCTGCCCCTGCGTAGCGGTCTGGGTG-GTGCTCCACT- GGGTCT GCGTCTGCCCCGG-GAGACCGACGAA G 3' (SEQ ID No. 39). The sequence of the antisense linker is: 5' CTTCGTCG-GTCTCCCGGGGCAGACGCAGACCCAGTGGAGCAC-CACCCAGA CCGCTACGCAGGGGCAGCCGGAT-GCCG 3' (SEQ ID No. 40). After annealing the phosphorylated linkers together in 0.1 M NaCl-10 mM Tris, pH 7.4 they were ligated into unique Cla I and Sma I sites in Hu-Asp2 in the vector pTAC. For inducible expression using induction with isopropyl b-D-thiogalactopyranoside (IPTG), bacterial cultures were grown in LB broth in the presence of ampicillin at 100 ug/ml, and induced in log phase growth at an OD600 of 0.6–1.0 with 1 mM IPTG for 4 hour at 37° C. The cell pellet was harvested by centrifugation.

To create a vector in which the leader sequences can be removed by limited proteolysis with caspase 8 such that this liberates a Hu-Asp2 polypeptide beginning with the N-terminal sequence GSFV (SEQ ID Nos. 27 and 28), the following procedure was followed. Two phosphorylated oligonucleotides containing the caspase 8 cleavage site IETD, #571=5' GATCGATGACTATCTCTGACTCTC-CGCTGGACTCTGGTATCGAAACCGACG (SEQ ID No. 41) and #572=GATCCGTCGGTTTCGATACCAGAGTC-CAGCGGAGAGTCAGAGATAGTCATC (SEQ D No. 42) were annealed and ligated into pET23a+ that had been opened with BamHI. After transformation into JM109, the purified vector DNA was recovered and orientation of the insert was confirmed by DNA sequence analysis.

The following oligonucleotides were used for amplification of the selected Hu-Asp2(a) sequence: #573= 5'AAGGATCCTTTGTGGAGATGGTGGACAACCTG, (SEQ ID No. 43) #554=GAAAGCTTTCATGACTCATCT-GTCTGTGGAATGTTG (SEQ ID No. 44) which placed BamHI and HindIII sites flanking the 5' and 3' ends of the insert, respectively. The Hu-Asp2(a) sequence was amplified from the full length Hu-Asp2(a) cDNA cloned into pcDNA3.1 using the Advantage-GC cDNA PCR [Clontech] following the manufacturer's supplied protocol using annealing & extension at 68° C. in a two-step PCR cycle for 25 cycles. The insert and vector were cut with BamHI and HindIII, purified by electrophoresis through an agarose gel, then ligated using the Rapid DNA Ligation kit [Boerhinger Mannheim]. The ligation reaction was used to transform the *E. coli* strain JM109 [Promega] and colonies were picked for the purification of plasmid (Qiagen, Qiaprep minispin) and DNA sequence analysis. For inducible expression using induction with isopropyl b-D-thiogalactopyranoside (IPTG), the expression vector was transferred into *E. coli* strain BL21 (Statagene). Bacterial cultures were grown in LB broth in the presence of ampicillin at 100 ug/ml, and induced in log phase growth at an OD600 of 0.6–1.0 with 1 mM IPTG for 4 hour at 37° C. The cell pellet was harvested by centrifugation.

To assist purification, a 6-His tag can be introduced into any of the above constructs following the T7 leader by opening the construct at the BamHI site and then ligating in the annealed, phosphorylated oligonucleotides containing the six histidine sequence #565= GATCGCATCATCACCATCACCATG (SEQ ID No. 45), #566=GATCCATGGTGATGGTGATGATGC (SEQ D No. 46). The 5' overhang for each set of oligonucleotides was designed such that it allowed ligation into the BamHI site but not subsequent digestion with BamHI.

Preparation of Bacterial Pellet:

36.34 g of bacterial pellet representing 10.8L of growth was dispersed into a total volume of 200 ml using a 20 mm tissue homogenizer probe at 3000 to 5000 rpm in 2M KCl, 0.1M Tris, 0.05M EDTA, 1 mM DTT. The conductivity adjusted to about 193 mMhos with water. After the pellet was dispersed, an additional amount of the KCl solution was added, bringing the total volume to 500 ml. This suspension was homogenized further for about 3 minutes at 5000 rpm using the same probe. The mixture was then passed through a Rannie high-pressure homogenizer at 10,000 psi.

In all cases, the pellet material was carried forward, while the soluble fraction was discarded. The resultant solution was centrifuged in a GSA rotor for 1 hour at 12,500 rpm. The pellet was resuspended in the same solution (without the DTT) using the same tissue homogenizer probe at 2,000 rpm. After homogenizing for 5 minutes at 3000 rpm, the volume was adjusted to 500 ml with the same solution, and spun for 1 hour at 12,500 rpm. The pellet was then resuspended as before, but this time the final volume was adjusted to 1.5L with the same solution prior to homogenizing for 5 minutes. After centrifuging at the same speed for 30 minutes, this procedure was repeated. The pellet was then resuspended into about 150 ml of cold water, pooling the pellets from the six centrifuge tubes used in the GSA rotor. The pellet has homogenized for 5 minutes at 3,000 rpm, volume adjusted to 250 ml with cold water, then spun for 30 minutes. Weight of the resultant pellet was 17.75 g.

Summary: Lysis of bacterial pellet in KCl solution, followed by centrifugation in a GSA-rotor was used to initially prepare the pellet. The same solution was then used an additional three times for resuspension/homogenization. A final water wash/homogenization was then performed to remove excess KCl and EDTA.

Solublization of Recombinant Hu-Asp2(a):

A ratio of 9–10 ml/gram of pellet was utilized for solubilizing the rHuAsp2L from the pellet previously described. 17.75 g of pellet was thawed, and 150 ml of SM guanidine HCl, 5 mM βME, 0.1% DEA, was added. 3M Tris was used to titrate the pH to 8.6. The pellet was initially resuspended into the guanidine solution using a 20 mm tissue homogenizer probe at 1000 rpm. The mixture was then stirred at 4° C. for 1 hour prior to centrifugation at 12,500 rpm for 1 hour in GSA rotor. The resultant supernatant was then centrifuged for 30 minutes at 40,000×g in an SS-34 rotor. The final supernatant was then stored at −20° C., except for 50 ml.

Immobilized Nickel Affinity Chromatography of Solubilized Recombinant Hu-Asp2(a):

The following solutions were utilized:

A) 6M Guanidine HCl, 0.1M NaP, pH 8.0, 0.01M Tris, 5 mM βME, 0.5 mM Imidazole

A') 6M Urea, 20 mM NaP, pH 6.80, 50 mM NaCl

B') 6M Urea, 20 mM NaP, pH 6.20, 50 mM NaCl, 12 mM Imidazole

C') 6M Urea, 20 mM NaP, pH 6.80, 50 mM NaCl, 300 mM Imidazole

Note: Buffers A' and C' were mixed at the appropriate ratios to give intermediate concentrations of Imidazole.

The 50 ml of solubilized material was combined with 50 ml of buffer A prior to adding to 100–125 ml Qiagen Ni-NTA SuperFlow (pre-equilibrated with buffer A) in a 5×10 cm Bio-Rad econo column. This was shaken gently overnight at 4° C. in the cold room.

Chromatography Steps:

Drained the resultant flow through.
Washed with 50 ml buffer A (collecting into flow through fraction)
Washed with 250 ml buffer A (wash 1)
Washed with 250 ml buffer A (wash 2)
Washed with 250 ml buffer A'
Washed with 250 ml buffer B'
Washed with 250 ml buffer A'
Eluted with 250 ml 75 mM Imidazole
Eluted with 250 ml 150 mM Imidazole (150-1)
Eluted with 250 ml 150 mM Imidazole (150-2)
Eluted with 250 ml 300 mM Imidazole (300-1)
Eluted with 250 ml 300 mM Imidazole (300-2)
Eluted with 250 ml 300 mM Imidazole (300-3)

Chromatography Results:

The Hu-Asp(a) eluted at 75 mM imidazole through 300 mM Imidazole. The 75 mM fraction, as well as the first 150 mM Imidazole (150-1) fraction contained contaminating proteins as visualized on Coomassie Blue stained gels. Therefore, fractions 150-2 and 300-1 will be utilized for refolding experiments since they contained the greatest amount of protein as visualized on a Coomassie Blue stained gel.

Refolding Experiments of Recombinant Hu-Asp2(a):

Experiment 1:

Forty ml of 150-2 was spiked with 1M DTT, 3M Tris, pH 7.4 and DEA to a final concentration of 6 mM, 50 mM, and 0.1% respectively. This was diluted suddenly (while stirring) with 200 ml of (4° C.) cold 20 mM NaP, pH 6.8, 150 mM NaCl. This dilution gave a final Urea concentration of 1M. This solution remained clear, even if allowed to set open to the air at room temperature (RT) or at 4° C.

After setting open to the air for 4–5 hours at 4° C., this solution was then dialyzed overnight against 20 mM NaP, pH 7.4, 150 mM NaCl, 200/a glycerol. This method effectively removes the urea in the solution without precipitation of the protein.

Experiment 2:

Some of the 150-2 eluate was concentrated 2× on an Amicon Centriprep, 10,000 MWCO, then treated as in Experiment 1. This material also stayed in solution, with no visible precipitation.

Experiment 3:

89 ml of the 150-2 eluate was spiked with 1M DTT, 3M Tris, pH 7.4 and DEA to a final concentration of 6 mM, 50 mM, and 0.1% respectively. This was diluted suddenly (while stirring) with 445 ml of (4° C.) cold 20 mM NaP, pH 6.8, 150 mM NaCl. This solution appeared clear, with no apparent precipitation. The solution was removed to RT and stirred for 10 minutes prior to adding MEA to a final concentration of 0.1 mM. This was stirred slowly at RT for 1 hour. Cystamine and $CuSO_4$ were then added to final concentrations of 1 mM and 10 µM respectively. The solution was stirred slowly at RT for 10 minutes prior to being moved to the 4° C. cold room and shaken slowly overnight, open to the air.

The following day, the solution (still clear, with no apparent precipitation) was centrifuged at 100,000×g for 1 hour. Supernatants from multiple runs were pooled, and the bulk of the stabilized protein was dialyzed against 20 mM NaP, pH 7.4, 150 mM NaCl, 20% glycerol. After dialysis, the material was stored at −20° C.

Some (about 10 ml) of the protein solution (still in 1M Urea) was saved back for biochemical analyses, and frozen at −20° C. for storage.

EXAMPLE 10

Expression of Hu-Asp2 and Derivatives in Insect Cells

Any materials (vectors, host cells, etc.) and methods that are useful to express Hu-Asp2(a) should in principle be equally effective for expression of Hu-Asp2(b).

Expression by Baculovirus Infection.

The coding sequence of Hu-Asp2(a) and Hu-ASp2(b) and several derivatives were engineered for expression in insect cells using the PCR. For the full-length sequence, a 5'-sense oligonucleotide primer that modified the translation initiation site to fit the Kozak consensus sequence was paired with a 3'-antisense primer that contains the natural translation termination codon in the Hu-Asp2 sequence. PCR amplification of the pcDNA3.1(hygro)/Hu-Asp2(a) template was used to prepare two derivatives of Hu-Asp2(a) or Hu-Asp(b) that delete the C-terminal transmembrane domain (SEQ ID Nos. 29–30 and 50–51, respectively) or delete the transmembrane domain and introduce a hexa-histidine tag at the C-terminus (SEQ ID Nos. 31–32 and 52–53) respectively, were also engineered using PCR. The same 5'-sense oligonucleotide primer described above was paired with either a 3'-antisense primer that (1) introduced a translation termination codon after codon 453 (SEQ ID No. 3) or (2) incorporated a hexa-histidine tag followed by a translation termination codon in the PCR using pcDNA3.1 (hygro)/Hu-Asp-2(a) as the template. In all cases, the PCR reactions were performed amplified for 15 cycles using PwoI DNA polymerase (Boehringer-Mannheim) as outlined by the supplier. The reaction products were digested to completion with BamHI and NotI and ligated to BamHI and NotI digested baculovirus transfer vector pVL1393 (Invitrogen). A portion of the ligations was used to transform competent *E coli* DH5 cells followed by antibiotic selection on LB-Amp. Plasmid DNA was prepared by standard alkaline lysis and banding in CsCl to yield the baculovirus transfer vectors pVL1393/Asp2(a), pVL1393/Asp2(a)ΔTM and pVL1393/Asp2(a)ΔTM(His)$_6$. Creation of recombinant baculoviruses and infection of sf9 insect cells was performed using standard methods.

Expression by Transfection

Transient and stable expression of Hu-Asp2(a)ΔTM and Hu-Asp2(a)ΔTM(His)$_6$ in High 5 insect cells was performed using the insect expression vector pIZ/V5-His. The DNA inserts from the expression plasmids vectors pVL1393/Asp2 (a), pVL1393/Asp2(a)ΔTM and pVL1393/Asp2(a)ΔTM (His)$_6$ were excised by double digestion with BamHI and NotI and subcloned into BamHI and NotI digested pIZ/V5-His using standard methods. The resulting expression plasmids, referred to as pIZ/Hu-Asp2ΔTM and pIZ/Hu-Asp2ΔTM(His)$_6$, were prepared as described above.

For transfection, High 5 insect cells were cultured in High Five serum free medium supplemented with 10 µg/ml gentamycin at 27° C. in sealed flasks. Transfections were performed using High five cells, High five serum free media supplemented with 10 µg/ml gentamycin, and InsectinPlus liposomes (Invitrogen, Carlsbad, Calif.) using standard methods.

For large scale transient transfections, $1.2 \times 10^7$ high five cells were plated in a 150 mm tissue culture dish and allowed to attach at room temperature for 15–30 minutes. During the attachment time the DNA/liposome mixture was prepared by mixing 6 ml of serum free media, 60 µg Hu-Asp2(a)ΔTM/pIZ (+/−His) DNA and 120 µl of Insectin Plus and incubating at room temperature for 15 minutes. The plating media was removed from the dish of cells and replaced with the DNA/liposome mixture for 4 hours at room temperature with constant rocking at 2 rpm. An additional 6 ml of media was added to the dish prior to incubation for 4 days at 27° C. in a humid incubator. Four days post transfection the media was harvested, clarified by centrifugation at 500×g, assayed for Hu-Asp2(a) expression by Western blotting. For stable expression, the cells were treated with 50 µg/ml Zeocin and the surviving pool used to prepared clonal cells by limiting dilution followed by analysis of the expression level as noted above.

Purification of Hu-Asp2(a)ΔTM and Hu-Asp2(a)ΔTM(His)$_6$

Removal of the transmembrane segment from Hu-Asp2 (a) resulted in the secretion of the polypeptide into the culture medium. Following protein production by either baculovirus infection or transfection, the conditioned medium was harvested, clarified by centrifugation, and dialyzed against Tris-HCl (pH 8.0). This material was then purified by successive chromatography by anion exchange (Tris-HCl, pH 8.0) followed by cation exchange chromatography (Acetate buffer at pH 4.5) using NaCl gradients. The elution profile was monitored by (1) Western blot analysis and (2) by activity assay using the peptide substrate described in Example 12. For the Hu-Asp2(a)ΔTM(His)$_6$, the conditioned medium was dialyzed against Tris buffer (pH A8.0) and purified by sequential chromatography on IMAC resin followed by anion 4; exchange chromatography.

Amino-terminal sequence analysis of the purified Hu-Asp2(a)ΔTM(His)$_r$ protein revealed that the signal peptide had been cleaved [TQHGIRLPLR, corresponding to SEQ ID NO: 32, residues 22–3].

EXAMPLE 11

Expression of Hu-Asp2(a) and Hu-Asp(b) in CHO Cells

The materials (vectors, host cells, etc.) and methods described herein for expression of Hu-Asp2(a) are intended to be equally applicable for expression of Hu-Asp2(b).

Heterologous Expression of Hu-Asp-2(a) in CHO-K1 Cells

The entire coding sequence of Hu-Asp2(a) was cloned into the mammalian expression vector pcDNA3.1(+)Hygro (Invitrogen, Carlsbad, Calif.) which contains the CMV immediate early promoter and bGH polyadenylation signal to drive over expression. The expression plasmid, pcDNA3.1(+)Hygro/Hu-Asp2(a), was prepared by alkaline lysis and banding in CsCl and completely sequenced on both strands to verify the integrity of the coding sequence.

Wild-type Chinese hamster ovary cells (CHO-K1) were obtained from the ATCC. The cells were maintained in monolayer cultures in α-MEM containing 10% FCS at 37° C. in 5% $CO_2$. Two 100 mm dishes of CHO-K1 cells (60% confluent) were transfected with pcDNA3.1 (+)/Hygro alone (mock) or pcDNA3.1(+)Hygro/Hu-Asp2(a) or pcDNA3.1 (+)Hygro/Hu-Asp2(b) using the cationic liposome DOTAP as recommended by the supplier (Roche, Indianapolis, Ind.). The cells were treated with the plasmid DNA/liposome mixtures for 15 hours and then the medium replaced with growth medium containing 500 Units/ml hygromycin B. In the case of pcDNA3.1(+)Hygro/Hu-Asp2(a) or (b) transfected CHO-K1 cells, individual hygromycin B-resistant cells were cloned by limiting dilution. Following clonal expansion of the individual cell lines, expression of Hu-Asp2(a) or Hu-Asp2(b) protein was assessed by Western blot analysis using a polyclonal rabbit antiserum raised against recombinant Hu-Asp2 prepared by expression in *E. coli*. Near confluent dishes of each cell line were harvested by scraping into PBS and the cells recovered by centrifugation. The cell pellets were resuspended in cold lysis buffer (25 mM Tris-HCl (pH 8.0)/5 mM EDTA) containing protease inhibitors and the cells lysed by sonication. The soluble and membrane fractions were separated by centrifugation (105,000×g, 60 min) and normalized amounts of protein from each fraction were then separated by SDS-PAGE. Following electrotransfer of the separated polypeptides to PVDF membranes, Hu-Asp-2(a) or Hu-Asp2(b) protein was detected using rabbit anti-Hu-Asp2 antiserum (1/1000 dilution) and the antibody-antigen complexes were visualized using alkaline phosphatase conjugated goat anti-rabbit antibodies (1/2500). A specific immunoreactive protein with an apparent Mr value of 65 kDa was detected in pcDNA3.1(+)Hygro/Hu-Asp2 transfected cells and not mock-transfected cells. Also, the Hu-Asp2 polypeptide was only detected in the membrane fraction, consistent with the presence of a signal peptide and single transmembrane domain in the predicted sequence. Based on this analysis, clone #5 had the highest expression level of Hu-Asp2(a) protein and this production cell lines was scaled up to provide material for purification.

Purification of Recombinant Hu-Asp-2(a) from CHO-K1/ Hu-ASp2 Clone #5

In a typical purification, clone #5 cell pellets derived from 20 150 mm dishes of confluent cells, were used as the starting material. The cell pellets were resuspended in 50 ml cold lysis buffer as described above. The cells were lysed by polytron homogenization (2×20 sec) and the lysate centrifuged at 338,000×g for 20 minutes. The membrane pellet was then resuspended in 20 ml of cold lysis buffer containing 50 mM β-octylglucoside followed by rocking at 4° C. for 1 hour. The detergent extract was clarified by centrifugation at 338,000×g for 20 minutes and the supernatant taken for further analysis.

The β-octylglucoside extract was applied to a Mono Q anion exchange column that was previously equilibrated with 25 mM Tris-HCl (pH 8.0)/50 mM β-octylglucoside. Following sample application, the column was eluted with a linear gradient of increasing NaCl concentration (0–1.0 M over 30 minutes) and individual fractions assayed by Western blot analysis and for β-secretase activity (see below). Fractions containing both Hu-Asp-2(a) immunoreactivity and β-secretase activity were pooled and dialyzed against 25 mM NaOAc (pH 4.5)/50 mM β-octylglucoside. Following dialysis, precipitated material was removed by centrifugation and the soluble material chromatographed on a MonoS cation exchange column that was previously equilibrated in 25 mM NaOAc (pH 4.5)/50 mM β-octylglucoside. The column was eluted using a linear gradient of increasing NaCl concentration (0–1.0 M over 30 minutes) and individual fractions assayed by Western blot analysis and for β-secretase activity. Fractions containing both Hu-Asp2 immunoreactivity and β-secretase activity were combined and determined to be >95% pure by SDS-PAGE/Coomassie Blue staining.

The same methods were used to express and purify Hu-Asp2(b).

EXAMPLE 12

Assay of Hu-Asp2 β-Secretase Activity Using Peptide Substrates

β-Secretase Assay

Recombinant human Asp2(a) prepared in CHO cells and purified as described in Example 11 was used to assay Asp2(a) proteolytic activity directly. Activity assays for Asp2(a) were performed using synthetic peptide substrates containing either the wild-type APP β-secretase site (SEVKM↓DAEFR SEQ ID NO: 64) the Swedish KM→NL mutation (SEVNL↓DAEFR SEQ ID NO: 63) or the Aβ40 and 42 γ-secretase sites (RRGGVV↓IA↓TVIVGER SEQ ID NO: 65). Reactions were performed in 50 mM 2-[N-morpholino]ethane-sulfonate ("Na-MES," pH 5.5) containing 1% β-octylglucoside, 70 mM peptide substrate, and recombinant Asp2(a) (1–5 μg protein) for various times at 37° C. The reaction products were quantified by RP-HPLC using a linear gradient from 0–70 B over 30 minutes (A=0.1% TFA in water, B=0.1% TFA/10% water/90% AcCN). The elution profile was monitored by absorbance at 214 nm. In preliminary experiments, the two product peaks which eluted before the intact peptide substrate, were confirmed to have the sequence DAEFR and SEVNL using both Edman sequencing and MADLI-TOF mass spectrometry. Percent hydrolysis of the peptide substrate was calculated by comparing the integrated peak areas for the two product peptides and the starting material derived from the absorbance at 214 nm. The sequence of cleavage/hydrolysis products was confirmed using Edman sequencing and MADLI-TOF mass spectrometry.

The behavior of purified Asp2(a) in the proteolysis assays was consistent with the prior anti-sense studies which indicated that Asp2(a) possesses β-secretase activity. Maximal proteolysis was seen with the Swedigh β-secretase peptide, which, after 6 hours, was about 10-fold higher than wild type APP.

The specificity of the protease cleavage reaction was determined by performing the β-secretase assay in the presence of 8 μM pepstatin A and the presence of a cocktail of protease inhibitors (10 μM leupeptin, 10 μM E64, and 5 mM EDTA). Proteolytic activity was insensitive to both the pepstatin and the cocktail, which are inhibitors of cathepsin D (and other aspartyl proteases), serine proteases, cysteinyl proteases, and metalloproteases, respectively.

Hu-Asp2(b) when similarly expressed in CHO cells and purified using identical conditions for extraction with β-octylglucoside and sequential chromatography over Mono Q and Mono S also cleaves the Swedish β-secretase peptide in proteolysis assays using identical assay conditions.

Collectively, this data establishes that both forms of Asp2 (Hu-Asp2(a) and Hu-Asp2(b)) act directly in cell-free assays to cleave synthetic APP peptides at the β-secretase site, and that the rate of cleavage is greatly increased by the Swedish KM→NL mutation that is associated with Alzheimer's disease.

An alternative β-secretase assay utilizes internally quenched fluorescent substrates to monitor enzyme activity using fluorescence spectroscopy in a single sample or multiwell format. Each reaction contained 50 mM Na-MES (pH 5.5), peptide substrate MCA-EVKMDAEF[K-DNP] (SEQ ID No:71) (BioSource International) (50 μM) and purified Hu-Asp-2 enzyme. These components were equilibrated to 37° C. for various times and the reaction initiated by addition of substrate. Excitation was performed at 330 nm and the reaction kinetics were monitored by measuring the fluorescence emission at 390 nm. To detect compounds that modulate Hu-Asp-2 activity, the test compounds were added during the preincubation phase of the reaction and the kinetics of the reaction monitored as described above. Activators are scored as compounds that increase the rate of appearance of fluorescence while inhibitors decrease the rate of appearance of fluorescence.

It will be clear that the invention may be practiced otherwise than as particularly described in the foregoing description and examples.

Numerous modifications and variations of the present invention are possible in light of the above teachings and, therefore, are within the scope of the invention. The entire disclosure of all publications cited herein are hereby incorporated by reference.

SEQUENCE LISTING

<160> NUMBER OF SEQ ID NOS: 73

<210> SEQ ID NO 1
<211> LENGTH: 1804
<212> TYPE: DNA
<213> ORGANISM: Homo sapiens

<400> SEQUENCE: 1

```
atgggcgcac tggcccgggc gctgctgctg cctctgctgg cccagtggct cctgcgcgcc      60
gccccggagc tggcccccgc gcccttcacg ctgcccctcc gggtggccgc ggccacgaac     120
cgcgtagttg cgcccacccc gggacccggg accccctgcc g agcgccacgc cgacggcttg    180
gcgctcgccc tggagcctgc cctggcgtcc cccgcgggcg ccgccaactt cttggccatg     240
gtagacaacc tgcaggggga ctctggccgc ggctactacc tggagatgct gatcgggacc     300
cccccgcaga agctacagat tctcgttgac actggaagca gtaactttgc cgtggcagga     360
accccgcact cctacataga cacgtacttt gacacagaga ggtctagcac ataccgctcc     420
aagggctttg acgtcacagt gaagtacaca caaggaagct ggacgggctt cgttggggaa     480
gacctcgtca ccatccccaa aggcttcaat acttcttttc ttgtcaacat tgccactatt     540
tttgaatcag agaatttctt tttgcctggg attaaatgga atggaatact tggcctagct     600
tatgccacac ttgccaagcc atcaagttct ctggagacct tcttcgactc cctggtgaca     660
caagcaaaca tccccaacgt tttctccatg cagatgtgtg gagccggctt gcccgttgct     720
ggatctggga ccaacggagg tagtcttgtc ttgggtggaa ttgaaccaag tttgtataaa     780
ggagacatct ggtatacccc tattaaggaa gagtggtact accagataga aattctgaaa     840
ttggaaattg gaggccaaag ccttaatctg gactgcagag agtataacgc agacaaggcc     900
atcgtggaca gtgcaccac gctgctgcgc ctgcccccaga aggtgtttga tgcggtggtg     960
gaagctgtgg cccgcgcatc tctgattcca gaattctctg atggtttctg gactgggtcc    1020
cagctggcgt gctggacgaa ttcggaaaca ccttggtctt acttccctaa aatctccatc    1080
tacctgagag atgagaactc cagcaggtca ttccgtatca caatcctgcc tcagctttac    1140
attcagccca tgatggggc cggcctgaat tatgaatgtt accgattcgg catttcccca    1200
tccacaaatg cgctggtgat cggtgccacg gtgatggagg gcttctacgt catcttcgac    1260
agagcccaga gagggtggg cttcgcagcg agccctgtg cagaaattgc aggtgctgca    1320
gtgtctgaaa tttccgggcc tttctcaaca gaggatgtag ccagcaactg tgtccccgct    1380
cagtctttga gcgagcccat tttgtggatt gtgtcctatg cgctcatgag cgtctgtgga    1440
gccatcctcc ttgtcttaat cgtcctgctg ctgctgccgt tccggtgtca gcgtcgcccc    1500
```

-continued

```
cgtgaccctg aggtcgtcaa tgatgagtcc tctctggtca gacatcgctg gaaatgaata       1560
gccaggcctg acctcaagca accatgaact cagctattaa gaaaatcaca tttccagggc       1620
agcagccggg atcgatggtg gcgctttctc ctgtgcccac ccgtcttcaa tctctgttct       1680
gctcccagat gccttctaga ttcactgtct tttgattctt gattttcaag cttttcaaatc      1740 ctccctactt ccaagaaaaa taattaaaaa aaaaacttca ttctaaacca aaaaaaaaa        1800 aaaa                                                                     1804
```

<210> SEQ ID NO 2
<211> LENGTH: 518
<212> TYPE: PRT
<213> ORGANISM: Homo sapiens

<400> SEQUENCE: 2

```
Met Gly Ala Leu Ala Arg Ala Leu Leu Pro Leu Leu Ala Gln Trp
1               5                   10                  15

Leu Leu Arg Ala Ala Pro Glu Leu Pro Ala Pro Phe Thr Leu Pro
                20                  25                  30

Leu Arg Val Ala Ala Ala Thr Asn Arg Val Val Ala Pro Thr Pro Gly
            35                  40                  45

Pro Gly Thr Pro Ala Glu Arg His Ala Asp Gly Leu Ala Leu Ala Leu
        50                  55                  60

Glu Pro Ala Leu Ala Ser Pro Ala Gly Ala Ala Asn Phe Leu Ala Met
65                  70                  75                  80

Val Asp Asn Leu Gln Gly Asp Ser Gly Arg Gly Tyr Tyr Leu Glu Met
                85                  90                  95

Leu Ile Gly Thr Pro Pro Gln Lys Leu Gln Ile Leu Val Asp Thr Gly
            100                 105                 110

Ser Ser Asn Phe Ala Val Ala Gly Thr Pro His Ser Tyr Ile Asp Thr
        115                 120                 125

Tyr Phe Asp Thr Glu Arg Ser Thr Tyr Arg Ser Lys Gly Phe Asp
        130                 135                 140

Val Thr Val Lys Tyr Thr Gln Gly Ser Trp Thr Gly Phe Val Gly Glu
145                 150                 155                 160

Asp Leu Val Thr Ile Pro Lys Gly Phe Asn Thr Ser Phe Leu Val Asn
                165                 170                 175

Ile Ala Thr Ile Phe Glu Ser Glu Asn Phe Phe Leu Pro Gly Ile Lys
            180                 185                 190

Trp Asn Gly Ile Leu Gly Leu Ala Tyr Ala Thr Leu Ala Lys Pro Ser
        195                 200                 205

Ser Ser Leu Glu Thr Phe Phe Asp Ser Leu Val Thr Gln Ala Asn Ile
        210                 215                 220

Pro Asn Val Phe Ser Met Gln Met Cys Gly Ala Gly Leu Pro Val Ala
225                 230                 235                 240

Gly Ser Gly Thr Asn Gly Gly Ser Leu Val Leu Gly Gly Ile Glu Pro
                245                 250                 255

Ser Leu Tyr Lys Gly Asp Ile Trp Tyr Thr Pro Ile Lys Glu Glu Trp
            260                 265                 270

Tyr Tyr Gln Ile Glu Ile Leu Lys Leu Glu Ile Gly Gly Gln Ser Leu
        275                 280                 285

Asn Leu Asp Cys Arg Glu Tyr Asn Ala Asp Lys Ala Ile Val Asp Ser
        290                 295                 300

Gly Thr Thr Leu Leu Arg Leu Pro Gln Lys Val Phe Asp Ala Val Val
305                 310                 315                 320
```

-continued

Glu Ala Val Ala Arg Ala Ser Leu Ile Pro Glu Phe Ser Asp Gly Phe
                325                 330                 335
Trp Thr Gly Ser Gln Leu Ala Cys Trp Thr Asn Ser Glu Thr Pro Trp
            340                 345                 350
Ser Tyr Phe Pro Lys Ile Ser Ile Tyr Leu Arg Asp Glu Asn Ser Ser
        355                 360                 365
Arg Ser Phe Arg Ile Thr Ile Leu Pro Gln Leu Tyr Ile Gln Pro Met
    370                 375                 380
Met Gly Ala Gly Leu Asn Tyr Glu Cys Tyr Arg Phe Gly Ile Ser Pro
385                 390                 395                 400
Ser Thr Asn Ala Leu Val Ile Gly Ala Thr Val Met Glu Gly Phe Tyr
                405                 410                 415
Val Ile Phe Asp Arg Ala Gln Lys Arg Val Gly Phe Ala Ala Ser Pro
            420                 425                 430
Cys Ala Glu Ile Ala Gly Ala Ala Val Ser Glu Ile Ser Gly Pro Phe
        435                 440                 445
Ser Thr Glu Asp Val Ala Ser Asn Cys Val Pro Ala Gln Ser Leu Ser
    450                 455                 460
Glu Pro Ile Leu Trp Ile Val Ser Tyr Ala Leu Met Ser Val Cys Gly
465                 470                 475                 480
Ala Ile Leu Leu Val Leu Ile Val Leu Leu Leu Pro Phe Arg Cys
                485                 490                 495
Gln Arg Arg Pro Arg Asp Pro Glu Val Val Asn Asp Glu Ser Ser Leu
            500                 505                 510
Val Arg His Arg Trp Lys
        515

<210> SEQ ID NO 3
<211> LENGTH: 2070
<212> TYPE: DNA
<213> ORGANISM: Homo sapiens

<400> SEQUENCE: 3
atggcccaag ccctgccctg gctcctgctg tggatgggcg cgggagtgct gcctgcccac      60
ggcacccagc acggcatccg gctgcccctg cgcagcggcc tggggggcgc cccctggggg     120
ctgcggctgc cccgggagac cgacgaagag cccgaggagc ccggccggag gggcagcttt     180
gtggagatgg tggacaacct gaggggcaag tcggggcagg gctactacgt ggagatgacc     240
gtgggcagcc ccccgcagac gctcaacatc ctggtggata caggcagcag taactttgca     300
gtgggtgctg ccccccaccc cttcctgcat cgctactacc agaggcagct gtccagcaca     360
taccgggacc tccggaaggg tgtgtatgtg ccctacaccc agggcaagtg ggaaggggag     420
ctgggcaccg acctggtaag catcccccat ggccccaacg tcactgtgcg tgccaacatt     480
gctgccatca ctgaatcaga caagttcttc atcaacggct ccaactggga aggcatcctg     540
gggctggcct atgctgagat tgccaggcct gacgactccc tggagccttt ctttgactct     600
ctggtaaagc agaccacgt tcccaacctc ttctccctgc agctttgtgg tgctggcttc     660
cccctcaacc agtctgaagt gctggcctct gtcggaggga gcatgatcat tggaggtatc     720
gaccactcgc tgtacacagg cagtctctgg tatacaccca tccggcggga gtggtattat     780
gaggtcatca ttgtgcgggt ggagatcaat ggacaggatc tgaaaatgga ctgcaaggag     840
tacaactatg acaagagcat tgtggacagt ggcaccacca accttcgttt gcccaagaaa     900
gtgtttgaag ctgcagtcaa atccatcaag gcagcctcct ccacggagaa gttccctgat     960

-continued

```
ggtttctggc taggagagca gctggtgtgc tggcaagcag gcaccacccc ttggaacatt   1020
ttcccagtca tctcactcta cctaatgggt gaggttacca accagtcctt ccgcatcacc   1080
atccttccgc agcaatacct gcggccagtg aagatgtgg ccacgtccca agacgactgt    1140
tacaagtttg ccatctcaca gtcatccacg ggcactgtta tgggagctgt tatcatggag   1200
ggcttctacg ttgtctttga tcgggcccga aaacgaattg gctttgctgt cagcgcttgc   1260
catgtgcacg atgagttcag gacggcagcg gtggaaggcc cttttgtcac cttggacatg   1320
gaagactgtg gctacaacat tccacagaca gatgagtcaa ccctcatgac catagcctat   1380
gtcatggctg ccatctgcgc cctcttcatg ctgccactct gcctcatggt gtgtcagtgg   1440
cgctgcctcc gctgcctgcg ccagcagcat gatgactttg ctgatgacat ctccctgctg   1500
aagtgaggag gcccatgggc agaagataga gattcccctg gaccacacct ccgtggttca   1560
ctttggtcac aagtaggaga cacagatggc acctgtggcc agagcacctc aggaccctcc   1620
ccacccacca aatgcctctg ccttgatgga gaaggaaaag gctggcaagg tgggttccag   1680
ggactgtacc tgtaggaaac agaaaagaga gaaagaagc actctgctgg cgggaatact    1740
cttggtcacc tcaaatttaa gtcgggaaat tctgctgctt gaaacttcag ccctgaacct   1800
ttgtccacca ttcctttaaa ttctccaacc caaagtattc ttcttttctt agtttcagaa   1860
gtactggcat cacacgcagg ttaccttggc gtgtgtccct gtggtaccct ggcagagaag   1920
agaccaagct tgtttccctg ctggccaaag tcagtaggag aggatgcaca gtttgctatt   1980
tgctttagag acagggactg tataaacaag cctaacattg gtgcaaagat tgcctcttga   2040
attaaaaaaa aaaaaaaaa aaaaaaaaa                                      2070
```

<210> SEQ ID NO 4
<211> LENGTH: 501
<212> TYPE: PRT
<213> ORGANISM: Homo sapiens

<400> SEQUENCE: 4

```
Met Ala Gln Ala Leu Pro Trp Leu Leu Leu Trp Met Gly Ala Gly Val
1               5                   10                  15

Leu Pro Ala His Gly Thr Gln His Gly Ile Arg Leu Pro Leu Arg Ser
                20                  25                  30

Gly Leu Gly Gly Ala Pro Leu Gly Leu Arg Leu Pro Arg Glu Thr Asp
            35                  40                  45

Glu Glu Pro Glu Glu Pro Gly Arg Arg Gly Ser Phe Val Glu Met Val
        50                  55                  60

Asp Asn Leu Arg Gly Lys Ser Gly Gln Gly Tyr Tyr Val Glu Met Thr
65                  70                  75                  80

Val Gly Ser Pro Pro Gln Thr Leu Asn Ile Leu Val Asp Thr Gly Ser
                85                  90                  95

Ser Asn Phe Ala Val Gly Ala Ala Pro His Pro Phe Leu His Arg Tyr
                100                 105                 110

Tyr Gln Arg Gln Leu Ser Ser Thr Tyr Arg Asp Leu Arg Lys Gly Val
            115                 120                 125

Tyr Val Pro Tyr Thr Gln Gly Lys Trp Glu Gly Glu Leu Gly Thr Asp
        130                 135                 140

Leu Val Ser Ile Pro His Gly Pro Asn Val Thr Val Arg Ala Asn Ile
145                 150                 155                 160

Ala Ala Ile Thr Glu Ser Asp Lys Phe Phe Ile Asn Gly Ser Asn Trp
                165                 170                 175
```

```
Glu Gly Ile Leu Gly Leu Ala Tyr Ala Glu Ile Ala Arg Pro Asp Asp
            180                 185                 190

Ser Leu Glu Pro Phe Phe Asp Ser Leu Val Lys Gln Thr His Val Pro
            195                 200                 205

Asn Leu Phe Ser Leu Gln Leu Cys Gly Ala Gly Phe Pro Leu Asn Gln
            210                 215                 220

Ser Glu Val Leu Ala Ser Val Gly Gly Ser Met Ile Gly Gly Ile
225                 230                 235                 240

Asp His Ser Leu Tyr Thr Gly Ser Leu Trp Tyr Thr Pro Ile Arg Arg
                245                 250                 255

Glu Trp Tyr Tyr Glu Val Ile Ile Val Arg Val Glu Ile Asn Gly Gln
                260                 265                 270

Asp Leu Lys Met Asp Cys Lys Glu Tyr Asn Tyr Asp Lys Ser Ile Val
            275                 280                 285

Asp Ser Gly Thr Thr Asn Leu Arg Leu Pro Lys Lys Val Phe Glu Ala
290                 295                 300

Ala Val Lys Ser Ile Lys Ala Ala Ser Ser Thr Glu Lys Phe Pro Asp
305                 310                 315                 320

Gly Phe Trp Leu Gly Glu Gln Leu Val Cys Trp Gln Ala Gly Thr Thr
                325                 330                 335

Pro Trp Asn Ile Phe Pro Val Ile Ser Leu Tyr Leu Met Gly Glu Val
                340                 345                 350

Thr Asn Gln Ser Phe Arg Ile Thr Ile Leu Pro Gln Gln Tyr Leu Arg
                355                 360                 365

Pro Val Glu Asp Val Ala Thr Ser Gln Asp Asp Cys Tyr Lys Phe Ala
370                 375                 380

Ile Ser Gln Ser Ser Thr Gly Thr Val Met Gly Ala Val Ile Met Glu
385                 390                 395                 400

Gly Phe Tyr Val Val Phe Asp Arg Ala Arg Lys Arg Ile Gly Phe Ala
                405                 410                 415

Val Ser Ala Cys His Val His Asp Glu Phe Arg Thr Ala Ala Val Glu
            420                 425                 430

Gly Pro Phe Val Thr Leu Asp Met Glu Asp Cys Gly Tyr Asn Ile Pro
            435                 440                 445

Gln Thr Asp Glu Ser Thr Leu Met Thr Ile Ala Tyr Val Met Ala Ala
            450                 455                 460

Ile Cys Ala Leu Phe Met Leu Pro Leu Cys Leu Met Val Cys Gln Trp
465                 470                 475                 480

Arg Cys Leu Arg Cys Leu Arg Gln Gln His Asp Asp Phe Ala Asp Asp
                485                 490                 495

Ile Ser Leu Leu Lys
            500

<210> SEQ ID NO 5
<211> LENGTH: 1977
<212> TYPE: DNA
<213> ORGANISM: Homo   sapiens

<400> SEQUENCE: 5
atggcccaag ccctgccctg gctcctgctg tggatgggcg cgggagtgct gcctgcccac     60
ggcacccagc acggcatccg gctgcccctg cgcagcggcc tggggggcgc ccccctgggg    120
ctgcggctgc cccgggagac cgacgaagag cccgaggagc ccggccggag gggcagcttt    180
gtggagatgg tggacaacct gagggggcaag tcggggcagg gctactacgt ggagatgacc    240
```

-continued

| | |
|---|---|
| gtgggcagcc ccccgcagac gctcaacatc ctggtggata caggcagcag taactttgca | 300 |
| gtgggtgctg ccccccaccc cttcctgcat cgctactacc agaggcagct gtccagcaca | 360 |
| taccgggacc tccggaaggg tgtgtatgtg ccctacaccc agggcaagtg ggaaggggag | 420 |
| ctgggcaccg acctggtaag catcccccat ggccccaacg tcactgtgcg tgccaacatt | 480 |
| gctgccatca ctgaatcaga caagttcttc atcaacggct ccaactggga aggcatcctg | 540 |
| gggctggcct atgctgagat tgccaggctt tgtggtgctg gcttcccccct caaccagtct | 600 |
| gaagtgctgg cctctgtcgg agggagcatg atcattggag gtatcgacca ctcgctgtac | 660 |
| acaggcagtc tctggtatac acccatccgg cgggagtggt attatgaggt gatcattgtg | 720 |
| cgggtggaga tcaatggaca ggatctgaaa atggactgca aggagtacaa ctatgacaag | 780 |
| agcattgtgg acagtggcac caccaacctt cgtttgccca agaaagtgtt tgaagctgca | 840 |
| gtcaaatcca tcaaggcagc ctcctccacg gagaagttcc ctgatggttt ctggctagga | 900 |
| gagcagctgg tgtgctggca agcaggcacc accccttgga acatttttccc agtcatctca | 960 |
| ctctacctaa tgggtgaggt taccaaccag tccttccgca tcaccatcct tccgcagcaa | 1020 |
| tacctgcggc cagtggaaga tgtggccacg tcccaagacg actgttacaa gtttgccatc | 1080 |
| tcacagtcat ccacgggcac tgttatggga gctgttatca tggagggctt ctacgttgtc | 1140 |
| tttgatcggg cccgaaaacg aattggcttt gctgtcagcg cttgccatgt gcacgatgag | 1200 |
| ttcaggacgg cagcggtgga aggcccttttt gtgaccttgg acatggaaga ctgtggctac | 1260 |
| aacattccac agacagatga gtcaaccctc atgaccatag cctatgtcat ggctgccatc | 1320 |
| tgcgccctct tcatgctgcc actctgcctc atggtgtgtc agtggcgctg cctccgctgc | 1380 |
| ctgcgccagc agcatgatga ctttgctgat gacatctccc tgctgaagtg aggaggccca | 1440 |
| tgggcagaag atagagattc ccctggacca cacctccgtg gttcactttg gtcacaagta | 1500 |
| ggagacacag atggcacctg tggccagagc acctcaggac cctccccacc caccaaatgc | 1560 |
| ctctgccttg atggagaagg aaaaggctgg caaggtgggt tccagggact gtacctgtag | 1620 |
| gaaacagaaa agagaagaaa gaagcactct gctggcggga atactcttgg tcacctcaaa | 1680 |
| tttaagtcgg gaaattctgc tgcttgaaac ttcagccctg aacctttgtc caccattcct | 1740 |
| ttaaattctc caacccaaag tattcttctt ttcttagttt cagaagtact ggcatcacac | 1800 |
| gcaggttacc ttggcgtgtg tccctgtggt accctggcag agaagagacc aagcttgttt | 1860 |
| ccctgctggc caaagtcagt aggagaggat gcacagtttg ctatttgctt tagagacagg | 1920 |
| gactgtataa acaagcctaa cattggtgca agattgcct cttgaaaaaa aaaaaaa | 1977 |

<210> SEQ ID NO 6
<211> LENGTH: 476
<212> TYPE: PRT
<213> ORGANISM: Homo sapiens

<400> SEQUENCE: 6

Met Ala Gln Ala Leu Pro Trp Leu Leu Leu Trp Met Gly Ala Gly Val
1               5                   10                  15

Leu Pro Ala His Gly Thr Gln His Gly Ile Arg Leu Pro Leu Arg Ser
            20                  25                  30

Gly Leu Gly Gly Ala Pro Leu Gly Leu Arg Leu Pro Arg Glu Thr Asp
        35                  40                  45

Glu Glu Pro Glu Glu Pro Gly Arg Arg Gly Ser Phe Val Glu Met Val
    50                  55                  60

```
Asp Asn Leu Arg Gly Lys Ser Gln Gly Tyr Tyr Val Glu Met Thr
 65                  70                  75                  80

Val Gly Ser Pro Pro Gln Thr Leu Asn Ile Leu Val Asp Thr Gly Ser
                 85                  90                  95

Ser Asn Phe Ala Val Gly Ala Ala Pro His Pro Phe Leu His Arg Tyr
            100                 105                 110

Tyr Gln Arg Gln Leu Ser Ser Thr Tyr Arg Asp Leu Arg Lys Gly Val
        115                 120                 125

Tyr Val Pro Tyr Thr Gln Gly Lys Trp Glu Gly Glu Leu Gly Thr Asp
130                 135                 140

Leu Val Ser Ile Pro His Gly Pro Asn Val Thr Val Arg Ala Asn Ile
145                 150                 155                 160

Ala Ala Ile Thr Glu Ser Asp Lys Phe Phe Ile Asn Gly Ser Asn Trp
                165                 170                 175

Glu Gly Ile Leu Gly Leu Ala Tyr Ala Glu Ile Ala Arg Leu Cys Gly
            180                 185                 190

Ala Gly Phe Pro Leu Asn Gln Ser Glu Val Leu Ala Ser Val Gly Gly
        195                 200                 205

Ser Met Ile Ile Gly Gly Ile Asp His Ser Leu Tyr Thr Gly Ser Leu
210                 215                 220

Trp Tyr Thr Pro Ile Arg Arg Glu Trp Tyr Tyr Glu Val Ile Ile Val
225                 230                 235                 240

Arg Val Glu Ile Asn Gly Gln Asp Leu Lys Met Asp Cys Lys Glu Tyr
                245                 250                 255

Asn Tyr Asp Lys Ser Ile Val Asp Ser Gly Thr Thr Asn Leu Arg Leu
            260                 265                 270

Pro Lys Lys Val Phe Glu Ala Ala Val Lys Ser Ile Lys Ala Ala Ser
        275                 280                 285

Ser Thr Glu Lys Phe Pro Asp Gly Phe Trp Leu Gly Glu Gln Leu Val
290                 295                 300

Cys Trp Gln Ala Gly Thr Thr Pro Trp Asn Ile Phe Pro Val Ile Ser
305                 310                 315                 320

Leu Tyr Leu Met Gly Glu Val Thr Asn Gln Ser Phe Arg Ile Thr Ile
                325                 330                 335

Leu Pro Gln Gln Tyr Leu Arg Pro Val Glu Asp Val Ala Thr Ser Gln
            340                 345                 350

Asp Asp Cys Tyr Lys Phe Ala Ile Ser Gln Ser Ser Thr Gly Thr Val
        355                 360                 365

Met Gly Ala Val Ile Met Glu Gly Phe Tyr Val Val Phe Asp Arg Ala
370                 375                 380

Arg Lys Arg Ile Gly Phe Ala Val Ser Ala Cys His Val His Asp Glu
385                 390                 395                 400

Phe Arg Thr Ala Ala Val Glu Gly Pro Phe Val Thr Leu Asp Met Glu
                405                 410                 415

Asp Cys Gly Tyr Asn Ile Pro Gln Thr Asp Glu Ser Thr Leu Met Thr
            420                 425                 430

Ile Ala Tyr Val Met Ala Ala Ile Cys Ala Leu Phe Met Leu Pro Leu
        435                 440                 445

Cys Leu Met Val Cys Gln Trp Arg Cys Leu Arg Cys Leu Arg Gln Gln
450                 455                 460

His Asp Asp Phe Ala Asp Asp Ile Ser Leu Leu Lys
465                 470                 475
```

<210> SEQ ID NO 7
<211> LENGTH: 2043
<212> TYPE: DNA
<213> ORGANISM: Mus musculus

<400> SEQUENCE: 7

| | | | | | |
|---|---|---|---|---|---|
| atggccccag | cgctgcactg | gctcctgcta | tgggtgggct | cgggaatgct | gcctgcccag | 60 |
| ggaacccatc | tcggcatccg | gctgcccctt | cgcagcggcc | tggcagggcc | acccctgggc | 120 |
| ctgaggctgc | cccgggagac | tgacgaggaa | tcggaggagc | ctggccggag | aggcagcttt | 180 |
| gtggagatgg | tggacaacct | gagggaaag | tccggccagg | gctactatgt | ggagatgacc | 240 |
| gtaggcagcc | ccccacagac | gctcaacatc | ctggtggaca | cgggcagtag | taactttgca | 300 |
| gtggggctg | ccccacaccc | tttcctgcat | cgctactacc | agaggcagct | gtccagcaca | 360 |
| tatcgagacc | tccgaaaggg | tgtgtatgtg | ccctacaccc | agggcaagtg | ggagggggaa | 420 |
| ctgggcaccg | acctggtgag | catccctcat | ggccccaacg | tcactgtgcg | tgccaacatt | 480 |
| gctgccatca | ctgaatcgga | caagttcttc | atcaatggtt | ccaactggga | gggcatccta | 540 |
| gggctggcct | atgctgagat | tgccaggccc | gacgactctt | tggagccctt | ctttgactcc | 600 |
| ctggtgaagc | agacccacat | tcccaacatc | ttttccctgc | agctctgtgg | cgctggcttc | 660 |
| cccctcaacc | agaccgaggc | actggcctcg | gtgggaggga | gcatgatcat | tggtggtatc | 720 |
| gaccactcgc | tatacacggg | cagtctctgg | tacacaccca | tccggcggga | gtggtattat | 780 |
| gaagtgatca | ttgtacgtgt | ggaaatcaat | ggtcaagatc | tcaagatgga | ctgcaaggag | 840 |
| tacaactacg | acaagagcat | tgtggacagt | gggaccacca | accttcgctt | gcccaagaaa | 900 |
| gtatttgaag | ctgccgtcaa | gtccatcaag | gcagcctcct | cgacggagaa | gttcccggat | 960 |
| ggcttttggc | taggggagca | gctggtgtgc | tggcaagcag | gcacgacccc | ttggaacatt | 1020 |
| ttcccagtca | tttcacttta | cctcatgggt | gaagtcacca | atcagtcctt | ccgcatcacc | 1080 |
| atccttcctc | agcaatacct | acggccggtg | gaggacgtgg | ccacgtccca | agacgactgt | 1140 |
| tacaagttcg | ctgtctcaca | gtcatccacg | ggcactgtta | tgggagccgt | catcatggaa | 1200 |
| ggtttctatg | tcgtcttcga | tcgagcccga | aagcgaattg | gctttgctgt | cagcgcttgc | 1260 |
| catgtgcacg | atgagttcag | gacggcggca | gtggaaggtc | cgtttgttac | ggcagacatg | 1320 |
| gaagactgtg | gctacaacat | tccccagaca | gatgagtcaa | cacttatgac | catagcctat | 1380 |
| gtcatggcgg | ccatctgcgc | cctcttcatg | ttgccactct | gcctcatggt | atgtcagtgg | 1440 |
| cgctgcctgc | gttgcctgcg | ccaccagcac | gatgactttg | ctgatgacat | ctccctgctc | 1500 |
| aagtaaggag | gctcgtgggc | agatgatgga | gacgcccctg | gaccacatct | gggtggttcc | 1560 |
| ctttggtcac | atgagttgga | gctatggatg | gtacctgtgg | ccagagcacc | tcaggaccct | 1620 |
| caccaacctg | ccaatgcttc | tggcgtgaca | gaacagagaa | atcaggcaag | ctggattaca | 1680 |
| gggcttgcac | ctgtaggaca | caggagaggg | aaggaagcag | cgttctggtg | gcaggaatat | 1740 |
| ccttaggcac | cacaaacttg | agttggaaat | tttgctgctt | gaagcttcag | ccctgaccct | 1800 |
| ctgcccagca | tcctttagag | tctccaacct | aaagtattct | ttatgtcctt | ccagaagtac | 1860 |
| tggcgtcata | ctcaggctac | ccggcatgtg | tccctgtggt | accctggcag | agaaagggcc | 1920 |
| aatctcattc | cctgctggcc | aaagtcagca | gaagaaggtg | aagtttgcca | gttgctttag | 1980 |
| tgatagggac | tgcagactca | agcctacact | ggtacaaaga | ctgcgtcttg | agataaacaa | 2040 |
| gaa | | | | | 2043 |

<210> SEQ ID NO 8

-continued

<211> LENGTH: 501
<212> TYPE: PRT
<213> ORGANISM: Mus musculus

<400> SEQUENCE: 8

```
Met Ala Pro Ala Leu His Trp Leu Leu Leu Trp Val Gly Ser Gly Met
1               5                   10                  15

Leu Pro Ala Gln Gly Thr His Leu Gly Ile Arg Leu Pro Leu Arg Ser
            20                  25                  30

Gly Leu Ala Gly Pro Pro Leu Gly Leu Arg Leu Pro Arg Glu Thr Asp
        35                  40                  45

Glu Glu Ser Glu Glu Pro Gly Arg Arg Gly Ser Phe Val Glu Met Val
    50                  55                  60

Asp Asn Leu Arg Gly Lys Ser Gly Gln Gly Tyr Tyr Val Glu Met Thr
65                  70                  75                  80

Val Gly Ser Pro Pro Gln Thr Leu Asn Ile Leu Val Asp Thr Gly Ser
                85                  90                  95

Ser Asn Phe Ala Val Gly Ala Ala Pro His Pro Phe Leu His Arg Tyr
            100                 105                 110

Tyr Gln Arg Gln Leu Ser Ser Thr Tyr Arg Asp Leu Arg Lys Gly Val
        115                 120                 125

Tyr Val Pro Tyr Thr Gln Gly Lys Trp Glu Gly Glu Leu Gly Thr Asp
    130                 135                 140

Leu Val Ser Ile Pro His Gly Pro Asn Val Thr Val Arg Ala Asn Ile
145                 150                 155                 160

Ala Ala Ile Thr Glu Ser Asp Lys Phe Phe Ile Asn Gly Ser Asn Trp
                165                 170                 175

Glu Gly Ile Leu Gly Leu Ala Tyr Ala Glu Ile Ala Arg Pro Asp Asp
            180                 185                 190

Ser Leu Glu Pro Phe Phe Asp Ser Leu Val Lys Gln Thr His Ile Pro
        195                 200                 205

Asn Ile Phe Ser Leu Gln Leu Cys Gly Ala Gly Phe Pro Leu Asn Gln
    210                 215                 220

Thr Glu Ala Leu Ala Ser Val Gly Gly Ser Met Ile Ile Gly Gly Ile
225                 230                 235                 240

Asp His Ser Leu Tyr Thr Gly Ser Leu Trp Tyr Thr Pro Ile Arg Arg
                245                 250                 255

Glu Trp Tyr Tyr Glu Val Ile Ile Val Arg Val Glu Ile Asn Gly Gln
            260                 265                 270

Asp Leu Lys Met Asp Cys Lys Glu Tyr Asn Tyr Asp Lys Ser Ile Val
        275                 280                 285

Asp Ser Gly Thr Thr Asn Leu Arg Leu Pro Lys Lys Val Phe Glu Ala
    290                 295                 300

Ala Val Lys Ser Ile Lys Ala Ala Ser Ser Thr Glu Lys Phe Pro Asp
305                 310                 315                 320

Gly Phe Trp Leu Gly Glu Gln Leu Val Cys Trp Gln Ala Gly Thr Thr
                325                 330                 335

Pro Trp Asn Ile Phe Pro Val Ile Ser Leu Tyr Leu Met Gly Glu Val
            340                 345                 350

Thr Asn Gln Ser Phe Arg Ile Thr Ile Leu Pro Gln Gln Tyr Leu Arg
        355                 360                 365

Pro Val Glu Asp Val Ala Thr Ser Gln Asp Asp Cys Tyr Lys Phe Ala
    370                 375                 380

Val Ser Gln Ser Ser Thr Gly Thr Val Met Gly Ala Val Ile Met Glu
```

```
              385                 390                 395                 400
Gly Phe Tyr Val Val Phe Asp Arg Ala Arg Lys Arg Ile Gly Phe Ala
                    405                 410                 415
Val Ser Ala Cys His Val His Asp Glu Phe Arg Thr Ala Ala Val Glu
                420                 425                 430
Gly Pro Phe Val Thr Ala Asp Met Glu Asp Cys Gly Tyr Asn Ile Pro
            435                 440                 445
Gln Thr Asp Glu Ser Thr Leu Met Thr Ile Ala Tyr Val Met Ala Ala
        450                 455                 460
Ile Cys Ala Leu Phe Met Leu Pro Leu Cys Leu Met Val Cys Gln Trp
465                 470                 475                 480
Arg Cys Leu Arg Cys Leu Arg His Gln His Asp Asp Phe Ala Asp Asp
                485                 490                 495
Ile Ser Leu Leu Lys
            500

<210> SEQ ID NO 9
<211> LENGTH: 2088
<212> TYPE: DNA
<213> ORGANISM: Homo sapiens

<400> SEQUENCE: 9
atgctgcccg gtttggcact gctcctgctg ccgcctggac ggctcgggc gctggaggta       60 cccactgatg gtaatgctgg cctgctggct gaacccccaga ttgccatgtt ctgtggcaga    120
ctgaacatgc acatgaatgt ccagaatggg aagtgggatt cagatccatc aggaccaaa     180 acctgcattg ataccaagga aggcatcctg cagtattgcc aagaagtcta ccctgaactg     240
cagatcacca atgtggtaga agccaaccaa ccagtgacca tccagaactg gtgcaagcgg     300
ggccgcaagc agtgcaagac ccatccccac tttgtgattc cctaccgctg cttagttggt     360
gagtttgtaa gtgatgccct ctctcgttcct gacaagtgca aattcttaca ccaggagagg     420
atggatgttt gcgaaactca tcttcactgg cacaccgtcg ccaaagagac atgcagtgag     480
aagagtacca acttgcatga ctacggcatg ttgctgccct gcggaattga caagttccga     540
ggggtagagt ttgtgtgttg cccactggct gaagaaagtg acaatgtgga ttctgctgat     600
gcggaggagg atgactcgga tgtctggtgg gcggagcag acacagacta tgcagatggg     660
agtgaagaca aagtagtaga agtagcagag gaggaagaag tggctgaggt ggaagaagaa     720
gaagccgatg atgacgagga cgatgaggat ggtgatgagg tagaggaaga ggctgaggaa     780
ccctacgaag aagccacaga gagaaccacc agcattgcca ccaccaccac caccaccaca     840
gagtctgtgg aagaggtggt tcgagttcct acaacagcag ccagtacccc tgatgccgtt     900
gacaagtatc tcgagacacc tggggatgag aatgaacatg cccattccca gaaagccaaa     960
gagaggcttg aggccaagca ccgagagaga atgtcccagg tcatgagaga tgggaagag    1020 gcagaacgtc aagcaaagaa cttgcctaaa gctgataaga aggcagttat ccagcatttc    1080
caggagaaag tggaatcttt ggaacaggaa gcagccaacg agagacagca gctggtggag    1140
acacacatgg ccagagtgga agccatgctc aatgaccgcc gccgcctggc cctggagaac    1200
tacatcaccg ctctgcaggc tgttcctcct cggcctcgtc acgtgttcaa tatgctaaag    1260
aagtatgtcc gcgcagaaca gaaggacaga cagcacaccc taaagcattt cgagcatgtg    1320
cgcatggtgg atcccaagaa agccgctcag atccggtccc aggttatgac acacctccgt    1380
gtgatttatg agcgcatgaa tcagtctctc tccctgctct acaacgtgcc tgcagtggcc    1440
```

-continued

```
gaggagattc aggatgaagt tgatgagctg cttcagaaag agcaaaacta ttcagatgac    1500
gtcttggcca acatgattag tgaaccaagg atcagttacg gaaacgatgc tctcatgcca    1560
tctttgaccg aaacgaaaac caccgtggag ctccttcccg tgaatggaga gttcagcctg    1620
gacgatctcc agccgtggca ttcttttggg gctgactctg tgccagccaa cacagaaaac    1680
gaagttgagc tgttgatgc ccgccctgct gccgaccgag gactgaccac tcgaccaggt    1740
tctgggttga caaatatcaa gacggaggag atctctgaag tgaagatgga tgcagaattc    1800
cgacatgact caggatatga agttcatcat caaaaattgg tgttctttgc agaagatgtg    1860
ggttcaaaca aggtgcaat cattggactc atggtgggcg tgttgtcat agcgacagtg     1920 atcgtcatca ccttggtgat gctgaagaag aaacagtaca catccattca tcatggtgtg    1980
gtggaggttg acgccgctgt caccccagag gagcgccacc tgtccaagat gcagcagaac    2040
ggctacgaaa atccaaccta caagttcttt gagcagatgc agaactag                2088
```

<210> SEQ ID NO 10
<211> LENGTH: 695
<212> TYPE: PRT
<213> ORGANISM: Homo sapiens

<400> SEQUENCE: 10

```
Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
                20                  25                  30

Gln Ile Ala Met Phe Cys Gly Arg Leu Asn Met His Met Asn Val Gln
            35                  40                  45

Asn Gly Lys Trp Asp Ser Asp Pro Ser Gly Thr Lys Thr Cys Ile Asp
        50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
```

-continued

```
                260                 265                 270
Ala Thr Thr Thr Thr Thr Thr Glu Ser Val Glu Val Val Arg
        275                 280                 285
Val Pro Thr Thr Ala Ala Ser Thr Pro Asp Ala Val Asp Lys Tyr Leu
290                 295                 300
Glu Thr Pro Gly Asp Glu Asn Glu His Ala His Phe Gln Lys Ala Lys
305                 310                 315                 320
Glu Arg Leu Glu Ala Lys His Arg Glu Arg Met Ser Gln Val Met Arg
                325                 330                 335
Glu Trp Glu Glu Ala Glu Arg Gln Ala Lys Asn Leu Pro Lys Ala Asp
            340                 345                 350
Lys Lys Ala Val Ile Gln His Phe Gln Glu Lys Val Glu Ser Leu Glu
                355                 360                 365
Gln Glu Ala Ala Asn Glu Arg Gln Gln Leu Val Glu Thr His Met Ala
            370                 375                 380
Arg Val Glu Ala Met Leu Asn Asp Arg Arg Arg Leu Ala Leu Glu Asn
385                 390                 395                 400
Tyr Ile Thr Ala Leu Gln Ala Val Pro Pro Arg Pro Arg His Val Phe
                405                 410                 415
Asn Met Leu Lys Lys Tyr Val Arg Ala Glu Gln Lys Asp Arg Gln His
            420                 425                 430
Thr Leu Lys His Phe Glu His Val Arg Met Val Asp Pro Lys Lys Ala
            435                 440                 445
Ala Gln Ile Arg Ser Gln Val Met Thr His Leu Arg Val Ile Tyr Glu
450                 455                 460
Arg Met Asn Gln Ser Leu Ser Leu Leu Tyr Asn Val Pro Ala Val Ala
465                 470                 475                 480
Glu Glu Ile Gln Asp Glu Val Asp Glu Leu Leu Gln Lys Glu Gln Asn
                485                 490                 495
Tyr Ser Asp Asp Val Leu Ala Asn Met Ile Ser Glu Pro Arg Ile Ser
            500                 505                 510
Tyr Gly Asn Asp Ala Leu Met Pro Ser Leu Thr Glu Thr Lys Thr Thr
            515                 520                 525
Val Glu Leu Leu Pro Val Asn Gly Glu Phe Ser Leu Asp Asp Leu Gln
530                 535                 540
Pro Trp His Ser Phe Gly Ala Asp Ser Val Pro Ala Asn Thr Glu Asn
545                 550                 555                 560
Glu Val Glu Pro Val Asp Ala Arg Pro Ala Ala Asp Arg Gly Leu Thr
                565                 570                 575
Thr Arg Pro Gly Ser Gly Leu Thr Asn Ile Lys Thr Glu Glu Ile Ser
            580                 585                 590
Glu Val Lys Met Asp Ala Glu Phe Arg His Asp Ser Gly Tyr Glu Val
            595                 600                 605
His His Gln Lys Leu Val Phe Phe Ala Glu Asp Val Gly Ser Asn Lys
            610                 615                 620
Gly Ala Ile Ile Gly Leu Met Val Gly Gly Val Val Ile Ala Thr Val
625                 630                 635                 640
Ile Val Ile Thr Leu Val Met Leu Lys Lys Lys Gln Tyr Thr Ser Ile
                645                 650                 655
His His Gly Val Val Glu Val Asp Ala Ala Val Thr Pro Glu Glu Arg
            660                 665                 670
His Leu Ser Lys Met Gln Gln Asn Gly Tyr Glu Asn Pro Thr Tyr Lys
            675                 680                 685
```

Phe Phe Glu Gln Met Gln Asn
    690             695

<210> SEQ ID NO 11
<211> LENGTH: 2088
<212> TYPE: DNA
<213> ORGANISM: Homo sapiens

<400> SEQUENCE: 11

| | | | | | |
|---|---|---|---|---|---|
| atgctgcccg | gtttggcact | gctcctgctg | gccgcctgga | cggctcgggc | gctggaggta | 60 |
| cccactgatg | gtaatgctgg | cctgctggct | gaacccagga | ttgccatgtt | ctgtggcaga | 120 |
| ctgaacatgc | acatgaatgt | ccagaatggg | aagtgggatt | cagatccatc | agggaccaaa | 180 |
| acctgcattg | ataccaagga | aggcatcctg | cagtattgcc | aagaagtcta | ccctgaactg | 240 |
| cagatcacca | atgtggtaga | agccaaccaa | ccagtgacca | tccagaactg | gtgcaagcgg | 300 |
| ggccgcaagc | agtgcaagac | ccatccccac | tttgtgattc | cctaccgctg | cttagttggt | 360 |
| gagtttgtaa | gtgatgccct | tctcgttcct | gacaagtgca | aattcttaca | ccaggagagg | 420 |
| atggatgttt | gcgaaactca | tcttcactgg | cacaccgtcg | ccaaagagac | atgcagtgag | 480 |
| aagagtacca | acttgcatga | ctacggcatg | ttgctgccct | gcggaattga | caagttccga | 540 |
| ggggtagagt | ttgtgtgttg | cccactggct | gaagaaagtg | acaatgtgga | ttctgctgat | 600 |
| gcggaggagg | atgactcgga | tgtctggtgg | ggcggagcag | acacagacta | tgcagatggg | 660 |
| agtgaagaca | aagtagtaga | agtagcagag | gaggaagaag | tggctgaggt | ggaagaagaa | 720 |
| gaagccgatg | atgacgagga | cgatgaggat | ggtgatgagg | tagaggaaga | ggctgaggaa | 780 |
| ccctacgaag | aagccacaga | gagaaccacc | agcattgcca | ccaccaccac | caccaccaca | 840 |
| gagtctgtgg | aagaggtggt | tcgagttcct | acaacagcag | ccagtacccc | tgatgccgtt | 900 |
| gacaagtatc | tcgagacacc | tggggatgag | aatgaacatg | cccatttcca | gaaagccaaa | 960 |
| gagaggcttg | aggccaagca | ccgagagaga | atgtcccagg | tcatgagaga | atgggaagag | 1020 |
| gcagaacgtc | aagcaaagaa | cttgcctaaa | gctgataaga | aggcagttat | ccagcatttc | 1080 |
| caggagaaag | tggaatcttt | ggaacaggaa | gcagccaacg | agagacagca | gctggtggag | 1140 |
| acacacatgg | ccagagtgga | agccatgctc | aatgaccgcc | gccgcctggc | cctggagaac | 1200 |
| tacatcaccg | ctctgcaggc | tgttcctcct | cggcctcgtc | acgtgttcaa | tatgctaaag | 1260 |
| aagtatgtcc | gcgcagaaca | gaaggacaga | cagcacaccc | taaagcattt | cgagcatgtg | 1320 |
| cgcatggtgg | atcccaagaa | agccgctcag | atccggtccc | aggttatgac | acacctccgt | 1380 |
| gtgatttatg | agcgcatgaa | tcagtctctc | tccctgctct | acaacgtgcc | tgcagtggcc | 1440 |
| gaggagattc | aggatgaagt | tgatgagctg | cttcagaaag | agcaaaacta | ttcagatgac | 1500 |
| gtcttggcca | acatgattag | tgaaccaagg | atcagttacg | gaaacgatgc | tctcatgcca | 1560 |
| tcttttgaccaa | aaacgaaaac | caccgtggag | ctccttcccg | tgaatggaga | gttcagcctg | 1620 |
| gacgatctcc | agccgtggca | ttcttttggg | gctgactctg | tgccagccaa | cacagaaaac | 1680 |
| gaagttgagc | ctgttgatgc | ccgccctgct | gccgaccgag | gactgaccac | tcgaccaggt | 1740 |
| tctgggttga | caaatatcaa | gacggaggag | atctctgaag | tgaatctgga | tgcagaattc | 1800 |
| cgacatgact | caggatatga | agttcatcat | caaaaattgg | tgttcttgc | agaagatgtg | 1860 |
| ggttcaaaca | aaggtgcaat | cattggactc | atggtgggcg | gtgttgtcat | agcgacagtg | 1920 |
| atcgtcatca | ccttggtgat | gctgaagaag | aaacagtaca | catccattca | tcatggtgtg | 1980 |
| gtggaggttg | acgccgctgt | cacccagag | gagcgccacc | tgtccaagat | gcagcagaac | 2040 |

```
ggctacgaaa atccaaccta caagttcttt gagcagatgc agaactag          2088
```

<210> SEQ ID NO 12
<211> LENGTH: 695
<212> TYPE: PRT
<213> ORGANISM: Homo sapiens

<400> SEQUENCE: 12

```
Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
            85                  90                  95

Trp Cys Lys Arg Gly Arg Lys Gln Cys Lys Thr His Pro His Phe Val
        100                 105                 110

Ile Pro Tyr Arg Cys Leu Val Gly Glu Phe Val Ser Asp Ala Leu Leu
    115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
            165                 170                 175

Asp Lys Phe Arg Gly Val Glu Phe Val Cys Cys Pro Leu Ala Glu Glu
        180                 185                 190

Ser Asp Asn Val Asp Ser Ala Asp Ala Glu Glu Asp Asp Ser Asp Val
    195                 200                 205

Trp Trp Gly Gly Ala Asp Thr Asp Tyr Ala Asp Gly Ser Glu Asp Lys
    210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
            245                 250                 255

Glu Ala Glu Glu Pro Tyr Glu Glu Ala Thr Glu Arg Thr Thr Ser Ile
        260                 265                 270

Ala Thr Thr Thr Thr Thr Thr Glu Ser Val Glu Glu Val Val Arg
        275                 280                 285

Val Pro Thr Thr Ala Ala Ser Thr Pro Asp Ala Val Asp Lys Tyr Leu
    290                 295                 300

Glu Thr Pro Gly Asp Glu Asn Glu His Ala His Phe Gln Lys Ala Lys
305                 310                 315                 320

Glu Arg Leu Glu Ala Lys His Arg Glu Arg Met Ser Gln Val Met Arg
            325                 330                 335

Glu Trp Glu Glu Ala Glu Arg Gln Ala Lys Asn Leu Pro Lys Ala Asp
        340                 345                 350

Lys Lys Ala Val Ile Gln His Phe Gln Glu Lys Val Glu Ser Leu Glu
    355                 360                 365
```

```
Gln Glu Ala Ala Asn Glu Arg Gln Gln Leu Val Glu Thr His Met Ala
    370                 375                 380

Arg Val Glu Ala Met Leu Asn Asp Arg Arg Leu Ala Leu Glu Asn
385                 390                 395                 400

Tyr Ile Thr Ala Leu Gln Ala Val Pro Pro Arg Pro His Val Phe
                405                 410                 415

Asn Met Leu Lys Lys Tyr Val Arg Ala Glu Gln Lys Asp Arg Gln His
                420                 425                 430

Thr Leu Lys His Phe Glu His Val Arg Met Val Asp Pro Lys Lys Ala
            435                 440                 445

Ala Gln Ile Arg Ser Gln Val Met Thr His Leu Arg Val Ile Tyr Glu
        450                 455                 460

Arg Met Asn Gln Ser Leu Ser Leu Leu Tyr Asn Val Pro Ala Val Ala
465                 470                 475                 480

Glu Glu Ile Gln Asp Glu Val Asp Glu Leu Leu Gln Lys Glu Gln Asn
                485                 490                 495

Tyr Ser Asp Asp Val Leu Ala Asn Met Ile Ser Glu Pro Arg Ile Ser
                500                 505                 510

Tyr Gly Asn Asp Ala Leu Met Pro Ser Leu Thr Glu Thr Lys Thr Thr
            515                 520                 525

Val Glu Leu Leu Pro Val Asn Gly Glu Phe Ser Leu Asp Asp Leu Gln
    530                 535                 540

Pro Trp His Ser Phe Gly Ala Asp Ser Val Pro Ala Asn Thr Glu Asn
545                 550                 555                 560

Glu Val Glu Pro Val Asp Ala Arg Pro Ala Ala Asp Arg Gly Leu Thr
                565                 570                 575

Thr Arg Pro Gly Ser Gly Leu Thr Asn Ile Lys Thr Glu Glu Ile Ser
            580                 585                 590

Glu Val Asn Leu Asp Ala Glu Phe Arg His Asp Ser Gly Tyr Glu Val
        595                 600                 605

His His Gln Lys Leu Val Phe Phe Ala Glu Asp Val Gly Ser Asn Lys
610                 615                 620

Gly Ala Ile Ile Gly Leu Met Val Gly Gly Val Val Ile Ala Thr Val
625                 630                 635                 640

Ile Val Ile Thr Leu Val Met Leu Lys Lys Lys Gln Tyr Thr Ser Ile
                645                 650                 655

His His Gly Val Val Glu Val Asp Ala Ala Val Thr Pro Glu Glu Arg
            660                 665                 670

His Leu Ser Lys Met Gln Gln Asn Gly Tyr Glu Asn Pro Thr Tyr Lys
        675                 680                 685

Phe Phe Glu Gln Met Gln Asn
    690                 695

<210> SEQ ID NO 13
<211> LENGTH: 2088
<212> TYPE: PRT
<213> ORGANISM: Homo sapiens

<400> SEQUENCE: 13

Ala Thr Gly Cys Thr Gly Cys Cys Gly Gly Thr Thr Gly Gly
1               5                   10                  15

Cys Ala Cys Thr Gly Cys Thr Cys Thr Gly Cys Thr Gly Gly Cys
                20                  25                  30

Cys Gly Cys Cys Thr Gly Gly Ala Cys Gly Gly Cys Thr Cys Gly Gly
```

-continued

```
        35                  40                  45

Gly Cys Gly Cys Thr Gly Gly Ala Gly Gly Thr Ala Cys Cys Cys Ala
    50                  55                  60

Cys Thr Gly Ala Thr Gly Gly Thr Ala Ala Thr Gly Cys Thr Gly Gly
65                  70                  75                  80

Cys Cys Thr Gly Cys Thr Gly Gly Cys Thr Gly Ala Ala Cys Cys Cys
                85                  90                  95

Cys Ala Gly Ala Thr Thr Gly Cys Cys Ala Thr Gly Thr Thr Cys Thr
            100                 105                 110

Gly Thr Gly Gly Cys Ala Gly Ala Cys Thr Gly Ala Ala Cys Ala Thr
        115                 120                 125

Gly Cys Ala Cys Ala Thr Gly Ala Ala Thr Gly Thr Cys Cys Ala Gly
    130                 135                 140

Ala Ala Thr Gly Gly Gly Ala Ala Gly Thr Gly Gly Gly Ala Thr Thr
145                 150                 155                 160

Cys Ala Gly Ala Thr Cys Cys Ala Thr Cys Ala Gly Gly Gly Ala Cys
                165                 170                 175

Cys Ala Ala Ala Ala Cys Cys Thr Gly Cys Ala Thr Thr Gly Ala Thr
            180                 185                 190

Ala Cys Cys Ala Ala Gly Gly Ala Ala Gly Gly Cys Ala Thr Cys Cys
        195                 200                 205

Thr Gly Cys Ala Gly Thr Ala Thr Thr Gly Cys Cys Ala Ala Gly Ala
    210                 215                 220

Ala Gly Thr Cys Thr Ala Cys Cys Cys Thr Gly Ala Ala Cys Thr Gly
225                 230                 235                 240

Cys Ala Gly Ala Thr Cys Ala Cys Cys Ala Ala Thr Gly Thr Gly Gly
                245                 250                 255

Thr Ala Gly Ala Ala Gly Cys Cys Ala Ala Cys Cys Ala Ala Cys Cys
            260                 265                 270

Ala Gly Thr Gly Ala Cys Cys Ala Thr Cys Cys Ala Gly Ala Ala Cys
        275                 280                 285

Thr Gly Gly Thr Gly Cys Ala Ala Gly Cys Gly Gly Gly Gly Cys Cys
    290                 295                 300

Gly Cys Ala Ala Gly Cys Ala Gly Thr Gly Cys Ala Ala Gly Ala Cys
305                 310                 315                 320

Cys Cys Ala Thr Cys Cys Cys Cys Ala Cys Thr Thr Thr Gly Thr Gly
                325                 330                 335

Ala Thr Thr Cys Cys Cys Thr Ala Cys Cys Gly Cys Thr Gly Cys Thr
            340                 345                 350

Thr Ala Gly Thr Thr Gly Gly Thr Gly Ala Gly Thr Thr Thr Gly Thr
        355                 360                 365

Ala Ala Gly Thr Gly Ala Thr Gly Cys Cys Cys Thr Thr Cys Thr Cys
    370                 375                 380

Gly Thr Thr Cys Cys Thr Gly Ala Cys Ala Ala Gly Thr Gly Cys Ala
385                 390                 395                 400

Ala Ala Thr Thr Cys Thr Thr Ala Cys Ala Cys Cys Ala Gly Gly Ala
                405                 410                 415

Gly Ala Gly Gly Ala Thr Gly Gly Ala Thr Gly Thr Thr Thr Gly Cys
            420                 425                 430

Gly Ala Ala Ala Cys Thr Cys Ala Thr Cys Thr Thr Cys Ala Cys Thr
        435                 440                 445

Gly Gly Cys Ala Cys Ala Cys Cys Gly Thr Cys Gly Cys Cys Ala Ala
    450                 455                 460
```

-continued

```
Ala Gly Ala Gly Ala Cys Ala Thr Gly Cys Ala Gly Thr Gly Ala Gly
465                 470                 475                 480

Ala Ala Gly Ala Gly Thr Ala Cys Cys Ala Ala Cys Thr Thr Gly Cys
                485                 490                 495

Ala Thr Gly Ala Cys Thr Ala Cys Gly Gly Cys Ala Thr Gly Thr Thr
            500                 505                 510

Gly Cys Thr Gly Cys Cys Cys Thr Gly Cys Gly Gly Ala Ala Thr Thr
        515                 520                 525

Gly Ala Cys Ala Ala Gly Thr Thr Cys Cys Gly Ala Gly Gly Gly Gly
    530                 535                 540

Thr Ala Gly Ala Gly Thr Thr Thr Gly Thr Gly Thr Gly Thr Thr Gly
545                 550                 555                 560

Cys Cys Cys Ala Cys Thr Gly Gly Cys Thr Gly Ala Ala Gly Ala Ala
                565                 570                 575

Ala Gly Thr Gly Ala Cys Ala Ala Thr Gly Thr Gly Gly Ala Thr Thr
            580                 585                 590

Cys Thr Gly Cys Thr Gly Ala Thr Gly Cys Gly Gly Ala Gly Gly Ala
        595                 600                 605

Gly Gly Ala Thr Gly Ala Cys Thr Cys Gly Gly Ala Thr Gly Thr Cys
    610                 615                 620

Thr Gly Gly Thr Gly Gly Gly Gly Cys Gly Gly Ala Gly Cys Ala Gly
625                 630                 635                 640

Ala Cys Ala Cys Ala Gly Ala Cys Thr Ala Thr Gly Cys Ala Gly Ala
                645                 650                 655

Thr Gly Gly Gly Ala Gly Thr Gly Ala Ala Gly Ala Cys Ala Ala Ala
            660                 665                 670

Gly Thr Ala Gly Thr Ala Gly Ala Ala Gly Thr Ala Gly Cys Ala Gly
        675                 680                 685

Ala Gly Gly Ala Gly Gly Ala Ala Gly Ala Ala Gly Thr Gly Gly Cys
    690                 695                 700

Thr Gly Ala Gly Gly Thr Gly Gly Ala Ala Gly Ala Ala Gly Ala Ala
705                 710                 715                 720

Gly Ala Ala Gly Cys Cys Gly Ala Thr Gly Ala Thr Gly Ala Cys Gly
                725                 730                 735

Ala Gly Gly Ala Cys Gly Ala Thr Gly Ala Gly Gly Ala Thr Gly Gly
            740                 745                 750

Thr Gly Ala Thr Gly Ala Gly Gly Thr Ala Gly Ala Gly Gly Ala Ala
        755                 760                 765

Gly Ala Gly Gly Cys Thr Gly Ala Gly Gly Ala Ala Cys Cys Cys Thr
    770                 775                 780

Ala Cys Gly Ala Ala Gly Ala Ala Gly Cys Cys Ala Cys Ala Gly Ala
785                 790                 795                 800

Gly Ala Gly Ala Ala Cys Cys Ala Cys Cys Ala Gly Cys Ala Thr Thr
                805                 810                 815

Gly Cys Cys Ala Cys Cys Ala Cys Cys Ala Cys Cys Ala Cys Cys Ala
            820                 825                 830

Cys Cys Ala Cys Cys Ala Cys Ala Gly Ala Gly Thr Cys Thr Gly Thr
        835                 840                 845

Gly Gly Ala Ala Gly Ala Gly Gly Thr Gly Gly Thr Thr Cys Gly Ala
    850                 855                 860

Gly Thr Thr Cys Cys Thr Ala Cys Ala Ala Cys Ala Gly Cys Ala Gly
865                 870                 875                 880
```

-continued

Cys Cys Ala Gly Thr Ala Cys Cys Thr Gly Ala Thr Gly Cys
            885             890             895

Cys Gly Thr Thr Gly Ala Cys Ala Ala Gly Thr Ala Thr Cys Thr Cys
            900             905             910

Gly Ala Gly Ala Cys Ala Cys Thr Gly Gly Gly Ala Thr Gly
            915             920             925

Ala Gly Ala Ala Thr Gly Ala Ala Cys Ala Thr Gly Cys Cys Ala
            930             935             940

Thr Thr Thr Cys Cys Ala Gly Ala Ala Gly Cys Cys Ala Ala Ala
945             950             955             960

Gly Ala Gly Ala Gly Gly Cys Thr Thr Gly Ala Gly Cys Cys Ala
            965             970             975

Ala Gly Cys Ala Cys Cys Gly Ala Gly Ala Gly Ala Ala Thr
            980             985             990

Gly Thr Cys Cys Cys Ala Gly Gly Thr Cys Ala Thr Gly Ala Gly Ala
            995             1000            1005

Gly Ala Ala Thr Gly Gly Gly Ala Ala Gly Ala Gly Gly Cys Ala
            1010            1015            1020

Gly Ala Ala Cys Gly Thr Cys Ala Ala Gly Cys Ala Ala Ala Gly
            1025            1030            1035

Ala Ala Cys Thr Thr Gly Cys Cys Thr Ala Ala Ala Gly Cys Thr
            1040            1045            1050

Gly Ala Thr Ala Ala Gly Ala Ala Gly Gly Cys Ala Gly Thr Thr
            1055            1060            1065

Ala Thr Cys Cys Ala Gly Cys Ala Thr Thr Thr Cys Cys Ala Gly
            1070            1075            1080

Gly Ala Gly Ala Ala Ala Gly Thr Gly Gly Ala Ala Thr Cys Thr
            1085            1090            1095

Thr Thr Gly Gly Ala Ala Cys Ala Gly Gly Ala Ala Gly Cys Ala
            1100            1105            1110

Gly Cys Cys Ala Ala Cys Gly Ala Gly Ala Gly Ala Cys Ala Gly
            1115            1120            1125

Cys Ala Gly Cys Thr Gly Gly Thr Gly Gly Ala Gly Ala Cys Ala
            1130            1135            1140

Cys Ala Cys Ala Thr Gly Gly Cys Cys Ala Gly Ala Gly Thr Gly
            1145            1150            1155

Gly Ala Ala Gly Cys Cys Ala Thr Gly Cys Thr Cys Ala Ala Thr
            1160            1165            1170

Gly Ala Cys Cys Gly Cys Cys Gly Cys Cys Gly Cys Cys Thr Gly
            1175            1180            1185

Gly Cys Cys Cys Thr Gly Gly Ala Gly Ala Ala Cys Thr Ala Cys
            1190            1195            1200

Ala Thr Cys Ala Cys Cys Gly Cys Thr Cys Thr Gly Cys Ala Gly
            1205            1210            1215

Gly Cys Thr Gly Thr Thr Cys Cys Thr Cys Cys Thr Cys Gly Gly
            1220            1225            1230

Cys Cys Thr Cys Gly Thr Cys Ala Cys Gly Thr Gly Thr Thr Cys
            1235            1240            1245

Ala Ala Thr Ala Thr Gly Cys Thr Ala Ala Ala Gly Ala Ala Gly
            1250            1255            1260

Thr Ala Thr Gly Thr Cys Cys Gly Cys Gly Cys Ala Gly Ala Ala
            1265            1270            1275

Cys Ala Gly Ala Ala Gly Gly Ala Cys Ala Gly Ala Cys Ala Gly

-continued

```
            1280                1285                1290
Cys Ala Cys Ala Cys Cys  Thr Ala Ala Gly  Cys Ala Thr
    1295            1300                1305
Thr Thr Cys Gly Ala Gly  Cys Ala Thr Gly  Thr Cys Gly Cys
    1310            1315                1320
Ala Thr Gly Gly Thr Gly  Ala Thr Cys Cys  Ala Ala Gly
    1325            1330                1335
Ala Ala Ala Gly Cys Cys  Gly Cys Thr Cys  Ala Gly Ala Thr Cys
    1340            1345                1350
Cys Gly Gly Thr Cys Cys  Cys Ala Gly Gly  Thr Thr Ala Thr Gly
    1355            1360                1365
Ala Cys Ala Cys Ala Cys  Cys Thr Cys Cys  Gly Thr Gly Thr Gly
    1370            1375                1380
Ala Thr Thr Thr Ala Thr  Gly Ala Gly Cys  Gly Cys Ala Thr Gly
    1385            1390                1395
Ala Ala Thr Cys Ala Gly  Thr Cys Thr Cys  Thr Cys Thr Cys Cys
    1400            1405                1410
Cys Thr Gly Cys Thr Cys  Thr Ala Cys Ala  Ala Cys Gly Thr Gly
    1415            1420                1425
Cys Cys Thr Gly Cys Ala  Gly Thr Gly Gly  Cys Cys Gly Ala Gly
    1430            1435                1440
Gly Ala Gly Ala Thr Thr  Cys Ala Gly Gly  Ala Thr Gly Ala Ala
    1445            1450                1455
Gly Thr Thr Gly Ala Thr  Gly Ala Gly Cys  Thr Gly Cys Thr Thr
    1460            1465                1470
Cys Ala Gly Ala Ala Ala  Gly Ala Gly Cys  Ala Ala Ala Ala Cys
    1475            1480                1485
Thr Ala Thr Thr Cys Ala  Gly Ala Thr Gly  Ala Cys Gly Thr Cys
    1490            1495                1500
Thr Thr Gly Gly Cys Cys  Ala Ala Cys Ala  Thr Gly Ala Thr Thr
    1505            1510                1515
Ala Gly Thr Gly Ala Ala  Cys Cys Ala Ala  Gly Gly Ala Thr Cys
    1520            1525                1530
Ala Gly Thr Thr Ala Cys  Gly Gly Ala Ala  Ala Cys Gly Ala Thr
    1535            1540                1545
Gly Cys Thr Cys Thr Cys  Ala Thr Gly Cys  Ala Thr Cys Thr
    1550            1555                1560
Thr Thr Gly Ala Cys Cys  Ala Ala Ala Cys  Gly Ala Ala Ala
    1565            1570                1575
Ala Cys Cys Ala Cys Cys  Gly Thr Gly Ala  Gly Cys Thr Cys
    1580            1585                1590
Cys Thr Thr Cys Cys Cys  Gly Thr Ala Ala  Thr Gly Gly Ala
    1595            1600                1605
Gly Ala Gly Thr Thr Cys  Ala Gly Cys Cys  Thr Gly Ala Cys
    1610            1615                1620
Gly Ala Thr Cys Thr Cys  Ala Gly Cys Cys  Gly Thr Gly Gly
    1625            1630                1635
Cys Ala Thr Thr Cys Thr  Thr Thr Gly Gly  Gly Gly Cys Thr
    1640            1645                1650
Gly Ala Cys Thr Cys Thr  Gly Thr Gly Cys  Cys Ala Gly Cys Cys
    1655            1660                1665
Ala Ala Cys Ala Cys Ala  Gly Ala Ala Ala  Cys Gly Ala Ala
    1670            1675                1680
```

-continued

```
Gly Thr Thr Gly Ala Gly Cys Cys Thr Gly Thr Gly Ala Thr
    1685                1690                1695

Gly Cys Cys Cys Gly Cys Cys Cys Thr Gly Cys Thr Gly Cys Cys
    1700                1705                1710

Gly Ala Cys Cys Gly Ala Gly Gly Ala Cys Thr Gly Ala Cys Cys
    1715                1720                1725

Ala Cys Thr Cys Gly Ala Cys Cys Ala Gly Gly Thr Thr Cys Thr
    1730                1735                1740

Gly Gly Gly Thr Thr Gly Ala Cys Ala Ala Thr Ala Thr Cys
    1745                1750                1755

Ala Ala Gly Ala Cys Gly Gly Ala Gly Gly Ala Gly Ala Thr Cys
    1760                1765                1770

Thr Cys Thr Gly Ala Ala Gly Thr Gly Ala Ala Gly Ala Thr Gly
    1775                1780                1785

Gly Ala Thr Gly Cys Ala Gly Ala Ala Thr Thr Cys Cys Gly Ala
    1790                1795                1800

Cys Ala Thr Gly Ala Cys Thr Cys Ala Gly Gly Ala Thr Ala Thr
    1805                1810                1815

Gly Ala Ala Gly Thr Thr Cys Ala Thr Cys Ala Thr Cys Ala Ala
    1820                1825                1830

Ala Ala Ala Thr Thr Gly Gly Thr Gly Thr Thr Cys Thr Thr Thr
    1835                1840                1845

Gly Cys Ala Gly Ala Ala Gly Ala Thr Gly Thr Gly Gly Gly Thr
    1850                1855                1860

Thr Cys Ala Ala Cys Ala Ala Ala Gly Gly Thr Gly Cys Ala
    1865                1870                1875

Ala Thr Cys Ala Thr Thr Gly Gly Ala Cys Thr Cys Ala Thr Gly
    1880                1885                1890

Gly Thr Gly Gly Gly Cys Gly Gly Thr Gly Thr Thr Gly Thr Cys
    1895                1900                1905

Ala Thr Ala Gly Cys Gly Ala Cys Ala Gly Thr Gly Ala Thr Cys
    1910                1915                1920

Thr Thr Cys Ala Thr Cys Ala Cys Cys Thr Thr Gly Gly Thr Gly
    1925                1930                1935

Ala Thr Gly Cys Thr Gly Ala Ala Gly Ala Ala Gly Ala Ala Ala
    1940                1945                1950

Cys Ala Gly Thr Ala Cys Ala Cys Ala Thr Cys Cys Ala Thr Thr
    1955                1960                1965

Cys Ala Thr Cys Ala Thr Gly Gly Thr Gly Thr Gly Gly Thr Gly
    1970                1975                1980

Gly Ala Gly Gly Thr Thr Gly Ala Cys Gly Cys Cys Gly Cys Thr
    1985                1990                1995

Gly Thr Cys Ala Cys Cys Cys Ala Gly Ala Gly Gly Ala Gly
    2000                2005                2010

Cys Gly Cys Cys Ala Cys Cys Thr Gly Thr Cys Ala Ala Gly
    2015                2020                2025

Ala Thr Gly Cys Ala Gly Cys Ala Gly Ala Ala Cys Gly Gly Cys
    2030                2035                2040

Thr Ala Cys Gly Ala Ala Ala Ala Thr Cys Cys Ala Ala Cys Cys
    2045                2050                2055

Thr Ala Cys Ala Ala Gly Thr Thr Cys Thr Thr Thr Gly Ala Gly
    2060                2065                2070
```

```
Cys Ala  Gly Ala Thr Gly Cys  Ala Gly Ala Ala Cys   Thr Ala Gly
    2075             2080                 2085

<210> SEQ ID NO 14
<211> LENGTH: 695
<212> TYPE: PRT
<213> ORGANISM: Homo sapiens

<400> SEQUENCE: 14

Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
                20                  25                  30

Gln Ile Ala Met Phe Cys Gly Arg Leu Asn Met His Met Asn Val Gln
            35                  40                  45

Asn Gly Lys Trp Asp Ser Asp Pro Ser Gly Thr Lys Thr Cys Ile Asp
        50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Glu Ser Val Glu Glu Val Val Arg
        275                 280                 285

Val Pro Thr Thr Ala Ala Ser Thr Pro Asp Ala Val Asp Lys Tyr Leu
        290                 295                 300

Glu Thr Pro Gly Asp Glu Asn Glu His Ala His Phe Gln Lys Ala Lys
305                 310                 315                 320

Glu Arg Leu Glu Ala Lys His Arg Glu Arg Met Ser Gln Val Met Arg
                325                 330                 335

Glu Trp Glu Glu Ala Glu Arg Gln Ala Lys Asn Leu Pro Lys Ala Asp
            340                 345                 350

Lys Lys Ala Val Ile Gln His Phe Gln Glu Lys Val Glu Ser Leu Glu
        355                 360                 365
```

```
Gln Glu Ala Ala Asn Glu Arg Gln Gln Leu Val Glu Thr His Met Ala
    370                 375                 380
Arg Val Glu Ala Met Leu Asn Asp Arg Arg Leu Ala Leu Glu Asn
385                 390                 395                 400
Tyr Ile Thr Ala Leu Gln Ala Val Pro Pro Arg Pro Arg His Val Phe
                405                 410                 415
Asn Met Leu Lys Lys Tyr Val Arg Ala Glu Gln Lys Asp Arg Gln His
                420                 425                 430
Thr Leu Lys His Phe Glu His Val Arg Met Val Asp Pro Lys Lys Ala
                435                 440                 445
Ala Gln Ile Arg Ser Gln Val Met Thr His Leu Arg Val Ile Tyr Glu
            450                 455                 460
Arg Met Asn Gln Ser Leu Ser Leu Leu Tyr Asn Val Pro Ala Val Ala
465                 470                 475                 480
Glu Glu Ile Gln Asp Glu Val Asp Glu Leu Leu Gln Lys Glu Gln Asn
                485                 490                 495
Tyr Ser Asp Asp Val Leu Ala Asn Met Ile Ser Glu Pro Arg Ile Ser
                500                 505                 510
Tyr Gly Asn Asp Ala Leu Met Pro Ser Leu Thr Glu Thr Lys Thr Thr
                515                 520                 525
Val Glu Leu Leu Pro Val Asn Gly Glu Phe Ser Leu Asp Asp Leu Gln
    530                 535                 540
Pro Trp His Ser Phe Gly Ala Asp Ser Val Pro Ala Asn Thr Glu Asn
545                 550                 555                 560
Glu Val Glu Pro Val Asp Ala Arg Pro Ala Ala Asp Arg Gly Leu Thr
                565                 570                 575
Thr Arg Pro Gly Ser Gly Leu Thr Asn Ile Lys Thr Glu Glu Ile Ser
                580                 585                 590
Glu Val Lys Met Asp Ala Glu Phe Arg His Asp Ser Gly Tyr Glu Val
            595                 600                 605
His His Gln Lys Leu Val Phe Phe Ala Glu Asp Val Gly Ser Asn Lys
            610                 615                 620
Gly Ala Ile Ile Gly Leu Met Val Gly Gly Val Val Ile Ala Thr Val
625                 630                 635                 640
Ile Phe Ile Thr Leu Val Met Leu Lys Lys Lys Gln Tyr Thr Ser Ile
                645                 650                 655
His His Gly Val Val Glu Val Asp Ala Ala Val Thr Pro Glu Glu Arg
                660                 665                 670
His Leu Ser Lys Met Gln Gln Asn Gly Tyr Glu Asn Pro Thr Tyr Lys
                675                 680                 685
Phe Phe Glu Gln Met Gln Asn
    690                 695

<210> SEQ ID NO 15
<211> LENGTH: 2094
<212> TYPE: DNA
<213> ORGANISM: Homo sapiens

<400> SEQUENCE: 15
atgctgcccg gtttggcact gctcctgctg gccgcctgga cggctcgggc gctggaggta      60
cccactgatg gtaatgctgg cctgctggct gaaccccaga ttgccatgtt ctgtggcaga     120
ctgaacatgc acatgaatgt ccagaatggg aagtgggatt cagatccatc aggaccaaa     180 acctgcattg ataccaagga aggcatcctg cagtattgcc aagaagtcta ccctgaactg     240
```

-continued

```
cagatcacca atgtggtaga agccaaccaa ccagtgacca tccagaactg gtgcaagcgg    300
ggccgcaagc agtgcaagac ccatccccac tttgtgattc cctaccgctg cttagttggt    360
gagtttgtaa gtgatgccct tctcgttcct gacaagtgca aattcttaca ccaggagagg    420
atggatgttt gcgaaactca tcttcactgg cacaccgtcg ccaaagagac atgcagtgag    480
aagagtacca acttgcatga ctacggcatg ttgctgccct gcggaattga caagttccga    540
ggggtagagt ttgtgtgttg cccactggct gaagaaagtg acaatgtgga ttctgctgat    600
gcggaggagg atgactcgga tgtctggtgg ggcggagcag acacagacta tgcagatggg    660
agtgaagaca agtagtaga agtagcagag gaggaagaag tggctgaggt ggaagaagaa    720
gaagccgatg atgacgagga cgatgaggat ggtgatgagg tagaggaaga ggctgaggaa    780
ccctacgaag aagccacaga gagaaccacc agcattgcca ccaccaccac caccaccaca    840
gagtctgtgg aagaggtggt tcgagttcct acaacagcag ccagtacccc tgatgccgtt    900
gacaagtatc tcgagacacc tggggatgag aatgaacatg cccatttcca gaaagccaaa    960
gagaggcttg aggccaagca ccgagagaga atgtcccagg tcatgagaga atgggaagag   1020
gcagaacgtc aagcaaagaa cttgcctaaa gctgataaga aggcagttat ccagcatttc   1080
caggagaaag tggaatcttt ggaacaggaa gcagccaacg agagacagca gctggtggag   1140
acacacatgg ccagagtgga agccatgctc aatgaccgcc gccgcctggc cctggagaac   1200
tacatcaccg ctctgcaggc tgttcctcct cggcctcgtc acgtgttcaa tatgctaaag   1260
aagtatgtcc gcgcagaaca gaaggacaga cagcacaccc taaagcattt cgagcatgtg   1320
cgcatggtgg atcccaagaa agccgctcag atccggtccc aggttatgac acacctccgt   1380
gtgatttatg agcgcatgaa tcagtctctc tccctgctct acaacgtgcc tgcagtggcc   1440
gaggagattc aggatgaagt tgatgagctg cttcagaaag gcaaaacta ttcagatgac   1500 gtcttggcca acatgattag tgaaccaagg atcagttacg aaacgatgc tctcatgcca   1560 tcttgaccg aaacgaaaac caccgtggag ctccttcccg tgaatggaga gttcagcctg   1620
gacgatctcc agccgtggca ttcttttggg gctgactctg tgccagccaa cacagaaaac   1680
gaagttgagc ctgttgatgc ccgccctgct gccgaccgag gactgaccac tcgaccaggt   1740
tctgggttga caaatatcaa gacggaggag atctctgaag tgaagatgga tgcagaattc   1800
cgacatgact caggatatga agttcatcat caaaaattgg tgttctttgc agaagatgtg   1860
ggttcaaaca aggtgcaat cattggactc atggtgggcg tgttgtcat agcgacagtg   1920 atcgtcatca ccttggtgat gctgaagaag aaacagtaca catccattca tcatggtgtg   1980
gtggaggttg acgccgctgt caccccagag gagcgccacc tgtccaagat gcagcagaac   2040
ggctacgaaa atccaaccta caagttcttt gagcagatgc agaacaagaa gtag        2094
```

<210> SEQ ID NO 16
<211> LENGTH: 697
<212> TYPE: PRT
<213> ORGANISM: Homo sapines

<400> SEQUENCE: 16

Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
                20                  25                  30

Gln Ile Ala Met Phe Cys Gly Arg Leu Asn Met His Met Asn Val Gln
            35                  40                  45

```
Asn Gly Lys Trp Asp Ser Asp Pro Ser Gly Thr Lys Thr Cys Ile Asp
     50                  55                  60

Thr Lys Glu Gly Ile Leu Gln Tyr Cys Gln Glu Val Tyr Pro Glu Leu
65                   70                  75                  80

Gln Ile Thr Asn Val Val Glu Ala Asn Gln Pro Val Thr Ile Gln Asn
                 85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
            115                 120                 125

Val Pro Asp Lys Cys Lys Phe Leu His Gln Glu Arg Met Asp Val Cys
130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
            195                 200                 205

Trp Trp Gly Gly Ala Asp Thr Asp Tyr Ala Asp Gly Ser Glu Asp Lys
            210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Glu Ser Val Glu Glu Val Val Arg
            275                 280                 285

Val Pro Thr Thr Ala Ala Ser Thr Pro Asp Ala Val Asp Lys Tyr Leu
290                 295                 300

Glu Thr Pro Gly Asp Glu Asn Glu His Ala His Phe Gln Lys Ala Lys
305                 310                 315                 320

Glu Arg Leu Glu Ala Lys His Arg Glu Arg Met Ser Gln Val Met Arg
                325                 330                 335

Glu Trp Glu Glu Ala Glu Arg Gln Ala Lys Asn Leu Pro Lys Ala Asp
            340                 345                 350

Lys Lys Ala Val Ile Gln His Phe Gln Glu Lys Val Glu Ser Leu Glu
            355                 360                 365

Gln Glu Ala Ala Asn Glu Arg Gln Gln Leu Val Glu Thr His Met Ala
370                 375                 380

Arg Val Glu Ala Met Leu Asn Asp Arg Arg Arg Leu Ala Leu Glu Asn
385                 390                 395                 400

Tyr Ile Thr Ala Leu Gln Ala Val Pro Pro Arg Pro Arg His Val Phe
                405                 410                 415

Asn Met Leu Lys Lys Tyr Val Arg Ala Glu Gln Lys Asp Arg Gln His
            420                 425                 430

Thr Leu Lys His Phe Glu His Val Arg Met Val Asp Pro Lys Lys Ala
            435                 440                 445

Ala Gln Ile Arg Ser Gln Val Met Thr His Leu Arg Val Ile Tyr Glu
450                 455                 460
```

-continued

```
Arg Met Asn Gln Ser Leu Ser Leu Leu Tyr Asn Val Pro Ala Val Ala
465                 470                 475                 480

Glu Glu Ile Gln Asp Glu Val Asp Glu Leu Leu Gln Lys Glu Gln Asn
            485                 490                 495

Tyr Ser Asp Asp Val Leu Ala Asn Met Ile Ser Glu Pro Arg Ile Ser
        500                 505                 510

Tyr Gly Asn Asp Ala Leu Met Pro Ser Leu Thr Glu Thr Lys Thr Thr
    515                 520                 525

Val Glu Leu Leu Pro Val Asn Gly Glu Phe Ser Leu Asp Asp Leu Gln
530                 535                 540

Pro Trp His Ser Phe Gly Ala Asp Ser Val Pro Ala Asn Thr Glu Asn
545                 550                 555                 560

Glu Val Glu Pro Val Asp Ala Arg Pro Ala Asp Arg Gly Leu Thr
            565                 570                 575

Thr Arg Pro Gly Ser Gly Leu Thr Asn Ile Lys Thr Glu Glu Ile Ser
        580                 585                 590

Glu Val Lys Met Asp Ala Glu Phe Arg His Asp Ser Gly Tyr Glu Val
    595                 600                 605

His His Gln Lys Leu Val Phe Phe Ala Glu Asp Val Gly Ser Asn Lys
    610                 615                 620

Gly Ala Ile Ile Gly Leu Met Val Gly Gly Val Val Ile Ala Thr Val
625                 630                 635                 640

Ile Val Ile Thr Leu Val Met Leu Lys Lys Lys Gln Tyr Thr Ser Ile
            645                 650                 655

His His Gly Val Val Glu Val Asp Ala Ala Val Thr Pro Glu Glu Arg
        660                 665                 670

His Leu Ser Lys Met Gln Gln Asn Gly Tyr Glu Asn Pro Thr Tyr Lys
    675                 680                 685

Phe Phe Glu Gln Met Gln Asn Lys Lys
    690                 695

<210> SEQ ID NO 17
<211> LENGTH: 2094
<212> TYPE: DNA
<213> ORGANISM: Homo sapiens

<400> SEQUENCE: 17
atgctgcccg gtttggcact gctcctgctg ccgcctggac ggctcgggc gctggaggta      60 cccactgatg gtaatgctgg cctgctggct gaaccccaga ttgccatgtt ctgtggcaga     120
ctgaacatgc acatgaatgt ccagaatggg aagtgggatt cagatccatc agggaccaaa    180
acctgcattg ataccaagga aggcatcctg cagtattgcc aagaagtcta ccctgaactg    240
cagatcacca atgtggtaga agccaaccaa ccagtgacca tccagaactg gtgcaagcgg    300
ggccgcaagc agtgcaagac ccatccccac tttgtgattc cctaccgctg cttagttggt    360
gagtttgtaa gtgatgccct tctcgttcct gacaagtgca attcttaca ccaggagagg     420 atggatgttt gcgaaactca tcttcactgg cacaccgtcg ccaaagagac atgcagtgag    480
aagagtacca acttgcatga ctacggcatg ttgctgccct gcggaattga caagttccga    540
ggggtagagt ttgtgtgttg cccactggct gaagaaagtg acaatgtgga ttctgctgat    600
gcggaggagg atgactcgga tgtctggtgg ggcggagcag acacagacta tgcagatggg    660
agtgaagaca agtagtagaa gtagcagag gaggaagaag tggctgaggt ggaagaagaa     720
gaagccgatg atgacgagga cgatgaggat ggtgatgagg tagaggaaga ggctgaggaa    780
```

-continued

```
ccctacgaag aagccacaga gagaaccacc agcattgcca ccaccaccac caccaccaca    840
gagtctgtgg aagaggtggt tcgagttcct acaacagcag ccagtacccc tgatgccgtt    900
gacaagtatc tcgagacacc tggggatgag aatgaacatg cccatttcca gaaagccaaa    960
gagaggcttg aggccaagca ccgagagaga atgtcccagg tcatgagaga atgggaagag   1020
gcagaacgtc aagcaaagaa cttgcctaaa gctgataaga aggcagttat ccagcatttc   1080
caggagaaag tggaatcttt ggaacaggaa gcagccaacg agacagca gctggtggag    1140
acacacatgg ccagagtgga agccatgctc aatgaccgcc gccgcctggc cctggagaac   1200
tacatcaccg ctctgcaggc tgttcctcct cggcctcgtc acgtgttcaa tatgctaaag   1260
aagtatgtcc gcgcagaaca gaaggacaga cagcacaccc taaagcattt cgagcatgtg   1320
cgcatggtgg atcccaagaa agccgctcag atccggtccc aggttatgac acacctccgt   1380
gtgatttatg agcgcatgaa tcagtctctc tccctgctct acaacgtgcc tgcagtggcc   1440
gaggagattc aggatgaagt tgatgagctg cttcagaaag agcaaaacta ttcagatgac   1500
gtcttggcca acatgattag tgaaccaagg atcagttacg aaacgatgc tctcatgcca    1560
tctttgaccg aaacgaaaac caccgtggag ctccttcccg tgaatggaga gttcagcctg   1620
gacgatctcc agccgtggca ttcttttggg gctgactctg tgccagccaa cacagaaaac   1680
gaagttgagc ctgttgatgc ccgccctgct gccgaccgag gactgaccac tcgaccaggt   1740
tctgggttga caaatatcaa gacggaggag atctctgaag tgaatctgga tgcagaattc   1800
cgacatgact caggatatga agttcatcat caaaaattgg tgttctttgc agaagatgtg   1860
ggttcaaaca aaggtgcaat cattggactc atggtgggcg gtgttgtcat agcgacagtg   1920
atcgtcatca ccttggtgat gctgaagaag aaacagtaca catccattca tcatggtgtg   1980
gtggaggttg acgccgctgt cacccagag gagcgccacc tgtccaagat gcagcagaac   2040
ggctacgaaa atccaaccta caagttcttt gagcagatgc agaacaagaa gtag         2094
```

<210> SEQ ID NO 18
<211> LENGTH: 697
<212> TYPE: PRT
<213> ORGANISM: Homo sapiens

<400> SEQUENCE: 18

```
Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
                20                  25                  30

Gln Ile Ala Met Phe Cys Gly Arg Leu Asn Met His Met Asn Val Gln
            35                  40                  45

Asn Gly Lys Trp Asp Ser Asp Pro Ser Gly Thr Lys Thr Cys Ile Asp
        50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140
```

-continued

```
Glu Thr His Leu His Trp His Thr Val Ala Lys Glu Thr Cys Ser Glu
145                 150                 155                 160

Lys Ser Thr Asn Leu His Asp Tyr Gly Met Leu Pro Cys Gly Ile
            165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
            195                 200                 205

Trp Trp Gly Gly Ala Asp Thr Asp Tyr Ala Asp Gly Ser Glu Asp Lys
210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Thr Glu Ser Val Glu Glu Val Val Arg
        275                 280                 285

Val Pro Thr Thr Ala Ala Ser Thr Pro Asp Ala Val Asp Lys Tyr Leu
        290                 295                 300

Glu Thr Pro Gly Asp Glu Asn Glu His Ala His Phe Gln Lys Ala Lys
305                 310                 315                 320

Glu Arg Leu Glu Ala Lys His Arg Glu Arg Met Ser Gln Val Met Arg
                325                 330                 335

Glu Trp Glu Glu Ala Glu Arg Gln Ala Lys Asn Leu Pro Lys Ala Asp
                340                 345                 350

Lys Lys Ala Val Ile Gln His Phe Gln Glu Lys Val Glu Ser Leu Glu
            355                 360                 365

Gln Glu Ala Ala Asn Glu Arg Gln Gln Leu Val Glu Thr His Met Ala
370                 375                 380

Arg Val Glu Ala Met Leu Asn Asp Arg Arg Arg Leu Ala Leu Glu Asn
385                 390                 395                 400

Tyr Ile Thr Ala Leu Gln Ala Val Pro Pro Arg Pro Arg His Val Phe
                405                 410                 415

Asn Met Leu Lys Lys Tyr Val Arg Ala Glu Gln Lys Asp Arg Gln His
            420                 425                 430

Thr Leu Lys His Phe Glu His Val Arg Met Val Asp Pro Lys Lys Ala
            435                 440                 445

Ala Gln Ile Arg Ser Gln Val Met Thr His Leu Arg Val Ile Tyr Glu
450                 455                 460

Arg Met Asn Gln Ser Leu Ser Leu Leu Tyr Asn Val Pro Ala Val Ala
465                 470                 475                 480

Glu Glu Ile Gln Asp Glu Val Asp Glu Leu Leu Gln Lys Glu Gln Asn
            485                 490                 495

Tyr Ser Asp Asp Val Leu Ala Asn Met Ile Ser Glu Pro Arg Ile Ser
            500                 505                 510

Tyr Gly Asn Asp Ala Leu Met Pro Ser Leu Thr Glu Thr Lys Thr Thr
            515                 520                 525

Val Glu Leu Leu Pro Val Asn Gly Glu Phe Ser Leu Asp Asp Leu Gln
            530                 535                 540

Pro Trp His Ser Phe Gly Ala Asp Ser Val Pro Ala Asn Thr Glu Asn
545                 550                 555                 560

Glu Val Glu Pro Val Asp Ala Arg Pro Ala Ala Asp Arg Gly Leu Thr
```

-continued

```
                565             570             575
Thr Arg Pro Gly Ser Gly Leu Thr Asn Ile Lys Thr Glu Glu Ile Ser
            580             585             590
Glu Val Asn Leu Asp Ala Glu Phe Arg His Asp Ser Gly Tyr Glu Val
        595             600             605
His His Gln Lys Leu Val Phe Phe Ala Glu Asp Val Gly Ser Asn Lys
    610             615             620
Gly Ala Ile Ile Gly Leu Met Val Gly Gly Val Val Ile Ala Thr Val
625             630             635             640
Ile Val Ile Thr Leu Val Met Leu Lys Lys Lys Gln Tyr Thr Ser Ile
            645             650             655
His His Gly Val Val Glu Val Asp Ala Ala Val Thr Pro Glu Glu Arg
        660             665             670
His Leu Ser Lys Met Gln Gln Asn Gly Tyr Glu Asn Pro Thr Tyr Lys
    675             680             685
Phe Phe Glu Gln Met Gln Asn Lys Lys
    690             695
```

<210> SEQ ID NO 19
<211> LENGTH: 2094
<212> TYPE: DNA
<213> ORGANISM: Homo sapiens

<400> SEQUENCE: 19

```
atgctgcccg gtttggcact gctcctgctg gccgcctgga cggctcgggc gctggaggta      60
cccactgatg gtaatgctgg cctgctggct gaaccccaga ttgccatgtt ctgtggcaga     120
ctgaacatgc acatgaatgt ccagaatggg aagtgggatt cagatccatc agggaccaaa     180
acctgcattg ataccaagga aggcatcctg cagtattgcc aagaagtcta ccctgaactg     240
cagatcacca atgtggtaga agccaaccaa ccagtgacca tccagaactg gtgcaagcgg     300
ggccgcaagc agtgcaagac ccatccccac tttgtgattc cctaccgctg cttagttggt     360
gagtttgtaa gtgatgccct tctcgttcct gacaagtgca aattcttaca ccaggagagg     420
atggatgttt gcgaaactca tcttcactgg cacaccgtcg ccaaagagac atgcagtgag     480
aagagtacca acttgcatga ctacggcatg ttgctgccct gcggaattga caagttccga     540
ggggtagagt ttgtgtgttg cccactggct gaagaaagtg acaatgtgga ttctgctgat     600
gcggaggagg atgactcgga tgtctggtgg ggcggagcag acacagacta tgcagatggg     660
agtgaagaca aagtagtaga agtagcagag gaggaagaag tggctgaggt ggaagaagaa     720
gaagccgatg atgacgagga cgatgaggat ggtgatgagg tagaggaaga ggctgaggaa     780
ccctacgaag aagccacaga gagaaccacc agcattgcca ccaccaccac caccaccaca     840
gagtctgtgg aagaggtggt tcgagttcct acaacagcag ccagtacccc tgatgccgtt     900
gacaagtatc tcgagacacc tggggatgag aatgaacatg cccatttcca aaagccaaa       960
gagaggcttg aggccaagca ccgagagaga atgtcccagg tcatgagaga atgggaagag    1020
gcagaacgtc aagcaaagaa cttgcctaaa gctgataaga aggcagttat ccagcatttc    1080
caggagaaag tggaatcttt ggaacaggaa gcagccaacg agagacagca gctggtggag    1140
acacacatgg ccagagtgga agccatgctc aatgaccgcc gcgcctggc cctggagaac    1200
tacatcaccg ctctgcaggc tgttcctcct cggcctcgtc acgtgttcaa tatgctaaag    1260
aagtatgtcc gcgcagaaca gaaggacaga cagcacaccc taaagcattt cgagcatgtg    1320
cgcatggtgg atcccaagaa agccgctcag atccggtccc aggttatgac acacctccgt    1380
```

-continued

```
gtgatttatg agcgcatgaa tcagtctctc tccctgctct acaacgtgcc tgcagtggcc      1440
gaggagattc aggatgaagt tgatgagctg cttcagaaag agcaaaacta ttcagatgac      1500
gtcttggcca acatgattag tgaaccaagg atcagttacg aaacgatgc tctcatgcca       1560 tctttgaccg aaacgaaaac caccgtggag ctccttcccg tgaatggaga gttcagcctg      1620
gacgatctcc agccgtggca ttcttttggg gctgactctg tgccagccaa cacagaaaac     1680
gaagttgagc ctgttgatgc ccgccctgct gccgaccgag gactgaccac tcgaccaggt     1740
tctgggttga caaatatcaa gacggaggag atctctgaag tgaagatgga tgcagaattc    1800
cgacatgact caggatatga agttcatcat caaaaattgg tgttctttgc agaagatgtg    1860
ggttcaaaca aggtgcaat cattggactc atggtgggcg tgttgtcat agcgacagtg       1920 atcttcatca ccttggtgat gctgaagaag aaacagtaca catccattca tcatggtgtg    1980
gtggaggttg acgccgctgt caccccagag gagcgccacc tgtccaagat gcagcagaac    2040
ggctacgaaa atccaaccta caagttcttt gagcagatgc agaacaagaa gtag           2094
```

<210> SEQ ID NO 20
<211> LENGTH: 697
<212> TYPE: PRT
<213> ORGANISM: Homo sapiens

<400> SEQUENCE: 20

```
Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
                20                  25                  30

Gln Ile Ala Met Phe Cys Gly Arg Leu Asn Met His Met Asn Val Gln
            35                  40                  45

Asn Gly Lys Trp Asp Ser Asp Pro Ser Gly Thr Lys Thr Cys Ile Asp
        50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Val Ala Glu Val Glu Glu
225                 230                 235                 240

Glu Ala Asp Asp Asp Glu Asp Asp Glu Asp Gly Asp Glu Val Glu Glu
```

-continued

```
                245                 250                 255
Glu Ala Glu Glu Pro Tyr Glu Glu Ala Thr Glu Arg Thr Thr Ser Ile
            260                 265                 270
Ala Thr Thr Thr Thr Thr Thr Thr Glu Ser Val Glu Glu Val Val Arg
            275                 280                 285
Val Pro Thr Thr Ala Ala Ser Thr Pro Asp Ala Val Asp Lys Tyr Leu
        290                 295                 300
Glu Thr Pro Gly Asp Glu Asn Glu His Ala His Phe Gln Lys Ala Lys
305                 310                 315                 320
Glu Arg Leu Glu Ala Lys His Arg Glu Arg Met Ser Gln Val Met Arg
                325                 330                 335
Glu Trp Glu Glu Ala Glu Arg Gln Ala Lys Asn Leu Pro Lys Ala Asp
            340                 345                 350
Lys Lys Ala Val Ile Gln His Phe Gln Glu Lys Val Glu Ser Leu Glu
            355                 360                 365
Gln Glu Ala Ala Asn Glu Arg Gln Gln Leu Val Glu Thr His Met Ala
        370                 375                 380
Arg Val Glu Ala Met Leu Asn Asp Arg Arg Arg Leu Ala Leu Glu Asn
385                 390                 395                 400
Tyr Ile Thr Ala Leu Gln Ala Val Pro Pro Arg Pro Arg His Val Phe
                405                 410                 415
Asn Met Leu Lys Lys Tyr Val Arg Ala Glu Gln Lys Asp Arg Gln His
            420                 425                 430
Thr Leu Lys His Phe Glu His Val Arg Met Val Asp Pro Lys Lys Ala
            435                 440                 445
Ala Gln Ile Arg Ser Gln Val Met Thr His Leu Arg Val Ile Tyr Glu
        450                 455                 460
Arg Met Asn Gln Ser Leu Ser Leu Leu Tyr Asn Val Pro Ala Val Ala
465                 470                 475                 480
Glu Glu Ile Gln Asp Glu Val Asp Glu Leu Leu Gln Lys Glu Gln Asn
                485                 490                 495
Tyr Ser Asp Asp Val Leu Ala Asn Met Ile Ser Glu Pro Arg Ile Ser
            500                 505                 510
Tyr Gly Asn Asp Ala Leu Met Pro Ser Leu Thr Glu Thr Lys Thr Thr
            515                 520                 525
Val Glu Leu Leu Pro Val Asn Gly Glu Phe Ser Leu Asp Asp Leu Gln
        530                 535                 540
Pro Trp His Ser Phe Gly Ala Asp Ser Val Pro Ala Asn Thr Glu Asn
545                 550                 555                 560
Glu Val Glu Pro Val Asp Ala Arg Pro Ala Ala Asp Arg Gly Leu Thr
                565                 570                 575
Thr Arg Pro Gly Ser Gly Leu Thr Asn Ile Lys Thr Glu Glu Ile Ser
            580                 585                 590
Glu Val Lys Met Asp Ala Glu Phe Arg His Asp Ser Gly Tyr Glu Val
            595                 600                 605
His His Gln Lys Leu Val Phe Phe Ala Glu Asp Val Gly Ser Asn Lys
        610                 615                 620
Gly Ala Ile Ile Gly Leu Met Val Gly Gly Val Val Ile Ala Thr Val
625                 630                 635                 640
Ile Phe Ile Thr Leu Val Met Leu Lys Lys Lys Gln Tyr Thr Ser Ile
                645                 650                 655
His His Gly Val Val Glu Val Asp Ala Ala Val Thr Pro Glu Glu Arg
            660                 665                 670
```

```
His Leu Ser Lys Met Gln Gln Asn Gly Tyr Glu Asn Pro Thr Tyr Lys
            675                 680                 685

Phe Phe Glu Gln Met Gln Asn Lys Lys
    690                 695

<210> SEQ ID NO 21
<211> LENGTH: 1341
<212> TYPE: DNA
<213> ORGANISM: Homo sapiens

<400> SEQUENCE: 21
atggctagca tgactggtgg acagcaaatg ggtcgcggat ccacccagca cggcatccgg      60
ctgcccctgc gcagcggcct ggggggcgcc cccctgggc tgcggctgcc ccggagacc      120
gacgaagagc ccgaggagcc cggccggagg ggcagctttg tggagatggt ggacaacctg    180
agggcaagt cggggcaggg ctactacgtg gagatgaccg tgggcagccc ccgcagacg      240
ctcaacatcc tggtggatac aggcagcagt aactttgcag tgggtgctgc ccccacccc    300
ttcctgcatc gctactacca gaggcagctg tccagcacat accggaccct ccggaagggt    360
gtgtatgtgc cctacaccca gggcaagtgg aaggggagc tgggcaccga cctggtaagc    420
atccccatg gccccaacgt cactgtgcgt gccaacattg ctgccatcac tgaatcagac    480
aagttcttca tcaacggctc caactgggaa ggcatcctgg gctggccta tgctgagatt    540
gccaggcctg acgactccct ggagcctttc tttgactctc tggtaaagca gacccacgtt    600
cccaacctct tctccctgca cctttgtggt gctggcttcc ccctcaacca gtctgaagtg    660
ctggcctctg tcggagggag catgatcatt ggaggtatcg accactcgct gtacacaggc    720
agtctctggt atacacccat ccggcgggag tggtattatg aggtcatcat tgtgcgggtg    780
gagatcaatg gacaggatct gaaaatggac tgcaaggagt acaactatga caagagcatt    840
gtggacagtg gcaccaccaa ccttcgtttg cccaagaaag tgtttgaagc tgcagtcaaa    900
tccatcaagg cagcctcctc acggagaag ttccctgatg gtttctggct aggagagcag    960
ctggtgtgct ggcaagcagg caccaccccct tggaacattt tcccagtcat ctcactctac   1020
ctaatgggtg aggttaccaa ccagtccttc cgcatcacca tccttccgca gcaataccg    1080
cggccagtgg aagatgtggc cacgtcccaa gacgactgtt acaagtttgc catctcacag    1140
tcatccacgg gcactgttat gggagctgtt atcatggagg gcttctacgt tgtctttgat    1200
cgggcccgaa acgaattggg ctttgctgtc agcgcttgcc atgtgcacga tgagttcagg    1260
acggcagcgg tggaaggccc ttttgtcacc ttggacatgg aagactgtgg ctacaacatt    1320
ccacagacag atgagtcatg a                                               1341

<210> SEQ ID NO 22
<211> LENGTH: 446
<212> TYPE: PRT
<213> ORGANISM: Homo sapiens

<400> SEQUENCE: 22

Met Ala Ser Met Thr Gly Gly Gln Gln Met Gly Arg Gly Ser Thr Gln
1               5                   10                  15

His Gly Ile Arg Leu Pro Leu Arg Ser Gly Leu Gly Gly Ala Pro Leu
            20                  25                  30

Gly Leu Arg Leu Pro Arg Glu Thr Asp Glu Glu Pro Glu Glu Pro Gly
        35                  40                  45

Arg Arg Gly Ser Phe Val Glu Met Val Asp Asn Leu Arg Gly Lys Ser
```

```
              50                  55                  60
Gly Gln Gly Tyr Tyr Val Glu Met Thr Val Gly Ser Pro Pro Gln Thr
 65                  70                  75                  80

Leu Asn Ile Leu Val Asp Thr Gly Ser Ser Asn Phe Ala Val Gly Ala
                     85                  90                  95

Ala Pro His Pro Phe Leu His Arg Tyr Tyr Gln Arg Gln Leu Ser Ser
                    100                 105                 110

Thr Tyr Arg Asp Leu Arg Lys Gly Val Tyr Val Pro Tyr Thr Gln Gly
                    115                 120                 125

Lys Trp Glu Gly Glu Leu Gly Thr Asp Leu Val Ser Ile Pro His Gly
130                 135                 140

Pro Asn Val Thr Val Arg Ala Asn Ile Ala Ala Ile Thr Glu Ser Asp
145                 150                 155                 160

Lys Phe Phe Ile Asn Gly Ser Asn Trp Glu Gly Ile Leu Gly Leu Ala
                    165                 170                 175

Tyr Ala Glu Ile Ala Arg Pro Asp Asp Ser Leu Glu Pro Phe Phe Asp
                    180                 185                 190

Ser Leu Val Lys Gln Thr His Val Pro Asn Leu Phe Ser Leu His Leu
                    195                 200                 205

Cys Gly Ala Gly Phe Pro Leu Asn Gln Ser Glu Val Leu Ala Ser Val
210                 215                 220

Gly Gly Ser Met Ile Ile Gly Gly Ile Asp His Ser Leu Tyr Thr Gly
225                 230                 235                 240

Ser Leu Trp Tyr Thr Pro Ile Arg Arg Glu Trp Tyr Tyr Glu Val Ile
                    245                 250                 255

Ile Val Arg Val Glu Ile Asn Gly Gln Asp Leu Lys Met Asp Cys Lys
                    260                 265                 270

Glu Tyr Asn Tyr Asp Lys Ser Ile Val Asp Ser Gly Thr Thr Asn Leu
                    275                 280                 285

Arg Leu Pro Lys Lys Val Phe Glu Ala Ala Val Lys Ser Ile Lys Ala
                    290                 295                 300

Ala Ser Ser Thr Glu Lys Phe Pro Asp Gly Phe Trp Leu Gly Glu Gln
305                 310                 315                 320

Leu Val Cys Trp Gln Ala Gly Thr Thr Pro Trp Asn Ile Phe Pro Val
                    325                 330                 335

Ile Ser Leu Tyr Leu Met Gly Glu Val Thr Asn Gln Ser Phe Arg Ile
                    340                 345                 350

Thr Ile Leu Pro Gln Gln Tyr Leu Arg Pro Val Glu Asp Val Ala Thr
                    355                 360                 365

Ser Gln Asp Asp Cys Tyr Lys Phe Ala Ile Ser Gln Ser Ser Thr Gly
                    370                 375                 380

Thr Val Met Gly Ala Val Ile Met Glu Gly Phe Tyr Val Val Phe Asp
385                 390                 395                 400

Arg Ala Arg Lys Arg Ile Gly Phe Ala Val Ser Ala Cys His Val His
                    405                 410                 415

Asp Glu Phe Arg Thr Ala Ala Val Glu Gly Pro Phe Val Thr Leu Asp
                    420                 425                 430

Met Glu Asp Cys Gly Tyr Asn Ile Pro Gln Thr Asp Glu Ser
                    435                 440                 445

<210> SEQ ID NO 23
<211> LENGTH: 1380
<212> TYPE: DNA
<213> ORGANISM: Homo sapiens
```

<400> SEQUENCE: 23

```
atggctagca tgactggtgg acagcaaatg ggtcgcggat cgatgactat ctctgactct    60
ccgcgtgaac aggacggatc cacccagcac ggcatccggc tgcccctgcg cagcggcctg   120
gggggcgccc ccctggggct gcggctgccc cgggagaccg acgaagagcc cgaggagccc   180
ggccggaggg gcagctttgt ggagatggtg acaacctga gggcaagtc ggggcagggc    240
tactacgtgg agatgaccgt gggcagcccc ccgcagacgc tcaacatcct ggtggataca   300
ggcagcagta actttgcagt gggtgctgcc cccacccct tcctgcatcg ctactaccag    360
aggcagctgt ccagcacata ccgggacctc cggaagggtg tgtatgtgcc ctacacccag   420
ggcaagtggg aaggggagct gggcaccgac ctggtaagca tccccatgg ccccaacgtc    480
actgtgcgtg ccaacattgc tgccatcact gaatcagaca agttcttcat caacggctcc   540
aactgggaag catcctgggg ctggcctat gctgagattg ccaggcctga cgactccctg    600
gagcctttct ttgactctct ggtaaagcag acccacgttc caacctctt ctccctgcac    660
ctttgtggtg ctggcttccc cctcaaccag tctgaagtgc tggcctctgt cggagggagc   720
atgatcattg gaggtatcga ccactcgctg tacacaggca gtctctggta tacacccatc   780
cggcgggagt ggtattatga ggtcatcatt gtgcgggtgg agatcaatgg acaggatctg   840
aaaatggact gcaaggagta caactatgac aagagcattg tggacagtgg caccaccaac   900
cttcgtttgc ccaagaaagt gtttgaagct gcagtcaaat ccatcaaggc agcctcctcc   960
acggagaagt tccctgatgg tttctggcta ggagagcagc tggtgtgctg gcaagcaggc  1020
accacccctt ggaacatttt cccagtcatc tcactctacc taatgggtga ggttaccaac  1080
cagtccttcc gcatcaccat ccttccgcag caatacctgc ggccagtgga agatgtggcc  1140
acgtcccaag acgactgtta caagtttgcc atctcacagt catccacggg cactgttatg  1200
ggagctgtta tcatggaggg cttctacgtt gtctttgatc gggcccgaaa acgaattggc  1260
tttgctgtca gcgcttgcca tgtgcacgat gagttcagga cggcagcggt ggaaggccct  1320
tttgtcacct tggacatgga agactgtggc tacaacattc cacagacaga tgagtcatga  1380
```

<210> SEQ ID NO 24
<211> LENGTH: 459
<212> TYPE: PRT
<213> ORGANISM: Homo sapiens

<400> SEQUENCE: 24

```
Met Ala Ser Met Thr Gly Gly Gln Gln Met Gly Arg Gly Ser Met Thr
1               5                  10                  15

Ile Ser Asp Ser Pro Arg Glu Gln Asp Gly Ser Thr Gln His Gly Ile
            20                  25                  30

Arg Leu Pro Leu Arg Ser Gly Leu Gly Gly Ala Pro Leu Gly Leu Arg
        35                  40                  45

Leu Pro Arg Glu Thr Asp Glu Glu Pro Glu Glu Pro Gly Arg Arg Gly
    50                  55                  60

Ser Phe Val Glu Met Val Asp Asn Leu Arg Gly Lys Ser Gly Gln Gly
65                  70                  75                  80

Tyr Tyr Val Glu Met Thr Val Gly Ser Pro Pro Gln Thr Leu Asn Ile
                85                  90                  95

Leu Val Asp Thr Gly Ser Ser Asn Phe Ala Val Gly Ala Ala Pro His
            100                 105                 110

Pro Phe Leu His Arg Tyr Tyr Gln Arg Gln Leu Ser Ser Thr Tyr Arg
```

```
                    115                 120                 125
Asp Leu Arg Lys Gly Val Tyr Val Pro Tyr Thr Gln Gly Lys Trp Glu
    130                 135                 140

Gly Glu Leu Gly Thr Asp Leu Val Ser Ile Pro His Gly Pro Asn Val
145                 150                 155                 160

Thr Val Arg Ala Asn Ile Ala Ala Ile Thr Glu Ser Asp Lys Phe Phe
                165                 170                 175

Ile Asn Gly Ser Asn Trp Glu Gly Ile Leu Gly Leu Ala Tyr Ala Glu
            180                 185                 190

Ile Ala Arg Pro Asp Asp Ser Leu Glu Pro Phe Phe Asp Ser Leu Val
        195                 200                 205

Lys Gln Thr His Val Pro Asn Leu Phe Ser Leu His Leu Cys Gly Ala
    210                 215                 220

Gly Phe Pro Leu Asn Gln Ser Glu Val Leu Ala Ser Val Gly Gly Ser
225                 230                 235                 240

Met Ile Ile Gly Gly Ile Asp His Ser Leu Tyr Thr Gly Ser Leu Trp
                245                 250                 255

Tyr Thr Pro Ile Arg Arg Glu Trp Tyr Tyr Glu Val Ile Ile Val Arg
            260                 265                 270

Val Glu Ile Asn Gly Gln Asp Leu Lys Met Asp Cys Lys Glu Tyr Asn
        275                 280                 285

Tyr Asp Lys Ser Ile Val Asp Ser Gly Thr Thr Asn Leu Arg Leu Pro
    290                 295                 300

Lys Lys Val Phe Glu Ala Ala Val Lys Ser Ile Lys Ala Ala Ser Ser
305                 310                 315                 320

Thr Glu Lys Phe Pro Asp Gly Phe Trp Leu Gly Glu Gln Leu Val Cys
                325                 330                 335

Trp Gln Ala Gly Thr Thr Pro Trp Asn Ile Phe Pro Val Ile Ser Leu
            340                 345                 350

Tyr Leu Met Gly Glu Val Thr Asn Gln Ser Phe Arg Ile Thr Ile Leu
        355                 360                 365

Pro Gln Gln Tyr Leu Arg Pro Val Glu Asp Val Ala Thr Ser Gln Asp
    370                 375                 380

Asp Cys Tyr Lys Phe Ala Ile Ser Gln Ser Ser Thr Gly Thr Val Met
385                 390                 395                 400

Gly Ala Val Ile Met Glu Gly Phe Tyr Val Val Phe Asp Arg Ala Arg
                405                 410                 415

Lys Arg Ile Gly Phe Ala Val Ser Ala Cys His Val His Asp Glu Phe
            420                 425                 430

Arg Thr Ala Ala Val Glu Gly Pro Phe Val Thr Leu Asp Met Glu Asp
        435                 440                 445

Cys Gly Tyr Asn Ile Pro Gln Thr Asp Glu Ser
    450                 455

<210> SEQ ID NO 25
<211> LENGTH: 1302
<212> TYPE: DNA
<213> ORGANISM: Homo sapiens

<400> SEQUENCE: 25
atgactcagc atggtattcg tctgccactg cgtagcggtc tgggtggtgc tccactgggt    60
ctgcgtctgc cccgggagac cgacgaagag cccgaggagc ccggccggag gggcagcttt   120
gtggagatgg tggacaacct gaggggcaag tcggggcagg gctactacgt ggagatgacc   180
```

-continued

```
gtgggcagcc ccccgcagac gctcaacatc ctggtggata caggcagcag taactttgca    240
gtgggtgctg cccccacccc cttcctgcat cgctactacc agaggcagct gtccagcaca    300
taccgggacc tccggaaggg tgtgtatgtg ccctacaccc agggcaagtg ggaaggggag    360
ctgggcaccg acctggtaag catcccccat ggccccaacg tcactgtgcg tgccaacatt    420
gctgccatca ctgaatcaga caagttcttc atcaacggct ccaactggga aggcatcctg    480
gggctggcct atgctgagat tgccaggcct gacgactccc tggagccttt ctttgactct    540
ctggtaaagc agaccacgt tcccaacctc ttctccctgc accttgtgg tgctggcttc     600 cccctcaacc agtctgaagt gctggcctct gtcggaggga gcatgatcat tggaggtatc    660
gaccactcgc tgtacacagg cagtctctgg tatacaccca tccggcggga gtggtattat    720
gaggtcatca ttgtgcgggt ggagatcaat ggacaggatc tgaaaatgga ctgcaaggag    780
tacaactatg acaagagcat tgtggacagt ggcaccacca accttcgttt gcccaagaaa    840
gtgtttgaag ctgcagtcaa atccatcaag gcagcctcct ccacggagaa gttccctgat    900
ggtttctggc taggagagca gctggtgtgc tggcaagcag gcaccacccc ttggaacatt    960
ttcccagtca tctcactcta cctaatgggt gaggttacca accagtcctt ccgcatcacc    1020
atccttccgc agcaatacct gcggccagtg aagatgtgg ccacgtccca agacgactgt    1080
tacaagtttg ccatctcaca gtcatccacg ggcactgtta tgggagctgt tatcatggag    1140
ggcttctacg ttgtctttga tcgggcccga aaacgaattg gctttgctgt cagcgcttgc    1200
catgtgcacg atgagttcag gacggcagcg gtggaaggcc cttttgtcac cttggacatg    1260
gaagactgtg gctacaacat tccacagaca gatgagtcat ga                      1302
```

<210> SEQ ID NO 26
<211> LENGTH: 433
<212> TYPE: PRT
<213> ORGANISM: Homo sapiens

<400> SEQUENCE: 26

```
Met Thr Gln His Gly Ile Arg Leu Pro Leu Arg Ser Gly Leu Gly Gly
1               5                  10                  15

Ala Pro Leu Gly Leu Arg Leu Pro Arg Glu Thr Asp Glu Glu Pro Glu
            20                  25                  30

Glu Pro Gly Arg Arg Gly Ser Phe Val Glu Met Val Asp Asn Leu Arg
        35                  40                  45

Gly Lys Ser Gly Gln Gly Tyr Tyr Val Glu Met Thr Val Gly Ser Pro
    50                  55                  60

Pro Gln Thr Leu Asn Ile Leu Val Asp Thr Gly Ser Ser Asn Phe Ala
65                  70                  75                  80

Val Gly Ala Ala Pro His Pro Phe Leu His Arg Tyr Tyr Gln Arg Gln
                85                  90                  95

Leu Ser Ser Thr Tyr Arg Asp Leu Arg Lys Gly Val Tyr Val Pro Tyr
            100                 105                 110

Thr Gln Gly Lys Trp Glu Gly Glu Leu Gly Thr Asp Leu Val Ser Ile
        115                 120                 125

Pro His Gly Pro Asn Val Thr Val Arg Ala Asn Ile Ala Ala Ile Thr
    130                 135                 140

Glu Ser Asp Lys Phe Phe Ile Asn Gly Ser Asn Trp Glu Gly Ile Leu
145                 150                 155                 160

Gly Leu Ala Tyr Ala Glu Ile Ala Arg Pro Asp Asp Ser Leu Glu Pro
                165                 170                 175
```

-continued

```
Phe Phe Asp Ser Leu Val Lys Gln Thr His Val Pro Asn Leu Phe Ser
            180                 185                 190
Leu His Leu Cys Gly Ala Gly Phe Pro Leu Asn Gln Ser Glu Val Leu
        195                 200                 205
Ala Ser Val Gly Gly Ser Met Ile Ile Gly Gly Ile Asp His Ser Leu
    210                 215                 220
Tyr Thr Gly Ser Leu Trp Tyr Thr Pro Ile Arg Arg Glu Trp Tyr Tyr
225                 230                 235                 240
Glu Val Ile Ile Val Arg Val Glu Ile Asn Gly Gln Asp Leu Lys Met
                245                 250                 255
Asp Cys Lys Glu Tyr Asn Tyr Asp Lys Ser Ile Val Asp Ser Gly Thr
            260                 265                 270
Thr Asn Leu Arg Leu Pro Lys Lys Val Phe Glu Ala Ala Val Lys Ser
        275                 280                 285
Ile Lys Ala Ala Ser Ser Thr Glu Lys Phe Pro Asp Gly Phe Trp Leu
    290                 295                 300
Gly Glu Gln Leu Val Cys Trp Gln Ala Gly Thr Thr Pro Trp Asn Ile
305                 310                 315                 320
Phe Pro Val Ile Ser Leu Tyr Leu Met Gly Glu Val Thr Asn Gln Ser
                325                 330                 335
Phe Arg Ile Thr Ile Leu Pro Gln Gln Tyr Leu Arg Pro Val Glu Asp
            340                 345                 350
Val Ala Thr Ser Gln Asp Asp Cys Tyr Lys Phe Ala Ile Ser Gln Ser
        355                 360                 365
Ser Thr Gly Thr Val Met Gly Ala Val Ile Met Glu Gly Phe Tyr Val
    370                 375                 380
Val Phe Asp Arg Ala Arg Lys Arg Ile Gly Phe Ala Val Ser Ala Cys
385                 390                 395                 400
His Val His Asp Glu Phe Arg Thr Ala Ala Val Glu Gly Pro Phe Val
                405                 410                 415
Thr Leu Asp Met Glu Asp Cys Gly Tyr Asn Ile Pro Gln Thr Asp Glu
            420                 425                 430
Ser
```

<210> SEQ ID NO 27
<211> LENGTH: 1278
<212> TYPE: DNA
<213> ORGANISM: Homo sapiens

<400> SEQUENCE: 27

```
atggctagca tgactggtgg acagcaaatg ggtcgcggat cgatgactat ctctgactct      60
ccgctggact ctggtatcga aaccgacgga tcctttgtgg agatggtgga caacctgagg     120
ggcaagtcgg ggcagggcta ctacgtggag atgaccgtgg gcagcccccc gcagacgctc     180
aacatcctgg tggatacagg cagcagtaac tttgcagtgg gtgctgcccc caccccttc      240
ctgcatcgct actaccagag gcagctgtcc agcacatacc gggacctccg aagggtgtg      300
tatgtgccct acacccaggg caagtgggaa ggggagctgg gcaccgacct ggtaagcatc     360
ccccatggcc ccaacgtcac tgtgcgtgcc aacattgctg ccatcactga atcagacaag     420
ttcttcatca acggctccaa ctgggaaggc atcctgggc tggcctatgc tgagattgcc      480
aggcctgacg actccctgga gcctttcttt gactctctgg taaagcagac ccacgttccc     540
aacctcttct ccctgcacct tgtggtgct ggcttccccc tcaaccagtc tgaagtgctg      600
gcctctgtcg gagggagcat gatcattgga ggtatcgacc actcgctgta cacaggcagt     660
```

-continued

```
ctctggtata cacccatccg gcgggagtgg tattatgagg tcatcattgt gcgggtggag     720
atcaatggac aggatctgaa aatggactgc aaggagtaca actatgacaa gagcattgtg     780
gacagtggca ccaccaacct tcgtttgccc aagaaagtgt ttgaagctgc agtcaaatcc     840
atcaaggcag cctcctccac ggagaagttc cctgatggtt tctggctagg agagcagctg     900
gtgtgctggc aagcaggcac cacccttgg  aacattttcc cagtcatctc actctaccta     960
atgggtgagg ttaccaacca gtccttccgc atcaccatcc ttccgcagca atacctgcgg    1020
ccagtggaag atgtggccac gtcccaagac gactgttaca gtttgccat  ctcacagtca    1080 tccacgggca ctgttatggg agctgttatc atggagggct ctacgttgt  ctttgatcgg    1140 gcccgaaaac gaattggctt tgctgtcagc gcttgccatg tgcacgatga gttcaggacg    1200
gcagcggtgg aaggcccttt tgtcaccttg gacatggaag actgtggcta caacattcca    1260
cagacagatg agtcatga                                                  1278
```

<210> SEQ ID NO 28
<211> LENGTH: 425
<212> TYPE: PRT
<213> ORGANISM: Homo sapiens

<400> SEQUENCE: 28

```
Met Ala Ser Met Thr Gly Gly Gln Gln Met Gly Arg Gly Ser Met Thr
1               5                   10                  15

Ile Ser Asp Ser Pro Leu Asp Ser Gly Ile Glu Thr Asp Gly Ser Phe
            20                  25                  30

Val Glu Met Val Asp Asn Leu Arg Gly Lys Ser Gly Gln Gly Tyr Tyr
        35                  40                  45

Val Glu Met Thr Val Gly Ser Pro Pro Gln Thr Leu Asn Ile Leu Val
    50                  55                  60

Asp Thr Gly Ser Ser Asn Phe Ala Val Gly Ala Ala Pro His Pro Phe
65                  70                  75                  80

Leu His Arg Tyr Tyr Gln Arg Gln Leu Ser Ser Thr Tyr Arg Asp Leu
                85                  90                  95

Arg Lys Gly Val Tyr Val Pro Tyr Thr Gln Gly Lys Trp Glu Gly Glu
            100                 105                 110

Leu Gly Thr Asp Leu Val Ser Ile Pro His Gly Pro Asn Val Thr Val
        115                 120                 125

Arg Ala Asn Ile Ala Ala Ile Thr Glu Ser Asp Lys Phe Phe Ile Asn
    130                 135                 140

Gly Ser Asn Trp Glu Gly Ile Leu Gly Leu Ala Tyr Ala Glu Ile Ala
145                 150                 155                 160

Arg Pro Asp Asp Ser Leu Glu Pro Phe Phe Asp Ser Leu Val Lys Gln
                165                 170                 175

Thr His Val Pro Asn Leu Phe Ser Leu His Leu Cys Gly Ala Gly Phe
            180                 185                 190

Pro Leu Asn Gln Ser Glu Val Leu Ala Ser Val Gly Gly Ser Met Ile
        195                 200                 205

Ile Gly Gly Ile Asp His Ser Leu Tyr Thr Gly Ser Leu Trp Tyr Thr
    210                 215                 220

Pro Ile Arg Arg Glu Trp Tyr Tyr Glu Val Ile Ile Val Arg Val Glu
225                 230                 235                 240

Ile Asn Gly Gln Asp Leu Lys Met Asp Cys Lys Glu Tyr Asn Tyr Asp
                245                 250                 255
```

```
Lys Ser Ile Val Asp Ser Gly Thr Thr Asn Leu Arg Leu Pro Lys Lys
            260                 265                 270

Val Phe Glu Ala Ala Val Lys Ser Ile Lys Ala Ala Ser Ser Thr Glu
            275                 280                 285

Lys Phe Pro Asp Gly Phe Trp Leu Gly Glu Gln Leu Val Cys Trp Gln
            290                 295                 300

Ala Gly Thr Thr Pro Trp Asn Ile Phe Pro Val Ile Ser Leu Tyr Leu
305                 310                 315                 320

Met Gly Glu Val Thr Asn Gln Ser Phe Arg Ile Thr Ile Leu Pro Gln
                325                 330                 335

Gln Tyr Leu Arg Pro Val Glu Asp Val Ala Thr Ser Gln Asp Asp Cys
                340                 345                 350

Tyr Lys Phe Ala Ile Ser Gln Ser Ser Thr Gly Thr Val Met Gly Ala
            355                 360                 365

Val Ile Met Glu Gly Phe Tyr Val Val Phe Asp Arg Ala Arg Lys Arg
370                 375                 380

Ile Gly Phe Ala Val Ser Ala Cys His Val His Asp Glu Phe Arg Thr
385                 390                 395                 400

Ala Ala Val Glu Gly Pro Phe Val Thr Leu Asp Met Glu Asp Cys Gly
            405                 410                 415

Tyr Asn Ile Pro Gln Thr Asp Glu Ser
            420                 425

<210> SEQ ID NO 29
<211> LENGTH: 1362
<212> TYPE: DNA
<213> ORGANISM: Homo sapiens

<400> SEQUENCE: 29
atggcccaag ccctgccctg gctcctgctg tggatgggcg cgggagtgct gcctgcccac     60
ggcacccagc acggcatccg gctgcccctg cgcagcggcc tggggggcgc ccccctgggg    120
ctgcggctgc cccgggagac cgacgaagag cccgaggagc ccggccggag gggcagcttt    180
gtggagatgg tggacaacct gaggggcaag tcggggcagg gctactacgt ggagatgacc    240
gtgggcagcc ccccgcagac gctcaacatc ctggtggata caggcagcag taactttgca    300
gtgggtgctg ccccccaccc cttcctgcat cgctactacc agaggcagct gtccagcaca    360
taccgggacc tccggaaggg tgtgtatgtg ccctacaccc agggcaagtg ggaaggggag    420
ctgggcaccg acctggtaag catcccccat ggccccaacg tcactgtgcg tgccaacatt    480
gctgccatca ctgaatcaga caagttcttc atcaacggct ccaactggga aggcatcctg    540
gggctggcct atgctgagat tgccaggcct gacgactccc tggagccttt ctttgactct    600
ctggtaaagc agacccacgt tcccaacctc ttctccctgc acctttgtgg tgctggcttc    660
cccctcaacc agtctgaagt gctggcctct gtcggaggga gcatgatcat tggaggtatc    720
gaccactcgc tgtacacagg cagtctctgg tatacaccca tccggcggga gtggtattat    780
gaggtcatca ttgtgcgggt ggagatcaat ggacaggatc tgaaaatgga ctgcaaggag    840
tacaactatg acaagagcat tgtggacagt ggcaccacca accttcgttt gcccaagaaa    900
gtgtttgaag ctgcagtcaa atccatcaag gcagcctcct ccacgagaa gttccctgat    960 ggtttctggc taggagagca gctggtgtgc tggcaagcag gcaccacccc ttggaacatt   1020
ttcccagtca tctcactcta cctaatgggt gaggttacca accagtcctt ccgcatcacc   1080
atccttccgc agcaatacct gcggccagtg gaagatgtgg ccacgtccca agacgactgt   1140
```

-continued

```
tacaagtttg ccatctcaca gtcatccacg ggcactgtta tgggagctgt tatcatggag    1200
ggcttctacg ttgtctttga tcgggcccga aaacgaattg gctttgctgt cagcgcttgc    1260
catgtgcacg atgagttcag gacggcagcg gtggaaggcc cttttgtcac cttggacatg    1320
gaagactgtg gctacaacat tccacagaca gatgagtcat ga                       1362
```

<210> SEQ ID NO 30
<211> LENGTH: 453
<212> TYPE: PRT
<213> ORGANISM: Homo sapiens

<400> SEQUENCE: 30

```
Met Ala Gln Ala Leu Pro Trp Leu Leu Leu Trp Met Gly Ala Gly Val
1               5                   10                  15

Leu Pro Ala His Gly Thr Gln His Gly Ile Arg Leu Pro Leu Arg Ser
                20                  25                  30

Gly Leu Gly Gly Ala Pro Leu Gly Leu Arg Leu Pro Arg Glu Thr Asp
            35                  40                  45

Glu Glu Pro Glu Glu Pro Gly Arg Arg Gly Ser Phe Val Glu Met Val
        50                  55                  60

Asp Asn Leu Arg Gly Lys Ser Gly Gln Gly Tyr Tyr Val Glu Met Thr
65                  70                  75                  80

Val Gly Ser Pro Pro Gln Thr Leu Asn Ile Leu Val Asp Thr Gly Ser
                85                  90                  95

Ser Asn Phe Ala Val Gly Ala Ala Pro His Pro Phe Leu His Arg Tyr
                100                 105                 110

Tyr Gln Arg Gln Leu Ser Ser Thr Tyr Arg Asp Leu Arg Lys Gly Val
            115                 120                 125

Tyr Val Pro Tyr Thr Gln Gly Lys Trp Glu Gly Glu Leu Gly Thr Asp
        130                 135                 140

Leu Val Ser Ile Pro His Gly Pro Asn Val Thr Val Arg Ala Asn Ile
145                 150                 155                 160

Ala Ala Ile Thr Glu Ser Asp Lys Phe Phe Ile Asn Gly Ser Asn Trp
                165                 170                 175

Glu Gly Ile Leu Gly Leu Ala Tyr Ala Glu Ile Ala Arg Pro Asp Asp
                180                 185                 190

Ser Leu Glu Pro Phe Phe Asp Ser Leu Val Lys Gln Thr His Val Pro
            195                 200                 205

Asn Leu Phe Ser Leu Gln Leu Cys Gly Ala Gly Phe Pro Leu Asn Gln
        210                 215                 220

Ser Glu Val Leu Ala Ser Val Gly Gly Ser Met Ile Ile Gly Gly Ile
225                 230                 235                 240

Asp His Ser Leu Tyr Thr Gly Ser Leu Trp Tyr Thr Pro Ile Arg Arg
                245                 250                 255

Glu Trp Tyr Tyr Glu Val Ile Ile Val Arg Val Glu Ile Asn Gly Gln
                260                 265                 270

Asp Leu Lys Met Asp Cys Lys Glu Tyr Asn Tyr Asp Lys Ser Ile Val
            275                 280                 285

Asp Ser Gly Thr Thr Asn Leu Arg Leu Pro Lys Lys Val Phe Glu Ala
        290                 295                 300

Ala Val Lys Ser Ile Lys Ala Ala Ser Ser Thr Glu Lys Phe Pro Asp
305                 310                 315                 320

Gly Phe Trp Leu Gly Glu Gln Leu Val Cys Trp Gln Ala Gly Thr Thr
                325                 330                 335
```

```
Pro Trp Asn Ile Phe Pro Val Ile Ser Leu Tyr Leu Met Gly Glu Val
            340                 345                 350

Thr Asn Gln Ser Phe Arg Ile Thr Ile Leu Pro Gln Gln Tyr Leu Arg
            355                 360                 365

Pro Val Glu Asp Val Ala Thr Ser Gln Asp Asp Cys Tyr Lys Phe Ala
            370                 375                 380

Ile Ser Gln Ser Ser Thr Gly Thr Val Met Gly Ala Val Ile Met Glu
385                 390                 395                 400

Gly Phe Tyr Val Val Phe Asp Arg Ala Arg Lys Arg Ile Gly Phe Ala
                405                 410                 415

Val Ser Ala Cys His Val His Asp Glu Phe Arg Thr Ala Ala Val Glu
            420                 425                 430

Gly Pro Phe Val Thr Leu Asp Met Glu Asp Cys Gly Tyr Asn Ile Pro
            435                 440                 445

Gln Thr Asp Glu Ser
    450
```

<210> SEQ ID NO 31
<211> LENGTH: 1380
<212> TYPE: DNA
<213> ORGANISM: Homo sapiens

<400> SEQUENCE: 31

```
atggcccaag ccctgccctg ctcctgctg tggatgggcg cgggagtgct gcctgcccac        60
ggcacccagc acggcatccg gctgcccctg cgcagcggcc tggggggcgc ccccctgggg       120
ctgcggctgc cccgggagac cgacgaagag cccgaggagc ccggccggag gggcagcttt       180
gtggagatgg tggacaacct gaggggcaag tcggggcagg gctactacgt ggagatgacc       240
gtgggcagcc ccccgcagac gctcaacatc ctggtggata caggcagcag taactttgca       300
gtgggtgctg cccccacc cttcctgcat cgctactacc agaggcagct gtccagcaca        360
taccgggacc tccggaaggg tgtgtatgtg ccctacaccc agggcaagtg ggaaggggag       420
ctgggcaccg acctggtaag catcccccat ggccccaacg tcactgtgcg tgccaacatt       480
gctgccatca ctgaatcaga caagttcttc atcaacggct ccaactggga aggcatcctg       540
gggctggcct atgctgagat tgccaggcct gacgactccc tggagccttt ctttgactct       600
ctggtaaagc agacccacgt tcccaacctc ttctccctgc acctttgtgg tgctggcttc       660
cccctcaacc agtctgaagt gctggcctct gtcggaggga gcatgatcat tggaggtatc       720
gaccactcgc tgtacacagg cagtctctgg tatacaccca tccggcggga gtggtattat       780
gaggtcatca ttgtgcgggt ggagatcaat ggacaggatc tgaaaatgga ctgcaaggag       840
tacaactatg acaagagcat tgtggacagt ggcaccacca accttcgttt gcccaagaaa       900
gtgtttgaag ctgcagtcaa atccatcaag gcagcctcct ccacggagaa gttccctgat       960
ggtttctggc taggagagca gctggtgtgc tggcaagcag gcaccacccc ttggaacatt      1020
ttcccagtca tctcactcta cctaatgggt gaggttacca accagtcctt ccgcatcacc      1080
atccttccgc agcaatacct gcggccagtg aagatgtgg ccacgtccca agacgactgt      1140
tacaagtttg ccatctcaca gtcatccacg ggcactgtta tgggagctgt tatcatggag      1200
ggcttctacg ttgtctttga tcgggcccga aaacgaattg gctttgctgt cagcgcttgc      1260
catgtgcacg atgagttcag gacggcagcg gtggaaggcc cttttgtcac cttggacatg      1320
gaagactgtg gctacaacat tccacagaca gatgagtcac agcagcagca gcagcagtga      1380
```

<210> SEQ ID NO 32
<211> LENGTH: 459
<212> TYPE: PRT
<213> ORGANISM: Homo sapiens

<400> SEQUENCE: 32

```
Met Ala Gln Ala Leu Pro Trp Leu Leu Leu Trp Met Gly Ala Gly Val
1               5                   10                  15

Leu Pro Ala His Gly Thr Gln His Gly Ile Arg Leu Pro Leu Arg Ser
            20                  25                  30

Gly Leu Gly Gly Ala Pro Leu Gly Leu Arg Leu Pro Arg Glu Thr Asp
        35                  40                  45

Glu Pro Glu Glu Pro Gly Arg Arg Gly Ser Phe Val Glu Met Val
50                  55                  60

Asp Asn Leu Arg Gly Lys Ser Gly Gln Gly Tyr Tyr Val Glu Met Thr
65                  70                  75                  80

Val Gly Ser Pro Pro Gln Thr Leu Asn Ile Leu Val Asp Thr Gly Ser
                85                  90                  95

Ser Asn Phe Ala Val Gly Ala Ala Pro His Pro Phe Leu His Arg Tyr
            100                 105                 110

Tyr Gln Arg Gln Leu Ser Ser Thr Tyr Arg Asp Leu Arg Lys Gly Val
        115                 120                 125

Tyr Val Pro Tyr Thr Gln Gly Lys Trp Glu Gly Glu Leu Gly Thr Asp
    130                 135                 140

Leu Val Ser Ile Pro His Gly Pro Asn Val Thr Val Arg Ala Asn Ile
145                 150                 155                 160

Ala Ala Ile Thr Glu Ser Asp Lys Phe Phe Ile Asn Gly Ser Asn Trp
                165                 170                 175

Glu Gly Ile Leu Gly Leu Ala Tyr Ala Glu Ile Ala Arg Pro Asp Asp
            180                 185                 190

Ser Leu Glu Pro Phe Phe Asp Ser Leu Val Lys Gln Thr His Val Pro
        195                 200                 205

Asn Leu Phe Ser Leu Gln Leu Cys Gly Ala Gly Phe Pro Leu Asn Gln
    210                 215                 220

Ser Glu Val Leu Ala Ser Val Gly Gly Ser Met Ile Ile Gly Gly Ile
225                 230                 235                 240

Asp His Ser Leu Tyr Thr Gly Ser Leu Trp Tyr Thr Pro Ile Arg Arg
                245                 250                 255

Glu Trp Tyr Tyr Glu Val Ile Ile Val Arg Val Glu Ile Asn Gly Gln
            260                 265                 270

Asp Leu Lys Met Asp Cys Lys Glu Tyr Asn Tyr Asp Lys Ser Ile Val
        275                 280                 285

Asp Ser Gly Thr Thr Asn Leu Arg Leu Pro Lys Lys Val Phe Glu Ala
    290                 295                 300

Ala Val Lys Ser Ile Lys Ala Ala Ser Ser Thr Glu Lys Phe Pro Asp
305                 310                 315                 320

Gly Phe Trp Leu Gly Glu Gln Leu Val Cys Trp Gln Ala Gly Thr Thr
                325                 330                 335

Pro Trp Asn Ile Phe Pro Val Ile Ser Leu Tyr Leu Met Gly Glu Val
            340                 345                 350

Thr Asn Gln Ser Phe Arg Ile Thr Ile Leu Pro Gln Gln Tyr Leu Arg
        355                 360                 365

Pro Val Glu Asp Val Ala Thr Ser Gln Asp Asp Cys Tyr Lys Phe Ala
    370                 375                 380
```

-continued

```
Ile Ser Gln Ser Ser Thr Gly Thr Val Met Gly Ala Val Ile Met Glu
385                 390                 395                 400

Gly Phe Tyr Val Val Phe Asp Arg Ala Arg Lys Arg Ile Gly Phe Ala
            405                 410                 415

Val Ser Ala Cys His Val His Asp Glu Phe Arg Thr Ala Ala Val Glu
        420                 425                 430

Gly Pro Phe Val Thr Leu Asp Met Glu Asp Cys Gly Tyr Asn Ile Pro
    435                 440                 445

Gln Thr Asp Glu Ser His His His His His
    450                 455
```

<210> SEQ ID NO 33
<211> LENGTH: 25
<212> TYPE: PRT
<213> ORGANISM: Homo sapiens

<400> SEQUENCE: 33

```
Ser Glu Gln Gln Arg Arg Pro Arg Asp Pro Glu Val Val Asn Asp Glu
1               5                   10                  15

Ser Ser Leu Val Arg His Arg Trp Lys
            20                  25
```

<210> SEQ ID NO 34
<211> LENGTH: 19
<212> TYPE: PRT
<213> ORGANISM: Homo sapiens

<400> SEQUENCE: 34

```
Ser Glu Gln Leu Arg Gln Gln His Asp Asp Phe Ala Asp Asp Ile Ser
1               5                   10                  15

Leu Leu Lys
```

<210> SEQ ID NO 35
<211> LENGTH: 29
<212> TYPE: DNA
<213> ORGANISM: Homo sapiens

<400> SEQUENCE: 35
gtggatccac ccagcacggc atccggctg                                  29

<210> SEQ ID NO 36
<211> LENGTH: 36
<212> TYPE: DNA
<213> ORGANISM: Homo sapiens

<400> SEQUENCE: 36
gaaagctttc atgactcatc tgtctgtgga atgttg                          36

<210> SEQ ID NO 37
<211> LENGTH: 39
<212> TYPE: DNA
<213> ORGANISM: Homo sapiens

<400> SEQUENCE: 37
gatcgatgac tatctctgac tctccgcgtg aacaggacg                       39

<210> SEQ ID NO 38
<211> LENGTH: 39
<212> TYPE: DNA
<213> ORGANISM: Homo sapiens

<400> SEQUENCE: 38

```
gatccgtcct gttcacgcgg agagtcagag atagtcatc          39
```

<210> SEQ ID NO 39
<211> LENGTH: 77
<212> TYPE: DNA
<213> ORGANISM: Artificial sequence
<220> FEATURE:
<223> OTHER INFORMATION: Hu-Asp2

<400> SEQUENCE: 39

```
cggcatccgg ctgcccctgc gtagcggtct gggtggtgct ccactgggtc tgcgtctgcc    60
ccgggagacc gacgaag                                                   77
```

<210> SEQ ID NO 40
<211> LENGTH: 77
<212> TYPE: DNA
<213> ORGANISM: Artificial sequence
<220> FEATURE:
<223> OTHER INFORMATION: Hu-Asp2

<400> SEQUENCE: 40

```
cttcgtcggt ctcccggggc agacgcagac ccagtggagc accacccaga ccgctacgca    60
ggggcagccg gatgccg                                                   77
```

<210> SEQ ID NO 41
<211> LENGTH: 51
<212> TYPE: DNA
<213> ORGANISM: Artificial sequence
<220> FEATURE:
<223> OTHER INFORMATION: Caspase-8 Cleavage Site

<400> SEQUENCE: 41

```
gatcgatgac tatctctgac tctccgctgg actctggtat cgaaaccgac g             51
```

<210> SEQ ID NO 42
<211> LENGTH: 51
<212> TYPE: DNA
<213> ORGANISM: Artificial sequence
<220> FEATURE:
<223> OTHER INFORMATION: Caspase-8 Cleavage Site

<400> SEQUENCE: 42

```
gatccgtcgg tttcgatacc agagtccagc ggagagtcag agatagtcat c             51
```

<210> SEQ ID NO 43
<211> LENGTH: 32
<212> TYPE: DNA
<213> ORGANISM: Homo sapiens

<400> SEQUENCE: 43

```
aaggatcctt tgtggagatg gtggacaacc tg                                  32
```

<210> SEQ ID NO 44
<211> LENGTH: 36
<212> TYPE: DNA
<213> ORGANISM: Homo sapiens

<400> SEQUENCE: 44

```
gaaagctttc atgactcatc tgtctgtgga atgttg                              36
```

<210> SEQ ID NO 45
<211> LENGTH: 24
<212> TYPE: DNA

```
<213> ORGANISM: Artificial sequence
<220> FEATURE:
<223> OTHER INFORMATION: 6-His tag

<400> SEQUENCE: 45
gatcgcatca tcaccatcac catg                                              24

<210> SEQ ID NO 46
<211> LENGTH: 24
<212> TYPE: DNA
<213> ORGANISM: Artificial sequence
<220> FEATURE:
<223> OTHER INFORMATION: 6-His tag

<400> SEQUENCE: 46
gatccatggt gatggtgatg atgc                                              24

<210> SEQ ID NO 47
<211> LENGTH: 22
<212> TYPE: DNA
<213> ORGANISM: Artificial sequence
<220> FEATURE:
<223> OTHER INFORMATION: Primer

<400> SEQUENCE: 47
gactgaccac tcgaccaggt tc                                                22

<210> SEQ ID NO 48
<211> LENGTH: 51
<212> TYPE: DNA
<213> ORGANISM: Artificial sequence
<220> FEATURE:
<223> OTHER INFORMATION: Primer

<400> SEQUENCE: 48
cgaattaaat tccagcacac tggctacttc ttgttctgca tctcaaagaa c                 51

<210> SEQ ID NO 49
<211> LENGTH: 26
<212> TYPE: DNA
<213> ORGANISM: Artificial sequence
<220> FEATURE:
<223> OTHER INFORMATION: Primer

<400> SEQUENCE: 49
cgaattaaat tccagcacac tggcta                                            26

<210> SEQ ID NO 50
<211> LENGTH: 1287
<212> TYPE: DNA
<213> ORGANISM: Artificial sequence
<220> FEATURE:
<223> OTHER INFORMATION: Hu-Asp2(b) delta TM

<400> SEQUENCE: 50
atggcccaag ccctgccctg gctcctgctg tggatgggcg cggagtgct gcctgcccac         60 ggcacccagc acggcatccg gctgcccctg cgcagcggcc tggggggcgc ccccctgggg       120
ctgcggctgc ccggagac cgacgaagag cccgaggagc ccggccggag gggcagcttt         180
gtggagatgg tggacaacct gaggggcaag tcggggcagg gctactacgt ggagatgacc       240
gtgggcagcc cccgcagac gctcaacatc ctggtggata caggcagcag taacttttgca       300 gtgggtgctg ccccccaccc cttcctgcat cgctactacc agaggcagct gtccagcaca       360
taccgggacc tccggaaggg tgtgtatatgt ccctacaccc agggcaagtg ggaaggggag       420
```

```
ctgggcaccg aacctggtaag catcccccat ggccccaacg tcactgtgcg tgccaacatt    480
gctgccatca ctgaatcaga caagttcttc atcaacggct ccaactggga aggcatcctg    540
gggctggcct atgctgagat tgccaggctt tgtggtgctg gcttcccct  caaccagtct    600
gaagtgctgg cctctgtcgg agggagcatg atcattggag gtatcgacca ctcgctgtac    660
acaggcagtc tctggtatac acccatccgg cgggagtggt attatgaggt catcattgtg    720
cgggtggaga tcaatggaca ggatctgaaa atggactgca aggagtacaa ctatgacaag    780
agcattgtgg acagtggcac caccaacctt cgtttgccca agaaagtgtt tgaagctgca    840
gtcaaatcca tcaaggcagc ctcctccacg gagaagttcc ctgatggttt ctggctagga    900
gagcagctgg tgtgctggca agcaggcacc acccttgga acattttccc agtcatctca    960
ctctacctaa tgggtgaggt taccaaccag tccttccgca tcaccatcct tccgcagcaa   1020
tacctgcggc cagtggaaga tgtggccacg tcccaagacg actgttacaa gtttgccatc   1080
tcacagtcat ccacgggcac tgttatggga gctgttatca tggagggctt ctacgttgtc   1140
tttgatcggg cccgaaaacg aattggcttt gctgtcagcg cttgccatgt gcacgatgag   1200
ttcaggacgg cagcggtgga aggccctttt gtcaccttgg acatggaaga ctgtggctac   1260
aacattccac agacagatga gtcatga                                         1287

<210> SEQ ID NO 51
<211> LENGTH: 428
<212> TYPE: PRT
<213> ORGANISM: Artificial sequence
<220> FEATURE:
<223> OTHER INFORMATION: Hu-Asp2(b) delta TM

<400> SEQUENCE: 51

Met Ala Gln Ala Leu Pro Trp Leu Leu Leu Trp Met Gly Ala Gly Val
1               5                   10                  15

Leu Pro Ala His Gly Thr Gln His Gly Ile Arg Leu Pro Leu Arg Ser
            20                  25                  30

Gly Leu Gly Gly Ala Pro Leu Gly Leu Arg Leu Pro Arg Glu Thr Asp
        35                  40                  45

Glu Glu Pro Glu Glu Pro Gly Arg Arg Gly Ser Phe Val Glu Met Val
    50                  55                  60

Asp Asn Leu Arg Gly Lys Ser Gly Gln Gly Tyr Tyr Val Glu Met Thr
65                  70                  75                  80

Val Gly Ser Pro Pro Gln Thr Leu Asn Ile Leu Val Asp Thr Gly Ser
                85                  90                  95

Ser Asn Phe Ala Val Gly Ala Ala Pro His Pro Phe Leu His Arg Tyr
            100                 105                 110

Tyr Gln Arg Gln Leu Ser Ser Thr Tyr Arg Asp Leu Arg Lys Gly Val
        115                 120                 125

Tyr Val Pro Tyr Thr Gln Gly Lys Trp Glu Gly Glu Leu Gly Thr Asp
    130                 135                 140

Leu Val Ser Ile Pro His Gly Pro Asn Val Thr Val Arg Ala Asn Ile
145                 150                 155                 160

Ala Ala Ile Thr Glu Ser Asp Lys Phe Phe Ile Asn Gly Ser Asn Trp
                165                 170                 175

Glu Gly Ile Leu Gly Leu Ala Tyr Ala Glu Ile Ala Arg Leu Cys Gly
            180                 185                 190

Ala Gly Phe Pro Leu Asn Gln Ser Glu Val Leu Ala Ser Val Gly Gly
        195                 200                 205
```

-continued

```
Ser Met Ile Ile Gly Gly Ile Asp His Ser Leu Tyr Thr Gly Ser Leu
    210                 215                 220
Trp Tyr Thr Pro Ile Arg Arg Glu Trp Tyr Tyr Glu Val Ile Ile Val
225                 230                 235                 240
Arg Val Glu Ile Asn Gly Gln Asp Leu Lys Met Asp Cys Lys Glu Tyr
                245                 250                 255
Asn Tyr Asp Lys Ser Ile Val Asp Ser Gly Thr Thr Asn Leu Arg Leu
            260                 265                 270
Pro Lys Lys Val Phe Glu Ala Ala Val Lys Ser Ile Lys Ala Ala Ser
        275                 280                 285
Ser Thr Glu Lys Phe Pro Asp Gly Phe Trp Leu Gly Glu Gln Leu Val
    290                 295                 300
Cys Trp Gln Ala Gly Thr Thr Pro Trp Asn Ile Phe Pro Val Ile Ser
305                 310                 315                 320
Leu Tyr Leu Met Gly Glu Val Thr Asn Gln Ser Phe Arg Ile Thr Ile
                325                 330                 335
Leu Pro Gln Gln Tyr Leu Arg Pro Val Glu Asp Val Ala Thr Ser Gln
            340                 345                 350
Asp Asp Cys Tyr Lys Phe Ala Ile Ser Gln Ser Ser Thr Gly Thr Val
        355                 360                 365
Met Gly Ala Val Ile Met Glu Gly Phe Tyr Val Val Phe Asp Arg Ala
    370                 375                 380
Arg Lys Arg Ile Gly Phe Ala Val Ser Ala Cys His Val His Asp Glu
385                 390                 395                 400
Phe Arg Thr Ala Ala Val Glu Gly Pro Phe Val Thr Leu Asp Met Glu
                405                 410                 415
Asp Cys Gly Tyr Asn Ile Pro Gln Thr Asp Glu Ser
            420                 425
```

<210> SEQ ID NO 52
<211> LENGTH: 1305
<212> TYPE: DNA
<213> ORGANISM: Artificial sequence
<220> FEATURE:
<223> OTHER INFORMATION: Hu-Asp2(b) delta TM

<400> SEQUENCE: 52

```
atggcccaag ccctgccctg ctcctgctg tggatgggcg cgggagtgct gcctgcccac    60
ggcacccagc acggcatccg gctgccctg cgcagcggcc tgggggcgc ccccctgggg   120
ctgcggctgc cccgggagac cgacgaagag cccgaggagc ccggccggag gggcagcttt   180
gtggagatgg tggacaacct gaggggcaag tcggggcagg gctactacgt ggagatgacc   240
gtgggcagcc ccccgcagac gctcaacatc ctggtggata caggcagcag taactttgca   300
gtgggtgctg ccccccaccc cttcctgcat cgctactacc agaggcagct gtccagcaca   360
taccgggacc tccggaaggg tgtgtatgtg ccctacaccc agggcaagtg ggaaggggag   420
ctgggcaccg acctggtaag catcccccat ggccccaacg tcactgtgcg tgccaacatt   480
gctgccatca ctgaatcaga caagttcttc atcaacggct ccaactggga aggcatcctg   540
gggctggcct atgctgagat tgccaggctt gtggtgctg gcttcccct caaccagtct   600
gaagtgctgg cctctgtcgg agggagcatg atcattggag gtatcgacca ctcgctgtac   660
acaggcagtc tctggtatac acccatccgg cgggagtggt attatgaggt catcattgtg   720
cgggtggaga tcaatggaca ggatctgaaa atggactgca aggagtacaa ctatgacaag   780
```

```
agcattgtgg acagtggcac caccaacctt cgtttgccca agaaagtgtt tgaagctgca    840
gtcaaatcca tcaaggcagc ctcctccacg gagaagttcc ctgatggttt ctggctagga    900
gagcagctgg tgtgctggca agcaggcacc acccttgga acattttccc agtcatctca    960
ctctacctaa tgggtgaggt taccaaccag tccttccgca tcaccatcct tccgcagcaa   1020
tacctgcggc cagtgaaga tgtggccacg tcccaagacg actgttacaa gtttgccatc   1080
tcacagtcat ccacgggcac tgttatggga gctgttatca tggagggctt ctacgttgtc   1140
tttgatcggg cccgaaaacg aattggcttt gctgtcagcg cttgccatgt gcacgatgag   1200
ttcaggacgg cagcggtgga aggccctttt gtcaccttgg acatggaaga ctgtggctac   1260
aacattccac agacagatga gtcacagcag cagcagcagc agtga               1305
```

<210> SEQ ID NO 53
<211> LENGTH: 434
<212> TYPE: PRT
<213> ORGANISM: Artificial sequence
<220> FEATURE:
<223> OTHER INFORMATION: Hu-Asp2(b) delta TM

<400> SEQUENCE: 53

```
Met Ala Gln Ala Leu Pro Trp Leu Leu Leu Trp Met Gly Ala Gly Val
  1               5                  10                  15

Leu Pro Ala His Gly Thr Gln His Gly Ile Arg Leu Pro Leu Arg Ser
                 20                  25                  30

Gly Leu Gly Gly Ala Pro Leu Gly Leu Arg Leu Pro Arg Glu Thr Asp
             35                  40                  45

Glu Glu Pro Glu Glu Pro Gly Arg Arg Gly Ser Phe Val Glu Met Val
         50                  55                  60

Asp Asn Leu Arg Gly Lys Ser Gly Gln Gly Tyr Tyr Val Glu Met Thr
 65                  70                  75                  80

Val Gly Ser Pro Pro Gln Thr Leu Asn Ile Leu Val Asp Thr Gly Ser
                 85                  90                  95

Ser Asn Phe Ala Val Gly Ala Ala Pro His Pro Phe Leu His Arg Tyr
            100                 105                 110

Tyr Gln Arg Gln Leu Ser Ser Thr Tyr Arg Asp Leu Arg Lys Gly Val
        115                 120                 125

Tyr Val Pro Tyr Thr Gln Gly Lys Trp Glu Gly Glu Leu Gly Thr Asp
    130                 135                 140

Leu Val Ser Ile Pro His Gly Pro Asn Val Thr Val Arg Ala Asn Ile
145                 150                 155                 160

Ala Ala Ile Thr Glu Ser Asp Lys Phe Phe Ile Asn Gly Ser Asn Trp
                165                 170                 175

Glu Gly Ile Leu Gly Leu Ala Tyr Ala Glu Ile Ala Arg Leu Cys Gly
            180                 185                 190

Ala Gly Phe Pro Leu Asn Gln Ser Glu Val Leu Ala Ser Val Gly Gly
        195                 200                 205

Ser Met Ile Ile Gly Gly Ile Asp His Ser Leu Tyr Thr Gly Ser Leu
    210                 215                 220

Trp Tyr Thr Pro Ile Arg Arg Glu Trp Tyr Tyr Glu Val Ile Ile Val
225                 230                 235                 240

Arg Val Glu Ile Asn Gly Gln Asp Leu Lys Met Asp Cys Lys Glu Tyr
                245                 250                 255

Asn Tyr Asp Lys Ser Ile Val Asp Ser Gly Thr Thr Asn Leu Arg Leu
            260                 265                 270
```

```
              Pro Lys Lys Val Phe Glu Ala Ala Val Lys Ser Ile Lys Ala Ala Ser
                  275                 280                 285

Ser Thr Glu Lys Phe Pro Asp Gly Phe Trp Leu Gly Glu Gln Leu Val
                  290                 295                 300

Cys Trp Gln Ala Gly Thr Thr Pro Trp Asn Ile Phe Pro Val Ile Ser
              305                 310                 315                 320

Leu Tyr Leu Met Gly Glu Val Thr Asn Gln Ser Phe Arg Ile Thr Ile
                                  325                 330                 335

Leu Pro Gln Gln Tyr Leu Arg Pro Val Glu Asp Val Ala Thr Ser Gln
                                  340                 345                 350

Asp Asp Cys Tyr Lys Phe Ala Ile Ser Gln Ser Ser Thr Gly Thr Val
                              355                 360                 365

Met Gly Ala Val Ile Met Glu Gly Phe Tyr Val Val Phe Asp Arg Ala
                          370                 375                 380

Arg Lys Arg Ile Gly Phe Ala Val Ser Ala Cys His Val His Asp Glu
              385                 390                 395                 400

Phe Arg Thr Ala Ala Val Glu Gly Pro Phe Val Thr Leu Asp Met Glu
                                  405                 410                 415

Asp Cys Gly Tyr Asn Ile Pro Gln Thr Asp Glu Ser His His His His
                              420                 425                 430

His His

<210> SEQ ID NO 54
<211> LENGTH: 2310
<212> TYPE: DNA
<213> ORGANISM: Homo sapiens

<400> SEQUENCE: 54
atgctgcccg gtttggcact gctcctgctg ccgcctggaa cggctcgggc gctggaggta      60
cccactgatg gtaatgctgg cctgctggct gaaccccaga ttgccatgtt ctgtggcaga     120
ctgaacatgc acatgaatgt ccagaatggg aagtgggatt cagatccatc agggaccaaa     180
acctgcattg ataccaagga aggcatcctg cagtattgcc aagaagtcta ccctgaactg     240
cagatcacca atgtggtaga agccaaccaa ccagtgacca tccagaactg gtgcaagcgg     300
ggccgcaagc agtgcaagac ccatccccac tttgtgattc cctaccgctg cttagttggt     360
gagtttgtaa gtgatgccct tctcgttcct gacaagtgca aattcttaca ccaggagagg     420
atggatgttt gcgaaactca tcttcactgg cacaccgtcg ccaaagagac atgcagtgag     480
aagagtacca acttgcatga ctacggcatg ttgctgccct gcggaattga caagttccga     540
ggggtagagt ttgtgtgttg cccactggct gaagaaagtg acaatgtgga ttctgctgat     600
gcggaggagg atgactcgga tgtctggtgg ggcggagcag acacagacta tgcagatggg     660
agtgaagaca agtagtagaa gtagcagagg aggaagaagt ggctgaggtg gaagaagaa      720 gaagccgatg atgacgagga cgatgaggat ggtgatgagg tagaggaaga ggctgaggaa     780
ccctacgaag aagccacaga gagaaccacc agcattgcca ccaccaccac caccaccaca     840
gagtctgtgg aagaggtggt tcgagaggtg tgctctgaac aagccgagac ggggccgtgc     900
cgagcaatga tctcccgctg gtactttgat gtgactgaag ggaagtgtgc cccattcttt     960
tacggcggat gtgcggcaa ccggaacaac tttgacacag aagagtactg catgccgtg     1020 tgtggcagcg ccatgtccca agtttactc aagactaccc aggaacctct ggccgagat     1080 cctgttaaac ttcctacaac agcagccagt cccctgatg ccgttgacaa gtatctcgag     1140
acacctgggg atgagaatga acatgcccat ttccagaaag ccaaagagag gcttgaggcc     1200
```

-continued

```
aagcaccgag agagaatgtc ccaggtcatg agagaatggg aagaggcaga acgtcaagca    1260
aagaacttgc ctaaagctga taagaaggca gttatccagc atttccagga gaaagtggaa    1320
tctttggaac aggaagcagc caacgagaga cagcagctgg tggagacaca catggccaga    1380
gtggaagcca tgctcaatga ccgccgccgc ctggccctgg agaactacat caccgctctg    1440
caggctgttc ctcctcggcc tcgtcacgtg ttcaatatgc taaagaagta tgtccgcgca    1500
gaacagaagg acagacagca cccctaaag catttcgagc atgtgcgcat ggtggatccc     1560
aagaaagccg ctcagatccg gtcccaggtt atgacacacc tccgtgtgat ttatgagcgc    1620
atgaatcagt ctctctccct gctctacaac gtgcctgcag tggccgagga gattcaggat    1680
gaagttgatg agctgcttca gaaagagcaa aactattcag atgacgtctt ggccaacatg    1740
attagtgaac caaggatcag ttacggaaac gatgctctca tgccatcttt gaccgaaacg    1800
aaaaccaccg tggagctcct tcccgtgaat ggagagttca gcctggacga tctccagccg    1860
tggcattctt ttggggctga ctctgtgcca gccaacacag aaaacgaagt tgagcctgtt    1920
gatgcccgcc ctgctgccga ccgaggacta ccactcgac caggttctgg gttgacaaat     1980
atcaagacgg aggagatctc tgaagtgaag atggatgcag aattccgaca tgactcagga    2040
tatgaagttc atcatcaaaa attggtgttc tttgcagaag atgtgggttc aaacaaaggt    2100
gcaatcattg gactcatggt gggcggtgtt gtcatagcga cagtgatcgt catcaccttg    2160
gtgatgctga agaagaaaca gtacacatcc attcatcatg gtgtggtgga ggttgacgcc    2220
gctgtcaccc cagaggagcg ccacctgtcc aagatgcagc agaacggcta cgaaaatcca    2280
acctacaagt tctttgagca gatgcagaac                                     2310
```

<210> SEQ ID NO 55
<211> LENGTH: 770
<212> TYPE: PRT
<213> ORGANISM: Homo sapiens

<400> SEQUENCE: 55

```
Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175
```

-continued

```
Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Ser Asp Val
        195                 200                 205

Trp Trp Gly Gly Ala Asp Thr Asp Tyr Ala Asp Gly Ser Glu Asp Lys
            210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Ala Thr Glu Arg Thr Thr Ser Ile
            260                 265                 270

Ala Thr Thr Thr Thr Thr Thr Glu Ser Val Glu Glu Val Val Arg
            275                 280                 285

Glu Val Cys Ser Glu Gln Ala Glu Thr Gly Pro Cys Arg Ala Met Ile
            290                 295                 300

Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
                325                 330                 335

Cys Met Ala Val Cys Gly Ser Ala Met Ser Gln Ser Leu Leu Lys Thr
            340                 345                 350

Thr Gln Glu Pro Leu Ala Arg Asp Pro Val Lys Leu Pro Thr Thr Ala
        355                 360                 365

Ala Ser Thr Pro Asp Ala Val Asp Lys Tyr Leu Glu Thr Pro Gly Asp
    370                 375                 380

Glu Asn Glu His Ala His Phe Gln Lys Ala Lys Glu Arg Leu Glu Ala
385                 390                 395                 400

Lys His Arg Glu Arg Met Ser Gln Val Met Arg Glu Trp Glu Glu Ala
                405                 410                 415

Glu Arg Gln Ala Lys Asn Leu Pro Lys Ala Asp Lys Lys Ala Val Ile
            420                 425                 430

Gln His Phe Gln Glu Lys Val Glu Ser Leu Glu Gln Glu Ala Ala Asn
        435                 440                 445

Glu Arg Gln Gln Leu Val Glu Thr His Met Ala Arg Val Glu Ala Met
    450                 455                 460

Leu Asn Asp Arg Arg Arg Leu Ala Leu Glu Asn Tyr Ile Thr Ala Leu
465                 470                 475                 480

Gln Ala Val Pro Pro Arg Pro Arg His Val Phe Asn Met Leu Lys Lys
                485                 490                 495

Tyr Val Arg Ala Glu Gln Lys Asp Arg Gln His Thr Leu Lys His Phe
            500                 505                 510

Glu His Val Arg Met Val Asp Pro Lys Lys Ala Ala Gln Ile Arg Ser
        515                 520                 525

Gln Val Met Thr His Leu Arg Val Ile Tyr Glu Arg Met Asn Gln Ser
    530                 535                 540

Leu Ser Leu Leu Tyr Asn Val Pro Ala Val Ala Glu Glu Ile Gln Asp
545                 550                 555                 560

Glu Val Asp Glu Leu Leu Gln Lys Glu Gln Asn Tyr Ser Asp Asp Val
                565                 570                 575

Leu Ala Asn Met Ile Ser Glu Pro Arg Ile Ser Tyr Gly Asn Asp Ala
            580                 585                 590
```

```
Leu Met Pro Ser Leu Thr Glu Thr Lys Thr Val Glu Leu Leu Pro
        595                 600                 605

Val Asn Gly Glu Phe Ser Leu Asp Asp Leu Gln Pro Trp His Ser Phe
    610                 615                 620

Gly Ala Asp Ser Val Pro Ala Asn Thr Glu Asn Glu Val Glu Pro Val
625                 630                 635                 640

Asp Ala Arg Pro Ala Ala Asp Arg Gly Leu Thr Thr Arg Pro Gly Ser
                645                 650                 655

Gly Leu Thr Asn Ile Lys Thr Glu Glu Ile Ser Glu Val Lys Met Asp
            660                 665                 670

Ala Glu Phe Arg His Asp Ser Gly Tyr Glu Val His His Gln Lys Leu
        675                 680                 685

Val Phe Phe Ala Glu Asp Val Gly Ser Asn Lys Gly Ala Ile Ile Gly
    690                 695                 700

Leu Met Val Gly Gly Val Val Ile Ala Thr Val Ile Val Ile Thr Leu
705                 710                 715                 720

Val Met Leu Lys Lys Lys Gln Tyr Thr Ser Ile His His Gly Val Val
                725                 730                 735

Glu Val Asp Ala Ala Val Thr Pro Glu Glu Arg His Leu Ser Lys Met
            740                 745                 750

Gln Gln Asn Gly Tyr Glu Asn Pro Thr Tyr Lys Phe Phe Glu Gln Met
        755                 760                 765

Gln Asn
    770

<210> SEQ ID NO 56
<211> LENGTH: 2253
<212> TYPE: DNA
<213> ORGANISM: Homo sapiens

<400> SEQUENCE: 56
atgctgcccg gtttggcact gctcctgctg ccgcctggac ggctcgggc gctggaggta      60 cccactgatg gtaatgctgg cctgctggct gaaccccaga ttgccatgtt ctgtggcaga    120
ctgaacatgc acatgaatgt ccagaatggg aagtgggatt cagatccatc agggaccaaa    180
acctgcattg ataccaagga aggcatcctg cagtattgcc aagaagtcta ccctgaactg    240
cagatcacca atgtggtaga agccaaccaa ccagtgacca tccagaactg gtgcaagcgg    300
ggccgcaagc agtgcaagac ccatccccac tttgtgattc cctaccgctg cttagttggt    360
gagtttgtaa gtgatgccct tctcgttcct gacaagtgca aattcttaca ccaggagagg    420
atggatgttt gcgaaactca tcttcactgg cacaccgtcg ccaaagagac atgcagtgag    480
aagagtacca acttgcatga ctacggcatg ttgctgccct gcggaattga caagttccga    540
ggggtagagt ttgtgtgttg cccactggct gaagaaagtg acaatgtgga ttctgctgat    600
gcggaggagg atgactcgga tgtctggtgg ggcggagcag acacagacta tgcagatggg    660
agtgaagaca agtagtagaa gtagcagag aggaagaag tggctgaggt ggaagaagaa    720
gaagccgatg atgacgagga cgatgaggat ggtgatgagg tagaggaaga ggctgaggaa    780
ccctacgaag aagccacaga gagaaccacc agcattgcca ccaccaccac caccaccaca    840
gagtctgtgg aagaggtggt tcgagaggtg tgctctgaac aagccgagac ggggccgtgc    900
cgagcaatga tctcccgctg gtactttgat gtgactgaag ggaagtgtgc cccattcttt    960
tacggcggat gtgcggcaa ccggaacaac tttgacacag aagagtactg catggccgtg   1020
tgtggcagcg ccattcctac aacagcagcc agtacccctg atgccgttga caagtatctc   1080
```

-continued

```
gagacacctg gggatgagaa tgaacatgcc catttccaga aagccaaaga gaggcttgag    1140
gccaagcacc gagagagaat gtcccaggtc atgagagaat gggaagaggc agaacgtcaa    1200
gcaaagaact tgcctaaagc tgataagaag gcagttatcc agcatttcca ggagaaagtg    1260
gaatctttgg aacaggaagc agccaacgag agacagcagc tggtggagac acacatggcc    1320
agagtggaag ccatgctcaa tgaccgccgc cgcctggccc tggagaacta catcaccgct    1380
ctgcaggctg ttcctcctcg gcctcgtcac gtgttcaata tgctaaagaa gtatgtccgc    1440
gcagaacaga aggacagaca gcacacccta aagcatttcg agcatgtgcg catggtggat    1500
cccaagaaag ccgctcagat ccggtcccag gttatgacac acctccgtgt gatttatgag    1560
cgcatgaatc agtctctctc cctgctctac aacgtgcctg cagtggccga ggagattcag    1620
gatgaagttg atgagctgct tcagaaagag caaaactatt cagatgacgt cttggccaac    1680
atgattagtg aaccaaggat cagttacgga acgatgctct catgccatc tttgaccgaa     1740 acgaaaacca ccgtggagct ccttcccgtg aatggagagt tcagcctgga cgatctccag    1800
ccgtggcatt cttttggggc tgactctgtg ccagccaaca cagaaaacga agttgagcct    1860
gttgatgccc gccctgctgc cgaccgagga ctgaccactc gaccaggttc tgggttgaca    1920
aatatcaaga cggaggagat ctctgaagtg aagatggatg cagaattccg acatgactca    1980
ggatatgaag ttcatcatca aaaattggtg ttcttgcag aagatgtggg ttcaaacaaa     2040
ggtgcaatca ttggactcat ggtgggcggt gttgtcatag cgacagtgat cgtcatcacc    2100
ttggtgatgc tgaagaagaa acagtacaca tccattcatc atggtgtggt ggaggttgac    2160
gccgctgtca ccccagagga gcgccacctg tccaagatgc agcagaacgg ctacgaaaat    2220
ccaacctaca agttctttga gcagatgcag aac                                 2253
```

<210> SEQ ID NO 57
<211> LENGTH: 751
<212> TYPE: PRT
<213> ORGANISM: Homo sapiens

<400> SEQUENCE: 57

```
Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
                20                  25                  30

Gln Ile Ala Met Phe Cys Gly Arg Leu Asn Met His Met Asn Val Gln
                35                  40                  45

Asn Gly Lys Trp Asp Ser Asp Pro Ser Gly Thr Lys Thr Cys Ile Asp
        50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
                100                 105                 110

Ile Pro Tyr Arg Cys Leu Val Gly Glu Phe Val Ser Asp Ala Leu Leu
            115                 120                 125

Val Pro Asp Lys Cys Lys Phe Leu His Gln Glu Arg Met Asp Val Cys
        130                 135                 140

Glu Thr His Leu His Trp His Thr Val Ala Lys Glu Thr Cys Ser Glu
145                 150                 155                 160
```

-continued

```
Lys Ser Thr Asn Leu His Asp Tyr Gly Met Leu Leu Pro Cys Gly Ile
            165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
            195                 200                 205

Trp Trp Gly Gly Ala Asp Thr Asp Tyr Ala Asp Gly Ser Glu Asp Lys
210                 215                 220

Val Val Glu Val Ala Glu Glu Glu Val Ala Glu Val Glu Glu Glu
225                 230                 235                 240

Glu Ala Asp Asp Glu Asp Asp Glu Asp Gly Asp Glu Val Glu Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Thr Glu Ser Val Glu Glu Val Val Arg
            275                 280                 285

Glu Val Cys Ser Glu Gln Ala Glu Thr Gly Pro Cys Arg Ala Met Ile
            290                 295                 300

Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
            325                 330                 335

Cys Met Ala Val Cys Gly Ser Ala Ile Pro Thr Thr Ala Ala Ser Thr
            340                 345                 350

Pro Asp Ala Val Asp Lys Tyr Leu Glu Thr Pro Gly Asp Glu Asn Glu
            355                 360                 365

His Ala His Phe Gln Lys Ala Lys Glu Arg Leu Glu Ala Lys His Arg
            370                 375                 380

Glu Arg Met Ser Gln Val Met Arg Glu Trp Glu Glu Ala Glu Arg Gln
385                 390                 395                 400

Ala Lys Asn Leu Pro Lys Ala Asp Lys Lys Ala Val Ile Gln His Phe
            405                 410                 415

Gln Glu Lys Val Glu Ser Leu Glu Gln Glu Ala Ala Asn Glu Arg Gln
            420                 425                 430

Gln Leu Val Glu Thr His Met Ala Arg Val Glu Ala Met Leu Asn Asp
            435                 440                 445

Arg Arg Arg Leu Ala Leu Glu Asn Tyr Ile Thr Ala Leu Gln Ala Val
450                 455                 460

Pro Pro Arg Pro Arg His Val Phe Asn Met Leu Lys Lys Tyr Val Arg
465                 470                 475                 480

Ala Glu Gln Lys Asp Arg Gln His Thr Leu Lys His Phe Glu His Val
            485                 490                 495

Arg Met Val Asp Pro Lys Lys Ala Ala Gln Ile Arg Ser Gln Val Met
            500                 505                 510

Thr His Leu Arg Val Ile Tyr Glu Arg Met Asn Gln Ser Leu Ser Leu
            515                 520                 525

Leu Tyr Asn Val Pro Ala Val Ala Glu Glu Ile Gln Asp Glu Val Asp
            530                 535                 540

Glu Leu Leu Gln Lys Glu Gln Asn Tyr Ser Asp Asp Val Leu Ala Asn
545                 550                 555                 560

Met Ile Ser Glu Pro Arg Ile Ser Tyr Gly Asn Asp Ala Leu Met Pro
                565                 570                 575

Ser Leu Thr Glu Thr Lys Thr Thr Val Glu Leu Leu Pro Val Asn Gly
```

-continued

```
                580             585             590
Glu Phe Ser Leu Asp Asp Leu Gln Pro Trp His Ser Phe Gly Ala Asp
            595                 600                 605

Ser Val Pro Ala Asn Thr Glu Asn Glu Val Glu Pro Val Asp Ala Arg
        610                 615                 620

Pro Ala Asp Arg Gly Leu Thr Thr Arg Pro Gly Ser Gly Leu Thr
625                 630                 635                 640

Asn Ile Lys Thr Glu Glu Ile Ser Glu Val Lys Met Asp Ala Glu Phe
                645                 650                 655

Arg His Asp Ser Gly Tyr Glu Val His His Gln Lys Leu Val Phe Phe
            660                 665                 670

Ala Glu Asp Val Gly Ser Asn Lys Gly Ala Ile Ile Gly Leu Met Val
        675                 680                 685

Gly Gly Val Val Ile Ala Thr Val Ile Val Ile Thr Leu Val Met Leu
    690                 695                 700

Lys Lys Lys Gln Tyr Thr Ser Ile His His Gly Val Val Glu Val Asp
705                 710                 715                 720

Ala Ala Val Thr Pro Glu Glu Arg His Leu Ser Lys Met Gln Gln Asn
                725                 730                 735

Gly Tyr Glu Asn Pro Thr Tyr Lys Phe Phe Glu Gln Met Gln Asn
            740                 745                 750
```

<210> SEQ ID NO 58
<211> LENGTH: 2316
<212> TYPE: DNA
<213> ORGANISM: Homo sapiens

<400> SEQUENCE: 58

```
atgctgcccg ttttggcact gctcctgctg ccgcctggca cggctcgggc gctggaggta      60
cccactgatg gtaatgctgg cctgctggct gaaccccaga ttgccatgtt ctgtggcaga     120
ctgaacatgc acatgaatgt ccagaatggg aagtgggatt cagatccatc agggaccaaa     180
acctgcattg ataccaagga aggcatcctg cagtattgcc aagaagtcta ccctgaactg     240
cagatcacca atgtggtaga agccaaccaa ccagtgacca tccagaactg gtgcaagcgg     300
ggccgcaagc agtgcaagac ccatccccac tttgtgattc cctaccgctg cttagttggt     360
gagtttgtaa gtgatgccct tctcgttcct gacaagtgca attcttaca ccaggagagg      420
atggatgttt gcgaaactca tcttcactgg cacaccgtcg ccaaagagac atgcagtgag     480
aagagtacca acttgcatga ctacggcatg ttgctgccct gcggaattga caagttccga     540
ggggtagagt ttgtgtgttg cccactggct gaagaaagtg acaatgtgga ttctgctgat     600
gcggaggagg atgactcgga tgtctggtgg ggcggagcag acacagacta tgcagatggg     660
agtgaagaca aagtagtaga agtagcagag gaggaagaag tggctgaggt ggaagaagaa     720
gaagccgatg atgacgagga cgatgaggat ggtgatgagg tagaggaaga ggctgaggaa     780
ccctacgaag aagccacaga gagaaccacc agcattgcca ccaccaccac caccaccaca     840
gagtctgtgg aagaggtggt tcgagaggtg tgctctgaac aagccgagac ggggccgtgc     900
cgagcaatga tctcccgctg gtactttgat gtgactgaag gaagtgtgc cccattcttt     960
tacggcggat gtgcggcaa ccggaacaac tttgacacag aagagtactg catgccgtg     1020
tgtggcagcg ccatgtccca agtttactc aagactaccc aggaacctct tggccgagat    1080
cctgttaaac ttcctacaac agcagccagt accctgatg ccgttgacaa gtatctcgag    1140
acacctgggg atgagaatga acatgcccat ttccagaaag ccaaagagag gcttgaggcc    1200
```

-continued

```
aagcaccgag agagaatgtc ccaggtcatg agagaatggg aagaggcaga acgtcaagca    1260
aagaacttgc ctaaagctga taagaaggca gttatccagc atttccagga gaaagtggaa    1320
tctttggaac aggaagcagc caacgagaga cagcagctgg tggagacaca catggccaga    1380
gtggaagcca tgctcaatga ccgccgccgc ctggccctgg agaactacat caccgctctg    1440
caggctgttc ctcctcggcc tcgtcacgtg ttcaatatgc taaagaagta tgtccgcgca    1500
gaacagaagg acagacagca caccctaaag catttcgagc atgtgcgcat ggtggatccc    1560
aagaaagccg ctcagatccg gtcccaggtt atgacacacc tccgtgtgat ttatgagcgc    1620
atgaatcagt ctctctccct gctctacaac gtgcctgcag tggccgagga gattcaggat    1680
gaagttgatg agctgcttca gaaagagcaa aactattcag atgacgtctt ggccaacatg    1740
attagtgaac caaggatcag ttacggaaac gatgctctca tgccatcttt gaccgaaacg    1800
aaaaccaccg tggagctcct cccgtgaat ggagagttca gcctggacga ctccagccg     1860 tggcattctt ttggggctga ctctgtgcca gccaacacag aaaacgaagt tgagcctgtt    1920
gatgcccgcc ctgctgccga ccgaggacta ccactcgac caggttctgg gttgacaaat     1980
atcaagacgg aggagatctc tgaagtgaag atggatgcag aattccgaca tgactcagga    2040
tatgaagttc atcatcaaaa attggtgttc tttgcagaag atgtgggttc aaacaaaggt    2100
gcaatcattg gactcatggt gggcggtgtt gtcatagcga cagtgatcgt catcaccttg    2160
gtgatgctga agaagaaaca gtacacatcc attcatcatg gtgtggtgga ggttgacgcc    2220
gctgtcaccc cagaggagcg ccacctgtcc aagatgcagc agaacggcta cgaaaatcca    2280
acctacaagt tctttgagca gatgcagaac aagaag                              2316
```

<210> SEQ ID NO 59
<211> LENGTH: 772
<212> TYPE: PRT
<213> ORGANISM: Homo sapiens

<400> SEQUENCE: 59

```
Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175
```

-continued

```
Asp Lys Phe Arg Gly Val Glu Phe Val Cys Cys Pro Leu Ala Glu Glu
            180                 185                 190

Ser Asp Asn Val Asp Ser Ala Asp Glu Glu Asp Ser Asp Val
        195                 200                 205

Trp Trp Gly Gly Ala Asp Thr Asp Tyr Ala Asp Gly Ser Glu Asp Lys
            210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
            245                 250                 255

Glu Ala Glu Glu Pro Tyr Glu Ala Thr Glu Arg Thr Thr Ser Ile
            260                 265                 270

Ala Thr Thr Thr Thr Thr Thr Glu Ser Val Glu Val Val Arg
            275                 280                 285

Glu Val Cys Ser Glu Gln Ala Glu Thr Gly Pro Cys Arg Ala Met Ile
            290                 295                 300

Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
            325                 330                 335

Cys Met Ala Val Cys Gly Ser Ala Met Ser Gln Ser Leu Leu Lys Thr
            340                 345                 350

Thr Gln Glu Pro Leu Ala Arg Asp Pro Val Lys Leu Pro Thr Thr Ala
            355                 360                 365

Ala Ser Thr Pro Asp Ala Val Asp Lys Tyr Leu Glu Thr Pro Gly Asp
            370                 375                 380

Glu Asn Glu His Ala His Phe Gln Lys Ala Lys Glu Arg Leu Glu Ala
385                 390                 395                 400

Lys His Arg Glu Arg Met Ser Gln Val Met Arg Glu Trp Glu Glu Ala
            405                 410                 415

Glu Arg Gln Ala Lys Asn Leu Pro Lys Ala Asp Lys Lys Ala Val Ile
            420                 425                 430

Gln His Phe Gln Glu Lys Val Glu Ser Leu Glu Gln Glu Ala Ala Asn
            435                 440                 445

Glu Arg Gln Gln Leu Val Glu Thr His Met Ala Arg Val Glu Ala Met
            450                 455                 460

Leu Asn Asp Arg Arg Arg Leu Ala Leu Glu Asn Tyr Ile Thr Ala Leu
465                 470                 475                 480

Gln Ala Val Pro Pro Arg Pro Arg His Val Phe Asn Met Leu Lys Lys
            485                 490                 495

Tyr Val Arg Ala Glu Gln Lys Asp Arg Gln His Thr Leu Lys His Phe
            500                 505                 510

Glu His Val Arg Met Val Asp Pro Lys Lys Ala Ala Gln Ile Arg Ser
            515                 520                 525

Gln Val Met Thr His Leu Arg Val Ile Tyr Glu Arg Met Asn Gln Ser
            530                 535                 540

Leu Ser Leu Leu Tyr Asn Val Pro Ala Val Ala Glu Glu Ile Gln Asp
545                 550                 555                 560

Glu Val Asp Glu Leu Leu Gln Lys Glu Gln Asn Tyr Ser Asp Asp Val
            565                 570                 575

Leu Ala Asn Met Ile Ser Glu Pro Arg Ile Ser Tyr Gly Asn Asp Ala
            580                 585                 590
```

```
Leu Met Pro Ser Leu Thr Glu Thr Lys Thr Thr Val Glu Leu Leu Pro
        595                 600                 605

Val Asn Gly Glu Phe Ser Leu Asp Asp Leu Gln Pro Trp His Ser Phe
    610                 615                 620

Gly Ala Asp Ser Val Pro Ala Asn Thr Glu Asn Glu Val Glu Pro Val
625                 630                 635                 640

Asp Ala Arg Pro Ala Ala Asp Arg Gly Leu Thr Thr Arg Pro Gly Ser
                645                 650                 655

Gly Leu Thr Asn Ile Lys Thr Glu Glu Ile Ser Glu Val Lys Met Asp
            660                 665                 670

Ala Glu Phe Arg His Asp Ser Gly Tyr Glu Val His His Gln Lys Leu
        675                 680                 685

Val Phe Phe Ala Glu Asp Val Gly Ser Asn Lys Gly Ala Ile Ile Gly
    690                 695                 700

Leu Met Val Gly Gly Val Val Ile Ala Thr Val Ile Val Ile Thr Leu
705                 710                 715                 720

Val Met Leu Lys Lys Lys Gln Tyr Thr Ser Ile His His Gly Val Val
                725                 730                 735

Glu Val Asp Ala Ala Val Thr Pro Glu Glu Arg His Leu Ser Lys Met
            740                 745                 750

Gln Gln Asn Gly Tyr Glu Asn Pro Thr Tyr Lys Phe Phe Glu Gln Met
        755                 760                 765

Gln Asn Lys Lys
    770

<210> SEQ ID NO 60
<211> LENGTH: 2259
<212> TYPE: DNA
<213> ORGANISM: Homo sapiens

<400> SEQUENCE: 60
atgctgcccg gtttggcact gctcctgctg gccgcctgga cggctcgggc gctggaggta      60
cccactgatg gtaatgctgg cctgctggct gaaccccaga ttgccatgtt ctgtggcaga     120
ctgaacatgc acatgaatgt ccagaatggg aagtgggatt cagatccatc agggaccaaa     180
acctgcattg ataccaagga aggcatcctg cagtattgcc aagaagtcta ccctgaactg     240
cagatcacca atgtggtaga agccaaccaa ccagtgacca tccagaactg gtgcaagcgg     300
ggccgcaagc agtgcaagac ccatccccac tttgtgattc cctaccgctg cttagttggt     360
gagtttgtaa gtgatgccct tctcgttcct gacaagtgca attcttaca ccaggagagg      420 atggatgttt gcgaaactca tcttcactgg cacaccgtcg ccaaagagac atgcagtgag     480
aagagtacca acttgcatga ctacggcatg ttgctgccct gcggaattga caagttccga     540
ggggtagagt ttgtgtgttg cccactggct gaagaaagtg acaatgtgga ttctgctgat     600
gcggaggagg atgactcgga tgtctggtgg ggcggagcag acacagacta tgcagatggg     660
agtgaagaca agtagtaga gtagcagag gaggaagaag tggctgaggt ggaagaagaa       720
gaagccgatg atgacgagga cgatgaggat ggtgatgagg tagaggaaga ggctgaggaa     780
ccctacgaag aagccacaga gagaaccacc agcattgcca ccaccaccac caccaccaca     840
gagtctgtgg aagaggtggt tcgagaggtg tgctctgaac aagccgagac ggggccgtgc     900
cgagcaatga tctcccgctg gtactttgat gtgactgaag ggaagtgtgc cccattcttt     960
tacggcggat gtgcggcaa ccggaacaac tttgacacag aagagtactg catggccgtg     1020
tgtggcagcg ccattcctac aacagcagcc agtacccctg atgccgttga caagtatctc    1080
```

-continued

```
gagacacctg gggatgagaa tgaacatgcc catttccaga aagccaaaga gaggcttgag    1140
gccaagcacc gagagagaat gtcccaggtc atgagagaat gggaagaggc agaacgtcaa    1200
gcaaagaact tgcctaaagc tgataagaag gcagttatcc agcatttcca ggagaaagtg    1260
gaatctttgg aacaggaagc agccaacgag agacagcagc tggtggagac acacatggcc    1320
agagtggaag ccatgctcaa tgaccgccgc cgcctggccc tggagaacta catcaccgct    1380
ctgcaggctg ttcctcctcg gcctcgtcac gtgttcaata tgctaaagaa gtatgtccgc    1440
gcagaacaga aggacagaca gcacacccta aagcatttcg agcatgtgcg catggtggat    1500
cccaagaaag ccgctcagat ccggtcccag gttatgacac acctccgtgt gatttatgag    1560
cgcatgaatc agtctctctc cctgctctac aacgtgcctg cagtggccga ggagattcag    1620
gatgaagttg atgagctgct tcagaaagag caaaactatt cagatgacgt cttggccaac    1680
atgattagtg aaccaaggat cagttacgga acgatgctct catgccatc tttgaccgaa     1740 acgaaaacca ccgtggagct ccttcccgtg aatggagagt tcagcctgga cgatctccag    1800
ccgtggcatt cttttggggc tgactctgtg ccagccaaca cagaaaacga agttgagcct    1860
gttgatgccc gccctgctgc cgaccgagga ctgaccactc gaccaggttc tgggttgaca    1920
aatatcaaga cggaggagat ctctgaagtg aagatggatg cagaattccg acatgactca    1980
ggatatgaag ttcatcatca aaaattggtg ttctttgcag aagatgtggg ttcaaacaaa    2040
ggtgcaatca ttggactcat ggtgggcggt gttgtcatag cgacagtgat cgtcatcacc    2100
ttggtgatgc tgaagaagaa acagtacaca tccattcatc atggtgtggt ggaggttgac    2160
gccgctgtca ccccagagga gcgccacctg tccaagatgc agcagaacgg ctacgaaaat    2220
ccaacctaca agttctttga gcagatgcag aacaagaag                           2259
```

<210> SEQ ID NO 61
<211> LENGTH: 753
<212> TYPE: PRT
<213> ORGANISM: Homo sapiens

<400> SEQUENCE: 61

```
Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160
```

-continued

Lys Ser Thr Asn Leu His Asp Tyr Gly Met Leu Leu Pro Cys Gly Ile
            165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
            195                 200                 205

Trp Trp Gly Gly Ala Asp Thr Asp Tyr Ala Asp Gly Ser Glu Asp Lys
210                 215                 220

Val Val Glu Val Ala Glu Glu Glu Val Ala Glu Val Glu Glu Glu
225                 230                 235                 240

Glu Ala Asp Asp Glu Asp Asp Glu Asp Gly Asp Glu Val Glu Glu
            245                 250                 255

Glu Ala Glu Glu Pro Tyr Glu Glu Ala Thr Glu Arg Thr Thr Ser Ile
            260                 265                 270

Ala Thr Thr Thr Thr Thr Thr Thr Glu Ser Val Glu Glu Val Val Arg
            275                 280                 285

Glu Val Cys Ser Glu Gln Ala Glu Thr Gly Pro Cys Arg Ala Met Ile
            290                 295                 300

Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
            325                 330                 335

Cys Met Ala Val Cys Gly Ser Ala Ile Pro Thr Thr Ala Ala Ser Thr
            340                 345                 350

Pro Asp Ala Val Asp Lys Tyr Leu Glu Thr Pro Gly Asp Glu Asn Glu
            355                 360                 365

His Ala His Phe Gln Lys Ala Lys Glu Arg Leu Glu Ala Lys His Arg
            370                 375                 380

Glu Arg Met Ser Gln Val Met Arg Glu Trp Glu Glu Ala Glu Arg Gln
385                 390                 395                 400

Ala Lys Asn Leu Pro Lys Ala Asp Lys Lys Ala Val Ile Gln His Phe
            405                 410                 415

Gln Glu Lys Val Glu Ser Leu Glu Gln Glu Ala Ala Asn Glu Arg Gln
            420                 425                 430

Gln Leu Val Glu Thr His Met Ala Arg Val Glu Ala Met Leu Asn Asp
            435                 440                 445

Arg Arg Arg Leu Ala Leu Glu Asn Tyr Ile Thr Ala Leu Gln Ala Val
450                 455                 460

Pro Pro Arg Pro Arg His Val Phe Asn Met Leu Lys Lys Tyr Val Arg
465                 470                 475                 480

Ala Glu Gln Lys Asp Arg Gln His Thr Leu Lys His Phe Glu His Val
            485                 490                 495

Arg Met Val Asp Pro Lys Lys Ala Ala Gln Ile Arg Ser Gln Val Met
            500                 505                 510

Thr His Leu Arg Val Ile Tyr Glu Arg Met Asn Gln Ser Leu Ser Leu
            515                 520                 525

Leu Tyr Asn Val Pro Ala Val Ala Glu Glu Ile Gln Asp Glu Val Asp
            530                 535                 540

Glu Leu Leu Gln Lys Glu Gln Asn Tyr Ser Asp Asp Val Leu Ala Asn
545                 550                 555                 560

Met Ile Ser Glu Pro Arg Ile Ser Tyr Gly Asn Asp Ala Leu Met Pro
            565                 570                 575

Ser Leu Thr Glu Thr Lys Thr Thr Val Glu Leu Leu Pro Val Asn Gly

```
                580             585             590
Glu Phe Ser Leu Asp Asp Leu Gln Pro Trp His Ser Phe Gly Ala Asp
            595                 600             605

Ser Val Pro Ala Asn Thr Glu Asn Glu Val Glu Pro Val Asp Ala Arg
        610                 615             620

Pro Ala Ala Asp Arg Gly Leu Thr Thr Arg Pro Gly Ser Gly Leu Thr
625                 630                 635                 640

Asn Ile Lys Thr Glu Glu Ile Ser Glu Val Lys Met Asp Ala Glu Phe
                645                 650                 655

Arg His Asp Ser Gly Tyr Glu Val His His Gln Lys Leu Val Phe Phe
            660                 665                 670

Ala Glu Asp Val Gly Ser Asn Lys Gly Ala Ile Ile Gly Leu Met Val
        675                 680                 685

Gly Gly Val Val Ile Ala Thr Val Ile Val Ile Thr Leu Val Met Leu
    690                 695                 700

Lys Lys Lys Gln Tyr Thr Ser Ile His His Gly Val Val Glu Val Asp
705                 710                 715                 720

Ala Ala Val Thr Pro Glu Glu Arg His Leu Ser Lys Met Gln Gln Asn
                725                 730                 735

Gly Tyr Glu Asn Pro Thr Tyr Lys Phe Phe Glu Gln Met Gln Asn Lys
            740                 745                 750

Lys

<210> SEQ ID NO 62
<211> LENGTH: 8
<212> TYPE: PRT
<213> ORGANISM: Artificial sequence
<220> FEATURE:
<223> OTHER INFORMATION: Synthesized  peptide

<400> SEQUENCE: 62

Leu Glu Val Leu Phe Gln Gly Pro
1               5

<210> SEQ ID NO 63
<211> LENGTH: 10
<212> TYPE: PRT
<213> ORGANISM: Artificial sequence
<220> FEATURE:
<223> OTHER INFORMATION: Synthesized peptide

<400> SEQUENCE: 63

Ser Glu Val Asn Leu Asp Ala Glu Phe Arg
1               5                   10

<210> SEQ ID NO 64
<211> LENGTH: 10
<212> TYPE: PRT
<213> ORGANISM: Artificial sequence
<220> FEATURE:
<223> OTHER INFORMATION: Synthesized peptide

<400> SEQUENCE: 64

Ser Glu Val Lys Met Asp Ala Glu Phe Arg
1               5                   10

<210> SEQ ID NO 65
<211> LENGTH: 15
<212> TYPE: PRT
<213> ORGANISM: Artificial sequence
<220> FEATURE:
```

```
<223> OTHER INFORMATION: Synthesized peptide

<400> SEQUENCE: 65

Arg Arg Gly Gly Val Val Ile Ala Thr Val Ile Val Gly Glu Arg
1               5                   10                  15

<210> SEQ ID NO 66
<211> LENGTH: 4
<212> TYPE: PRT
<213> ORGANISM: Artificial sequence
<220> FEATURE:
<223> OTHER INFORMATION: Synthesized peptide

<400> SEQUENCE: 66

Asn Leu Asp Ala
1

<210> SEQ ID NO 67
<211> LENGTH: 8
<212> TYPE: PRT
<213> ORGANISM: Artificial sequence
<220> FEATURE:
<223> OTHER INFORMATION: Synthesized peptide

<400> SEQUENCE: 67

Glu Val Lys Met Asp Ala Glu Phe
1               5

<210> SEQ ID NO 68
<211> LENGTH: 5
<212> TYPE: PRT
<213> ORGANISM: Artificial sequence
<220> FEATURE:
<223> OTHER INFORMATION: Synthesized peptide

<400> SEQUENCE: 68

Gly Arg Arg Gly Ser
1               5

<210> SEQ ID NO 69
<211> LENGTH: 6
<212> TYPE: PRT
<213> ORGANISM: Artificial sequence
<220> FEATURE:
<223> OTHER INFORMATION: Synthesized peptide

<400> SEQUENCE: 69

Thr Gln His Gly Ile Arg
1               5

<210> SEQ ID NO 70
<211> LENGTH: 6
<212> TYPE: PRT
<213> ORGANISM: Artificial sequence
<220> FEATURE:
<223> OTHER INFORMATION: Synthesized peptide

<400> SEQUENCE: 70

Glu Thr Asp Glu Glu Pro
1               5

<210> SEQ ID NO 71
<211> LENGTH: 15
<212> TYPE: PRT
<213> ORGANISM: Artificial sequence
<220> FEATURE:
<223> OTHER INFORMATION: Synthesized peptide
```

-continued

```
<400> SEQUENCE: 71

Met Cys Ala Glu Val Lys Met Asp Ala Glu Phe Lys Asp Asn Pro
1               5                   10                  15

<210> SEQ ID NO 72
<211> LENGTH: 4
<212> TYPE: PRT
<213> ORGANISM: Artificial sequence
<220> FEATURE:
<223> OTHER INFORMATION: Synthesized Peptide
<220> FEATURE:
<221> NAME/KEY: misc_feature
<222> LOCATION: (1)
<223> OTHER INFORMATION: Xaa = Lys or Asn
<220> FEATURE:
<221> NAME/KEY: misc_feature
<222> LOCATION: (2)
<223> OTHER INFORMATION: Xaa = Met or Leu
<220> FEATURE:
<221> NAME/KEY: misc_feature
<222> LOCATION: (3)
<223> OTHER INFORMATION: Xaa = Asp
<220> FEATURE:
<221> NAME/KEY: misc_feature
<222> LOCATION: (4)
<223> OTHER INFORMATION: Xaa = Asp

<400> SEQUENCE: 72

Xaa Xaa Xaa Xaa
1

<210> SEQ ID NO 73
<211> LENGTH: 476
<212> TYPE: PRT
<213> ORGANISM: Mus musculus

<400> SEQUENCE: 73

Met Ala Pro Ala Leu His Trp Leu Leu Leu Trp Val Gly Ser Gly Met
1               5                   10                  15

Leu Pro Ala Gln Gly Thr His Leu Gly Ile Arg Leu Pro Leu Arg Ser
            20                  25                  30

Gly Leu Ala Gly Pro Pro Leu Gly Leu Arg Leu Pro Arg Glu Thr Asp
        35                  40                  45

Glu Glu Ser Glu Glu Pro Gly Arg Arg Gly Ser Phe Val Glu Met Val
    50                  55                  60

Asp Asn Leu Arg Gly Lys Ser Gly Gln Gly Tyr Tyr Val Glu Met Thr
65                  70                  75                  80

Val Gly Ser Pro Pro Gln Thr Leu Asn Ile Leu Val Asp Thr Gly Ser
                85                  90                  95

Ser Asn Phe Ala Val Gly Ala Ala Pro His Pro Phe Leu His Arg Tyr
            100                 105                 110

Tyr Gln Arg Gln Leu Ser Ser Thr Tyr Arg Asp Leu Arg Lys Gly Val
        115                 120                 125

Tyr Val Pro Tyr Thr Gln Gly Lys Trp Glu Gly Glu Leu Gly Thr Asp
    130                 135                 140

Leu Val Ser Ile Pro His Gly Pro Asn Val Thr Val Arg Ala Asn Ile
145                 150                 155                 160

Ala Ala Ile Thr Glu Ser Asp Lys Phe Phe Ile Asn Gly Ser Asn Trp
                165                 170                 175

Glu Gly Ile Leu Gly Leu Ala Tyr Ala Glu Ile Ala Arg Leu Cys Gly
            180                 185                 190
```

```
                        -continued

Ala Gly Phe Pro Leu Asn Gln Thr Glu Ala Leu Ala Ser Val Gly Gly
            195                 200                 205

Ser Met Ile Ile Gly Gly Ile Asp His Ser Leu Tyr Thr Gly Ser Leu
    210                 215                 220

Trp Tyr Thr Pro Ile Arg Arg Glu Trp Tyr Tyr Glu Val Ile Ile Val
225                 230                 235                 240

Arg Val Glu Ile Asn Gly Gln Asp Leu Lys Met Asp Cys Lys Glu Tyr
                245                 250                 255

Asn Tyr Asp Lys Ser Ile Val Asp Ser Gly Thr Thr Asn Leu Arg Leu
            260                 265                 270

Pro Lys Lys Val Phe Glu Ala Ala Val Lys Ser Ile Lys Ala Ala Ser
        275                 280                 285

Ser Thr Glu Lys Phe Pro Asp Gly Phe Trp Leu Gly Glu Gln Leu Val
    290                 295                 300

Cys Trp Gln Ala Gly Thr Thr Pro Trp Asn Ile Phe Pro Val Ile Ser
305                 310                 315                 320

Leu Tyr Leu Met Gly Glu Val Thr Asn Gln Ser Phe Arg Ile Thr Ile
                325                 330                 335

Leu Pro Gln Gln Tyr Leu Arg Pro Val Glu Asp Val Ala Thr Ser Gln
            340                 345                 350

Asp Asp Cys Tyr Lys Phe Ala Val Ser Gln Ser Ser Thr Gly Thr Val
        355                 360                 365

Met Gly Ala Val Ile Met Glu Gly Phe Tyr Val Val Phe Asp Arg Ala
370                 375                 380

Arg Lys Arg Ile Gly Phe Ala Val Ser Ala Cys His Val His Asp Glu
385                 390                 395                 400

Phe Arg Thr Ala Ala Val Glu Gly Pro Phe Val Thr Ala Asp Met Glu
                405                 410                 415

Asp Cys Gly Tyr Asn Ile Pro Gln Thr Asp Glu Ser Thr Leu Met Thr
            420                 425                 430

Ile Ala Tyr Val Met Ala Ala Ile Cys Ala Leu Phe Met Leu Pro Leu
        435                 440                 445

Cys Leu Met Val Cys Gln Trp Arg Cys Leu Arg Cys Leu Arg His Gln
    450                 455                 460

His Asp Asp Phe Ala Asp Asp Ile Ser Leu Leu Lys
465                 470                 475
```

What is claimed is:

1. A purified or isolated polypeptide comprising an amino acid sequence that is at least 95% identical to a fragment of the Asp2 protein amino acid sequence of SEQ ID NO: 4,
   wherein said fragment is a contiguous fragment that includes the aspartyl protease active site tripeptides DTG and DSG and exhibits aspartyl protease activity involved in processing APP into amyloid beta,
   wherein said polypeptide lacks a transmembrane domain, and
   wherein said polypeptide exhibits aspartyl protease activity involved in processing APP into amyloid beta.

2. A purified or isolated polypeptide according to claim 1, wherein said polypeptide further includes a heterologous peptide tag.

3. A method for identifying an agent that decreases the protease activity of the aspartyl protease polypeptide of claim 1 or 2 comprising steps of:
   (a) measuring proteolytic activity of said polypeptide in the presence and absence of a test agent; and
   (b) comparing proteolytic activity of the polypeptide in the presence and absence of the test agent, wherein decreased proteolytic activity in the presence of the test agent identifies the test agent as an agent that decreases the protease activity of the aspartyl protease polypeptide.

4. A method according to claim 3 wherein step (a) comprises measuring the proteolytic activity of the polypeptide toward an amyloid precursor protein (APP) substrate.

* * * * *

UNITED STATES PATENT AND TRADEMARK OFFICE
CERTIFICATE OF CORRECTION

PATENT NO. : 6,825,023 B1
DATED : November 30, 2004
INVENTOR(S) : Mark E. Gurney et al.

It is certified that error appears in the above-identified patent and that said Letters Patent is hereby corrected as shown below:

Title page,
Item [*] Notice, please insert -- This patent is subject to a terminal disclaimer. --.

Column 1,
Line 62, please delete "αβ-secretase" and insert -- α-secretase --.

Column 2,
Line 24, please insert -- , in -- before "addition".
Line 46, please delete "two-sets" and insert -- two sets --.

Column 3,
Line 12, please delete "led" and insert -- linked --.
Line 56, please insert -- of -- before "those".

Column 5,
Line 10, please insert -- to -- after "linked".
Line 49, please insert -- of -- before "those".

Column 6,
Line 1, please delete "(p)" and insert -- (β) --.
Line 28, please delete "lease" and insert -- least --.

Column 8,
Line 39, please delete "has" and insert -- as --.
Line 46, please delete "βsecretase" and insert -- β-secretase --.
Line 62, please delete "a,".

Column 9,
Line 10, please delete "calorimetric" and insert -- colorimetric --.
Line 18, please delete "KM-NL" and insert -- KM→NL --.
Line 24, please insert -- which is associated -- before "with".
Line 38, please delete "construct" and insert -- constructed --.
Line 40, please delete "streches" and insert -- stretches --.

UNITED STATES PATENT AND TRADEMARK OFFICE
CERTIFICATE OF CORRECTION

PATENT NO. : 6,825,023 B1
DATED : November 30, 2004
INVENTOR(S) : Mark E. Gurney et al.

It is certified that error appears in the above-identified patent and that said Letters Patent is hereby corrected as shown below:

Column 10,
Line 5, please delete "carboxy-terminal" and insert -- amino-terminal --.
Line 12, please delete "hyrdrophobic" and insert -- hydrophobic --.
Line 21, please delete "NLDA" and insert -- NLDA. --.
Lines 26-27, please delete "comprises" and insert -- comprise --.
Line 49, please delete "P secretase" and insert -- β-secretase --.
Line 59, please delete "a." and insert -- a --.

Column 11,
Line 22, please delete "β-secrete" and insert -- β-secretase --.
Line 53, please delete "on" and insert -- one --.
Lines 66-67, please delete "that that the β-expresses" and insert -- that expresses --.

Column 12,
Line 27, please delete "If)" and insert -- ID --.
Line 50, please delete "C3".
Line 59, please delete "binds" and insert -- bind --.
Line 64, please delete "describes" and insert -- describe --.

Column 15,
Line 16, please delete "KM-NL" and insert -- KM→NL --.
Line 43, please delete "shows".
Line 55, please delete "(SEQ ID NO: 9)" and insert -- (SEQ ID NO: 8) --.
Line 56, please delete "shows".
Line 67, please delete "mRNA" and insert -- mRNA. --.

Column 16,
Line 4, please delete "farther" and insert -- further --.
Line 32, please delete "exists" and insert -- exist --.
Line 50, please delete "530532" and insert -- 530-532 --.
Line 57, please delete "PAP or PAP" and insert -- βAP or βAP --.
Line 62, please delete "abreviations" and insert -- abbreviations --.

Column 17,
Line 45, please delete "β-secretase" and insert -- γ-secretase --.

Column 18,
Line 58, please delete "Hu-Asp2)" and insert -- Hu-Asp2(b) --.

UNITED STATES PATENT AND TRADEMARK OFFICE
CERTIFICATE OF CORRECTION

PATENT NO. : 6,825,023 B1
DATED : November 30, 2004
INVENTOR(S) : Mark E. Gurney et al.

It is certified that error appears in the above-identified patent and that said Letters Patent is hereby corrected as shown below:

Column 20,
Line 4, please insert -- the -- before "amino-terminus".
Line 34, please delete "4;".
Line 64, please delete "D" and insert -- ID --.

Column 21,
Line 58, please delete "at." and insert -- al. --.

Column 24,
Line 16, please delete "__yeast" and insert -- yeast --.
Line 45, please delete "comprises" and insert -- comprise --.

Column 25,
Line 12, please delete "embyonic" and insert -- embryonic --.

Column 26,
Line 16, please insert -- which KM -- after "in".

Column 27,
Line 26, please delete "24" and insert -- 2-4 --.
Line 26, please delete "4 peptide" and insert -- Aβ peptide --.

Column 28,
Lines 1-2, please delete "$D^{y+}_{25}TG$" and insert -- $D^{Y+25}TG$ --.
Line 58, please delete "a".
Line 63, please delete "MV" and insert -- HIV --.

Column 29,
Line 45, please delete "CI1D2.2" and insert -- C11D2.2 --.

Column 31,
Line 12, please delete "sequence" and insert -- sequenced --.
Line 55, please delete "contains" and insert -- contain --.

Column 32,
Line 32, please insert -- to -- before "contain".
Line 62, please delete "1" and insert -- I --.
Line 66, please delete "manufacture" and insert -- manufacturer --.

UNITED STATES PATENT AND TRADEMARK OFFICE
CERTIFICATE OF CORRECTION

PATENT NO. : 6,825,023 B1
DATED : November 30, 2004
INVENTOR(S) : Mark E. Gurney et al.

It is certified that error appears in the above-identified patent and that said Letters Patent is hereby corrected as shown below:

Column 33,
Line 52, please delete "is" and insert -- in --.
Line 55, please delete "MR" and insert -- IMR --.

Column 34,
Lines 30-31, please delete "#275 CGAATTMATTCCAGCACACTGGCTA" and insert -- #275 CGAATTAAATTCCAGCACACTGGCTA --.

Column 35,
Line 23, please delete "AP" and insert -- Aβ --.

Column 36,
Line 43, please delete "prorietary" and insert -- proprietary --.
Line 56, please delete "λg/ml" and insert -- mg/ml --.

Column 38,
Line 26, please delete "V717-F" and insert -- V717→F --.
Line 62, please delete "V717-F. The V717-F" and insert -- V717→F. The V717→F --.

Column 39,
Line 14, please delete "KM-NL" and insert -- KM→NL --.
Line 27, please delete "D" and insert -- ID --.

Column 40,
Line 28, please delete "KM-NL" and insert -- KM→NL --.
Line 44, please delete "AP" and insert -- Aβ --.
Line 65, please delete "Ab" and insert -- Aβ --.

Column 41,
Line 5, please delete "V717-F" and insert -- V717→F --.
Line 30, please delete "D" and insert -- ID --.
Line 62, please delete "if".

Column 43,
Line 22, please delete "D" and insert -- ID --.
Line 63, please delete "SM" and insert -- 8M --.

Column 44,
Line 57, please delete "200/a" and insert -- 20% --.

UNITED STATES PATENT AND TRADEMARK OFFICE
CERTIFICATE OF CORRECTION

PATENT NO.    : 6,825,023 B1
DATED         : November 30, 2004
INVENTOR(S)   : Mark E. Gurney et al.

It is certified that error appears in the above-identified patent and that said Letters Patent is hereby corrected as shown below:

Column 45,
Line 30, please delete "Hu-ASp2(b)" and insert -- Hu-Asp2(b) --.

Column 46,
Line 46, please delete "A8.0" and insert -- 8.0 --.
Line 47, please delete "anion 4;" and insert -- anion --.
Line 50, please delete "(His)" and insert -- (His)$_6$ --.

Column 47,
Line 45, please delete "ASp" and insert -- Asp --.

Column 48,
Line 46, please delete "Swedigh" and insert -- Swedish --.

Signed and Sealed this

Twenty-seventh Day of September, 2005

JON W. DUDAS
*Director of the United States Patent and Trademark Office*